US011554157B2

(12) United States Patent
Rogelj et al.

(10) Patent No.: US 11,554,157 B2
(45) Date of Patent: Jan. 17, 2023

(54) ANTI-INFECTIVE FORMULATIONS

(71) Applicant: NEW MEXICO TECH UNIVERSITY RESEARCH PARK CORPORATION, Socorro, NM (US)

(72) Inventors: Snezna Rogelj, Socorro, NM (US); Danielle Nicole Turner, Socorro, NM (US)

(73) Assignee: NEW MEXICO TECH UNIVERSITY RESEARCH PARK CORPORATION, Socorro, NM (US)

( * ) Notice: Subject to any disclaimer, the term of this patent is extended or adjusted under 35 U.S.C. 154(b) by 0 days.

(21) Appl. No.: 17/046,271

(22) PCT Filed: Apr. 11, 2019

(86) PCT No.: PCT/US2019/026866
§ 371 (c)(1),
(2) Date: Oct. 8, 2020

(87) PCT Pub. No.: WO2019/200025
PCT Pub. Date: Oct. 17, 2019

(65) Prior Publication Data
US 2021/0361737 A1  Nov. 25, 2021

Related U.S. Application Data

(60) Provisional application No. 62/656,111, filed on Apr. 11, 2018, provisional application No. 62/749,309, filed on Oct. 23, 2018.

(51) Int. Cl.
| | | |
|---|---|---|
| *A61K 31/14* | (2006.01) | |
| *A61K 31/198* | (2006.01) | |
| *A61K 38/12* | (2006.01) | |
| *A61P 31/04* | (2006.01) | |
| *A61P 31/10* | (2006.01) | |
| *A61K 47/18* | (2017.01) | |
| *A61K 47/44* | (2017.01) | |

(52) U.S. Cl.
CPC ............. *A61K 38/12* (2013.01); *A61K 31/14* (2013.01); *A61K 31/198* (2013.01); *A61K 47/183* (2013.01); *A61K 47/186* (2013.01); *A61K 47/44* (2013.01); *A61P 31/04* (2018.01); *A61P 31/10* (2018.01)

(58) Field of Classification Search
CPC ...... A61K 31/14; A61K 31/198; A61K 38/12; A61P 31/00; A61P 31/04–08; A61P 31/12–22
See application file for complete search history.

(56) References Cited

U.S. PATENT DOCUMENTS

| | | | | |
|---|---|---|---|---|
| 3,507,796 A | * | 4/1970 | Voss ......................... | C11D 3/48 424/54 |
| 3,888,947 A | * | 6/1975 | Stephenson ......... | C07C 279/265 562/567 |
| 6,322,992 B1 | * | 11/2001 | Friedman ......... | G01N 33/54386 435/7.92 |
| 8,735,054 B1 | * | 5/2014 | Sun ...................... | A01N 1/0294 435/1.1 |
| 2004/0037895 A1 | * | 2/2004 | Zhu ........................ | A61K 31/58 424/697 |
| 2008/0317702 A1 | | 12/2008 | Edgington et al. | |
| 2014/0271757 A1 | | 9/2014 | Agrawal et al. | |
| 2020/0046664 A1 | * | 2/2020 | Patel .................... | A61K 31/198 |

FOREIGN PATENT DOCUMENTS

| | | |
|---|---|---|
| CN | 104877806 A | 9/2015 |
| WO | WO-2018035183 A1 | 2/2018 |

OTHER PUBLICATIONS

Wikipedia, "Propylene glycol", Dec. 6, 2017 (Dec. 6, 2017), retrieved on Jun. 3, 2019 from https://en.wikipedia.org/w/index.php?title=Propylene_glycol&oldid=-81 4001880.
Wikipedia, "Glycerol", Dec. 23, 2017 (Dec. 23, 2017), retrieved on Jun. 3, 2019 from https://enswikipedia.org/w/index.php?title.Glycerol&oldid=816765979.
Extended European Search Report issued in European Patent Application No. 19784691.8 dated Feb. 4, 2022.
Qiu et al. In vitro inhibition of bacterial growth by iron chelators. FEMS Microbiol Lett. Jan. 2011;314(2):107-11. doi: 10.1111/j.1574-6968.2010.02153.x. Epub Nov. 29, 2010. PMID: 21114684.
Vieira et al. Cationic lipids and surfactants as antifungal agents: mode of action. J Antimicrob Chemother. Oct. 2006;58(4):760-7. doi: 10.1093/jac/dkl312. Epub Aug. 2, 2006. PMID: 16885181.

* cited by examiner

*Primary Examiner* — Jeffrey E. Russel
(74) *Attorney, Agent, or Firm* — Wilson Sonsini Goodrich & Rosati

(57) ABSTRACT

The present disclosure provides pharmaceutical compositions for treating fungal and bacterial infections. The pharmaceutical compositions of the disclosure comprise a cationic surfactant, a chelating agent, and at least one solvent. The pharmaceutical compositions of the disclosure can be used to treat drug-sensitive or multi drug-resistant bacterial or fungal infections.

20 Claims, 100 Drawing Sheets

Day 2

Day 7

Day 1

Day 5

FIG. 97

ANTI-INFECTIVE FORMULATIONS

CROSS REFERENCE

This application is a National Stage Entry of PCT/US2019/026866 filed Apr. 11, 2019, which claims the benefit of U.S. Provisional Application No. 62/656,111, filed Apr. 11, 2018, and U.S. Provisional Application No. 62/749,309, filed Oct. 23, 2018, each of which is incorporated herein by reference in its entirety.

BACKGROUND

Fungi are primitive organisms that live in air, water, soil, and on other surfaces. Some types of fungus reproduce by sending spores through the air. When the spores land on and grow on the body, the spores can cause fungal infections. People with weakened immune systems or people taking medicines, such as antibiotics or corticosteroids, are at increased risk for fungal skin infections. Fungal infections are often difficult to treat, and treatment requires antifungal agents specific to the type of fungus that is causing the infection.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the disclosure provides a pharmaceutical composition comprising, in a unit dosage form: a) a cationic surfactant, wherein the cationic surfactant is a cetyltrimethylammonium halide; b) a chelating agent, wherein the chelating agent is diethylenetriaminepentaacetic acid (DTPA) or a pharmaceutically-acceptable salt thereof; and c) a solvent.

In some embodiments, the disclosure provides a method of killing a microorganism comprising administering to the microorganism a therapeutically-effective amount of a pharmaceutical composition, wherein the pharmaceutical composition comprises, in a unit dosage form: a) a cationic surfactant, wherein the cationic surfactant is a cetyltrimethylammonium halide; b) a chelating agent, wherein the chelating agent is diethylenetriaminepentaacetic acid (DTPA) or a pharmaceutically-acceptable salt thereof; and c) a solvent.

In some embodiments, the disclosure provides a method of treating an infection comprising administering to a subject in need thereof a therapeutically-effective amount of a pharmaceutical composition, wherein the pharmaceutical composition comprises, in unit dosage form: a) a cationic surfactant, wherein the cationic surfactant is cetyltrimethylammonium halide; b) a chelating agent, wherein the chelating agent is diethylenetriaminepentaacetic acid (DTPA) or a pharmaceutically-acceptable salt thereof: and c) a solvent.

In some embodiments, the disclosure provides a method of disinfecting a surface comprising administering to a surface in need thereof a therapeutically-effective amount of a pharmaceutical composition, wherein the pharmaceutical composition comprises, in unit dosage form: a) a cationic surfactant, wherein the cationic surfactant is cetyltrimethylammonium halide; b) a chelating agent, wherein the chelating agent is diethylenetriaminepentaacetic acid (DTPA) or a pharmaceutically-acceptable salt thereof; and c) a solvent.

In some embodiments, the disclosure provides a method of disinfecting an agricultural product, the method comprising contacting the agricultural product with an effective amount of a composition, wherein the composition comprises, in unit dosage form: a) a cationic surfactant, wherein the cationic surfactant is a cetyltrimethylammonium halide; b) a chelating agent, wherein the chelating agent is diethylenetriaminepentaacetic acid (DTPA) or a pharmaceutically-acceptable salt thereof; and c) a solvent.

Figure 8:
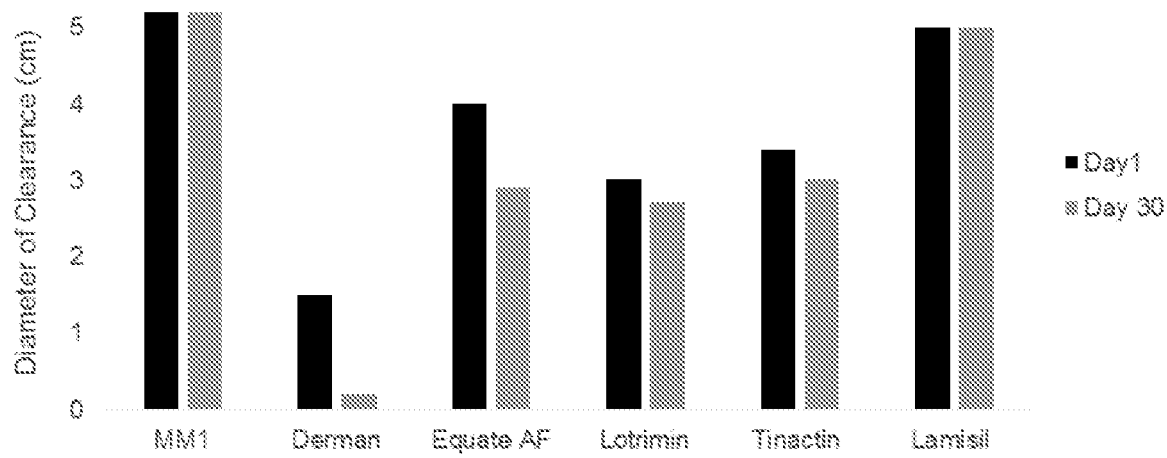

FIG. 8 compares the effects of the formulations in killing *Trichophyton rubrum*. The data show that MM1 was more effective at killing *Trichophyton rubrum* than Derman® Antifungal Cream, Equate® Athlete's Foot, Lotrimin® Ultra Athlete's Foot Cream, Tinactin® Athlete's Foot Cream, and Lamisil® Athlete's Foot Cream 12 days after application and 30 days after application.

Figure 9:
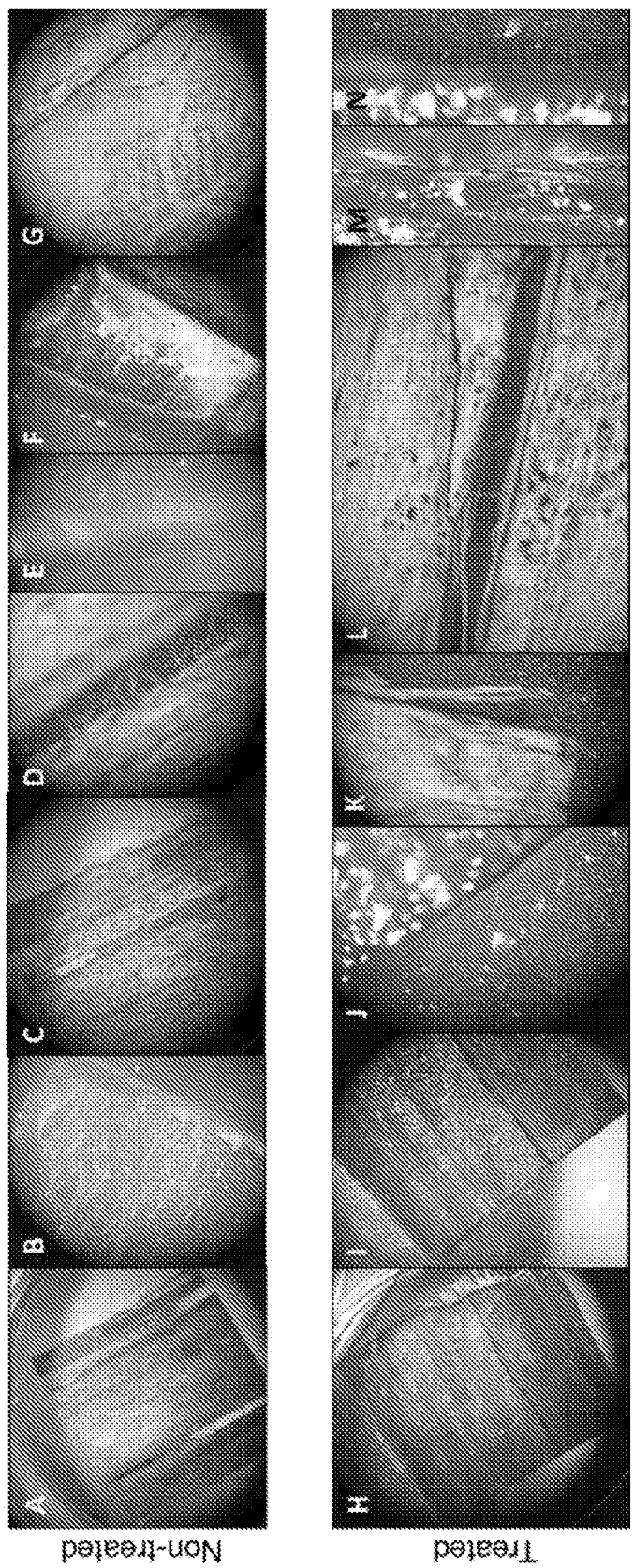

FIG. 9 PANEL A-G show images of the untreated *Aspergillus niger*-infected wood sample. PANEL H-M show images of the *Aspergillus niger*-infected wood sample treated with MM1.

Figure 10:
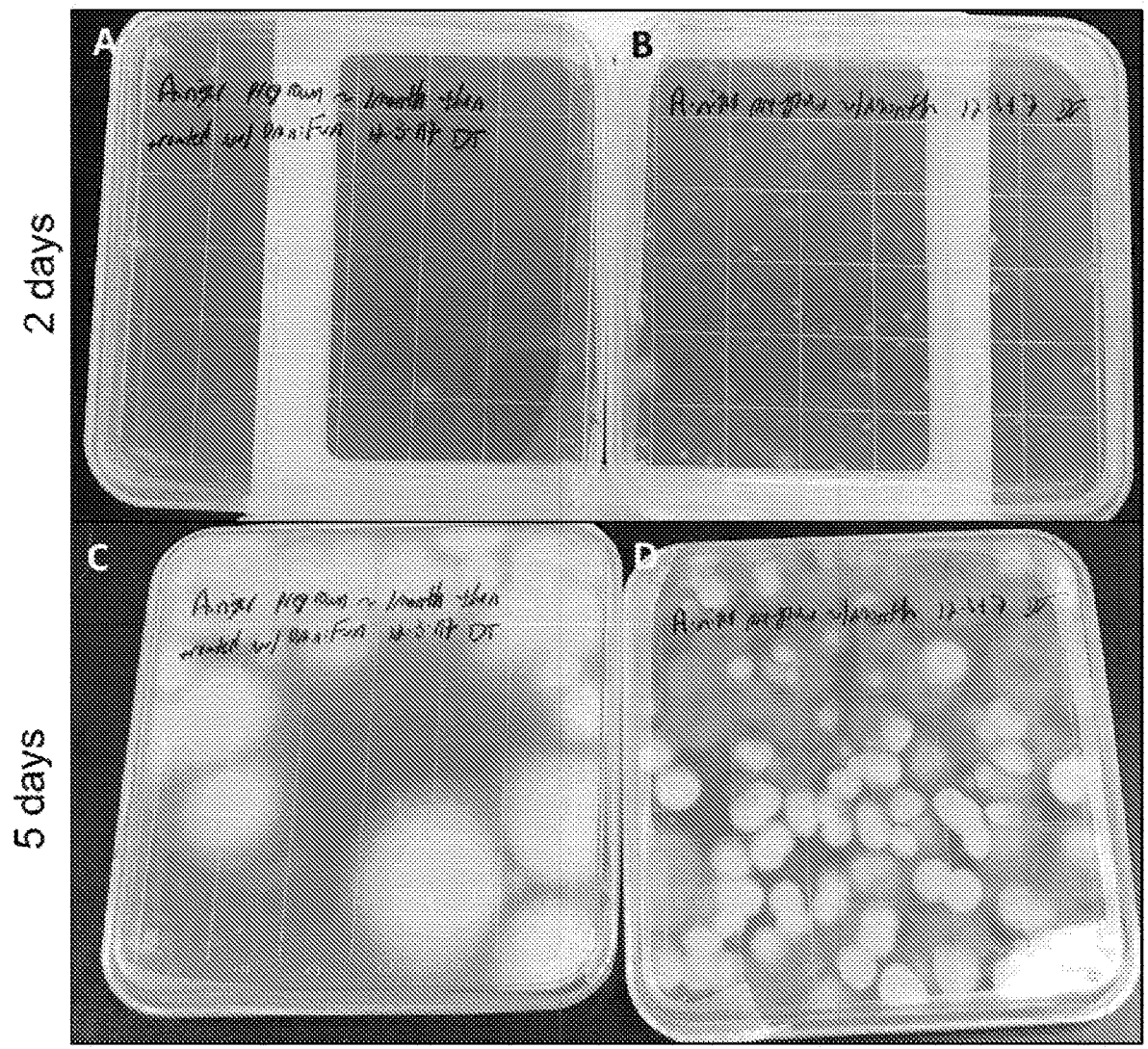

FIG. 10 PANEL A shows an MHA plate swabbed with a MM1-treated wood sample after 2 days. PANEL B shows an MHA plate swabbed with an untreated wood sample after 2 days. PANEL C shows an MHA plate swabbed with a MM1-treated wood sample after 5 days. PANEL D shows an MHA plate swabbed with an untreated wood sample after 5 days.

Figure 11:
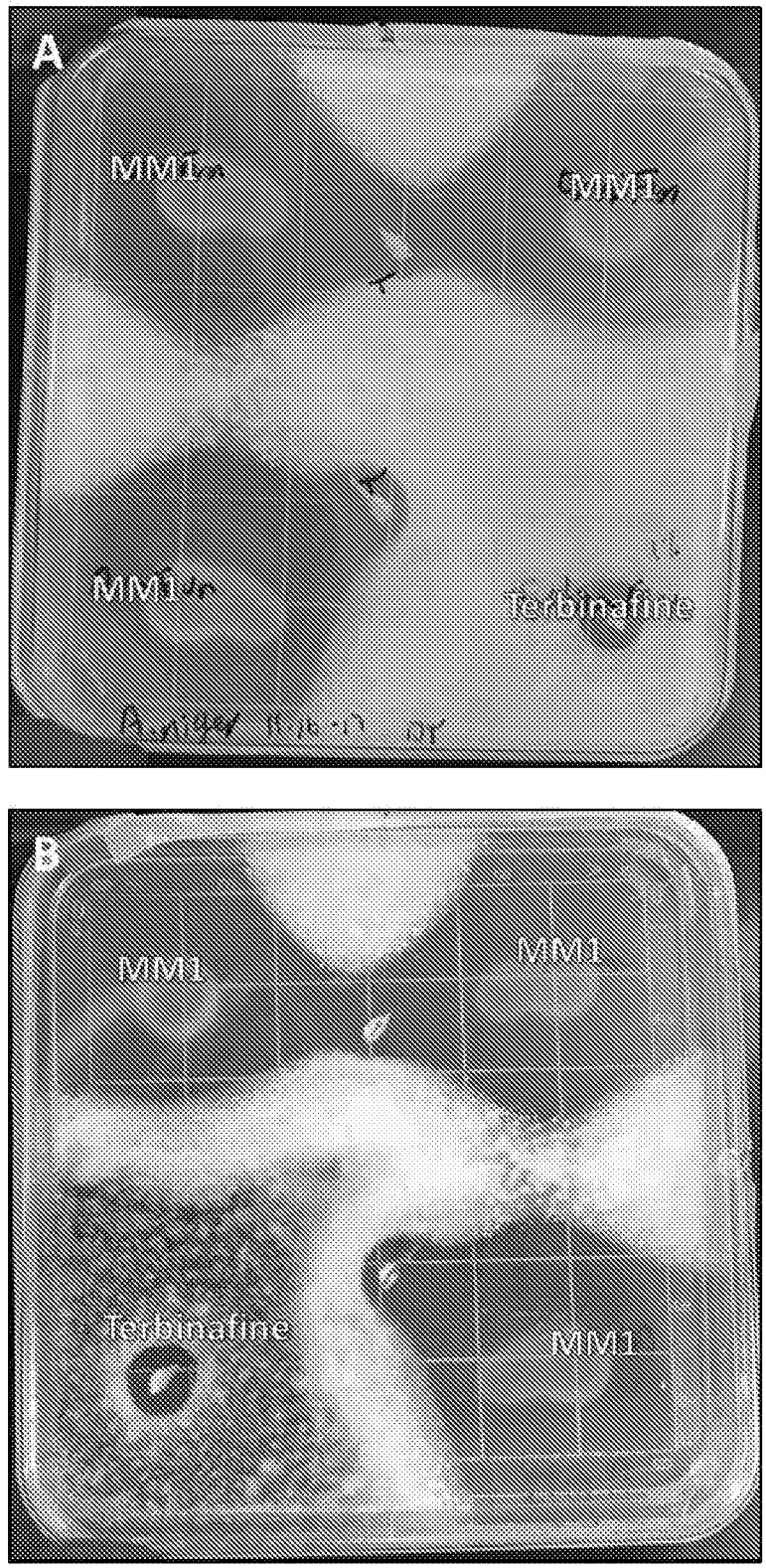

FIG. 11 PANEL A shows the front of the *Aspergillus niger*-infected MHA plate treated with MM1 and Lamisil® Ultra Athlete's Foot Cream after incubation for 5 days. PANEL B shows the back of the *Aspergillus niger*-infected MHA plate treated with MM1 and Lamisil® Ultra Athlete's Foot Cream after incubation for 5 days.

Figure 12:
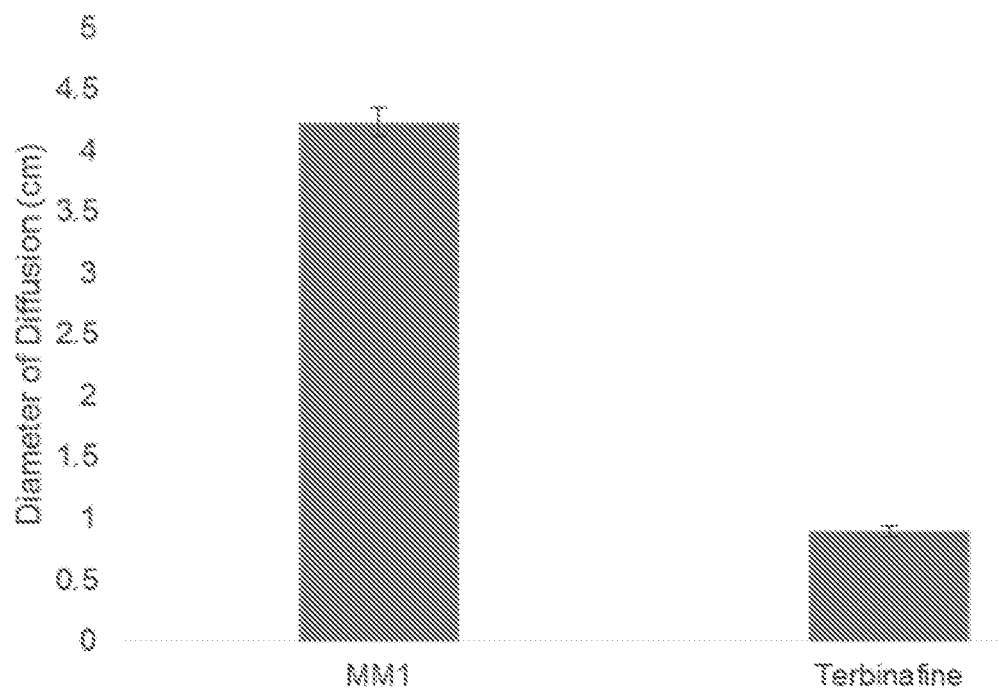

FIG. 12 compares the diameter of diffusion (cm) of the spots of the *Aspergillus niger*-infected MHA plate treated with MM1 and Lamisil® Ultra Athlete's Foot Cream.

Figure 13:
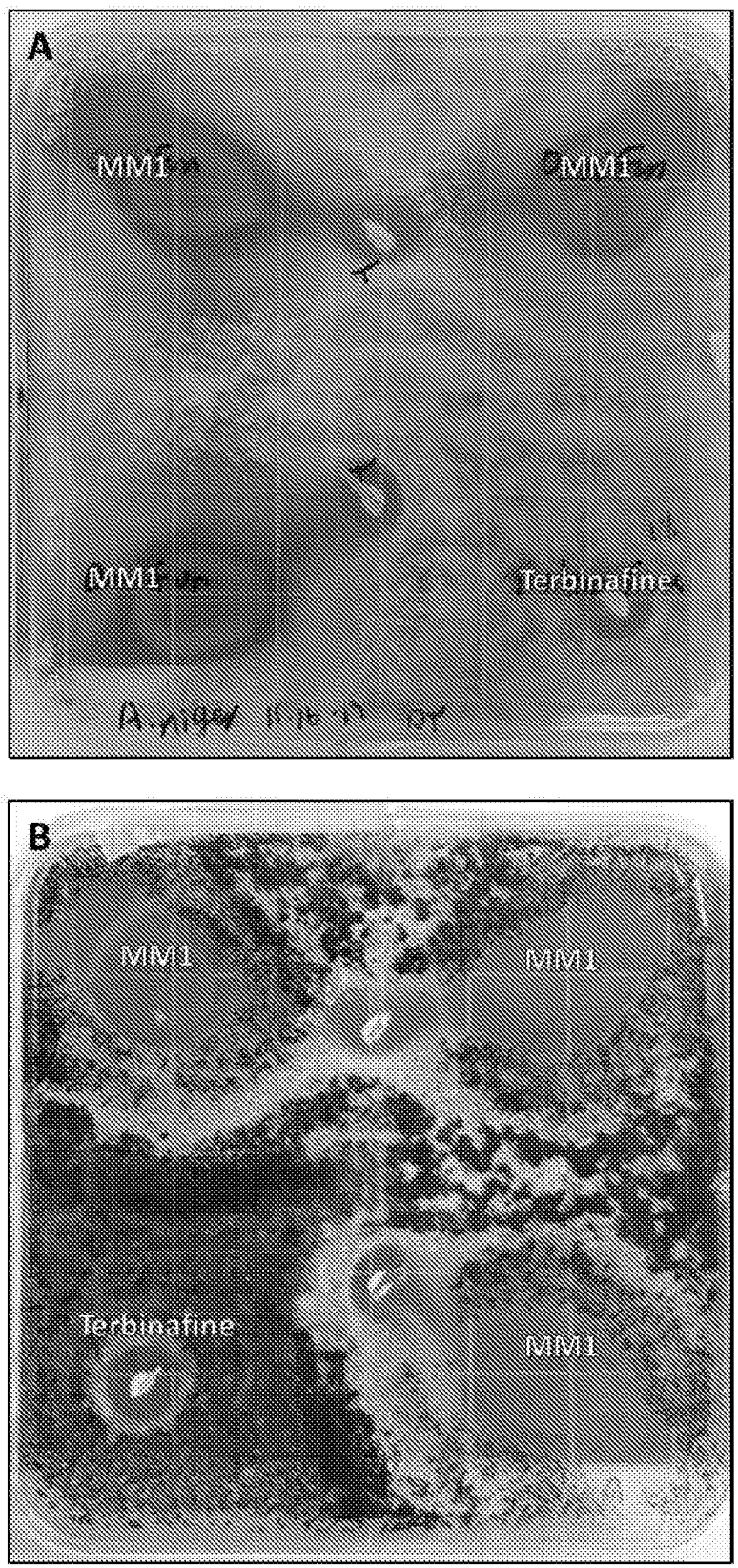

FIG. 13 PANEL A shows the front of the *Aspergillus niger*-infected MHA plate treated with MM1 and Lamisil® Ultra Athlete's Foot Cream after an incubation time of 32 days. PANEL B shows the back of the *Aspergillus niger*-infected MHA plate treated with MM1 and Lamisil® Ultra Athlete's Foot Cream after an incubation time of 32 days.

Figure 14:
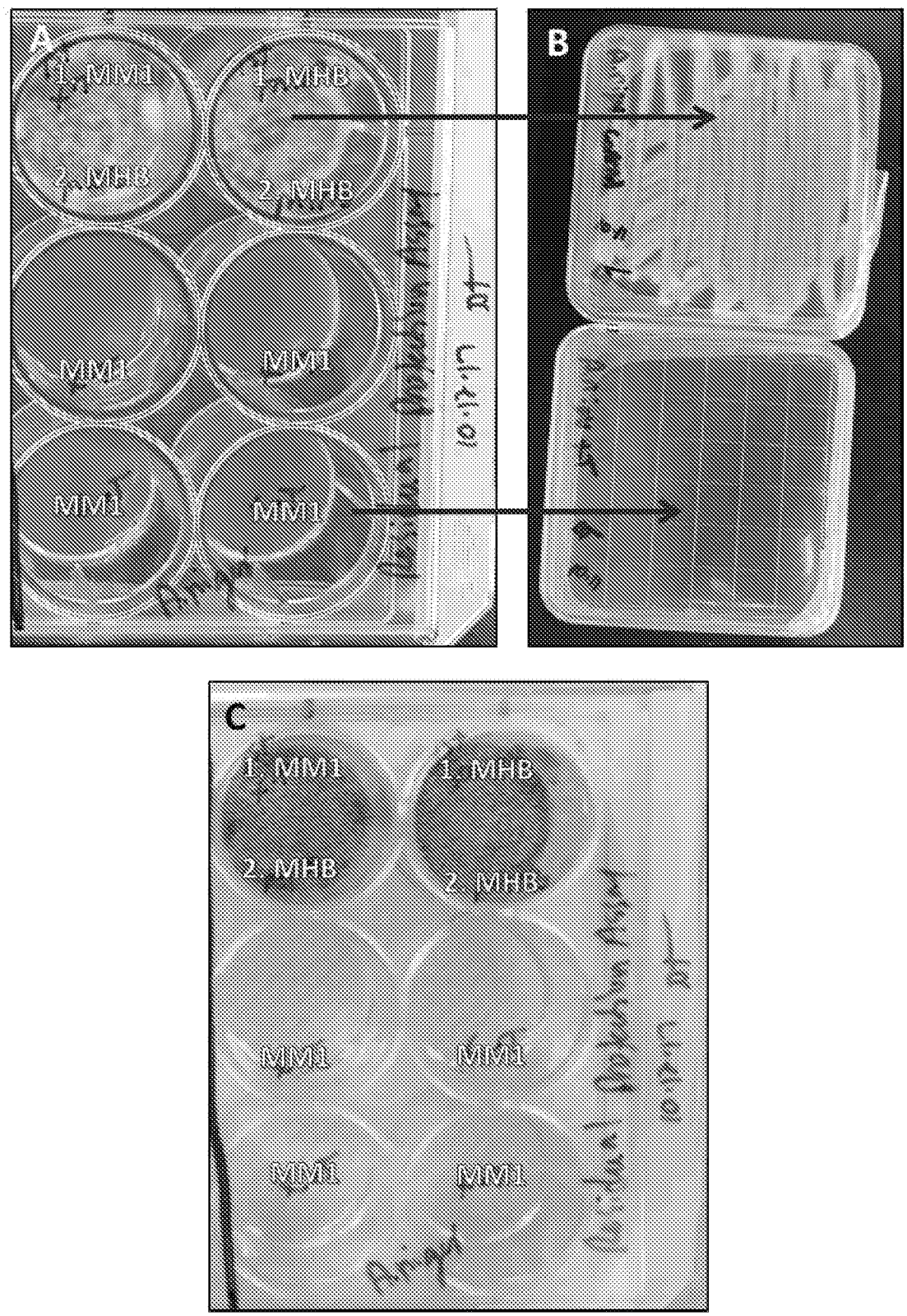

FIG. 14 PANEL A shows the 6-well plate with 3 wells pre-treated with MM1 and 3 wells pre-treated with an MHB control. PANEL B TOP PANEL shows the MHA plate swabbed with the well treated with MHB, inoculated with *Aspergillus niger*, and further treated with MHB. PANEL B BOTTOM PANEL shows the MHA plate swabbed with the well pre-treated with MHB, inoculated with *Aspergillus niger*, and treated with MM1. PANEL C shows the 6-well plate after incubation for 7 days.

Figure 15:
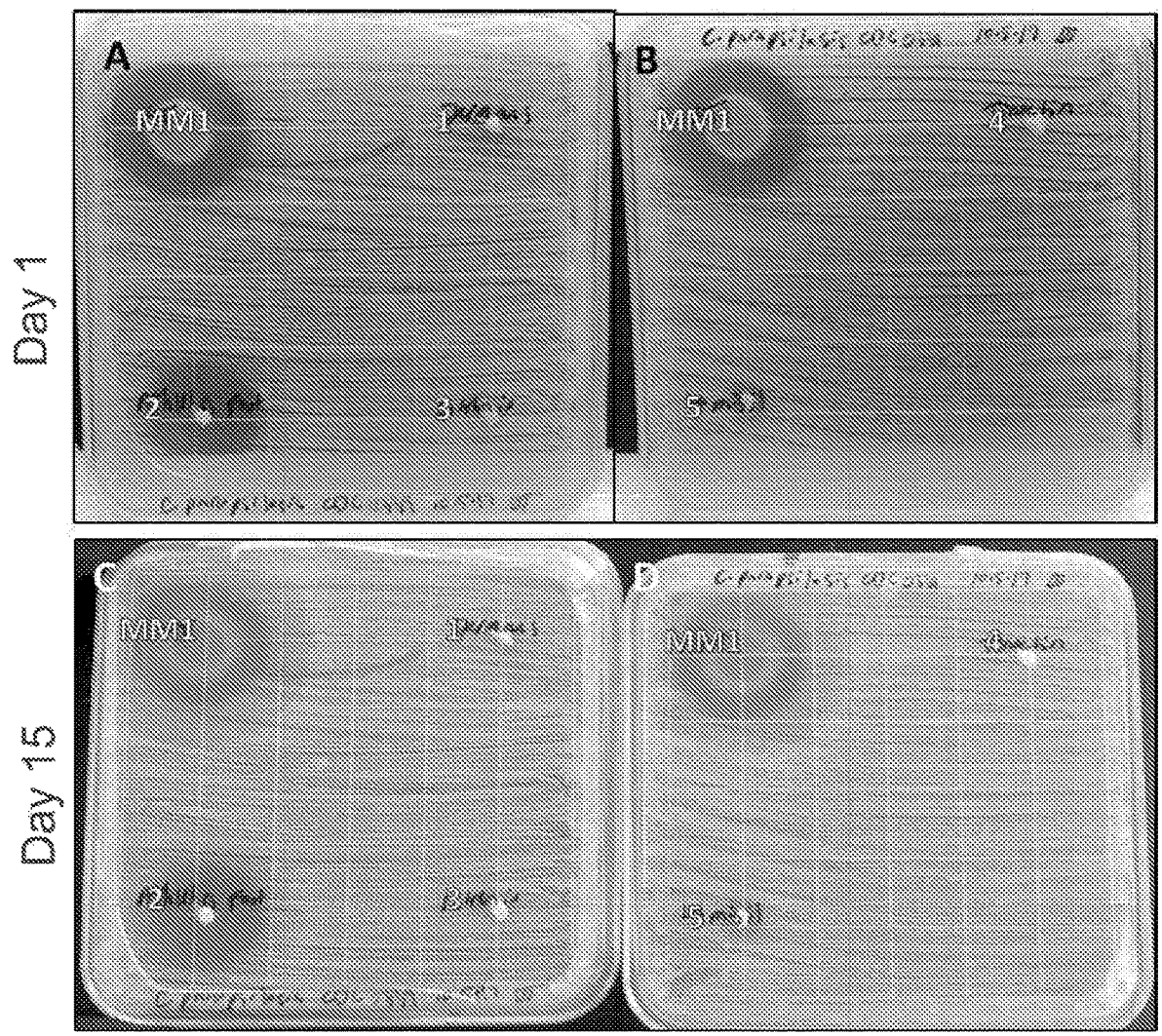

FIG. 15 PANEL A shows the extent of clearing of drug-resistant *Candida parapsilosis* when treated with MM1, Derman® Antifungal Cream (1), Equate® Athlete's Foot Cream (2), or Lotrimin® Ultra Athlete's Foot Cream (3) after 1 day. PANEL B shows the extent of clearing of drug-resistant *Candida parapsilosis* when treated with MM1, Tinactin® Athlete's Foot Cream (4), or Lamisil® Athlete's Foot Cream (5) after 1 day. PANEL C shows the extent of clearing of drug-resistant *Candida parapsilosis* when treated with MM1, Derman® Antifungal Cream (1), Equate® Athlete's Foot Cream (2), or Lotrimin® Ultra Athlete's Foot Cream (3) after 15 days. PANEL D shows the extent of clearing of drug-resistant *Candida parapsilosis* when treated with MM1, Tinactin® Athlete's Foot Cream (4), or Lamisil® Athlete's Foot Cream (5) after 15 days.

Figure 16:
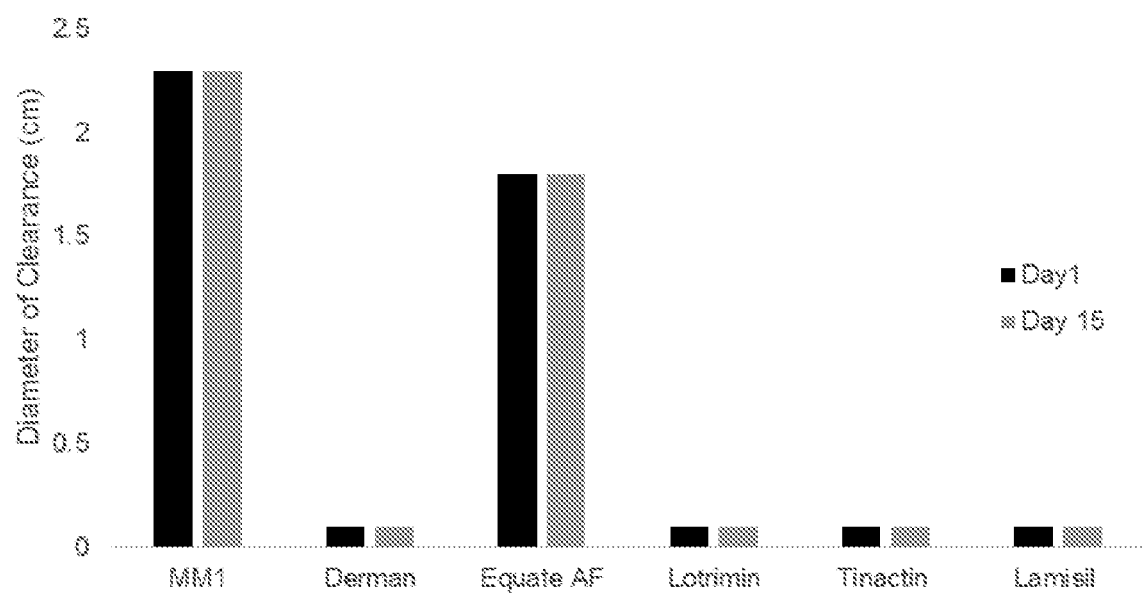

FIG. 16 compares the effectiveness of MM1 and commercially available formulations in killing drug-resistant *Candida parapsilosis* after 1 day and 15 days of treatment.

Figure 17:
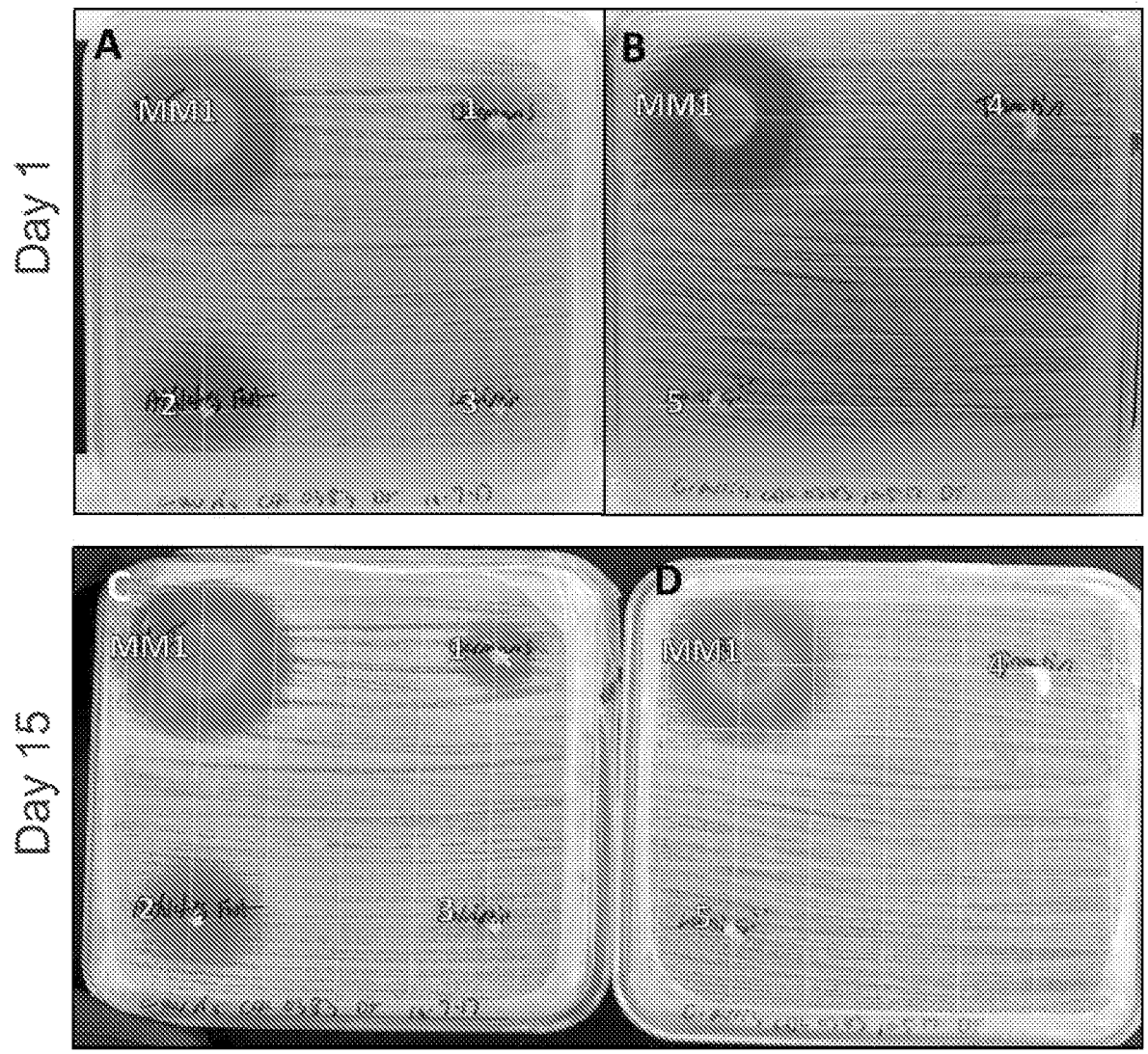

FIG. 17 PANEL A shows the diameter of clearing (cm) of drug-resistant *Candida auris* (CDC 0383) when treated with MM1, Derman® Antifungal Cream (1), Equate® Athlete's Foot Cream (2), or Lotrimin® Ultra Athlete's Foot Cream (3) after 1 day. PANEL B shows the diameter of clearing (cm) of drug-resistant *Candida auris* (CDC 0383) when treated with MM1, Tinactin® Athlete's Foot Cream (4), or Lamisil® Athlete's Foot Cream (5) after 1 day. PANEL C shows the diameter of clearing (cm) of drug-resistant *Candida auris* (CDC 0383) when treated with MM1, Derman® Antifungal Cream (1), Equate® Athlete's Foot Cream (2), or Lotrimin® Ultra Athlete's Foot Cream (3) after 15 days. PANEL D shows the diameter of clearing (cm) of drug-resistant *Candida auris* (CDC 0383) when treated with MM1, Tinactin® Athlete's Foot Cream (4), or Lamisil® Athlete's Foot Cream (5) after 15 days.

Figure 18:
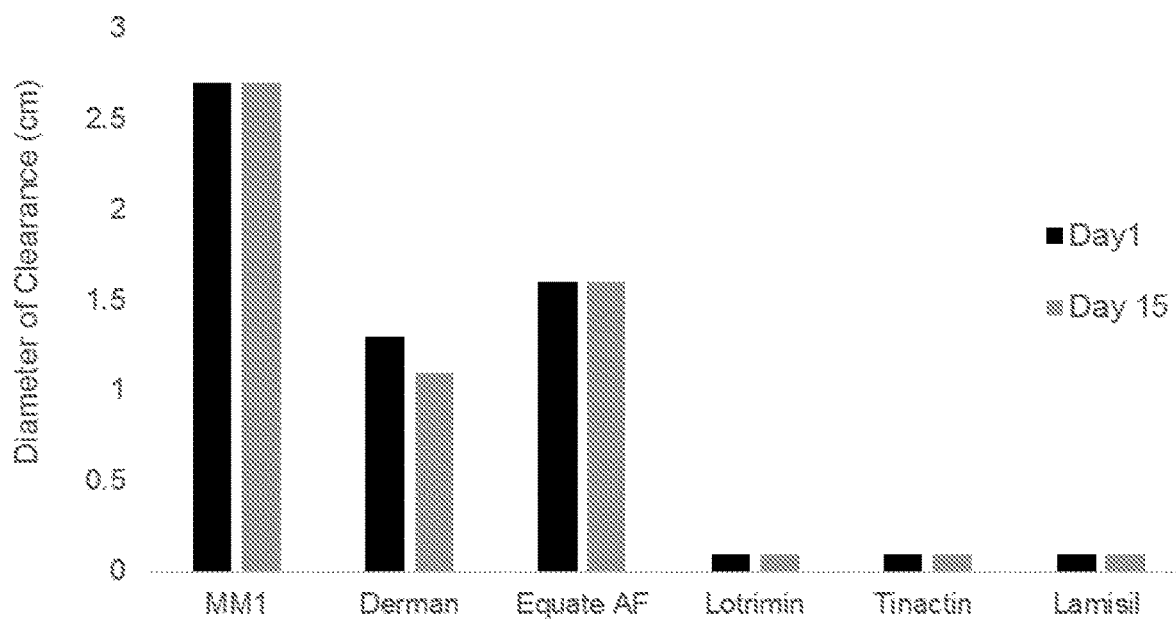

FIG. 18 compares the effectiveness of MM1 and commercially available formulations in killing drug-resistant *Candida auris* (CDC 0383) after 1 day and 15 days of treatment.

Figure 19:
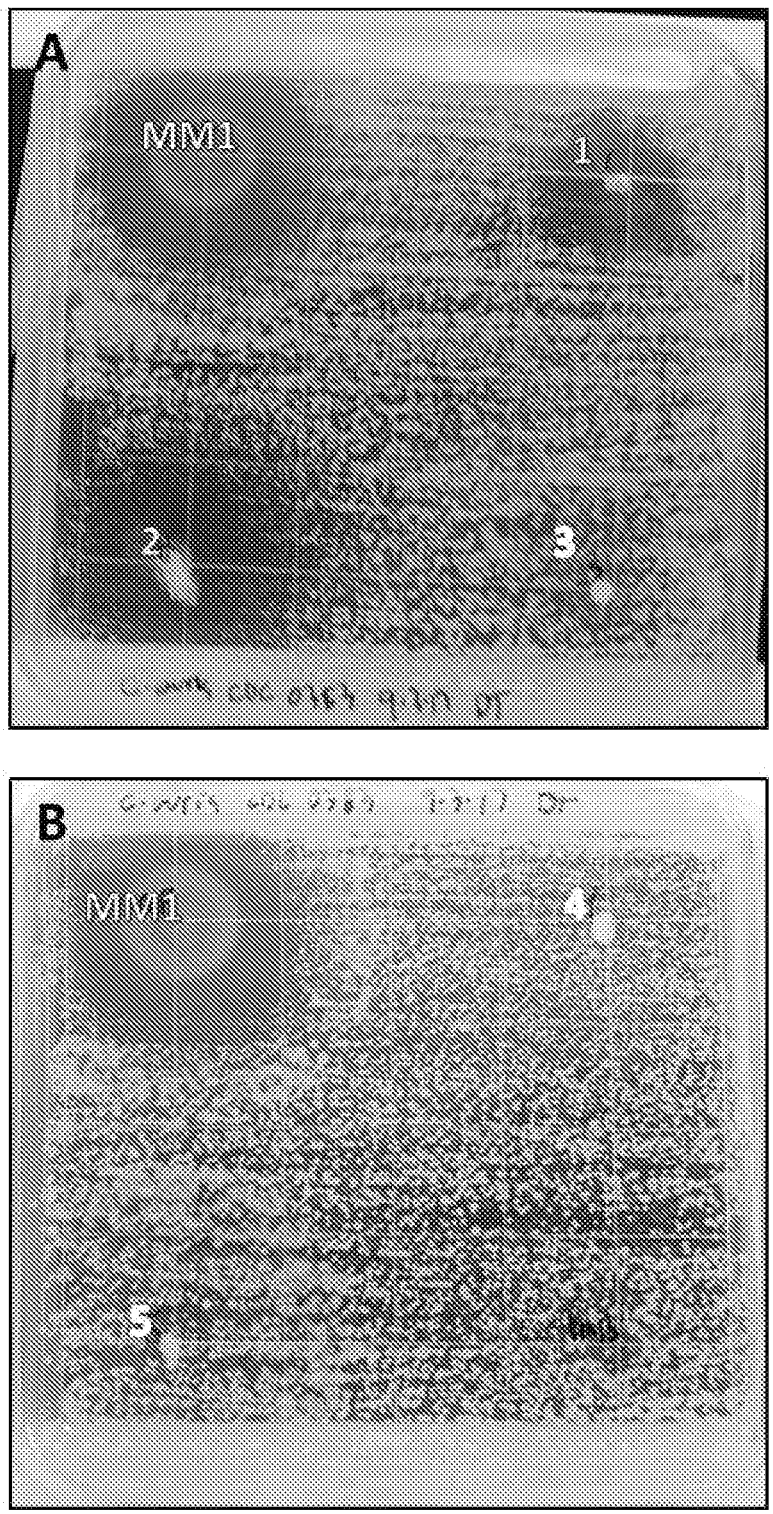

FIG. 19 PANEL A shows the diameter of clearing (cm) of drug-resistant *Candida auris* (CDC 0383) when treated with MM1, Derman® Antifungal Cream (1), Equate® Athlete's Foot Cream (2), or Lotrimin® Ultra Athlete's Foot Cream (3). PANEL B shows the diameter of clearing (cm) of drug-resistant *Candida auris* (CDC 0383) when treated with MM1, Tinactin® Athlete's Foot Cream (4), or Lamisil® Athlete's Foot Cream (5).

Figure 20:
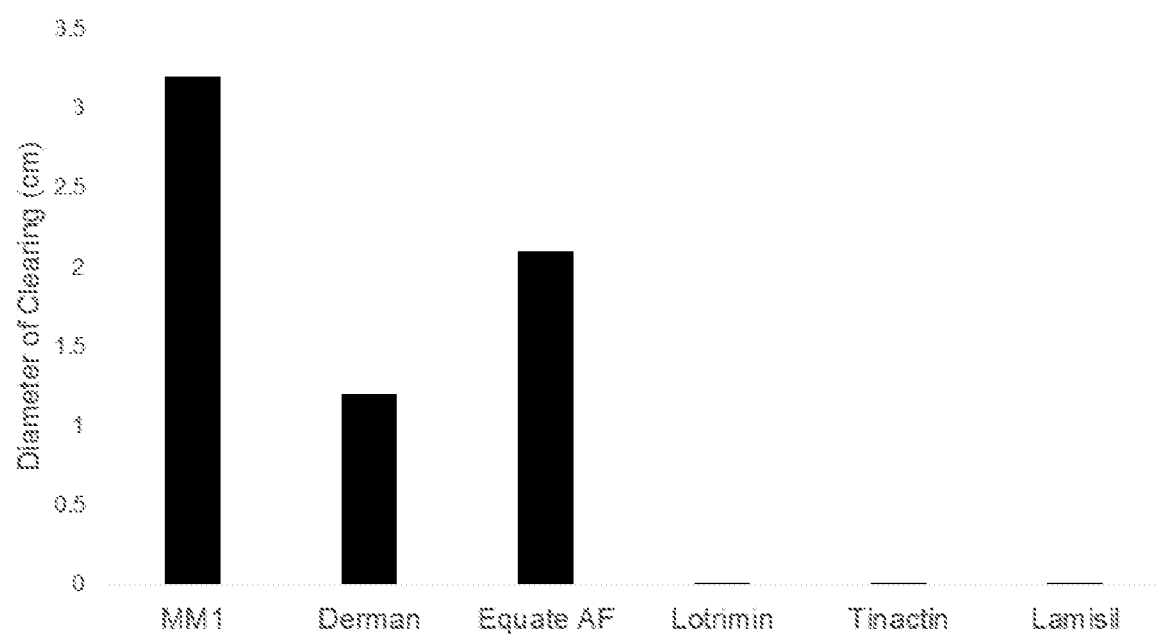

FIG. 20 compares the effectiveness of MM1 and commercially available formulations in killing drug-resistant *Candida auris* (CDC 0383).

Figure 21:
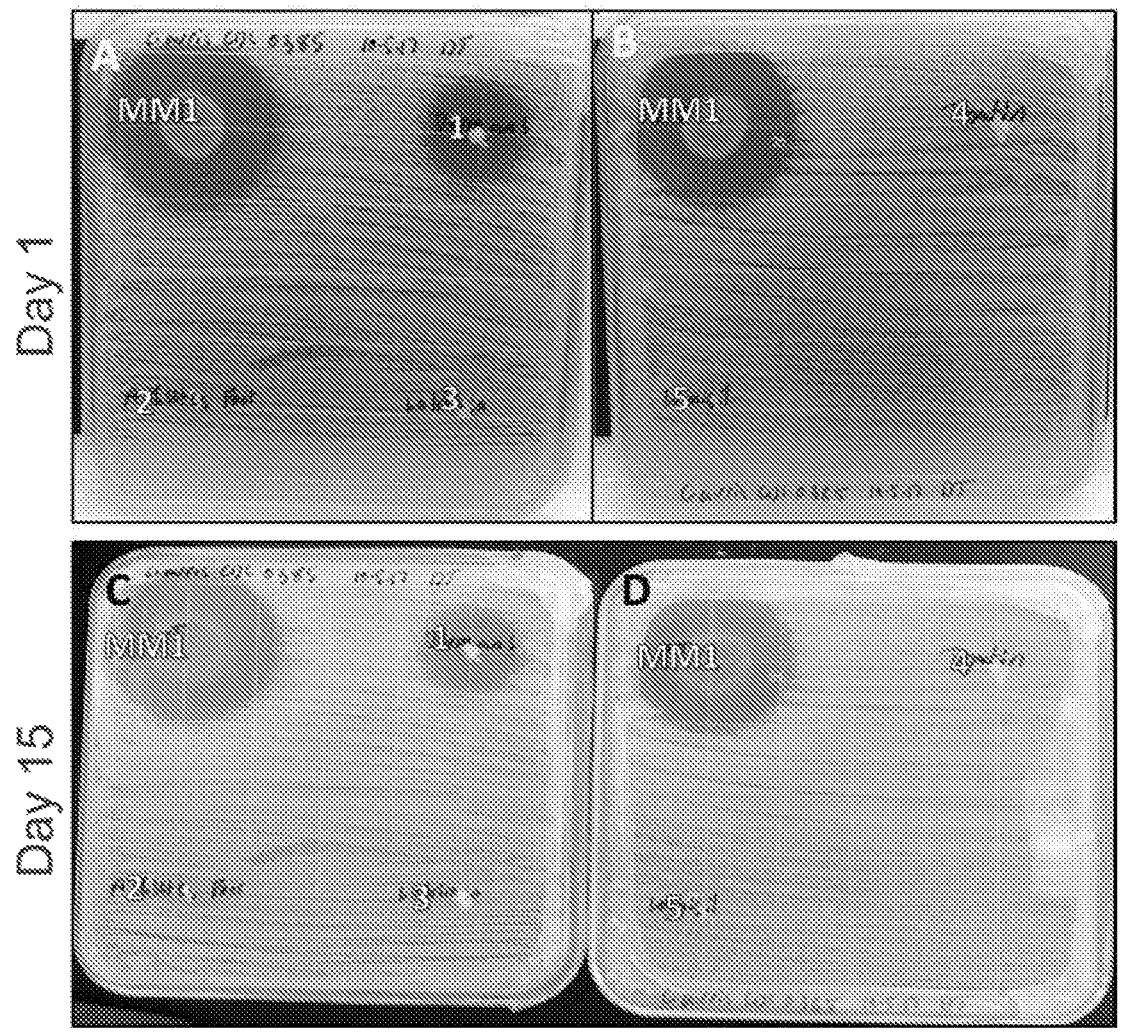

FIG. 21 PANEL A shows the diameter of clearing (cm) of multi drug-resistant *Candida auris* (CDC 0385) when treated with MM1, Derman® Antifungal Cream (1), Equate® Athlete's Foot Cream (2), or Lotrimin® Ultra Athlete's Foot Cream (3) after 1 day. PANEL B shows the diameter of clearing (cm) of multi drug-resistant *Candida auris* (CDC 0385) when treated with MM1, Tinactin® Athlete's Foot Cream (4), or Lamisil® Athlete's Foot Cream (5) after 1 day. PANEL C shows the diameter of clearing (cm) of multi drug-resistant *Candida auris* (CDC 0385) when treated with MM1, Derman® Antifungal Cream (1), Equate® Athlete's Foot Cream (2), or Lotrimin® Ultra Athlete's Foot Cream (3) after 15 days. PANEL D shows the diameter of clearing (cm) of multi drug-resistant *Candida auris* (CDC 0385) when treated with MM1, Tinactin® Athlete's Foot Cream (4), or Lamisil® Athlete's Foot Cream (5) after 15 days.

Figure 22:
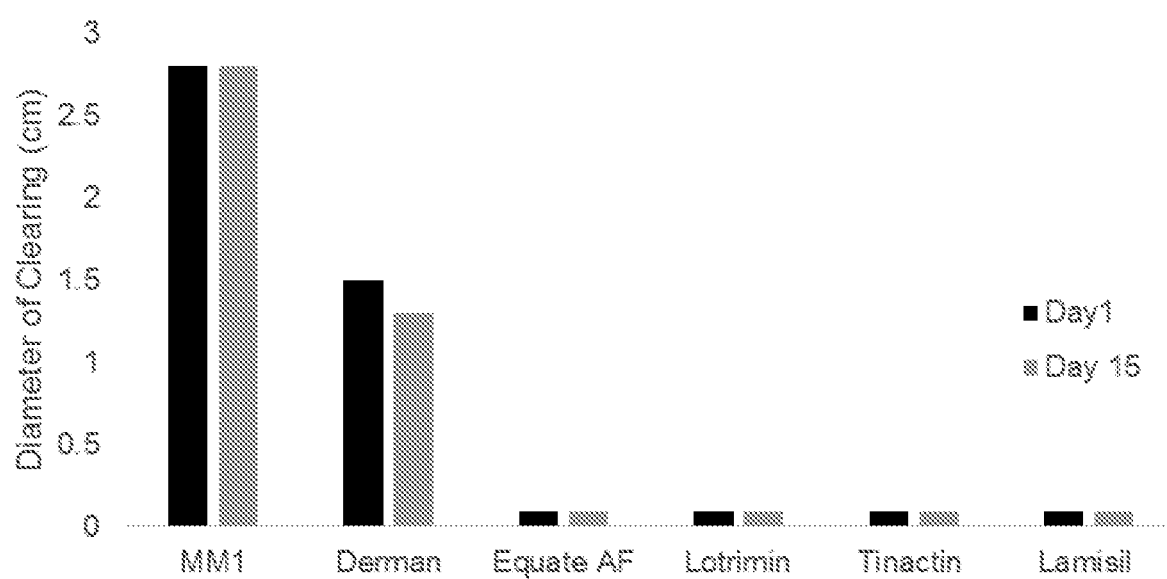

FIG. 22 compares the effectiveness of MM1 and commercially available formulations in killing multi drug-resistant *Candida auris* (CDC 0385) after 1 day or 15 days of treatment.

Figure 23:
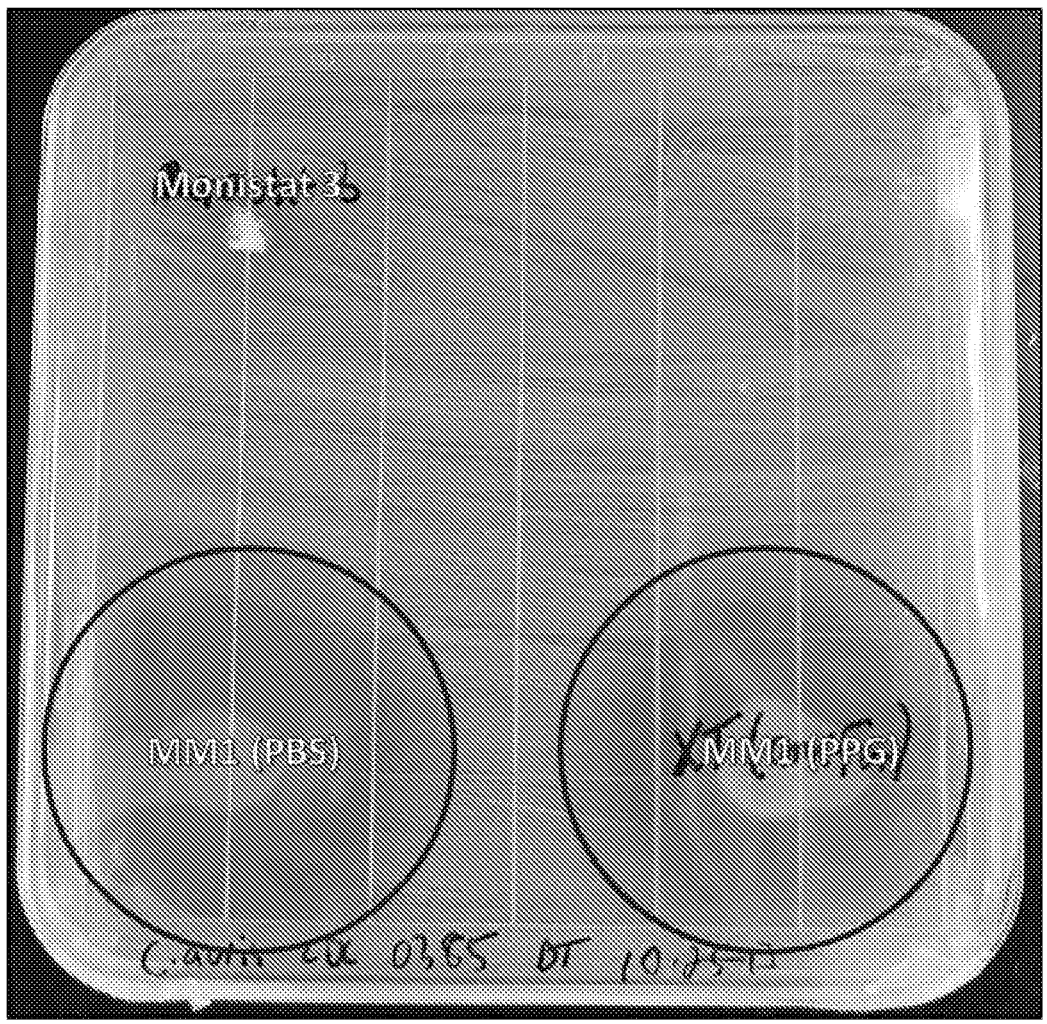

FIG. 23 compares the effectiveness of Monistat® 3 Complete Therapy System, MM1 prepared in PBS, and MM1 prepared in PG in killing multi-drug resistant *Candida auris* (CDC 0385).

Figure 24:
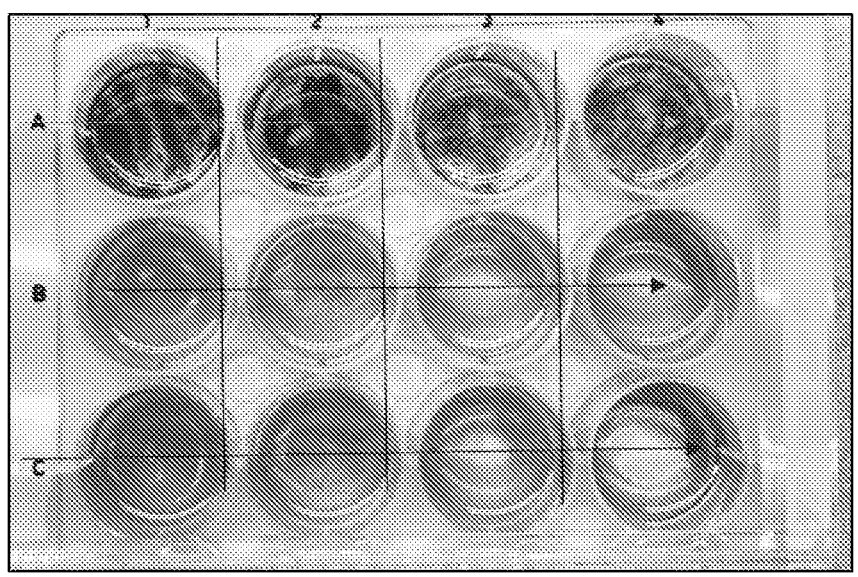

FIG. 24 shows the 12-well plate used to simulate the use of MM1 as a mouthwash and a douche.

Figure 25:
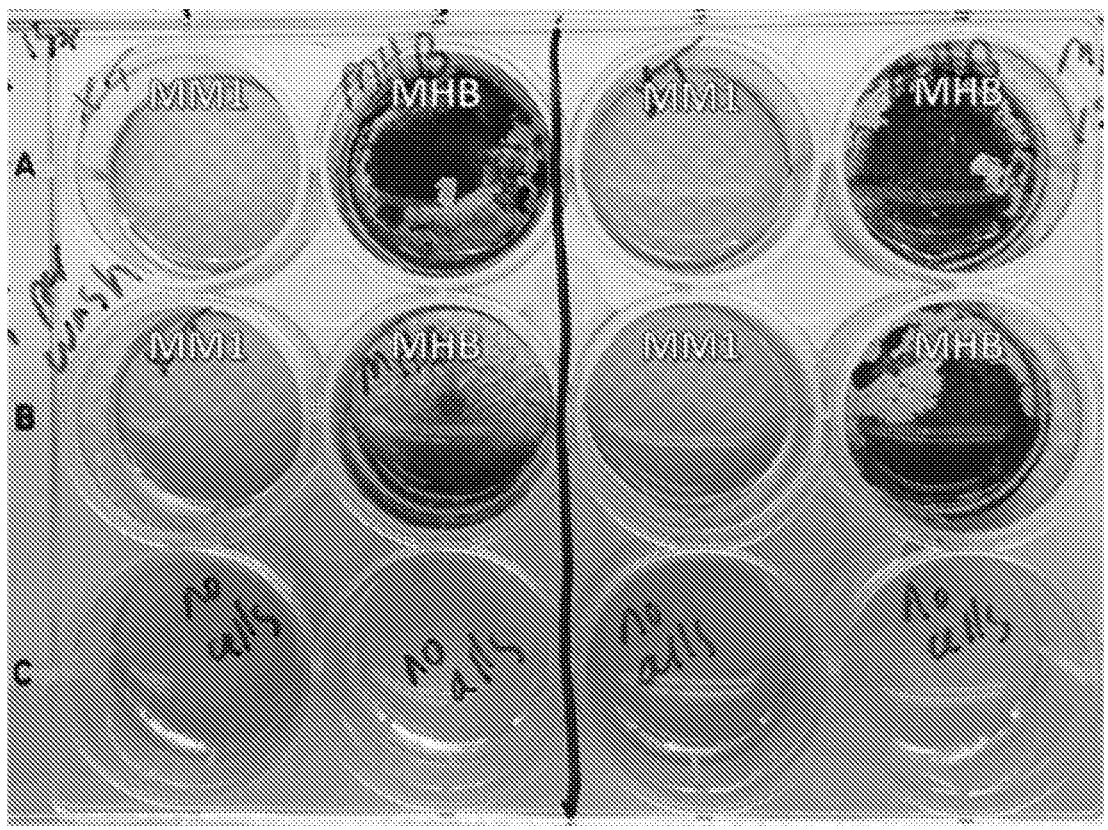

FIG. 25 shows the results of 1) wells pre-treated with MM1 and inoculated with multi-drug resistant *Candida auris* (CDC 0385), 2) wells pre-treated with MHB and inoculated with multi-drug resistant *Candida auris* (CDC 0385), 3) wells inoculated with multi-drug resistant *Candida auris* (CDC 0385) and treated with MM1, and 4) well inoculated with multi-drug resistant *Candida auris* (CDC 0385) and treated with MHB.

Figure 26:
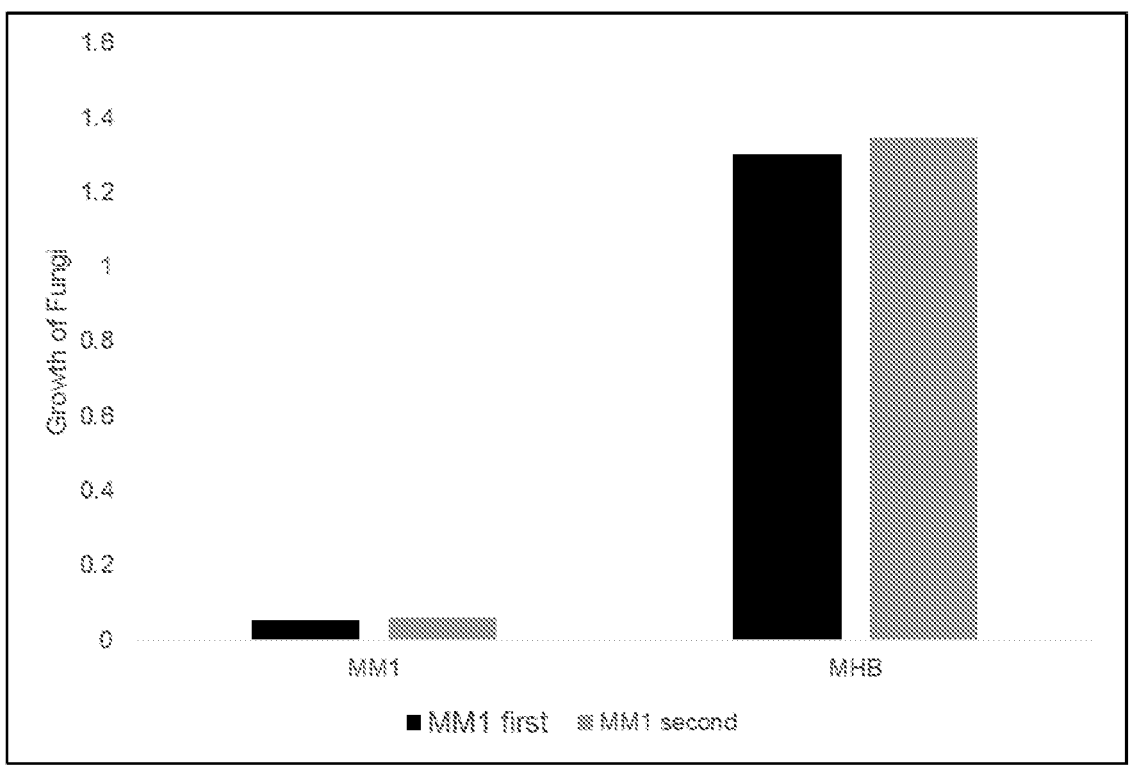

FIG. 26 compares the effect of MM1 and the MHB control on the growth of multi-drug resistant *Candida auris* (CDC 0385) when applied to a surface prior to inoculation of multi-drug resistant *Candida auris* (CDC 0385) (black), or when applied to a surface after the surface was inoculated with multi-drug resistant *Candida auris* (CDC 0385).

Figure 27:
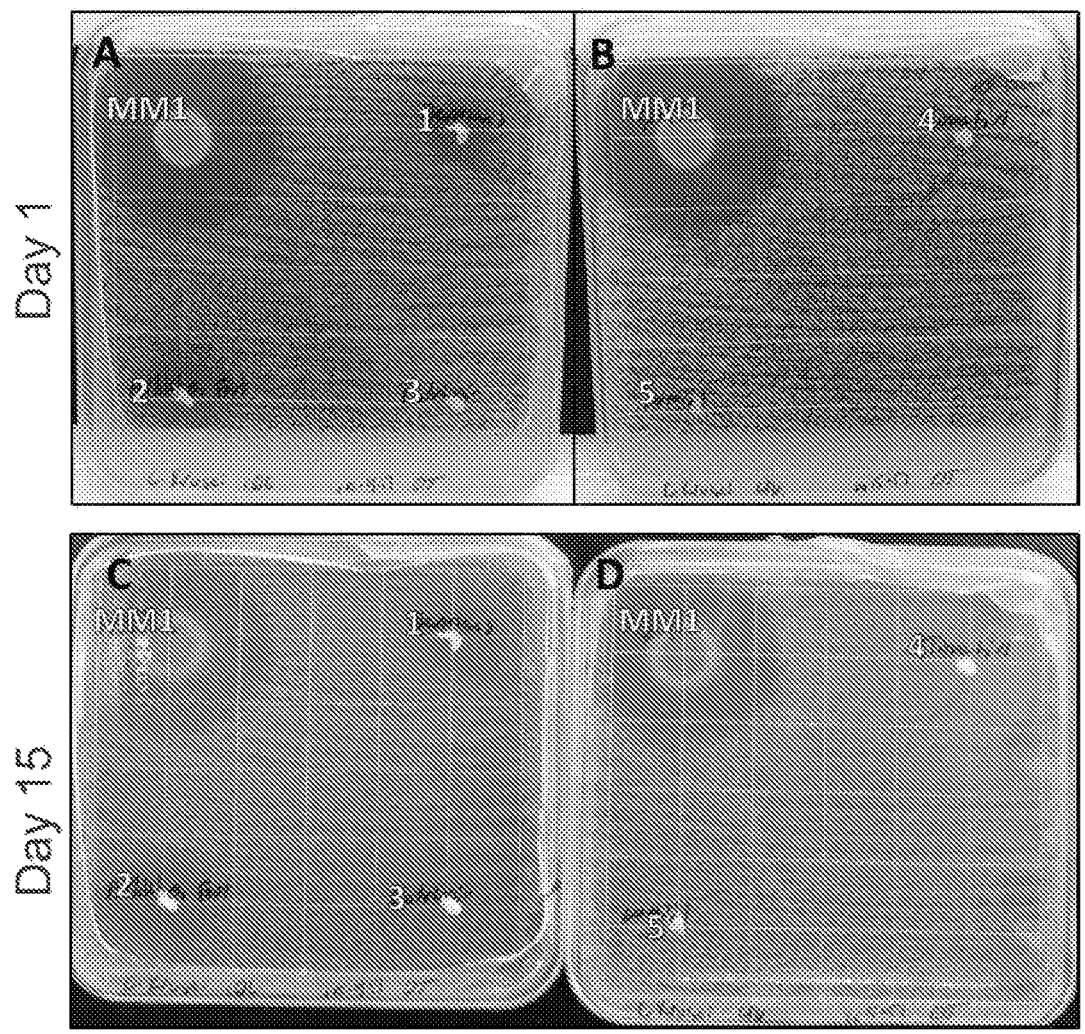

FIG. 27 PANEL A shows the clearing of *Candida krusei* (CDC 0397) when treated with MM1, Derman® Antifungal Cream (1), Equate® Athlete's Foot Cream (2), or Lotrimin® Ultra Athlete's Foot Cream (3) after 1 day. PANEL B shows the clearing of *Candida krusei* (CDC 0397) when treated with MM1, Tinactin® Athlete's Foot Cream (4), or Lamisil® Athlete's Foot Cream (5) after 1 day. PANEL C shows the clearing of *Candida krusei* (CDC 0397) when treated with MM1, Derman® Antifungal Cream (1), Equate® Athlete's Foot Cream (2), or Lotrimin® Ultra Athlete's Foot Cream (3) after 15 days. PANEL D shows the clearing of *Candida krusei* (CDC 0397) when treated with a single dose of MM1, Tinactin® Athlete's Foot Cream (4), or Lamisil® Athlete's Foot Cream (5) after 15 days.

Figure 28:
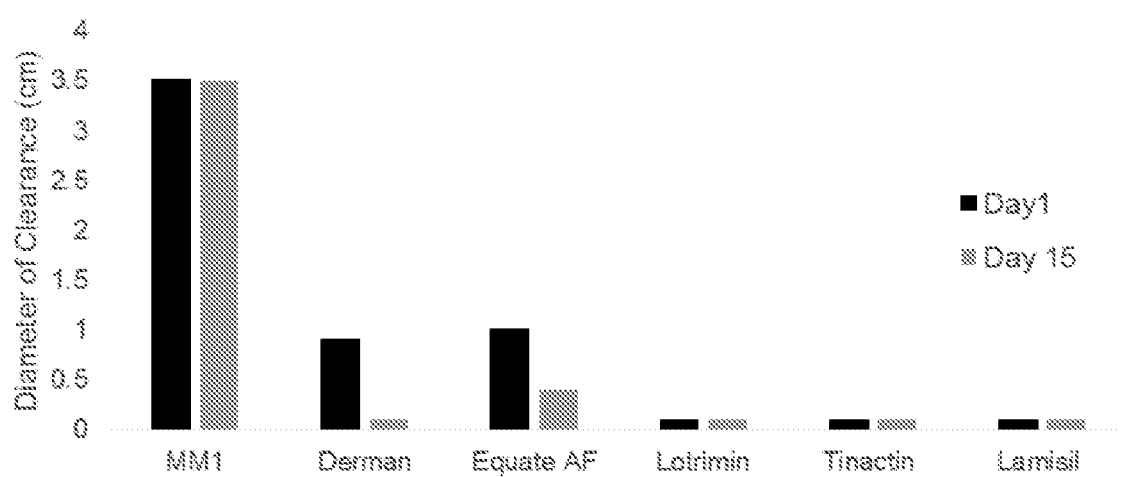

FIG. 28 compares the effectiveness of MM1 and commercially available formulations in killing *Candida krusei* (CDC 0397).

Figure 29:
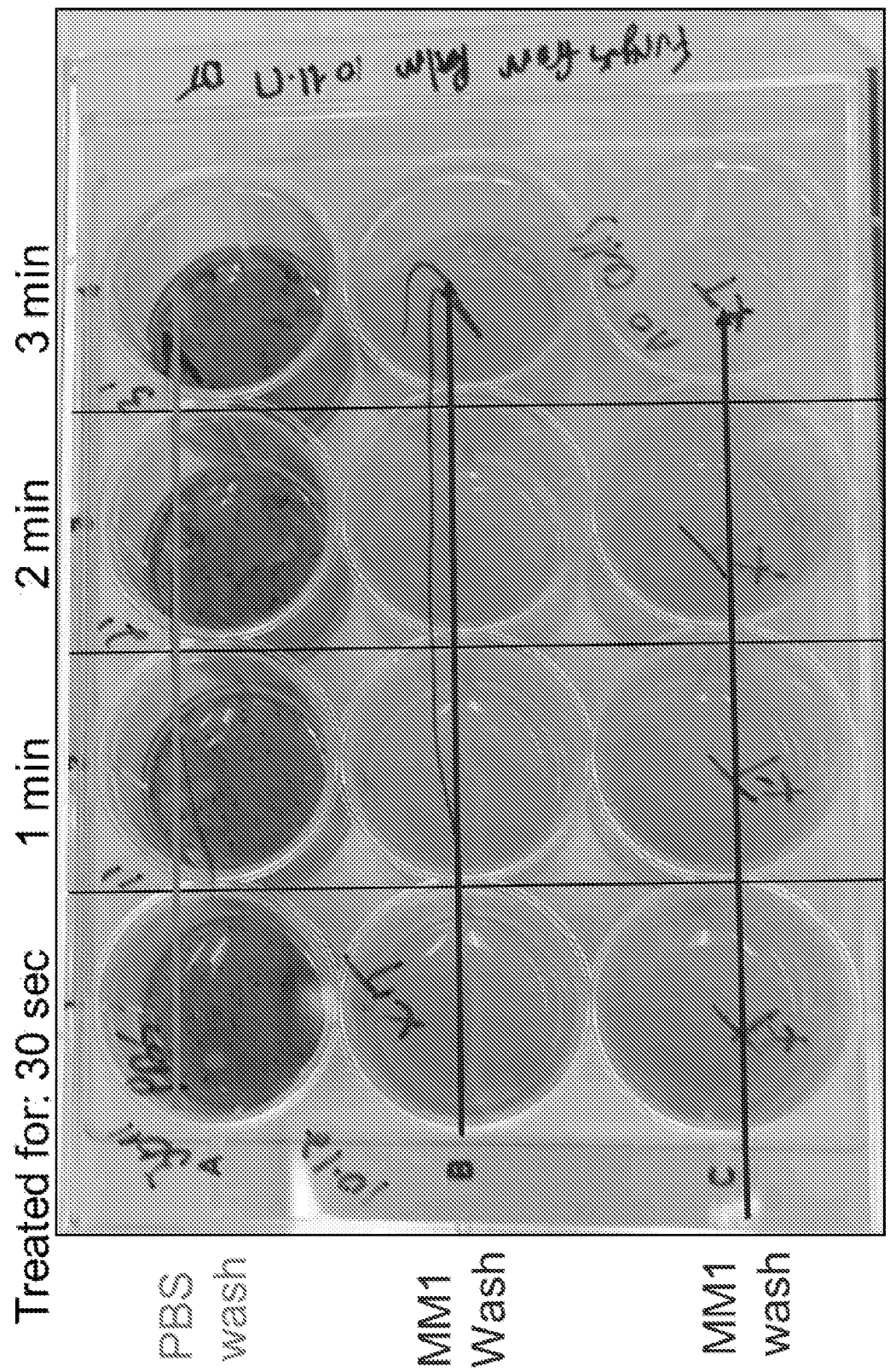

FIG. 29 shows the 12-well plate used to treat an unidentified plant fungus with MM1.

Figure 30:
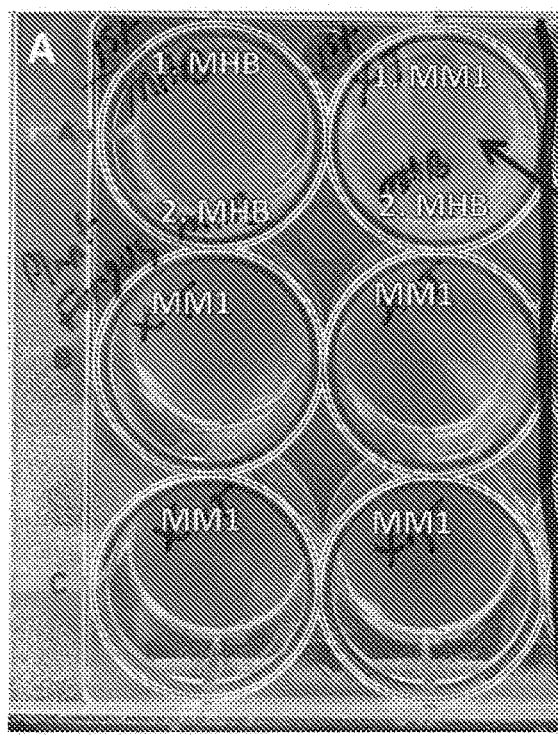
Figure 30:
Figure 30:
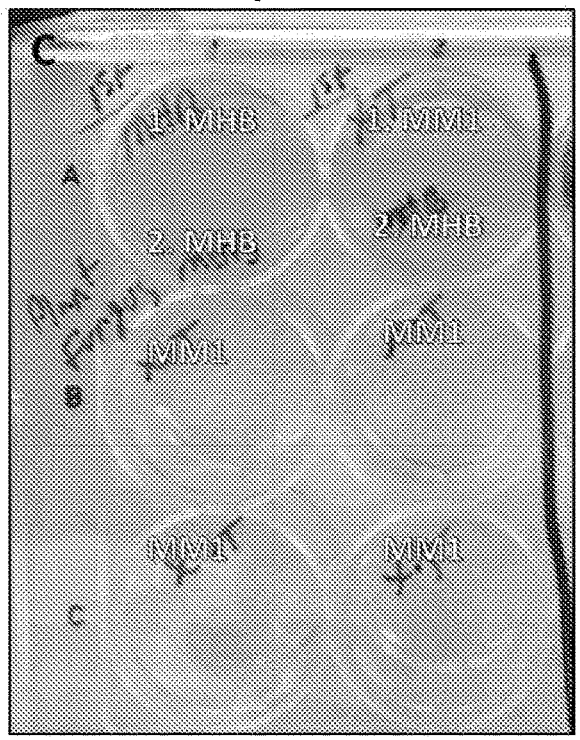

FIG. 30 PANEL A shows a 6-well plate with 2 wells pre-treated with MM1 with no subsequent washes, 2 wells pre-treated with an MM1 and then washed with MHB to remove any remaining MM1, or 2 wells washed with only MHB which served as a positive growth control after 2 days of incubation. PANEL B shows the unidentified plant fungus that was used for the residual protection assay. PANEL C shows the 6-well plate with 4 wells pre-treated with MM1 and 2 wells pre-treated with an MHB control after 7 days of incubation.

Figure 31:
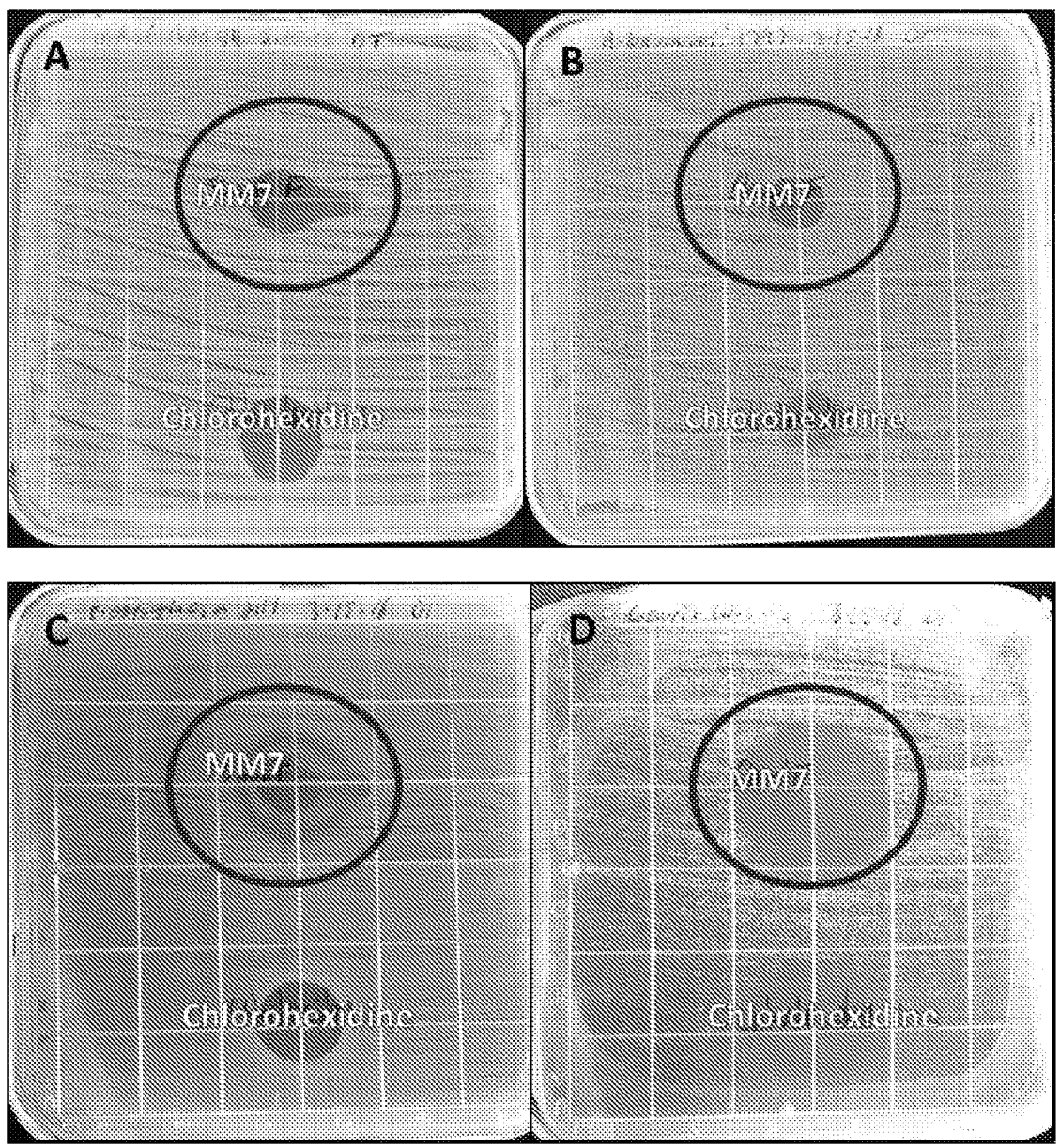

FIG. 31 PANEL A shows the abilities of MM7 and the chlorohexidine gluconate 0.12% oral rinse in killing MRSA (BAA-44). PANEL B shows the abilities of MM7 and the chlorohexidine gluconate 0.12% oral rinse in killing *Acinetobacter baumannii* (ATCC 1797). PANEL C shows the abilities of MM7 and the chlorohexidine gluconate 0.12% oral rinse in killing *Pseudomonas aeruginosa* (ATCC 2114). PANEL D shows the abilities of MM7 and the chlorohexidine gluconate 0.12% oral rinse in killing multi-drug resistant *Candida auris* (CDC 0385).

Figure 32:
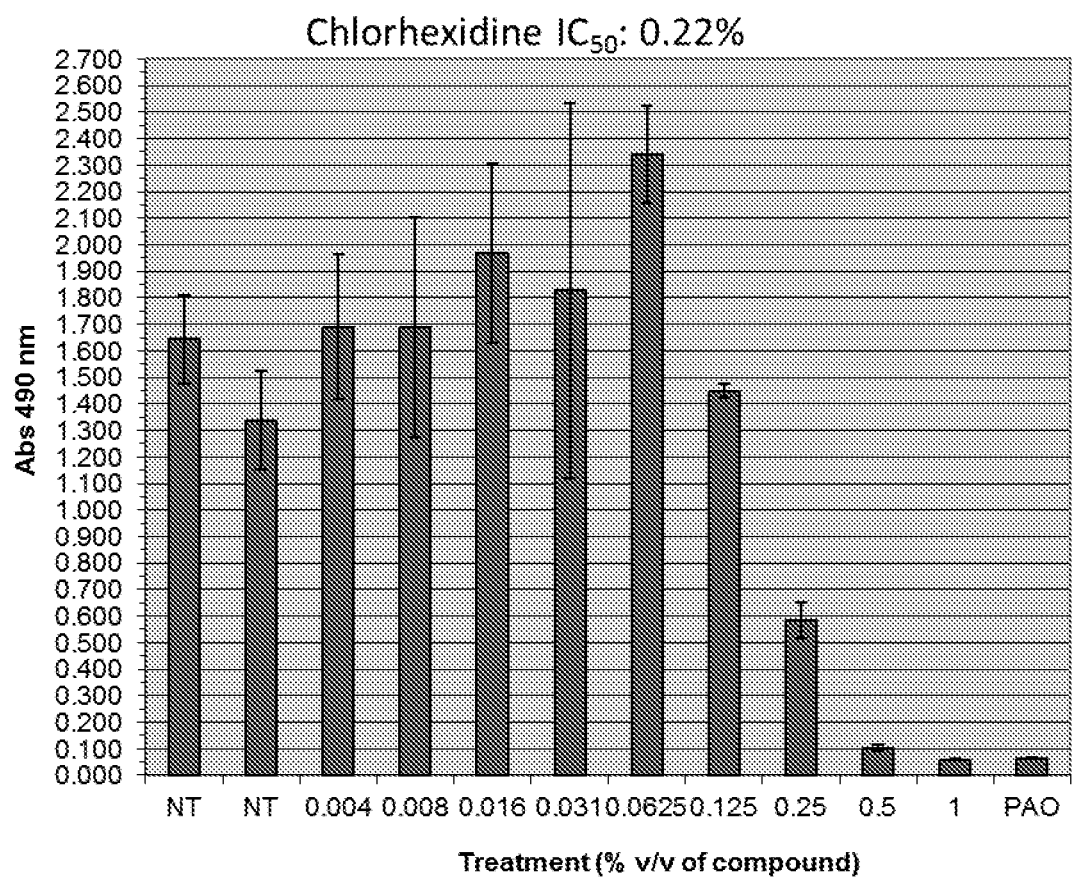

FIG. 32 shows the toxicity of chlorohexidine gluconate 0.12% oral rinse against HeLa cells.

Figure 33:
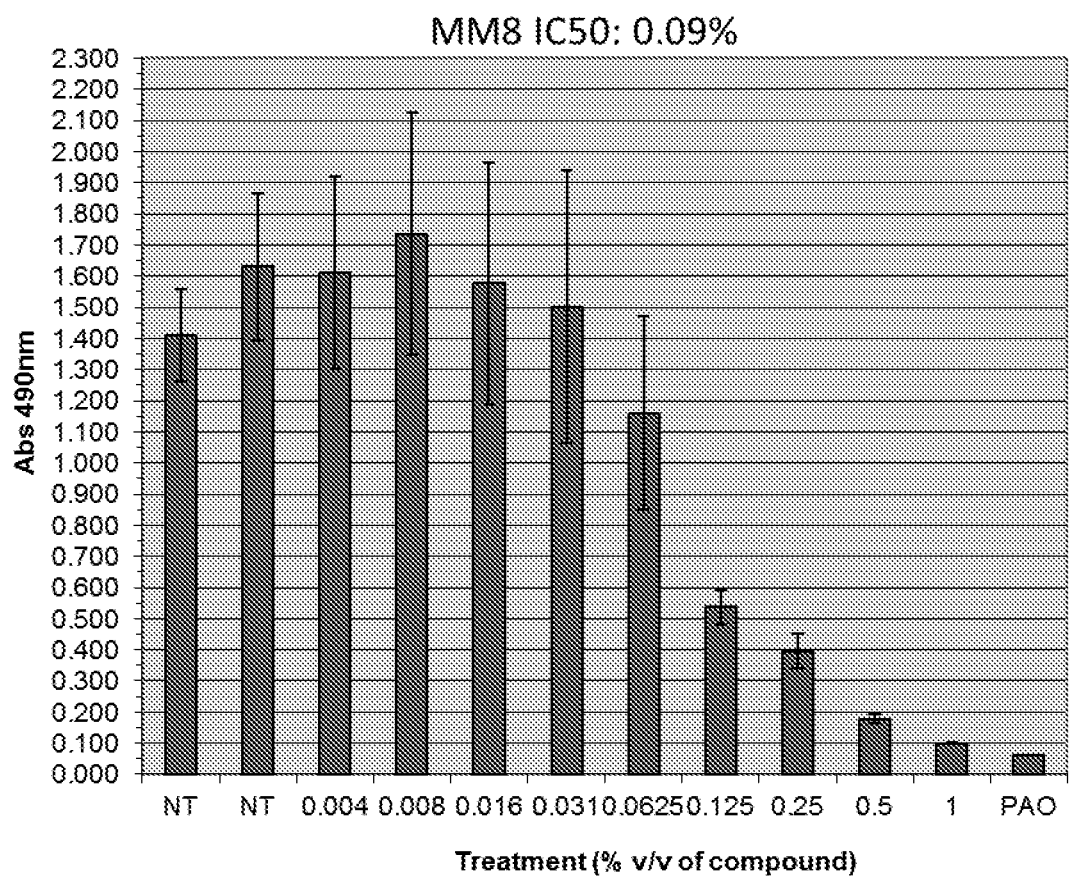

FIG. 33 shows the toxicity of MM8 against HeLa cells. MM8 had an $IC_{50}$ ($GI_{50}$) of 0.22% v/v of the compound.

Figure 34:
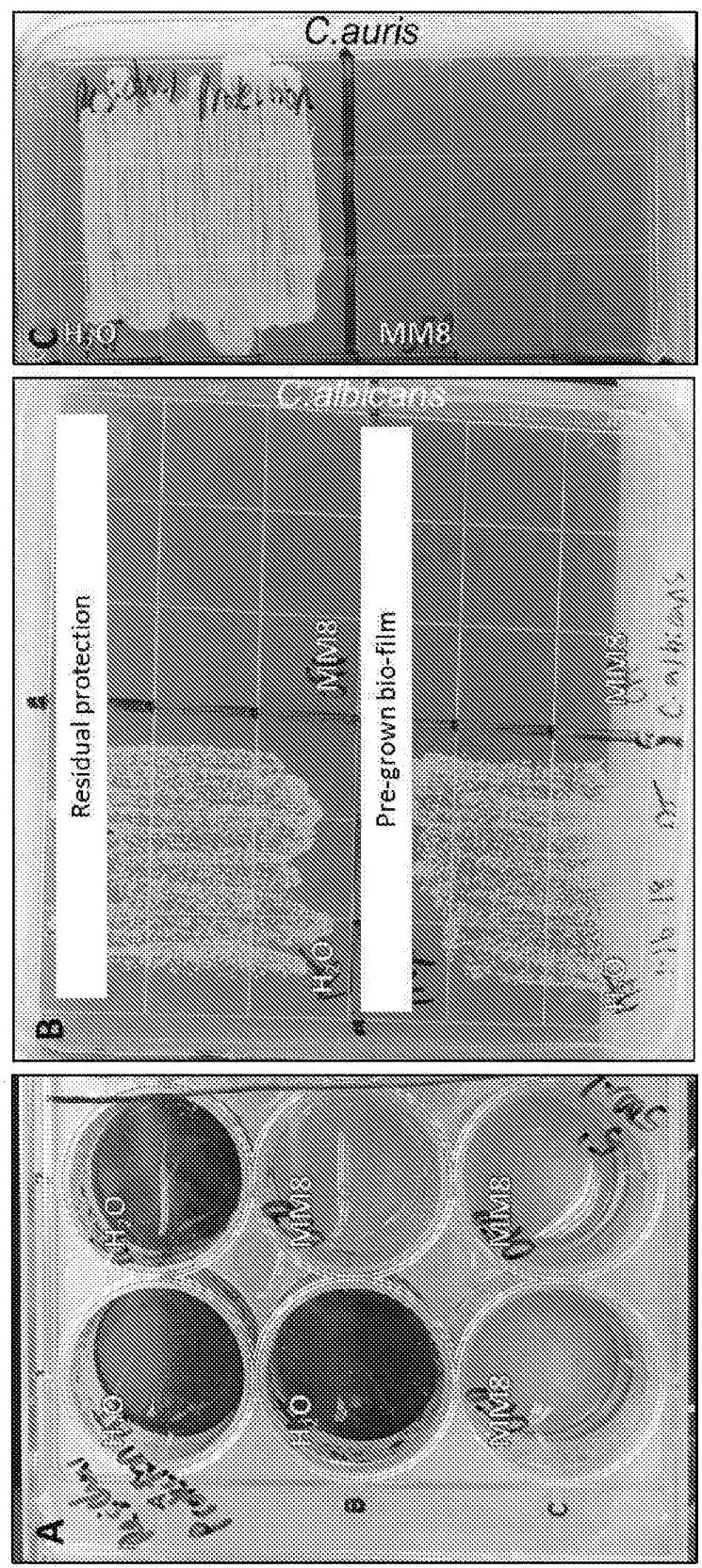

FIG. 34 PANEL A shows that wells that received treatment with water exhibited no protection from *Candida albicans*, while wells treated with MM8 exhibited residual protection. PANEL B TOP RIGHT PANEL shows that the well pre-treated with MM8 and inoculated with *Candida albicans* exhibited residual protection from the fungus. PANEL B BOTTOM LEFT PANEL shows that the *Candida albicans*-infected MHA plate treated with water did not exhibit protection against the fungus. PANEL B BOTTOM RIGHT PANEL shows that the *Candida albicans*-infected MHA plate treated with MM8 exhibited protection against the fungus. PANEL C shows that the *C. auris*-infected MHA plate treated with MM8 exhibited protection against *C. auris*.

Figure 35:
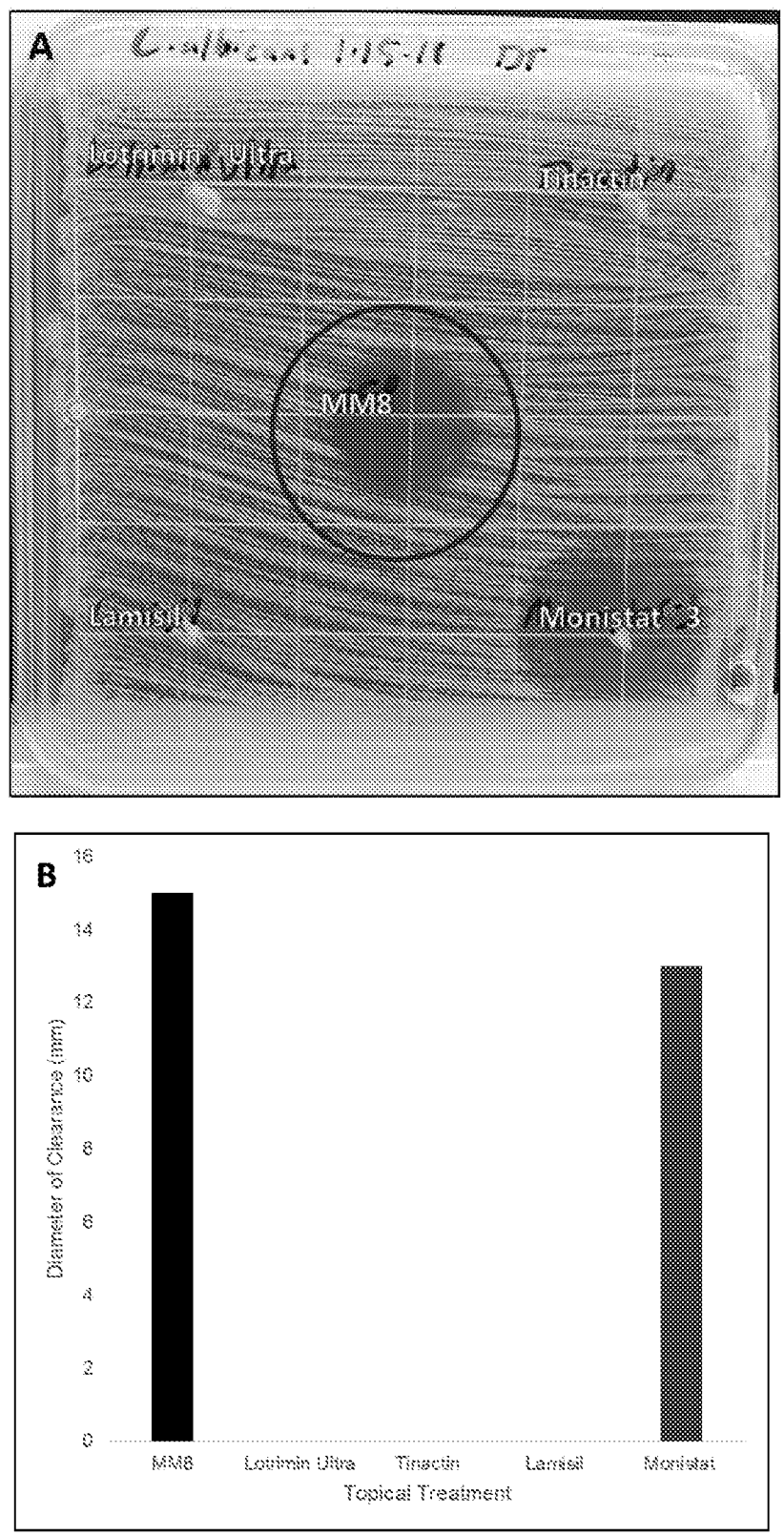

FIG. 35 PANEL A shows that MM8 and Monistat® 3 killed *Candida albicans*, while Lotrimin® Ultra Athlete's Foot Cream, Tinactin® Athlete's Foot Cream, and Lamisil® Athlete's Foot Cream did not kill *Candida albicans*. PANEL B compares the diameter of clearance (mm) of MM8, Lotrimin® Ultra Athlete's Foot Cream, Tinactin® Athlete's Foot Cream, Lamisil® Athlete's Foot Cream, and Monistat® 3 Complete Therapy System when used to treat *Candida albicans*.

Figure 36:

FIG. 36 shows that treatment with Monistat® 3 Complete Therapy System resulted in invasion of the colonies at the border of the diameter of clearance, resulting in a smaller diameter of clearance than MM8.

Figure 37:
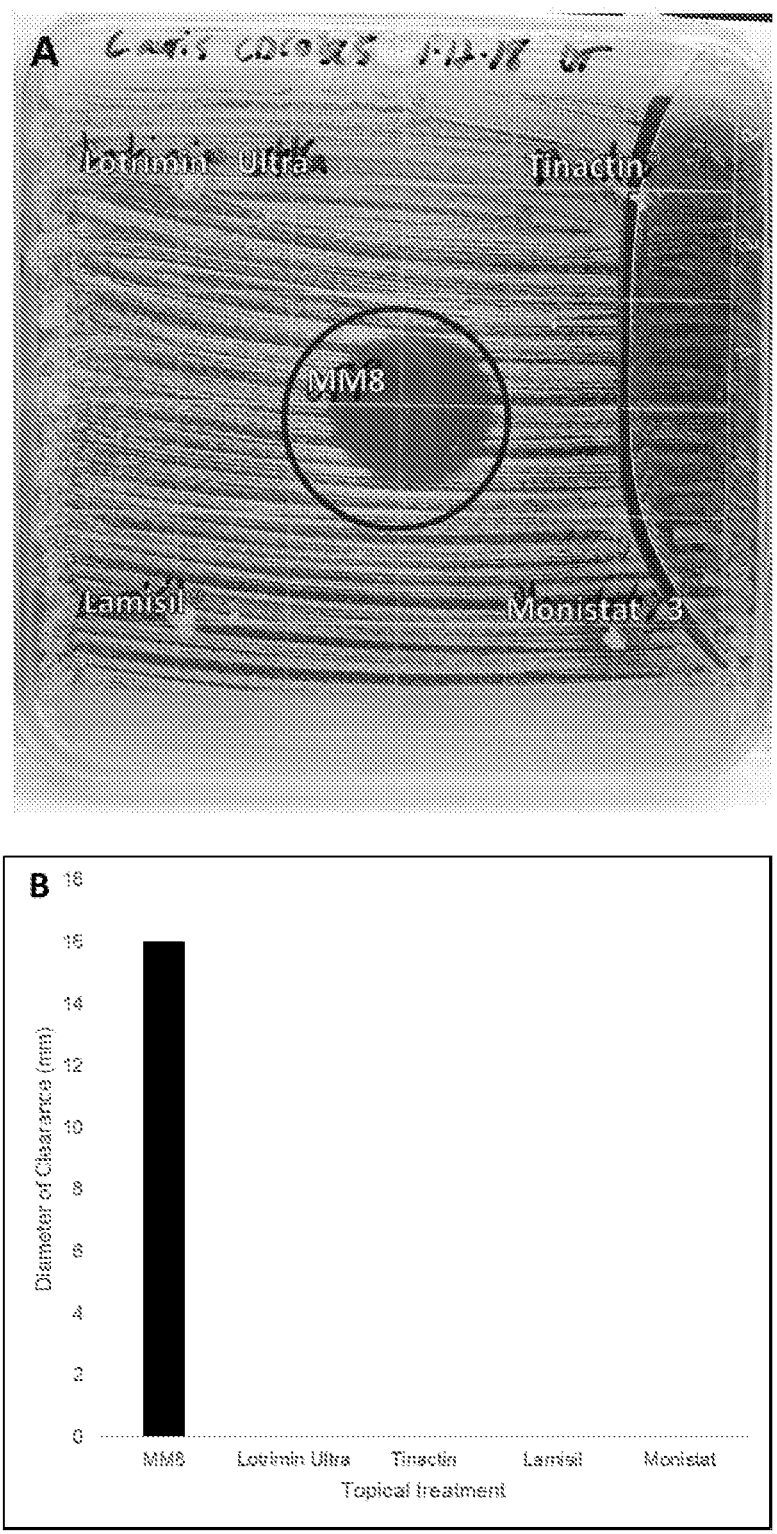

FIG. 37 PANEL A shows that MM8 and Monistat® 3 killed multi-drug resistant *Candida auris* (CDC 0385), while Lotrimin® Ultra Athlete's Foot Cream, Tinactin® Athlete's Foot Cream, and Lamisil® Athlete's Foot Cream did not kill multi-drug resistant *Candida auris* (CDC 0385). PANEL B compares the diameter of clearance (mm) of MM8, Lotrimin® Ultra Athlete's Foot Cream, Tinactin® Athlete's Foot Cream, Lamisil® Athlete's Foot Cream, and Monistat® 3 Complete Therapy System when used to treat multi-drug resistant *Candida auris* (CDC 0385).

Figure 38:
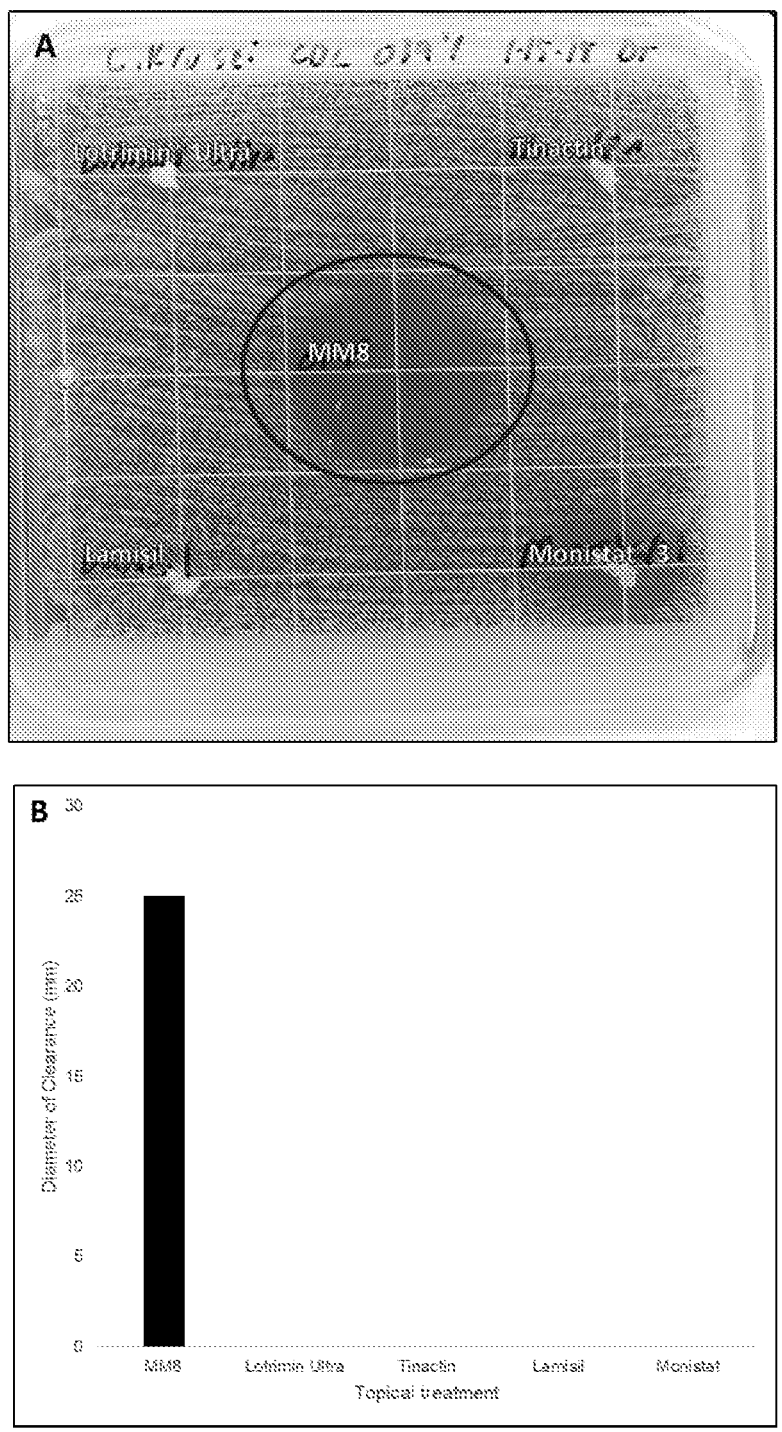

FIG. 38 PANEL A shows that MM8 and Monistat® 3 killed *Candida krusei* (CDC 0397), while Lotrimin® Ultra Athlete's Foot Cream, Tinactin® Athlete's Foot Cream, and Lamisil® Athlete's Foot Cream did not kill multi-drug resistant *Candida krusei* (CDC 0397). PANEL B compares the diameter of clearance (mm) of MM8, Lotrimin® Ultra Athlete's Foot Cream, Tinactin® Athlete's Foot Cream, Lamisil® Athlete's Foot Cream, and Monistat® 3 Complete Therapy System when used to treat multi drug-resistant *Candida auris* (CDC 0385).

Figure 39:
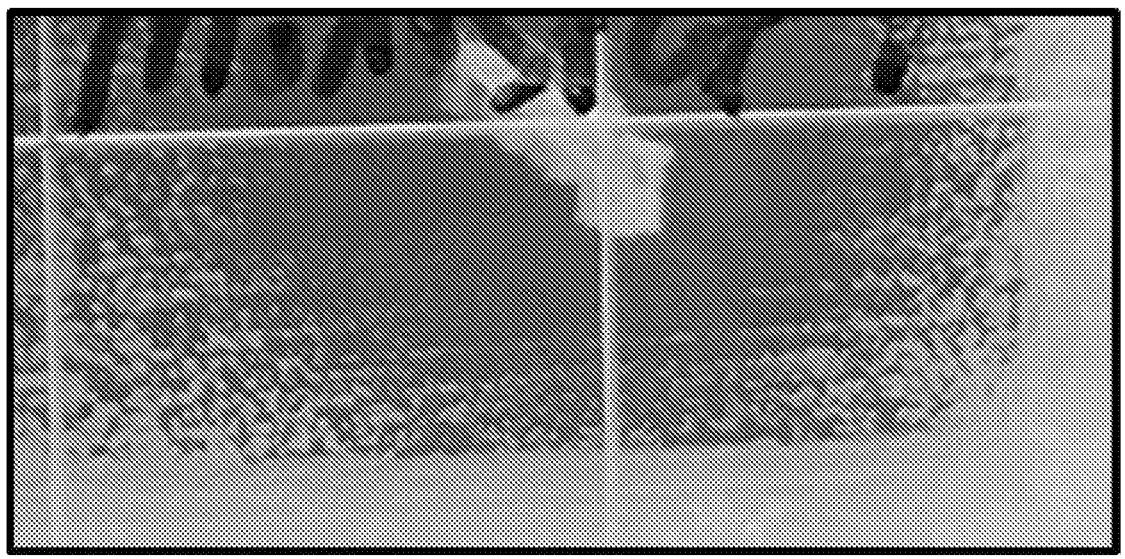

FIG. 39 shows that treatment with Monistat® 3 Complete Therapy System resulted in invasion of the colonies at the border of the diameter of clearance, resulting in a smaller diameter of clearance than MM8.

Figure 40:
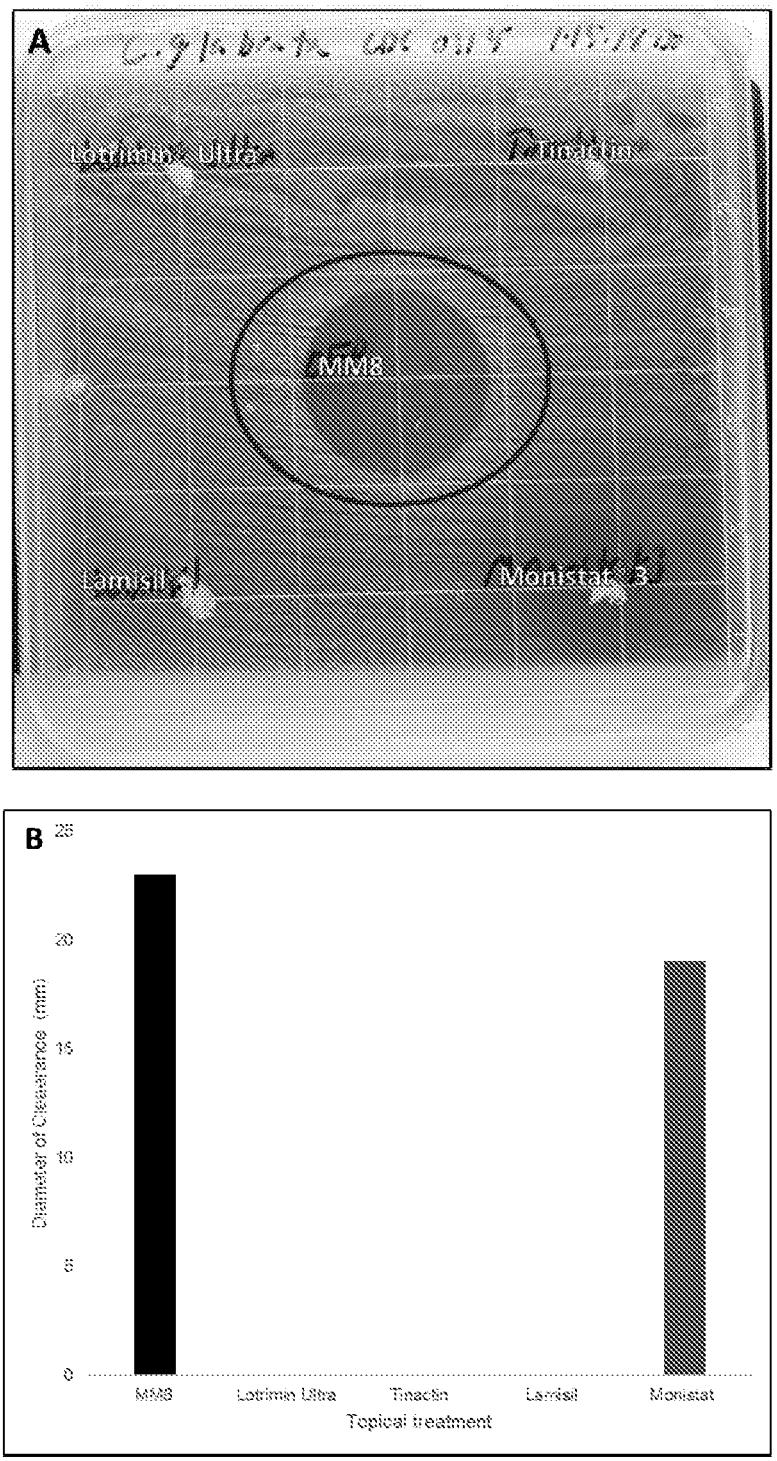

FIG. 40 PANEL A shows that MM8 and Monistat® 3 Complete Therapy System killed *Candida glabrata* (CDC 0315), while Lotrimin® Ultra Athlete's Foot Cream, Tinactin® Athlete's Foot Cream, and Lamisil® Athlete's Foot Cream did not kill multi-drug resistant *Candida glabrata* (CDC 0315). PANEL B compares the diameter of clearance (mm) of MM8, Lotrimin® Ultra Athlete's Foot Cream, Tinactin® Athlete's Foot Cream, Lamisil® Athlete's Foot Cream, and Monistat® 3 Complete Therapy System when used to treat multi-drug resistant *Candida glabrata* (CDC 0315).

Figure 41:
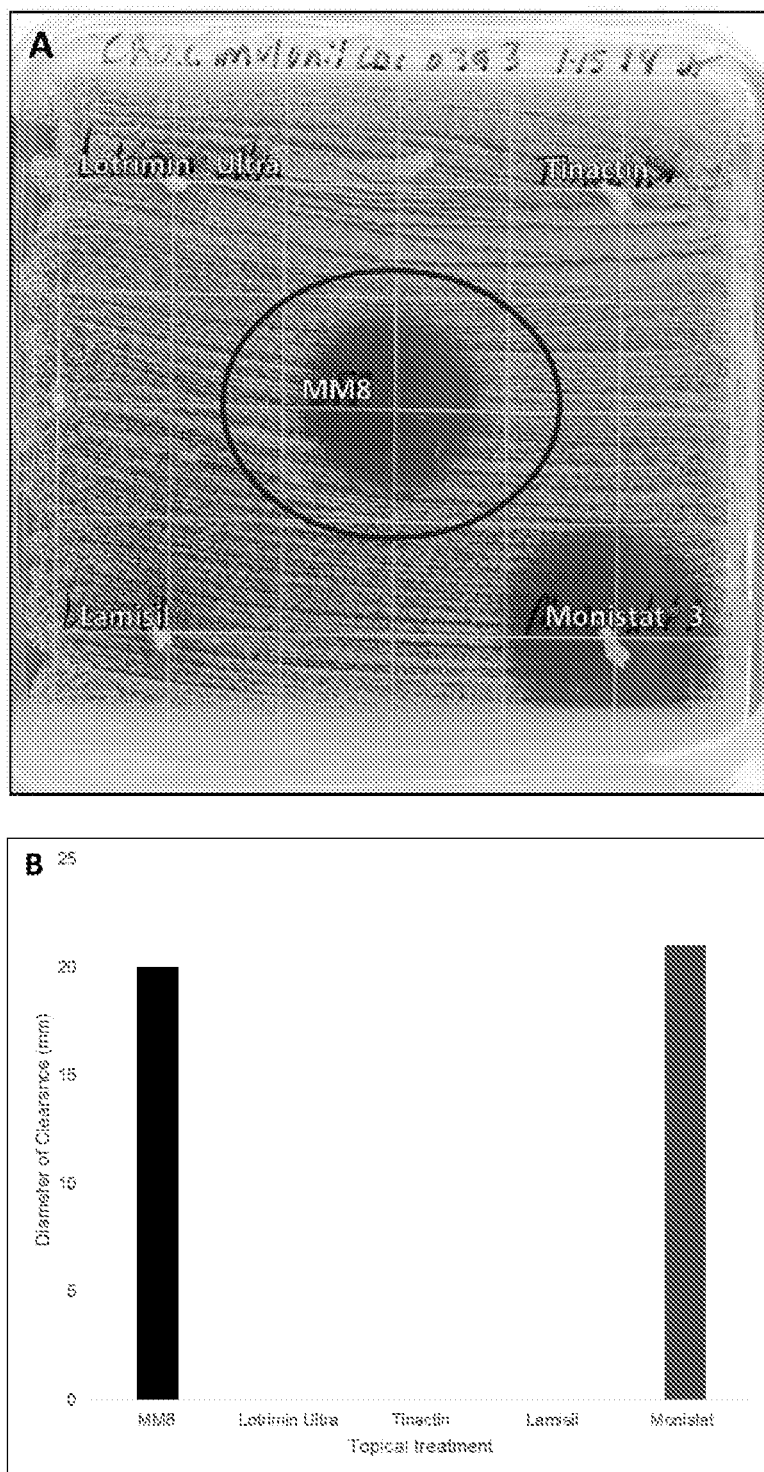

FIG. 41 PANEL A shows that MM8 and Monistat® 3 Complete Therapy System killed *Candida haemulonii* (CDC 0393), while Lotrimin® Ultra Athlete's Foot Cream, Tinactin® Athlete's Foot Cream, and Lamisil® Athlete's Foot Cream did not kill multi-drug resistant *Candida haemulonii* (CDC 0393). FIG. 41 PANEL B compares the diameter of clearance (mm) of MM8, Lotrimin® Ultra Athlete's Foot Cream, Tinactin® Athlete's Foot Cream, Lamisil® Athlete's Foot Cream, and Monistat® 3 Complete Therapy System when used to treat multi-drug resistant *Candida haemulonii* (CDC 0393).

Figure 42:
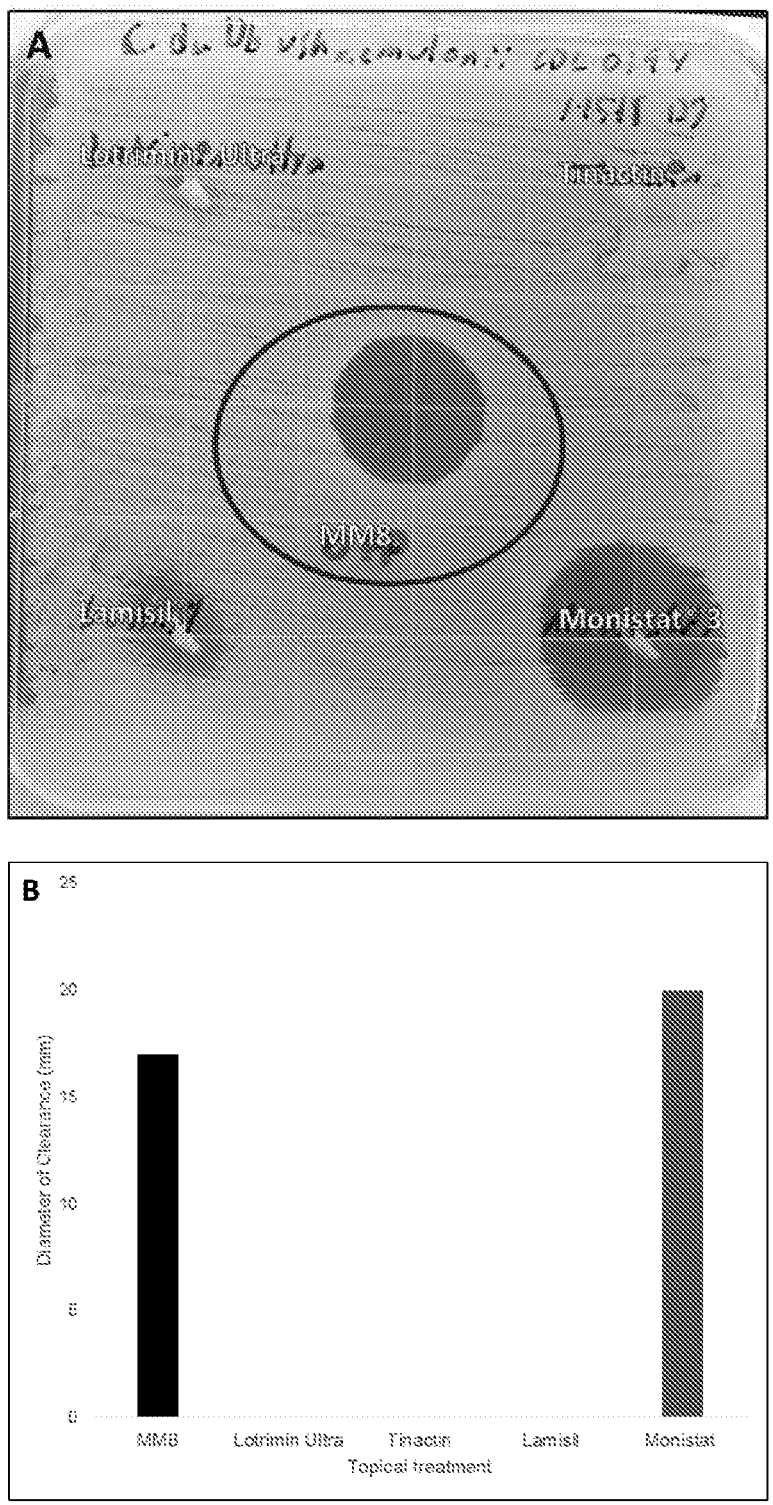

FIG. 42 PANEL A shows that MM8, Lamisil® Athlete's Foot Cream, and Monistat® 3 Complete Therapy System killed *Candida duobshaemulonii* (CDC 0394), while Lotrimin® Ultra Athlete's Foot Cream and Tinactin® Athlete's Foot Cream did not kill *Candida duobshaemulonii* (CDC 0394). PANEL B compares the diameter of clearance (mm) of MM8, Lotrimin® Ultra Athlete's Foot Cream, Tinactin® Athlete's Foot Cream, Lamisil® Athlete's Foot Cream, and Monistat® 3 Complete Therapy System when used to treat *Candida duobshaemulonii* (CDC 0394).

Figure 43:
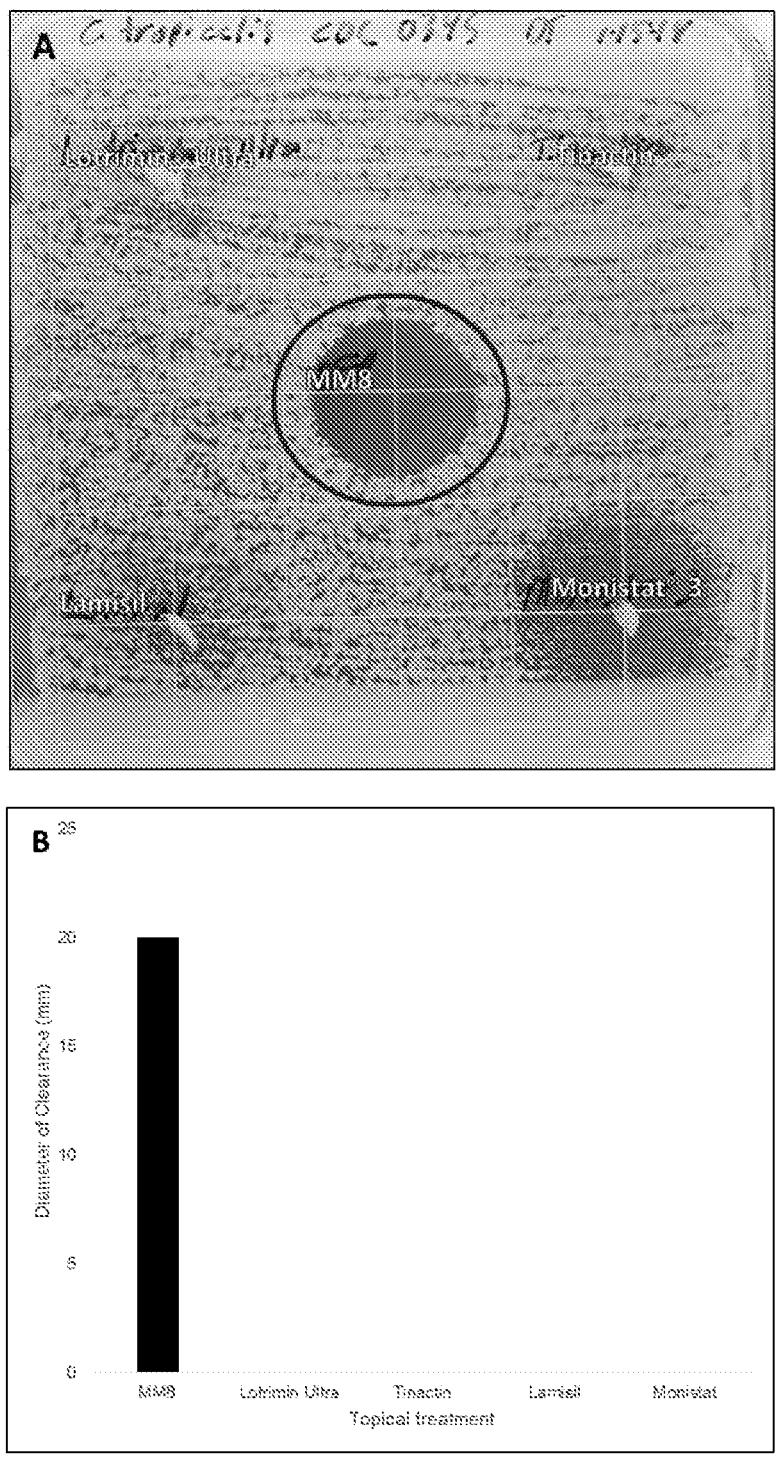

FIG. 43 PANEL A shows that MM8 and Monistat® 3 Complete Therapy System killed *Candida tropicalis* (CDC 0345), while Lotrimin® Ultra Athlete's Foot Cream, Tinactin® Athlete's Foot Cream, and Lamisil® Athlete's Foot Cream did not kill *Candida tropicalis* (CDC 0345). PANEL B compares the diameter of clearance (mm) of MM8, Lotrimin® Ultra Athlete's Foot Cream, Tinactin® Athlete's Foot Cream, Lamisil® Athlete's Foot Cream, and Monistat® 3 Complete Therapy System when used to treat *Candida tropicalis* (CDC 0345).

Figure 44:

FIG. 44 shows that treatment with Monistat® 3 Complete Therapy System resulted in invasion of the colonies at the border of the diameter of clearance, resulting in a diameter of clearance of zero mm.

Figure 45:
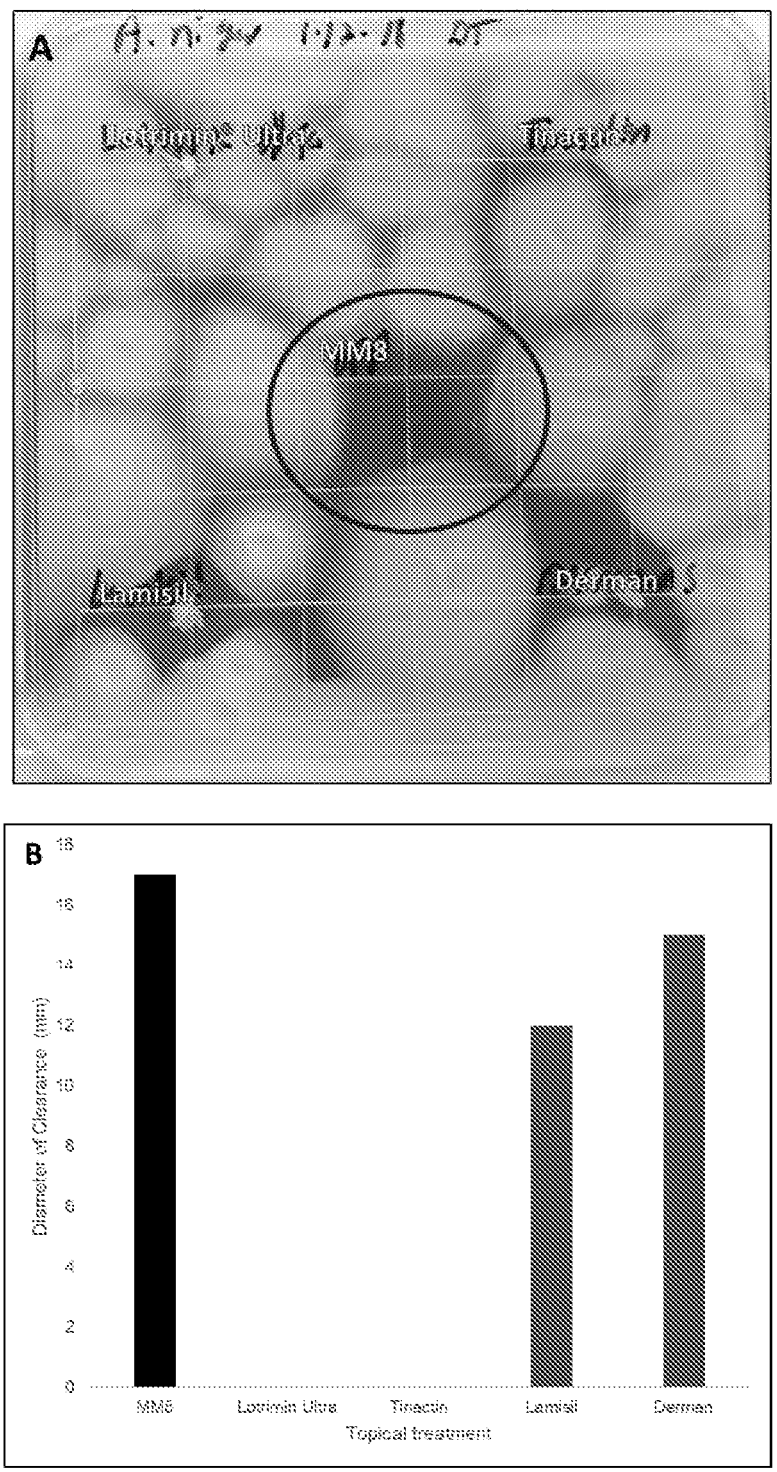

FIG. 45 PANEL A shows that MM8, Lamisil® Athlete's Foot Cream, and Derman® Antifungal Cream killed *Aspergillus niger*, while Lotrimin® Ultra Athlete's Foot Cream and Tinactin® Athlete's Foot Cream did not kill *Aspergillus niger*. PANEL B compares the diameter of clearance (mm) of MM8, Lotrimin® Ultra Athlete's Foot Cream, Tinactin® Athlete's Foot Cream, Lamisil® Athlete's Foot Cream, and Derman® Antifungal Cream when used to treat *Aspergillus niger*.

Figure 46:
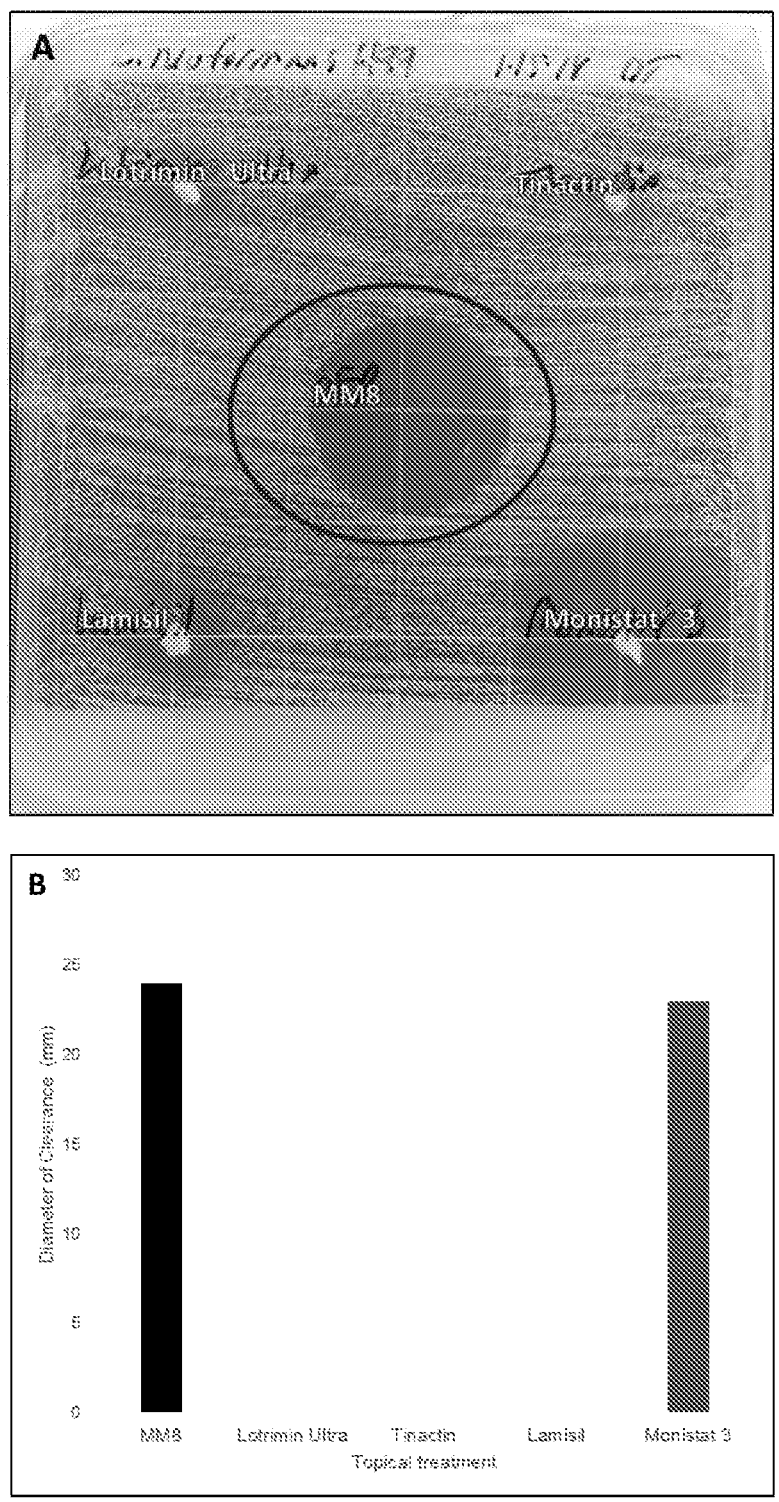

FIG. 46 PANEL A shows that MM8 and Monistat® 3 killed *Cryptococcus neoformans* (H99), while Lotrimin® Ultra Athlete's Foot Cream, Tinactin® Athlete's Foot Cream, and Lamisil® Athlete's Foot Cream did not kill *Cryptococcus neoformans* (H99). PANEL B compares the diameter of clearance (mm) of MM8, Lotrimin® Ultra Athlete's Foot Cream, Tinactin® Athlete's Foot Cream, Lamisil® Athlete's Foot Cream, and Monistat® 3 Complete Therapy System when used to treat *Cryptococcus neoformans* (H99).

Figure 47:
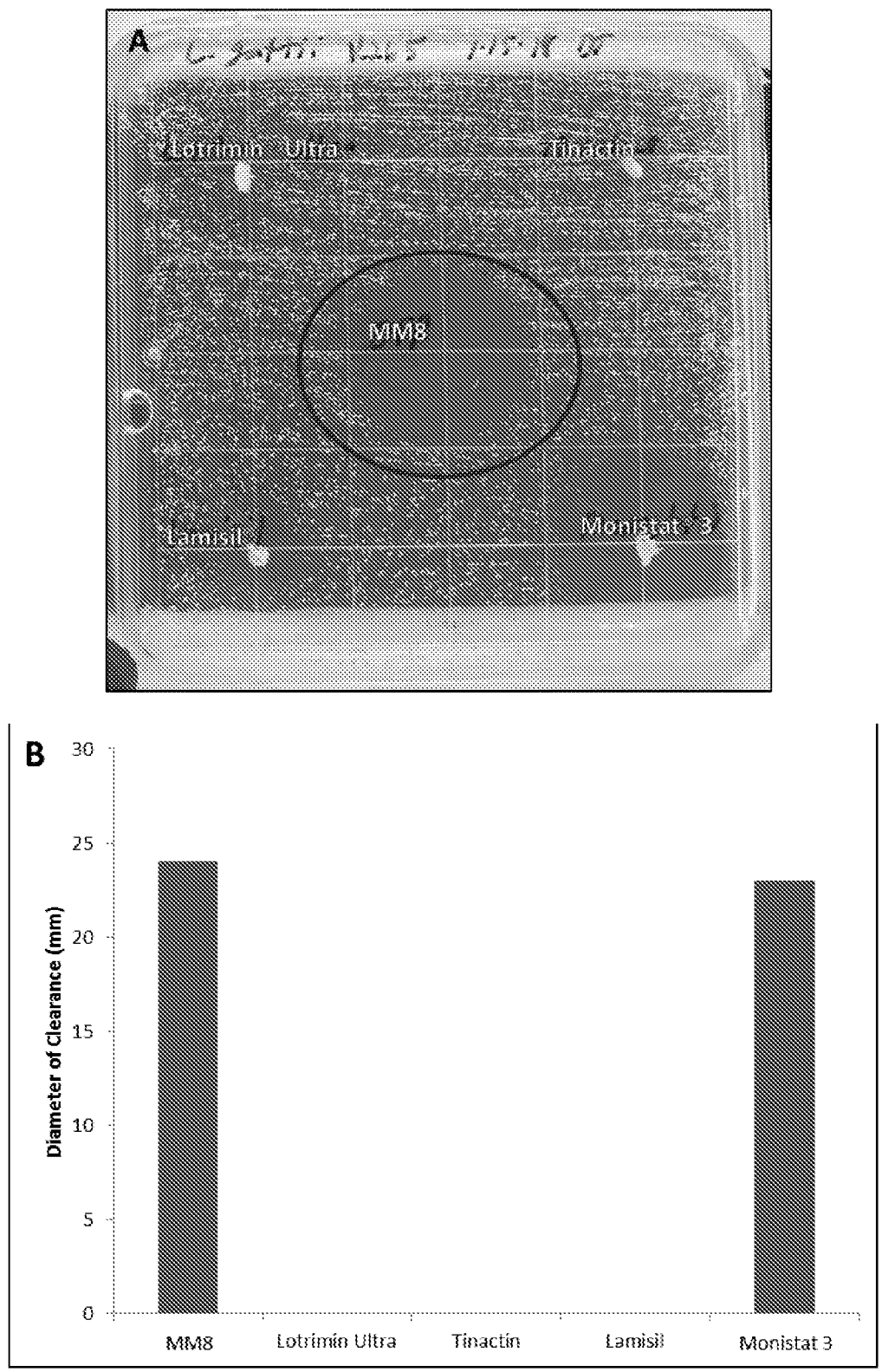

FIG. 47 PANEL A shows that MM8 and Monistat® 3 Complete Therapy System killed *Cryptococcus gattii* (K265), while Lotrimin® Ultra Athlete's Foot Cream, Tinactin® Athlete's Foot Cream, and Lamisil® Athlete's Foot Cream did not kill *Cryptococcus gattii* (K265). PANEL B compares the diameter of clearance (mm) of MM8, Lotrimin® Ultra Athlete's Foot Cream, Tinactin® Athlete's Foot Cream, Lamisil® Athlete's Foot Cream, and Monistat® 3 Complete Therapy System when used to treat *Cryptococcus gattii* (K265).

Figure 48:
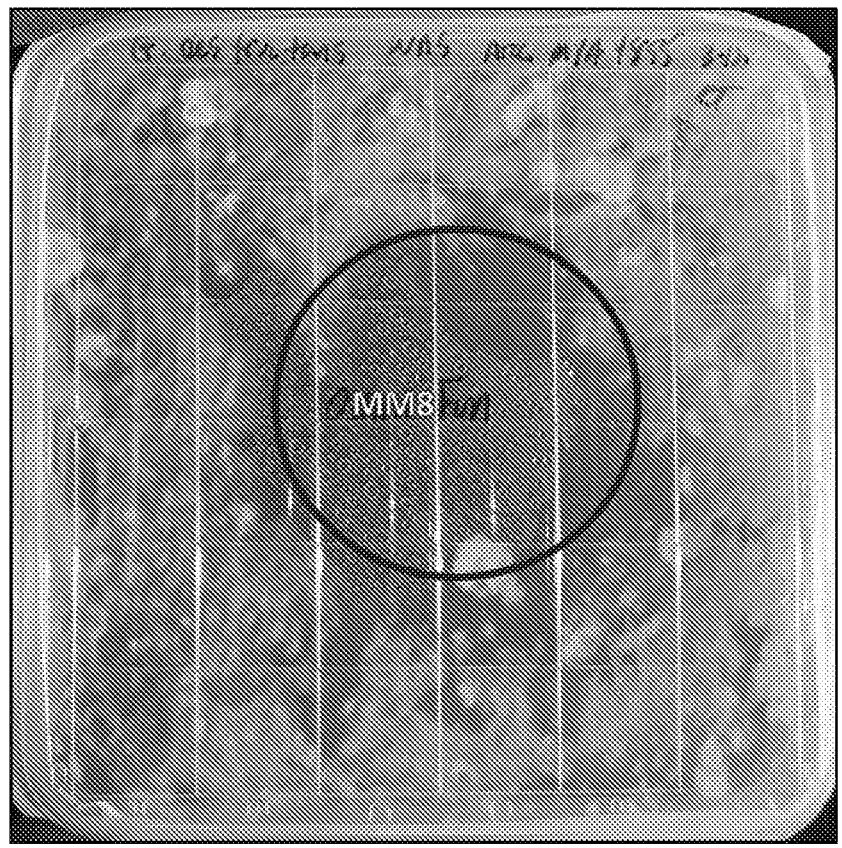

FIG. 48 shows that MM8 killed *Geomyces destructans*.

Figure 49:
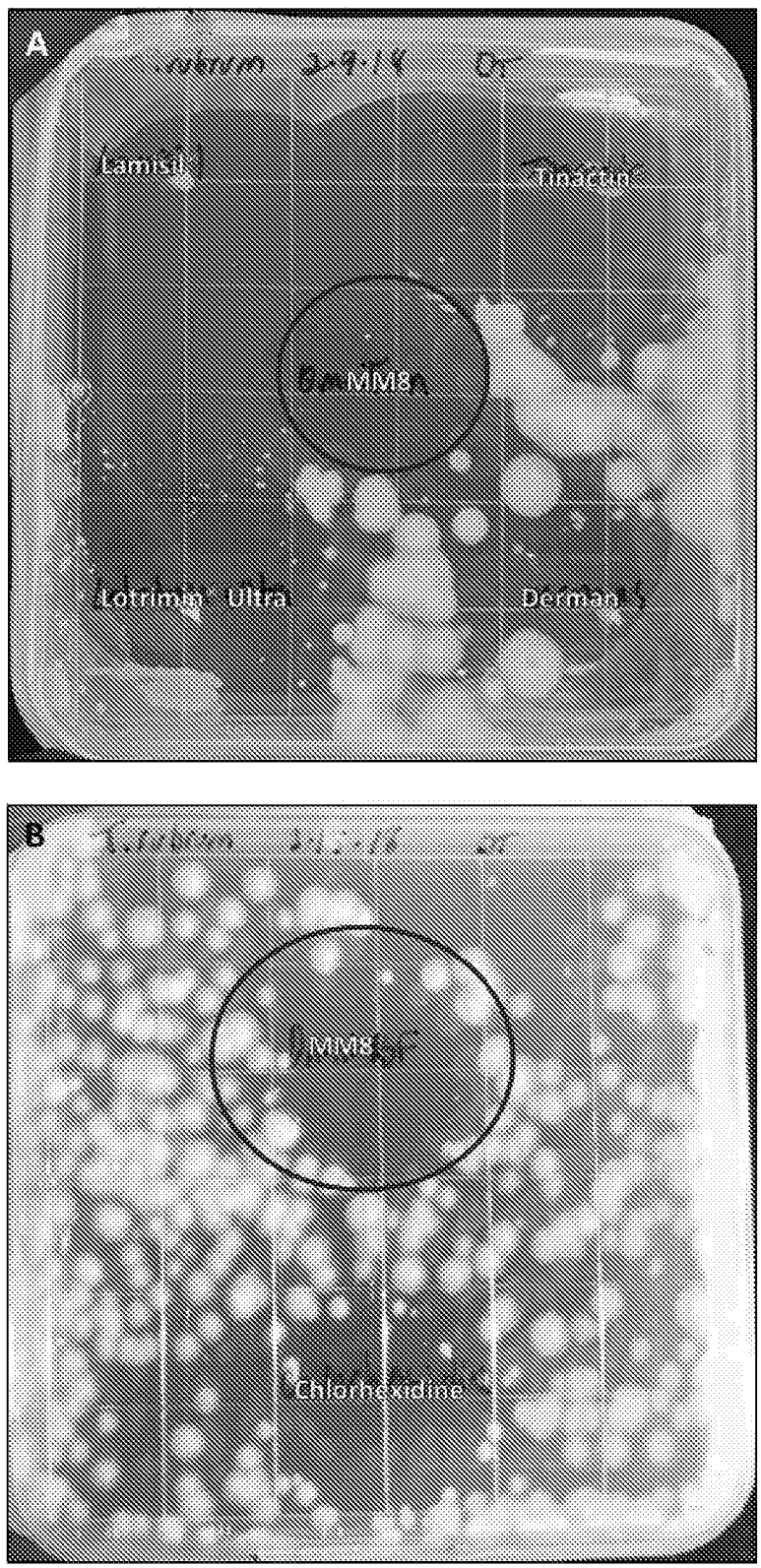

FIG. 49 PANEL A shows that MM8, Lamisil® Athlete's Foot Cream, Tinactin® Athlete's Foot Cream, and Derman® Antifungal Cream killed *Trichophyton rubrum*. Lamisil® Athlete's Foot Cream was the most effective at killing *Trichophyton rubrum*. PANEL B shows that MM8 was as effective at killing *Trichophyton rubrum* as a chlorohexidine gluconate 0.12% oral rinse.

Figure 50:
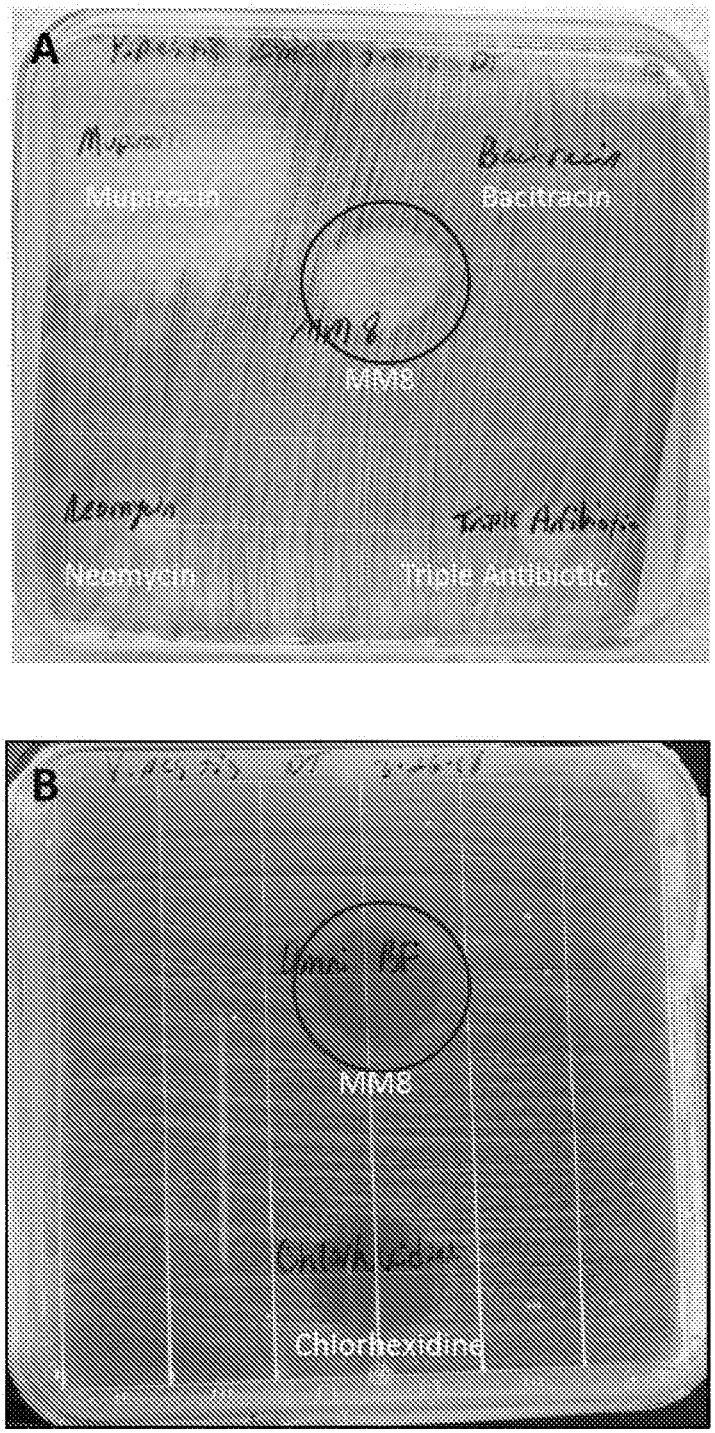

FIG. 50 PANEL A shows the circle enclosing the diameter of clearance created by treatment with MM8 and demonstrates that while mupirocin and neomycin were more effective than MM8 was, MM8 was more effective than bacitracin and the triple antibiotic ointment were after an incubation period of 1 day. PANEL B shows that MM8 and the chlorhexidine gluconate 0.12% oral rinse were about equally toxic to *Yesenia pestis* (Kimo 6).

FIG. 51 PANEL A shows that MM8 and bacitracin killed VRE after an incubation period of 1 day. The circle encloses the diameter of clearance created by treatment with MM8 and demonstrates that MM8 was the most efficacious treatment compared to mupirocin, bacitracin, neomycin, and a triple antibiotic ointment. PANEL B shows that after 7 days of incubation, the area of VRE treated with MM8 was the only remaining diameter of clearance, indicating that one treatment with MM8 had long-lasting effects against VRE.

FIG. 52 PANEL A shows that MM8 and mupirocin killed MRSA after an incubation period of 1 day. PANEL B shows that after 4 days of incubation, MM8 and mupirocin were the only formulations that killed VRSA.

FIG. 53 PANEL A shows that MM8 and mupirocin killed CRE NDM-1 MDR after an incubation period of 1 day. PANEL B shows that after 5 days of incubation, MM8 and mupirocin were the only formulations that killed CRE NDM-1 MDR.

FIG. 54 shows that MM8 and mupirocin killed *A. baumannii* after an incubation period of 1 day.

FIG. 55 shows that MM8 and mupirocin killed multi-drug resistant *Pseudomonas aeruginosa* after an incubation period of 1 day.

FIG. 56 PANEL A shows that MM8, mupirocin, neomycin, and the triple antibiotic ointment killed *Escherichia coli* (O157:H7) after an incubation period of 1 day. PANEL B shows that after 5 days of incubation, MM8, mupirocin, neomycin, and the triple antibiotic ointment were the only formulations that killed *Escherichia coli* (O157:H7).

FIG. 57 PANEL A shows that MM8 was the only formulation to kill multi-drug resistant *Burkholderia cepacia* after an incubation period of 1 day. PANEL B shows that after 4 days of incubation, MM8 was the only formulation that killed multi-drug resistant *Burkholderia cepacia.*

FIG. 58 PANEL A shows that MM8, mupirocin, neomycin, and the triple antibiotic ointment killed *Streptococcus pyogenes* after an incubation period of 1 day. PANEL B shows that after 7 days of incubation, MM8, mupirocin, neomycin, and the triple antibiotic ointment further killed *S. pyogenes.*

FIG. 59 shows that the *S. pyogenes* colonies invaded the areas treated with neomycin and the triple antibiotic, but the area treated with MM8 did not exhibit regrowth of the *Streptococcus pyogenes* colonies.

FIG. 60 shows that MM8 killed polymyxin E-resistant *Stenotrophomonas maltophilia* after an incubation period of 1 day.

FIG. 61 shows that MM8, mupirocin, neomycin, and the triple antibiotic ointment killed *Bacillus subtilis* after an incubation period of 1 day.

FIG. 62 PANEL A shows that MM8 was the only formulation that killed *Mycobacterium abscessus*. PANEL B shows an image of the MHA stained with MTT.

FIG. 63 PANEL A shows that MM8 and mupirocin killed MRSA BAA-1717 (USA 300). PANEL B shows that MM8, mupirocin, neomycin, and the triple antibiotic ointment killed multi-drug resistant *Burkholderia cepacia.*

FIG. 64 PANEL A shows that MM8 and chlorhexidine gluconate 0.12% oral rinse killed MRSA BAA-1717 (USA 300). PANEL B shows that MM8 and chlorhexidine gluconate 0.12% oral rinse killed MRSA BAA-44.

FIG. 65 PANEL A shows that MM8 and chlorhexidine gluconate 0.12% oral rinse killed *Acinetobacter baumannii* (ATCC 1797). PANEL B shows that MM8 and chlorhexidine gluconate 0.12% oral rinse killed *Pseudomonas aeruginosa* (ATCC 2114).

FIG. 66 PANEL A shows that MM8 and chlorhexidine gluconate 0.12% oral rinse killed multi-drug resistant *Burkholderia cepacia*. PANEL B shows that MM8 and chlorhexidine gluconate 0.12% oral rinse killed multi-drug resistant *Candida auris.*

FIG. 67 PANEL A shows that MM8 and chlorhexidine gluconate 0.12% oral rinse killed *Candida albicans* (ATCC 26555). PANEL B shows that MM8 and chlorhexidine gluconate 0.12% oral rinse killed *Candida auris* (CDC 0383) after an incubation period of 2 days.

FIG. 68 PANEL A shows that MM8 and chlorhexidine gluconate 0.12% oral rinse killed *Candida tropicalis* (CDC 0345) after an incubation period of 2 days. PANEL B shows that MM8 and chlorhexidine gluconate 0.12% oral rinse killed *Candida glabrata* (CDC 0315) after an incubation period of 2 days.

Figure 69:
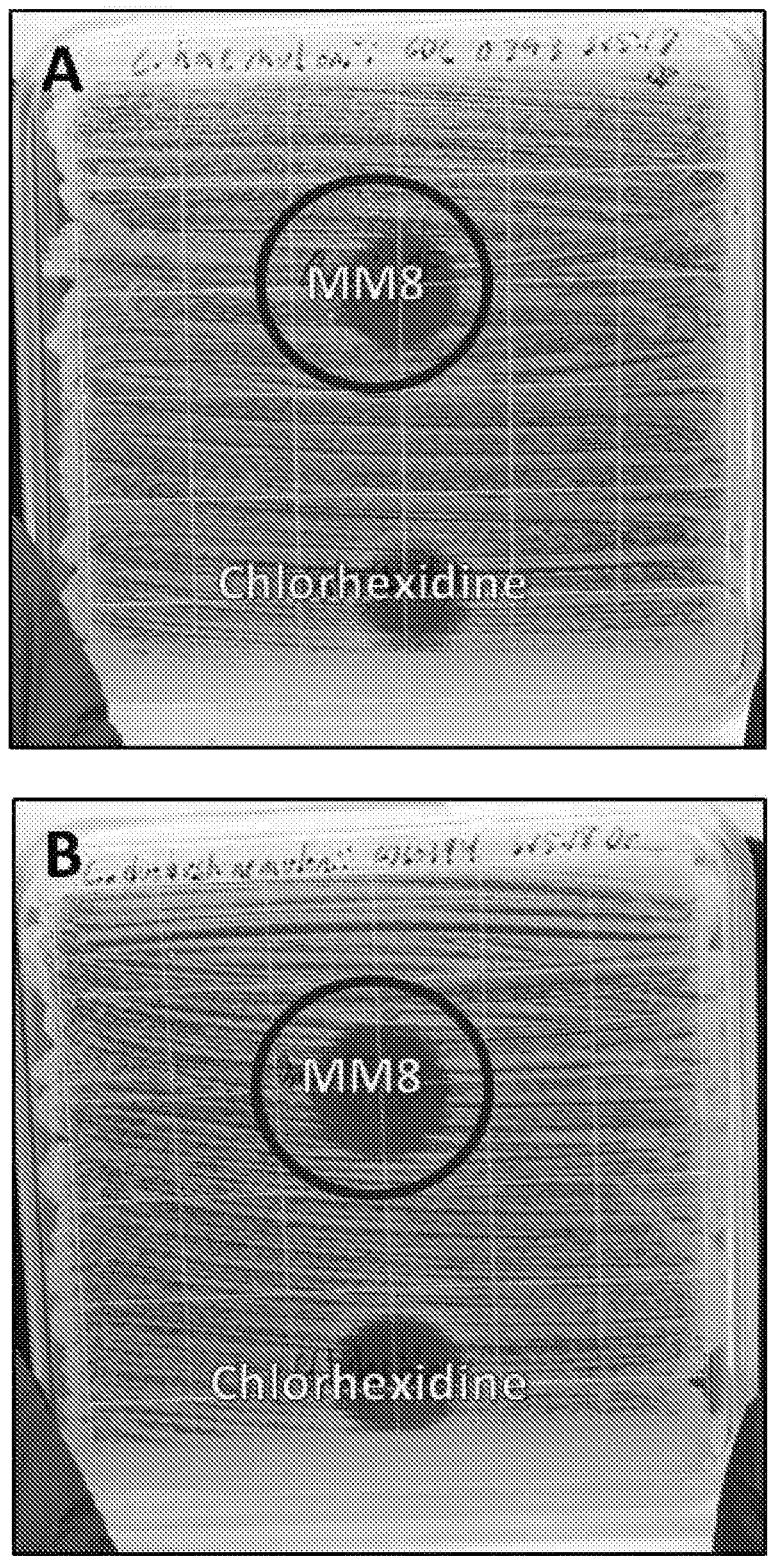

FIG. 69 PANEL A shows that MM8 and chlorhexidine gluconate 0.12% oral rinse killed *Candida haemulonii* (CDC 0393) after an incubation period of 2 days. PANEL B shows that MM8 and chlorhexidine gluconate 0.12% oral rinse killed *Candida duobushaemulonii* (CDC 0339) after an incubation period of 2 days.

Figure 70:
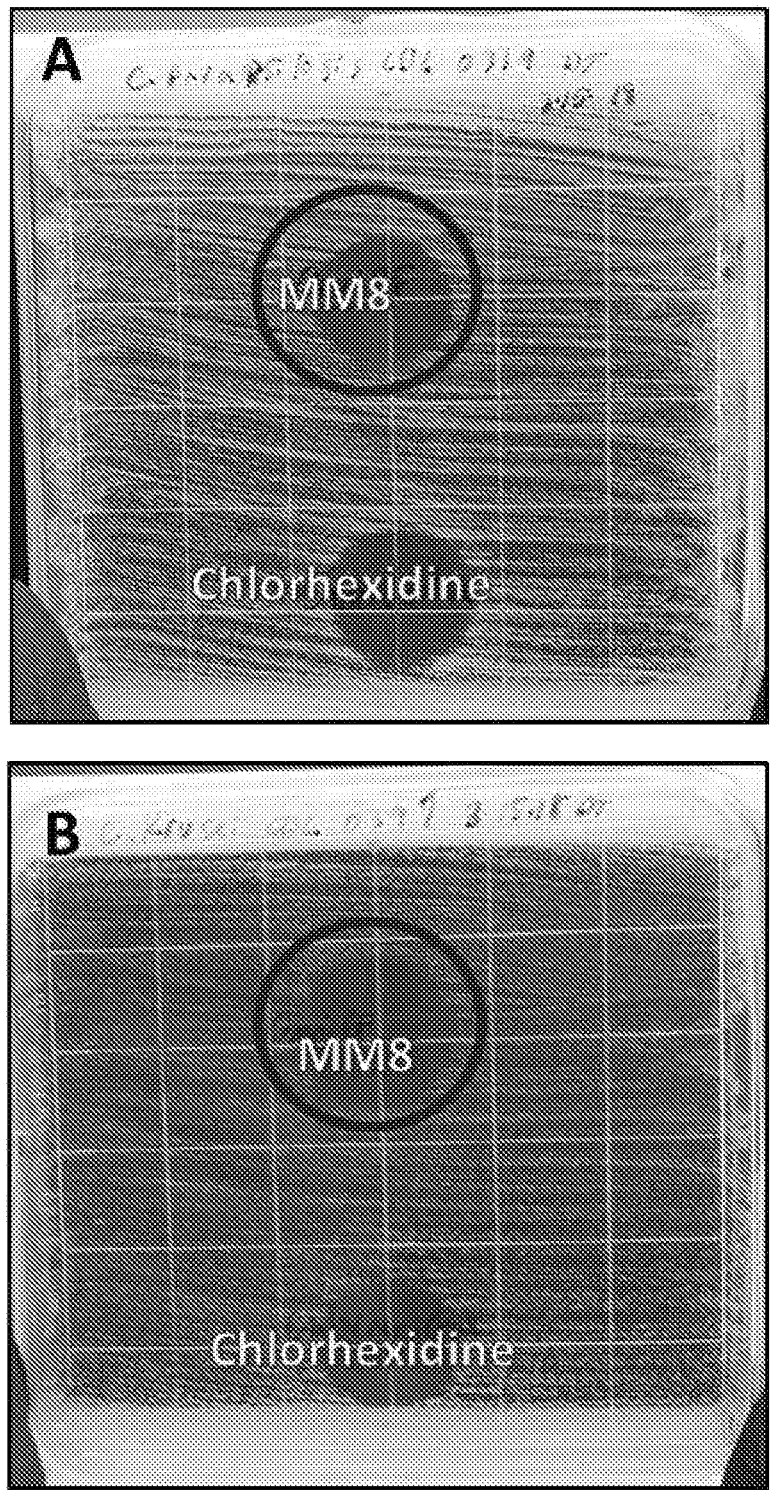

FIG. 70 PANEL A shows that MM8 and chlorhexidine gluconate 0.12% oral rinse killed *Candida parapsilosis* (CDC 0339) after an incubation period of 2 days. PANEL B shows that MM8 and chlorhexidine gluconate 0.12% oral rinse killed *Candida krusei* (CDC 0397) after an incubation period of 2 days.

Figure 71:
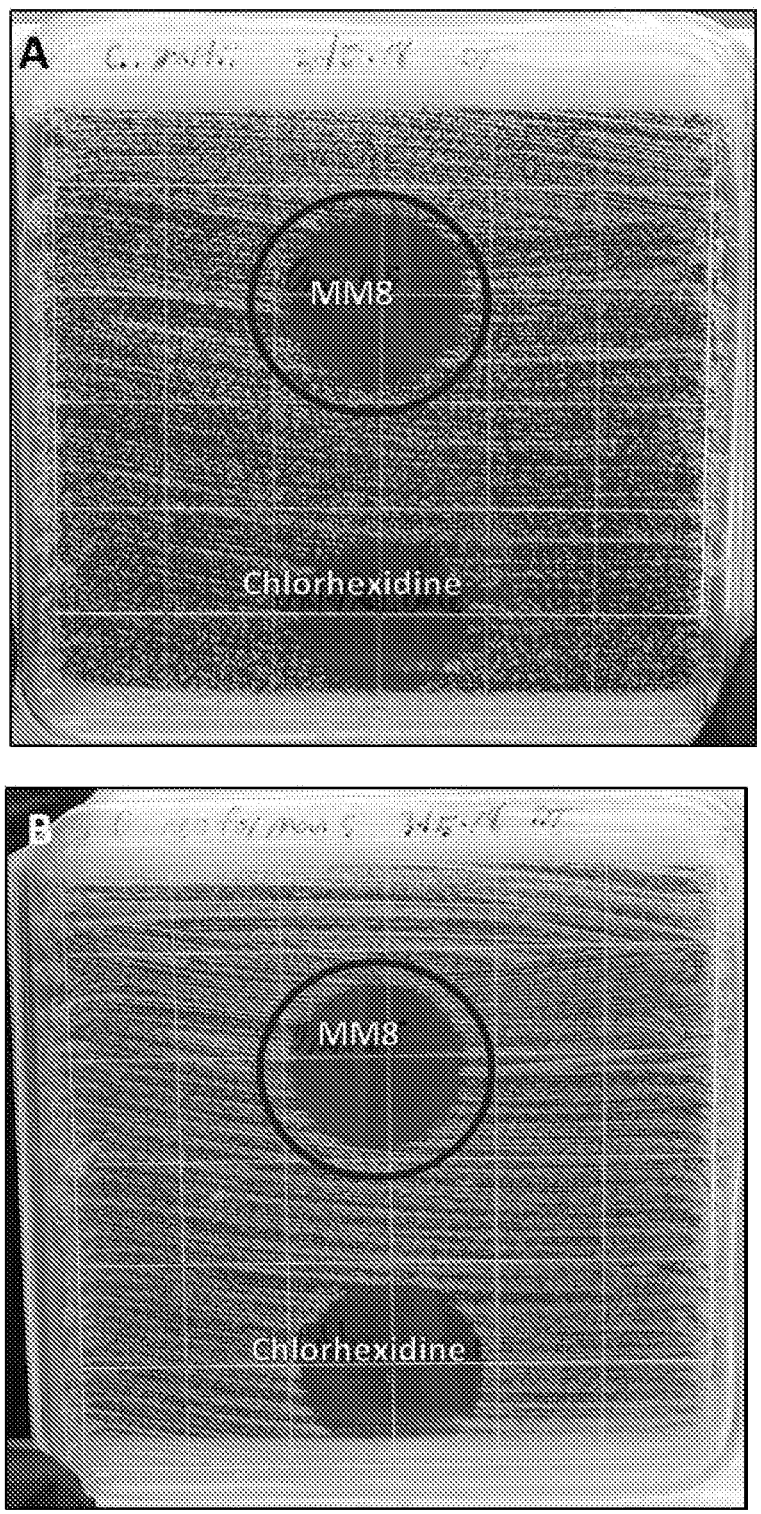

FIG. 71 PANEL A shows that MM8 and chlorhexidine gluconate 0.12% oral rinse killed *Cryptococcus gattii*. PANEL B shows that MM8 and chlorhexidine gluconate 0.12% oral rinse killed *Cryptococcus neoformans*.

Figure 72:
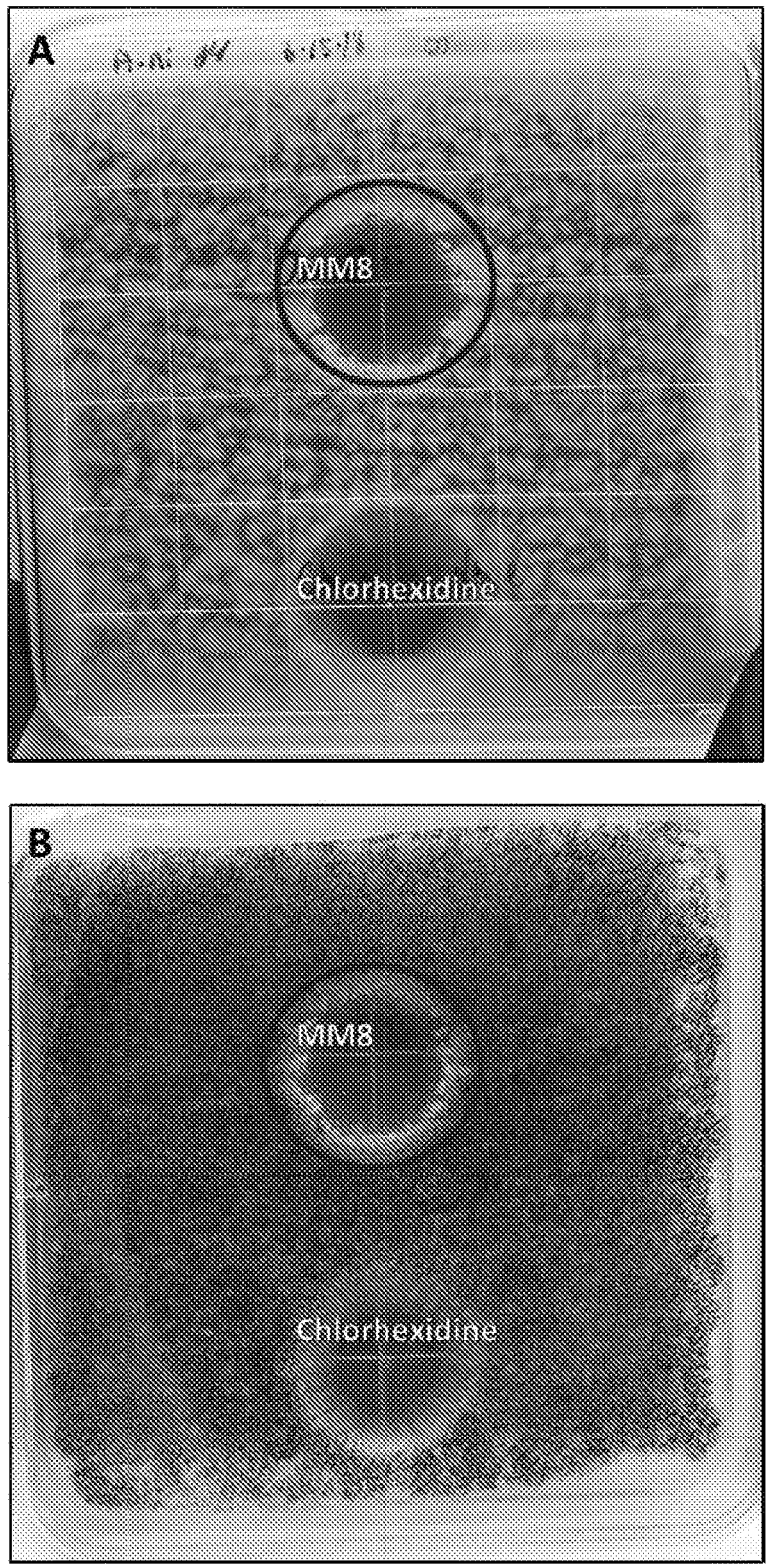

FIG. 72 PANEL A shows the front side of an MHA plate infected with *Aspergillus niger*, which shows that MM8 and chlorhexidine gluconate 0.12% oral rinse killed *Aspergillus niger*. PANEL B shows the back side of an MHA plate infected with *Aspergillus niger*, which shows that MM8 and chlorhexidine gluconate 0.12% oral rinse killed *Aspergillus niger*.

Figure 73:
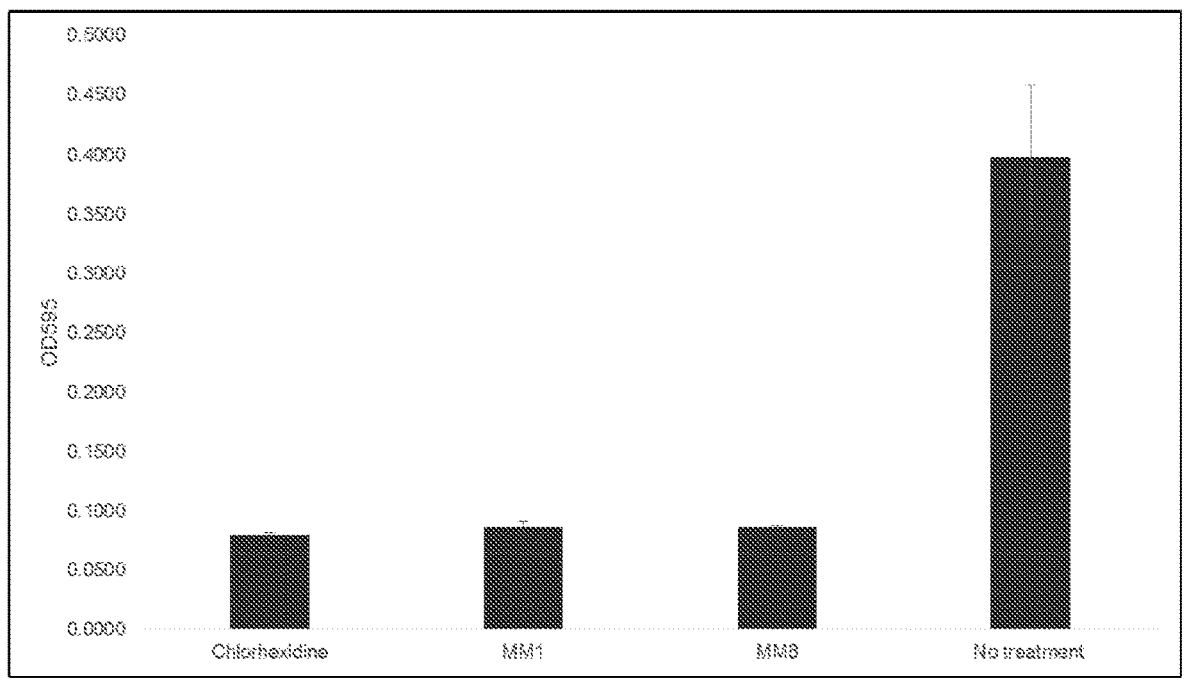

FIG. 73 shows that chlorhexidine gluconate 0.12% oral rinse, MM1, and MM8 were equally effective at a pre-established *Staphylococcus epidermis* biofilm after 15 minutes of treatment.

Figure 74:
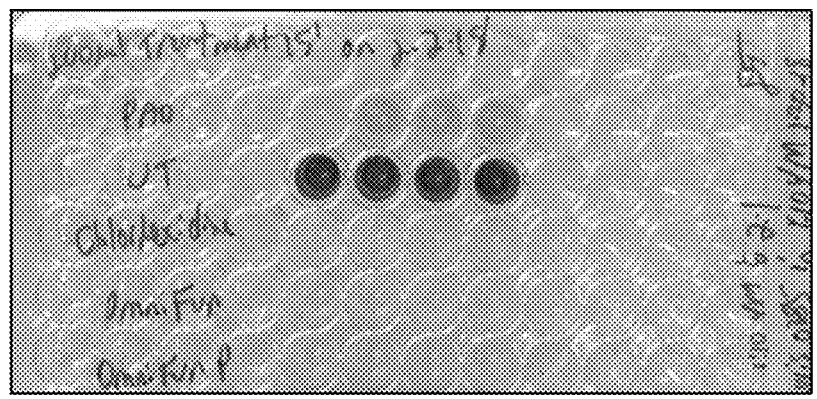
Figure 74:
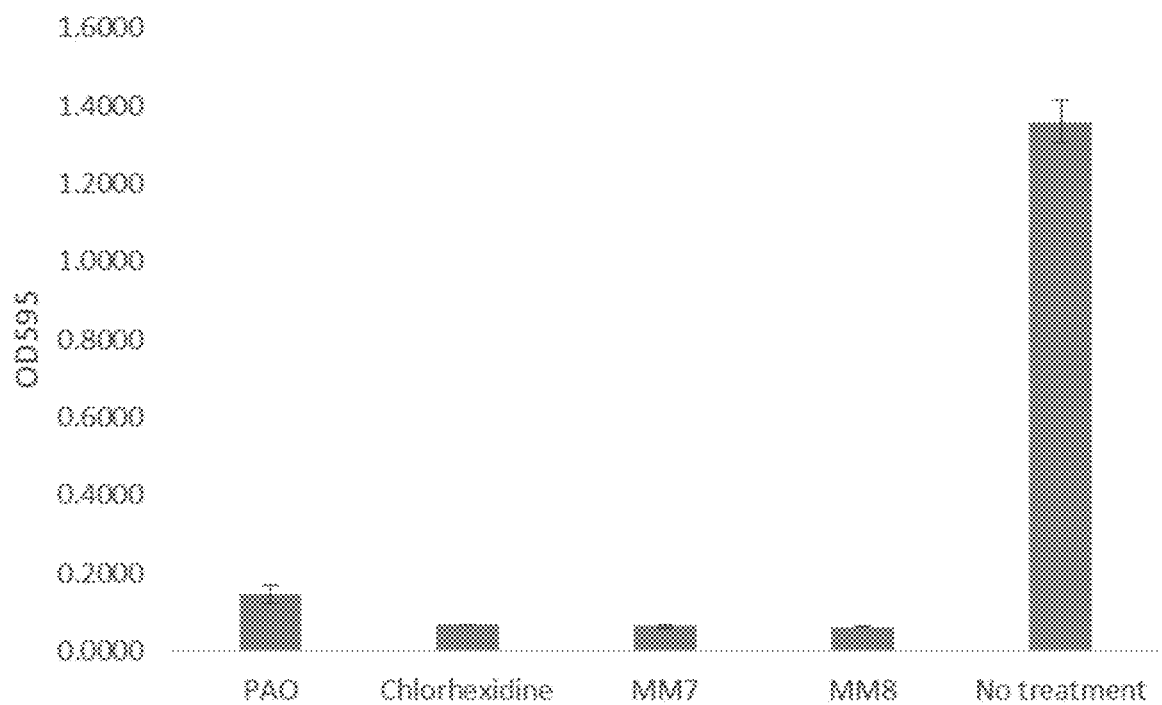

FIG. 74 PANEL A shows the colorimetric results of treating an 8-day old biofilm of *Candida auris* with PAO, no treatment, chlorhexidine gluconate 0.12% oral rinse, MM7, or MM8. PANEL B shows that chlorhexidine gluconate 0.12% oral rinse, MM7, and MM8 were the most effective at killing a pre-established, multi-drug resistant *Candida auris* biofilm.

Figure 75:
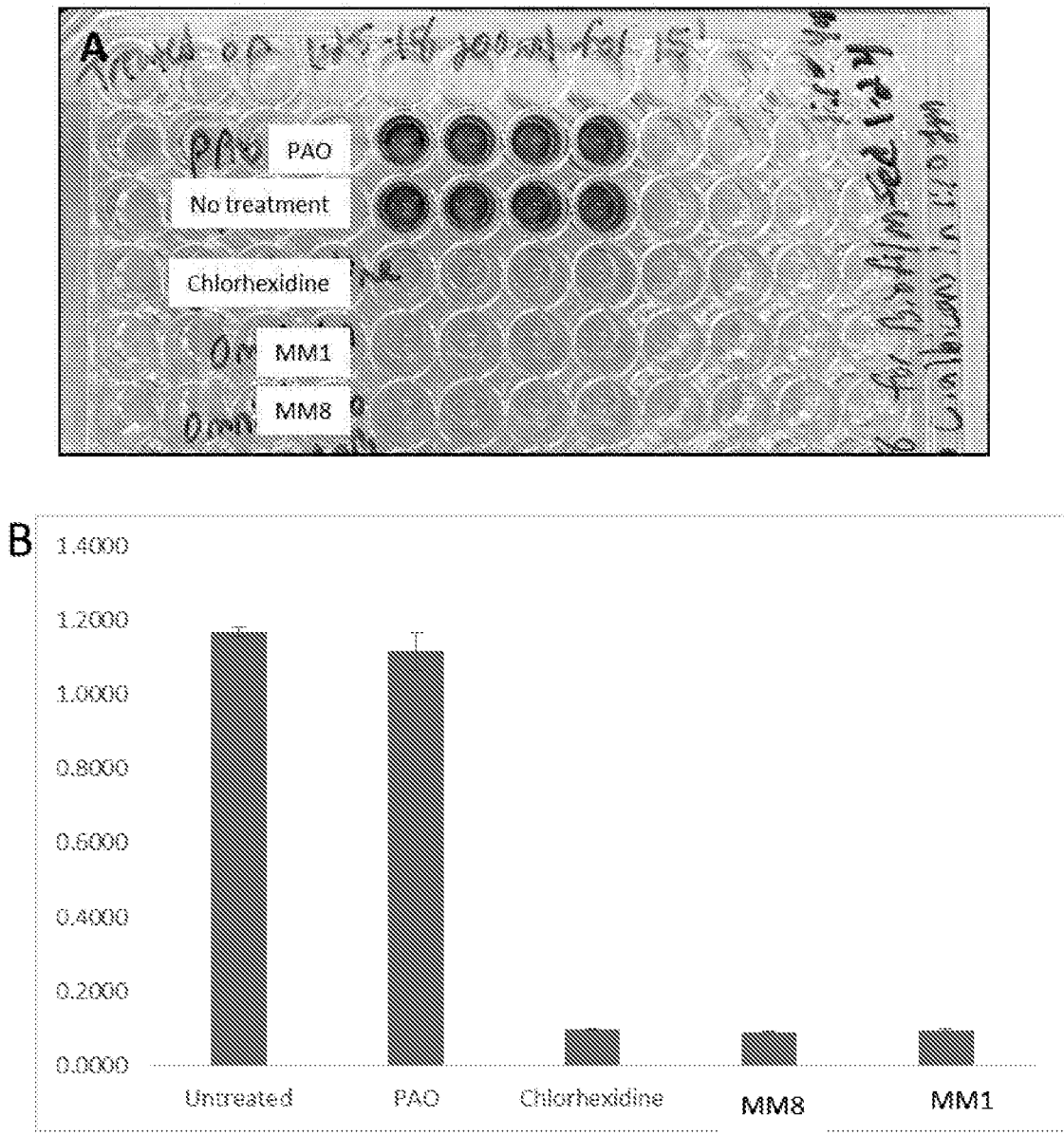

FIG. 75 PANEL A shows the colorimetric results of treating a 6-day old biofilm of *Candida albicans* with PAO, no treatment, chlorhexidine gluconate 0.12% oral rinse, MM1, and MM8. PANEL B shows that chlorhexidine gluconate 0.12% oral rinse, MM1, and MM8 were the most effective at killing a pre-established, multi-drug resistant *Candida albicans* biofilm.

Figure 76:
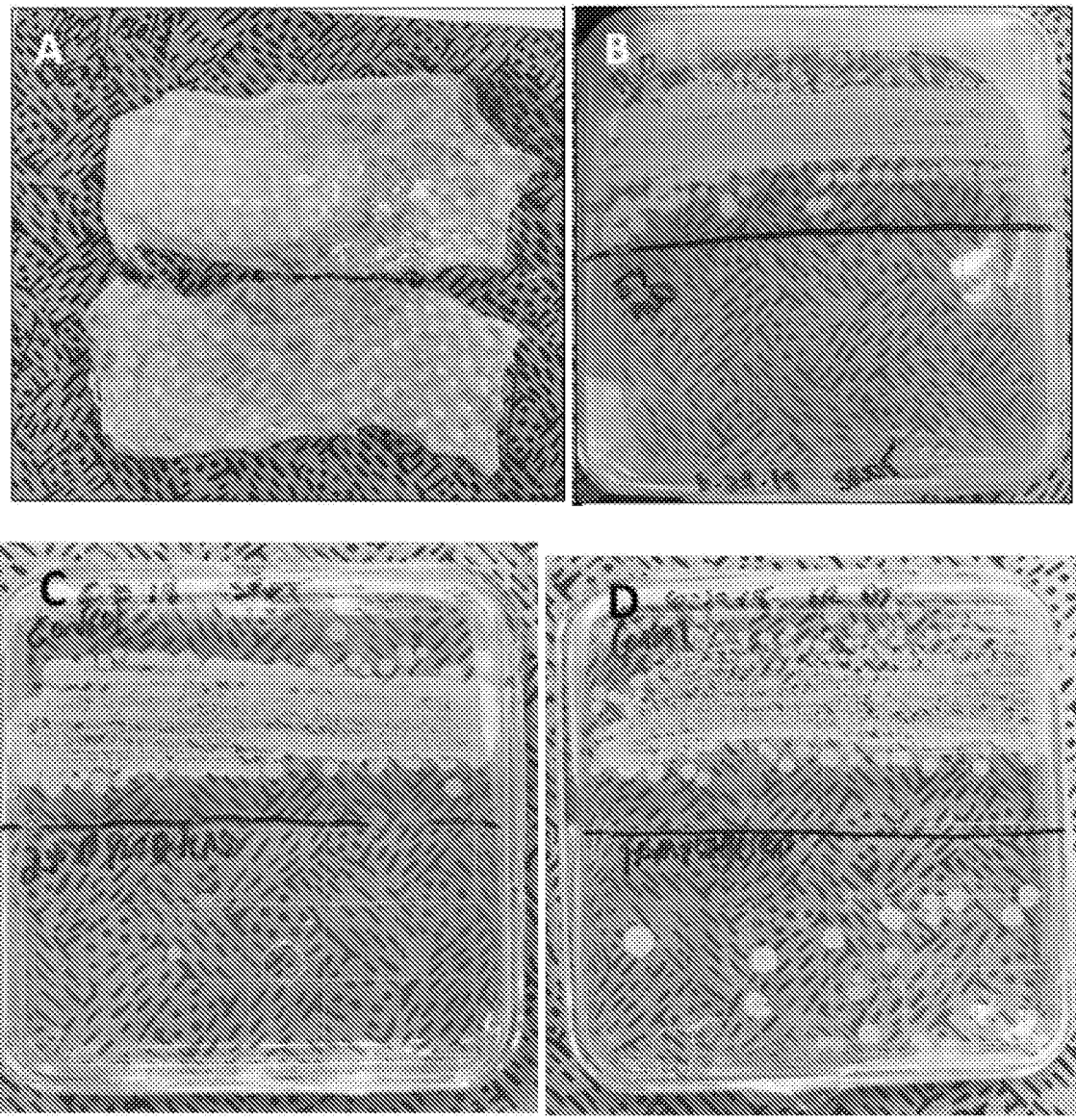

FIG. 76 PANEL A shows chicken skin samples that were infected with *B. subtilis* and decontaminated using concentrated MM8. PANEL B shows the colony counts post treatment with water (TOP) and 5× concentrated MM8 (BOTTOM). PANEL C shows colony counts post treatment with water (TOP) or 2× concentrated MM8 (BOTTOM). PANEL D shows colony counts post treatment with water (TOP) or 1×MM8 (BOTTOM).

Figure 77:
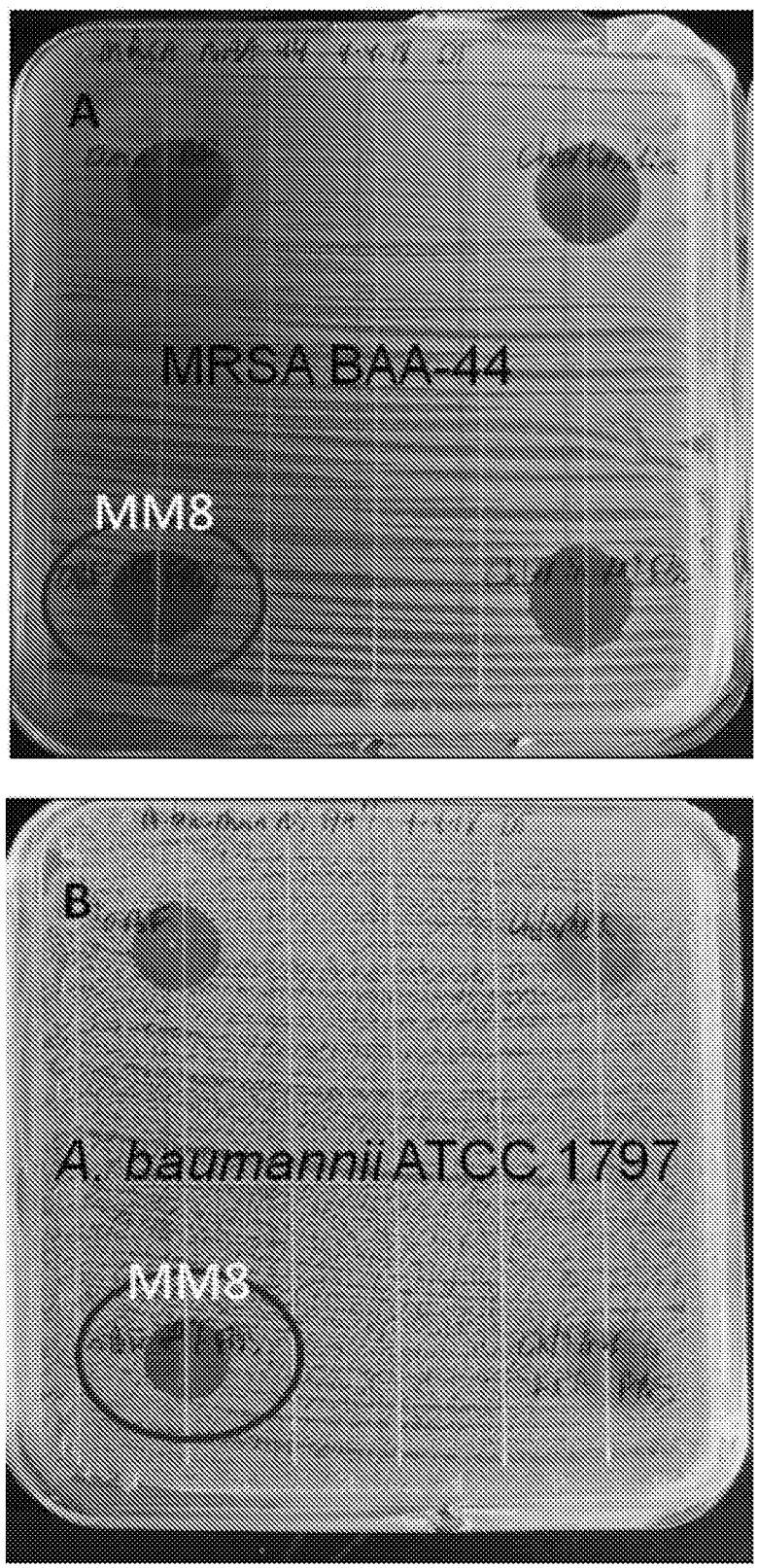

FIG. 77 PANEL A shows that 20% FBS did not decrease the efficacy of MM8 or chlorhexidine gluconate 0.12% oral rinse in Gram-positive MRSA. PANEL B shows that 20% FBS did not decrease MM8 killing efficiency in Gram-negative multi drug-resistant *A. baumannii*, but that 20% FBS decreased the efficacy of chlorhexidine gluconate 0.12% oral rinse in multi drug-resistant *A. baumannii*.

Figure 78:
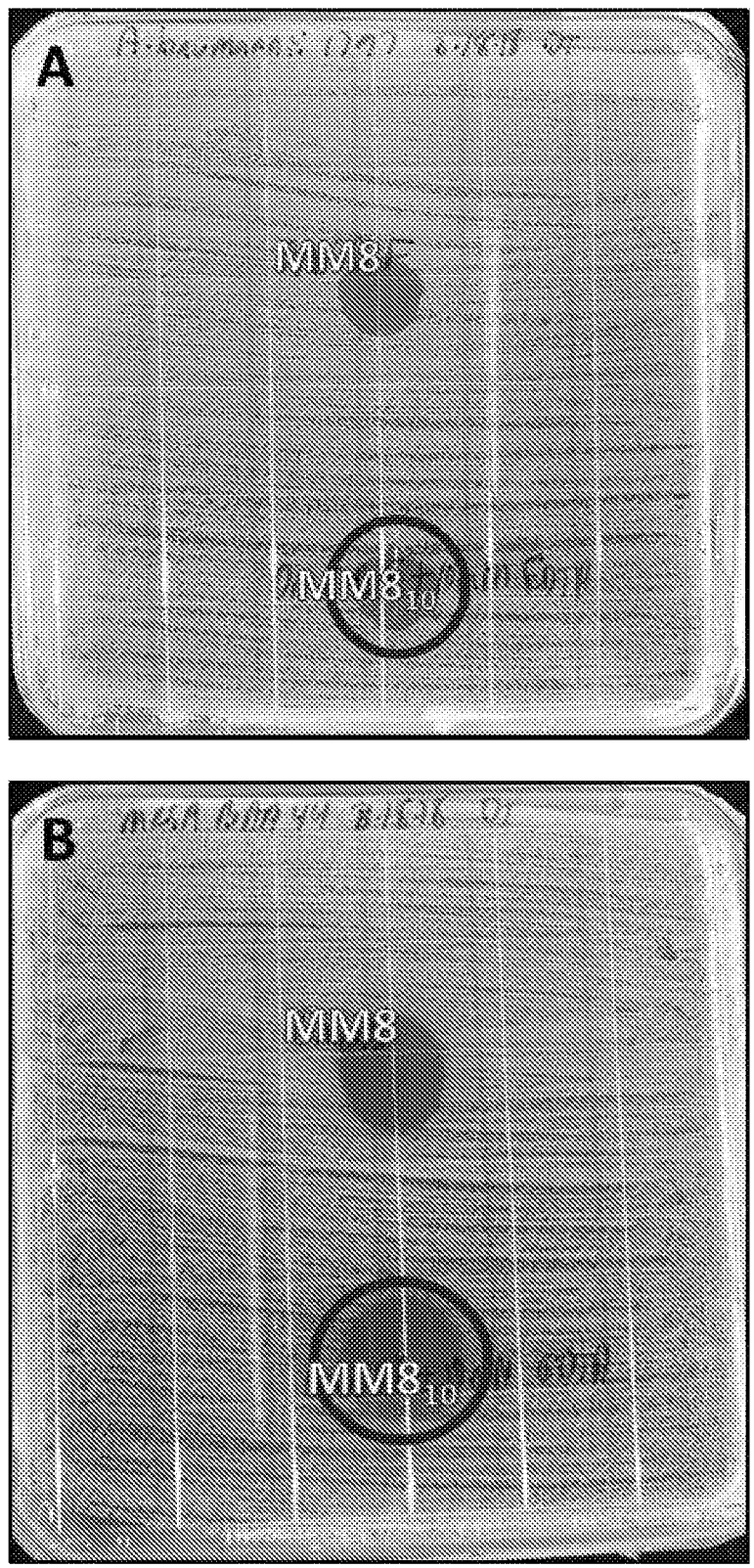

FIG. 78 PANEL A shows that $MM8_{10}$ was not more effective at killing *Acinetobacter baumannii* (ATCC 1797) than was MM8 alone. PANEL B shows that $MM8_{10}$ was not more effective at killing MRSA BAA-44 than was MM8 alone.

Figure 79:
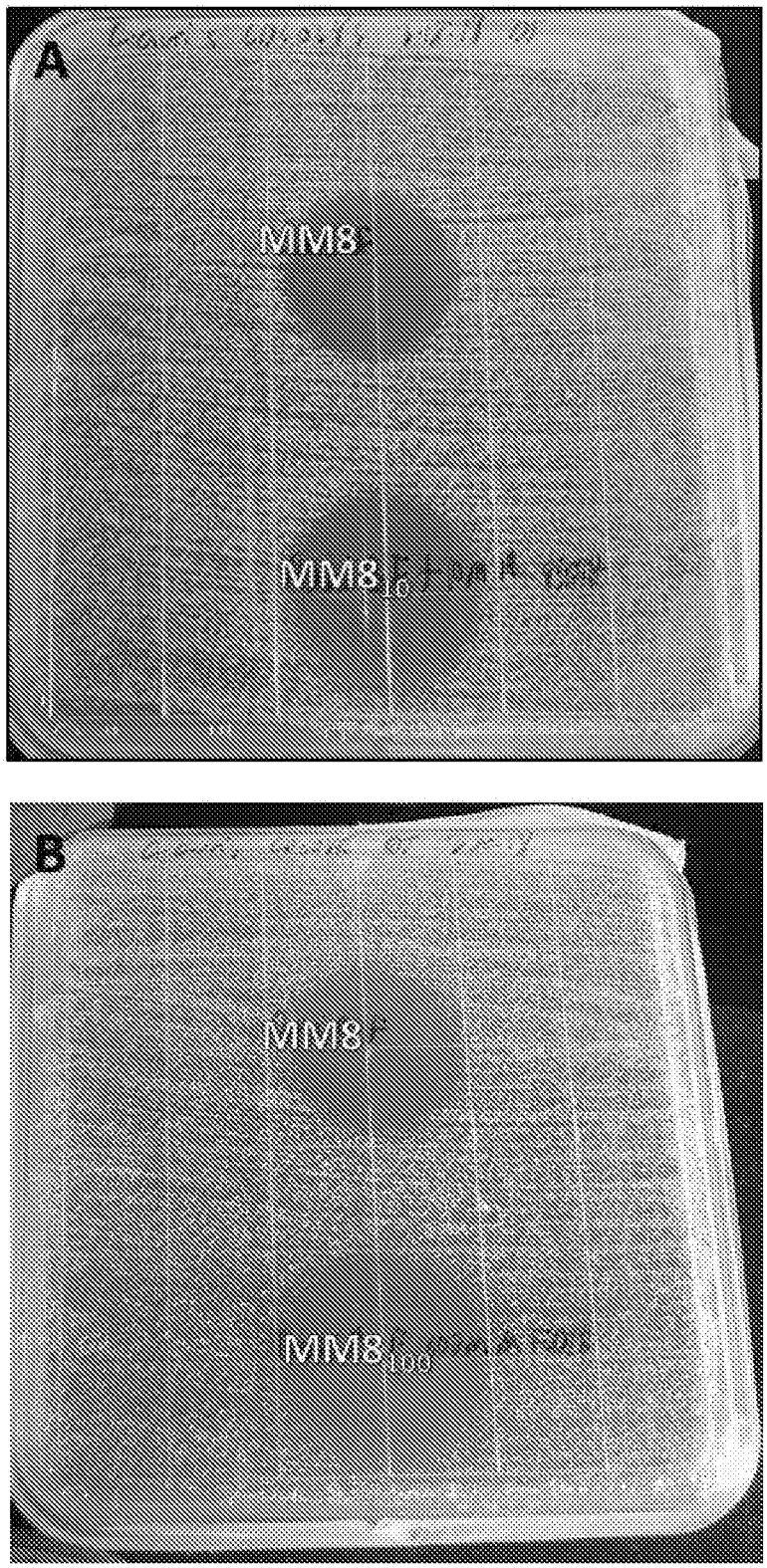

FIG. 79 PANEL A shows that $MM8_{10}$ was more effective at killing multi-drug resistant *Candida auris* than was MM8 alone. PANEL B shows that $MM8_{100}$ was more effective at killing multi-drug resistant *Candida auris* than was MM8 alone.

Figure 80:
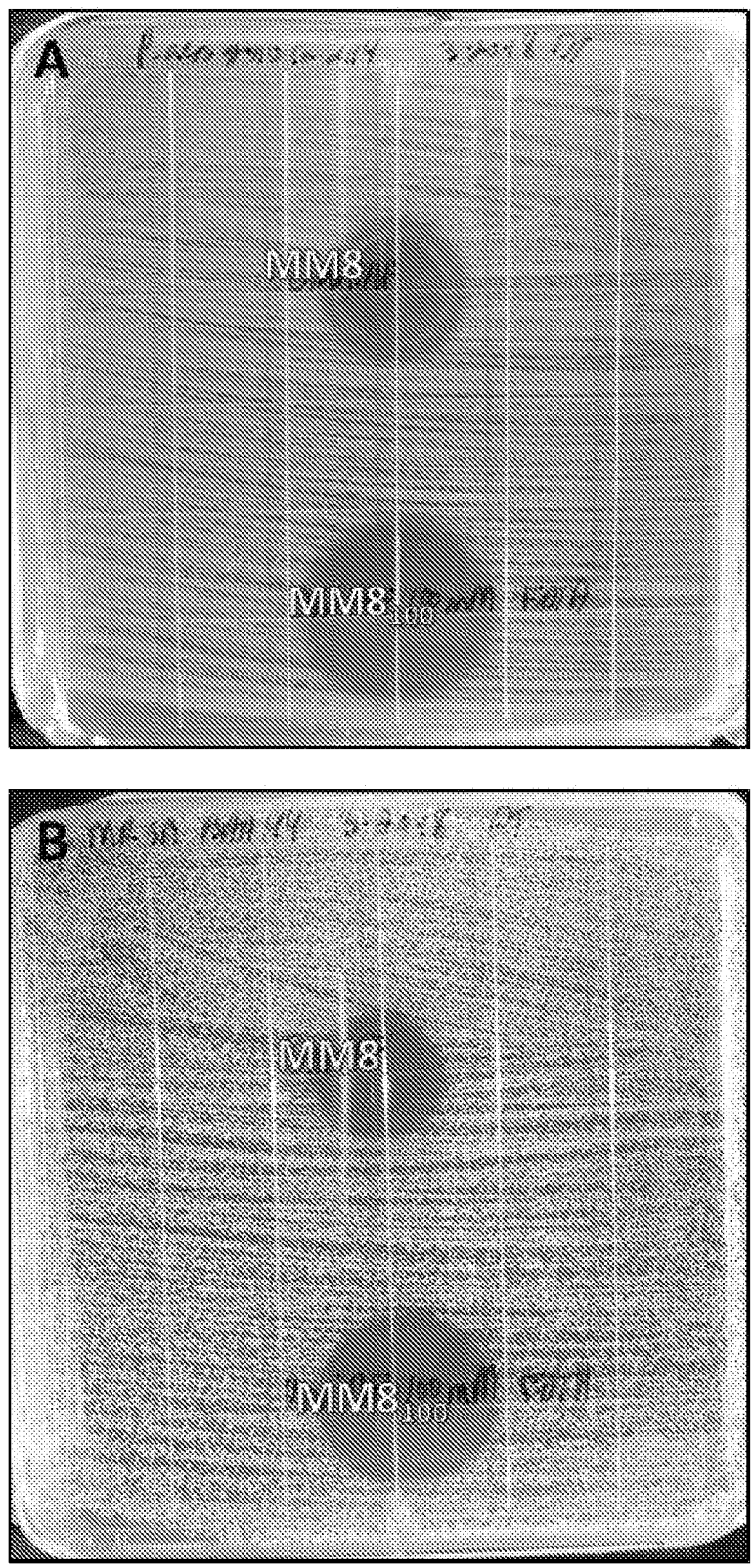

FIG. 80 PANEL A shows that $MM8_{100}$ was more effective at killing *P. aeruginosa* (ATCC 2114) than was MM8 alone. PANEL B shows that $MM8_{100}$ was more effective at killing MMRSA BAA-44 than was MM8 alone.

Figure 81:
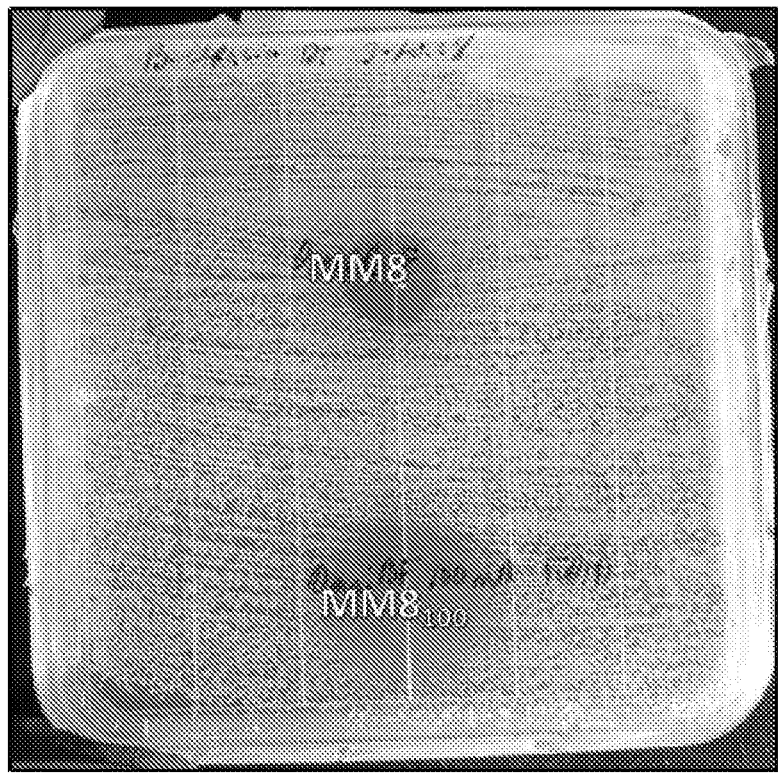

FIG. 81 shows that $MM8_{100}$ shows that $MM8_{100}$ was more effective at killing *Burkholderia cepacia* (ATCC 10856) than was MM8 alone.

Figure 82:
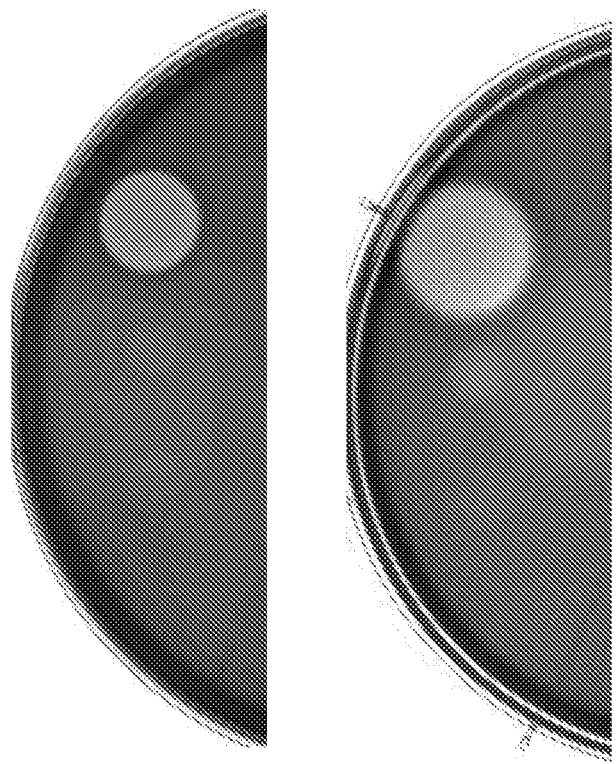

FIG. 82 shows that CellLytic® B created a dramatic clearance while chlorhexidine gluconate 0.12% oral rinse and MM8 did not affect the color of the plate.

Figure 83:
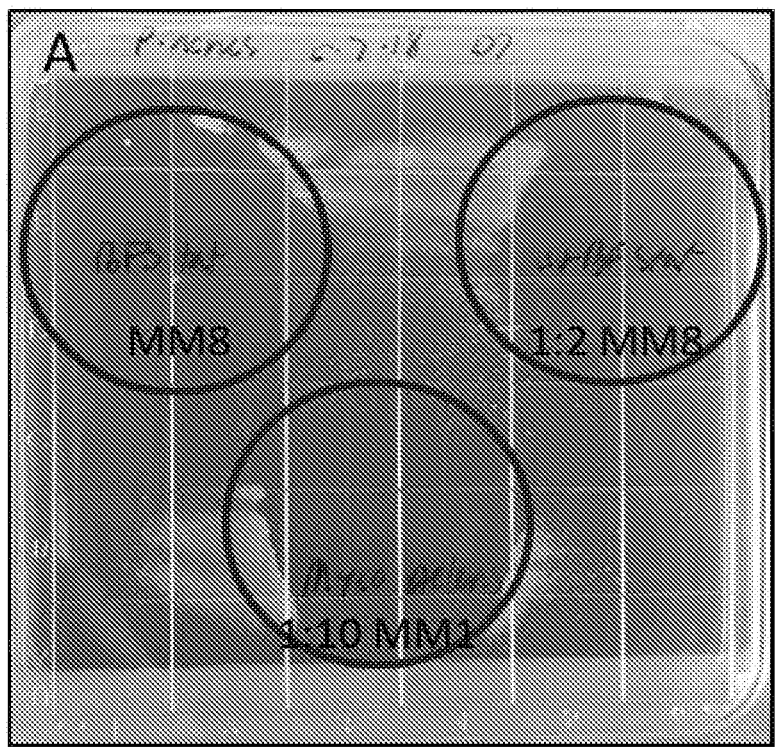
Figure 83:
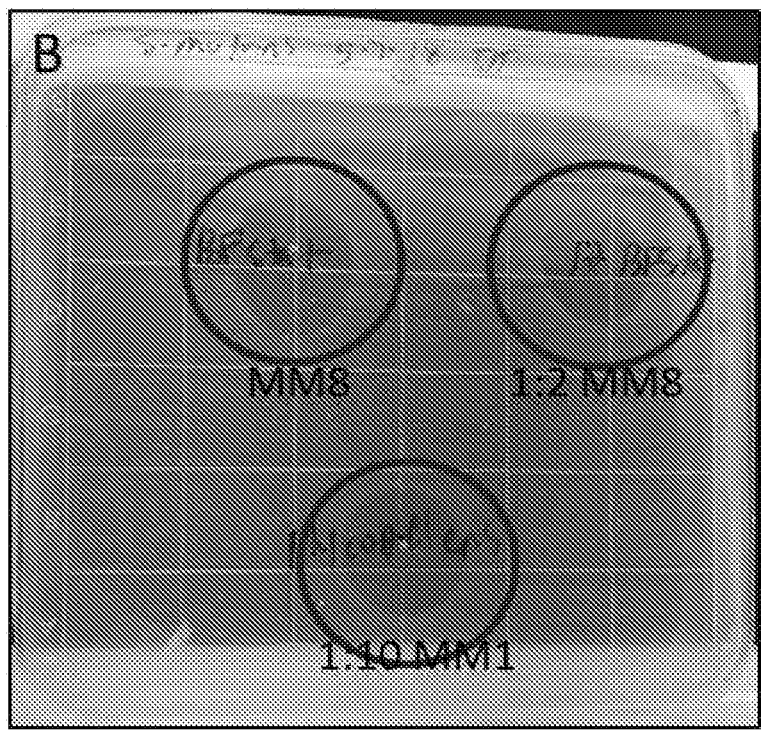

FIG. 83 PANEL A shows that MM8, a 1:2 aqueous dilution of MM8, and a 1:10 aqueous dilution of MM1 were equally effective in killing anaerobic bacteria *Propionibacterium acnes* (ATCC 6919). PANEL B shows that MM8, a 1:2 aqueous dilution of MM8, and a 1:10 aqueous dilution of MM1 were equally effective in killing *Streptococcus mutans* (85 W 2357).

Figure 84:
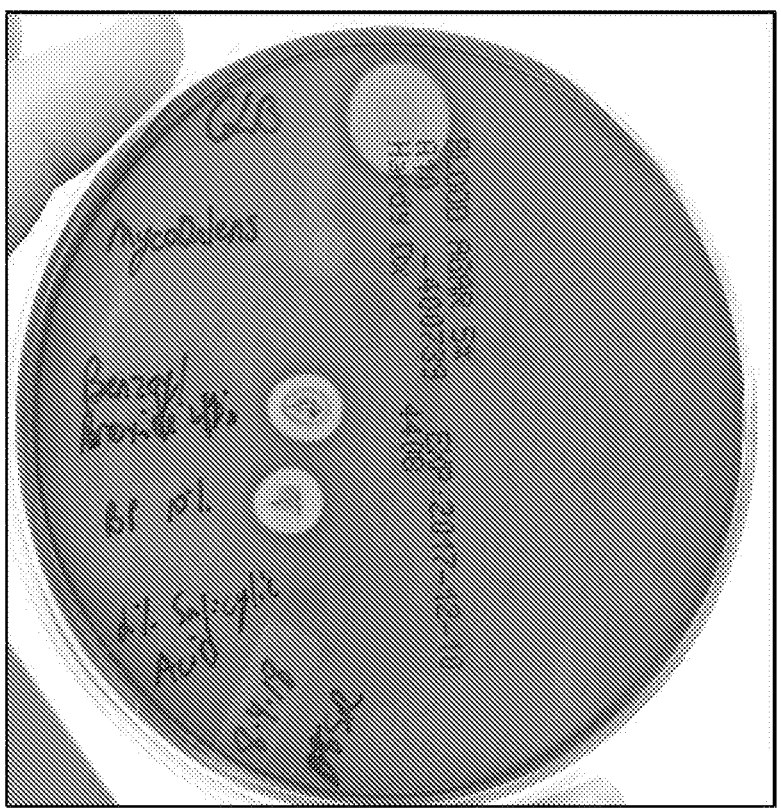

FIG. 84 shows a blood agar plate spotted with cell lysis buffer, MM7, 4% benzoyl peroxide, 10% benzoyl peroxide, and 2% salicylic acid.

Figure 85:
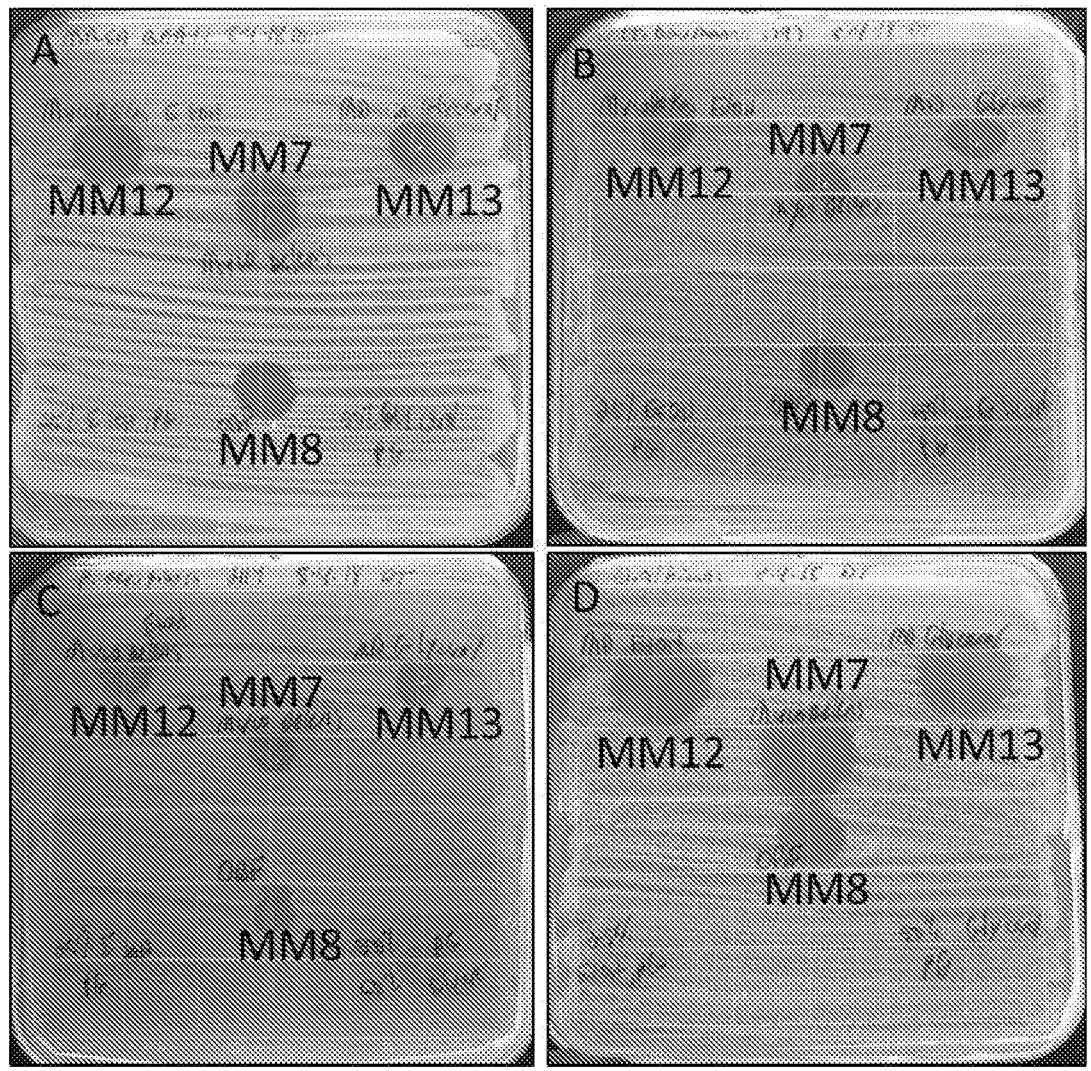

FIG. 85 PANEL A shows an MHA plate of MRSA BAA-44 treated with MM7, MM8, MM12, MM13, and vehicle controls. PANEL B shows an MHA plate of *A. baumannii* treated with MM7, MM8, MM12, MM13, and vehicle controls. PANEL C shows an MHA plate of *P. aeruginosa* treated with MM7, MM8, MM12, MM13, and vehicle controls. PANEL D shows an MHA plate of *C. albicans* treated with MM7, MM8, MM12, MM13, and vehicle controls.

Figure 86:
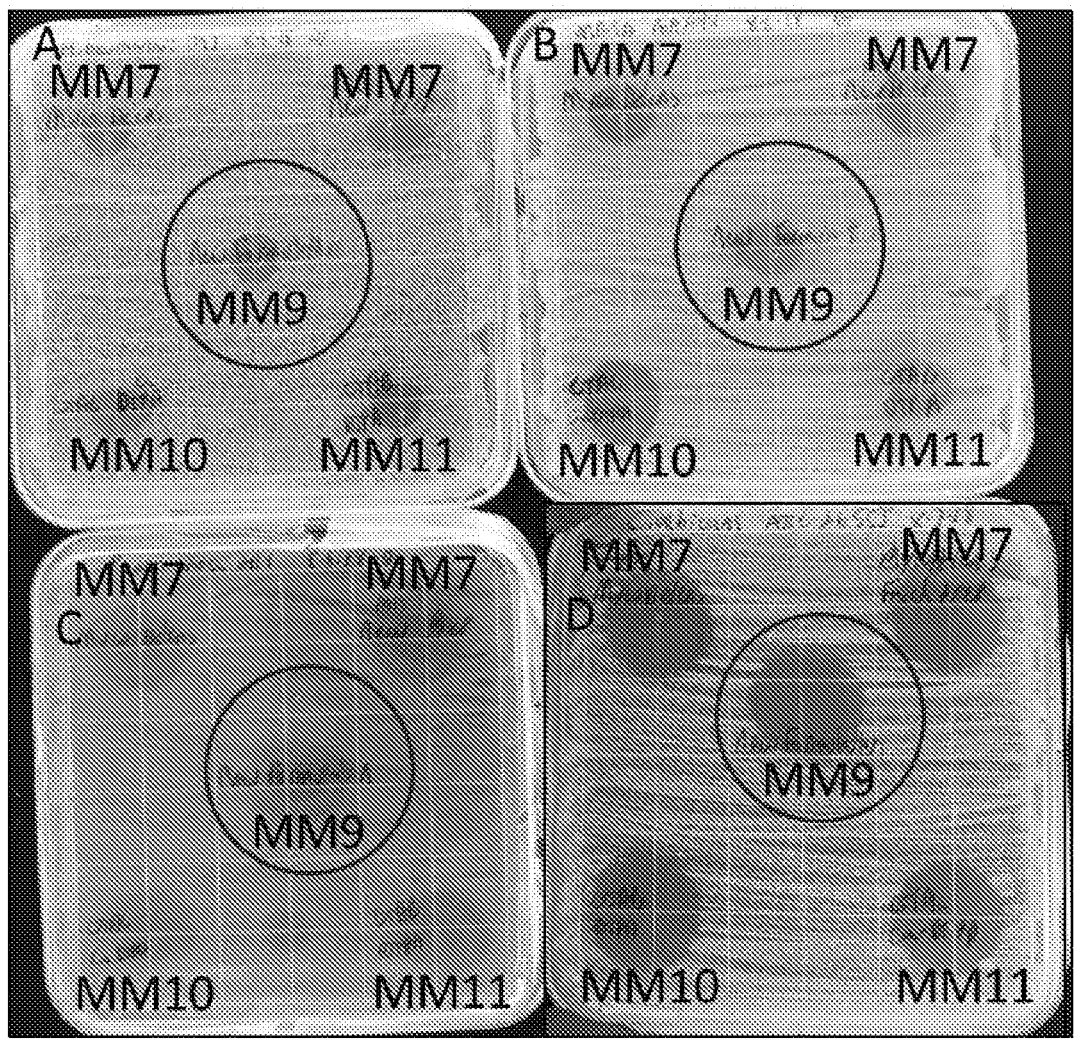

FIG. 86 PANEL A shows an MHA plate of *A. baumannii* treated with MM7, MM9, MM10, and MM11. PANEL B shows an MHA plate of MRSA BAA-44 treated with MM7, MM9, MM10, and MM11. PANEL C shows an MHA plate of *P. aeruginosa* treated with MM7, MM9, MM10, and MM11. PANEL D shows an MHA plate of *C. albicans* treated with MM7, MM9, MM10, and MM11.

Figure 87:
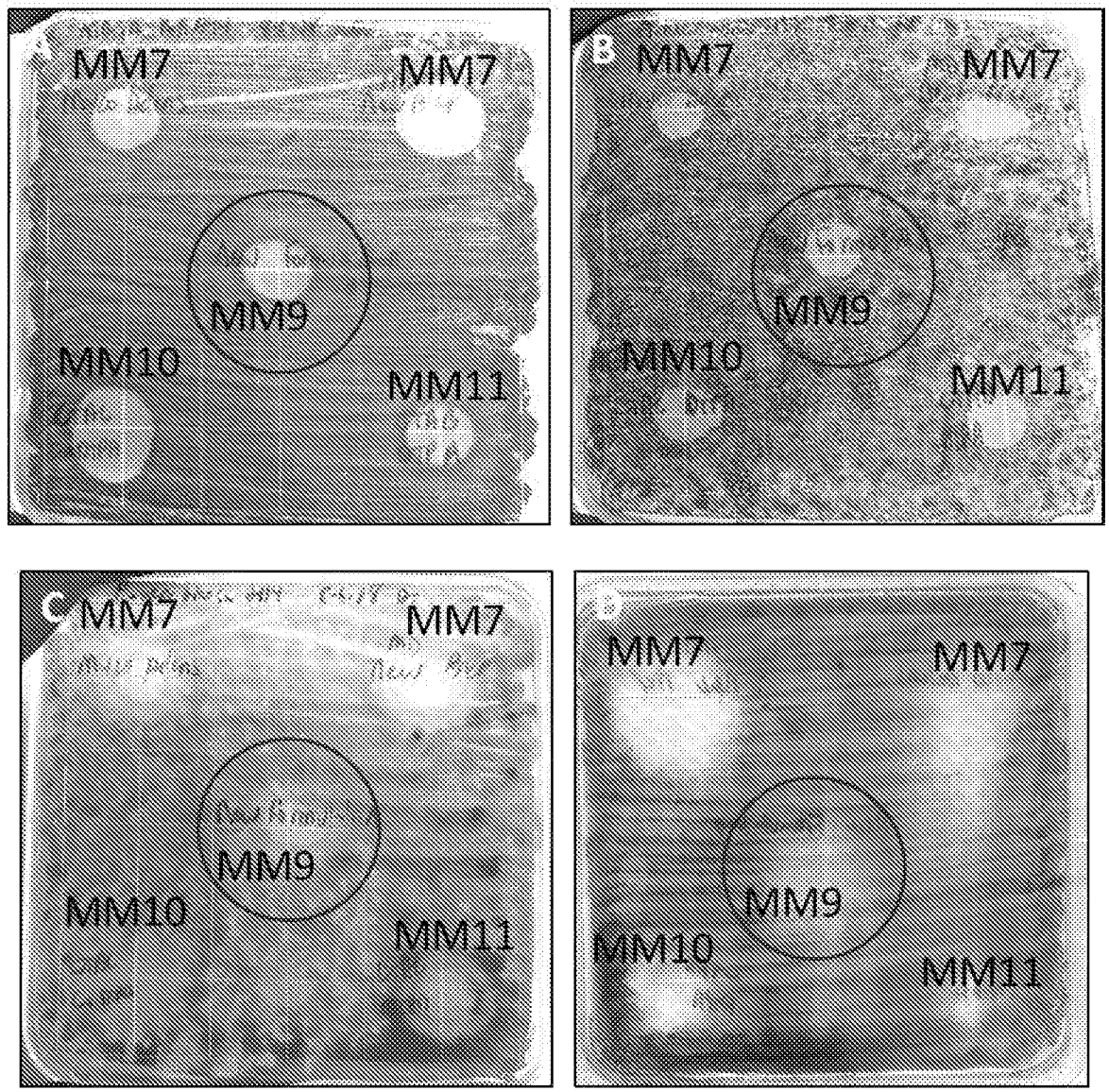

FIG. 87 PANEL A shows an MHA plate of MRSA BAA-44 treated with MM7, MM9, MM10, and MM11. PANEL B shows an MHA plate of *A. baumannii* (ATCC 1797) treated with MM7, MM9, MM10, and MM11. PANEL C shows an MHA plate of *P. aeruginosa* (ATCC 2114) treated with MM7, MM9, MM10, and MM11. PANEL D shows an MHA plate of *C. albicans* treated with MM7, MM9, MM10, and MM11.

Figure 88:
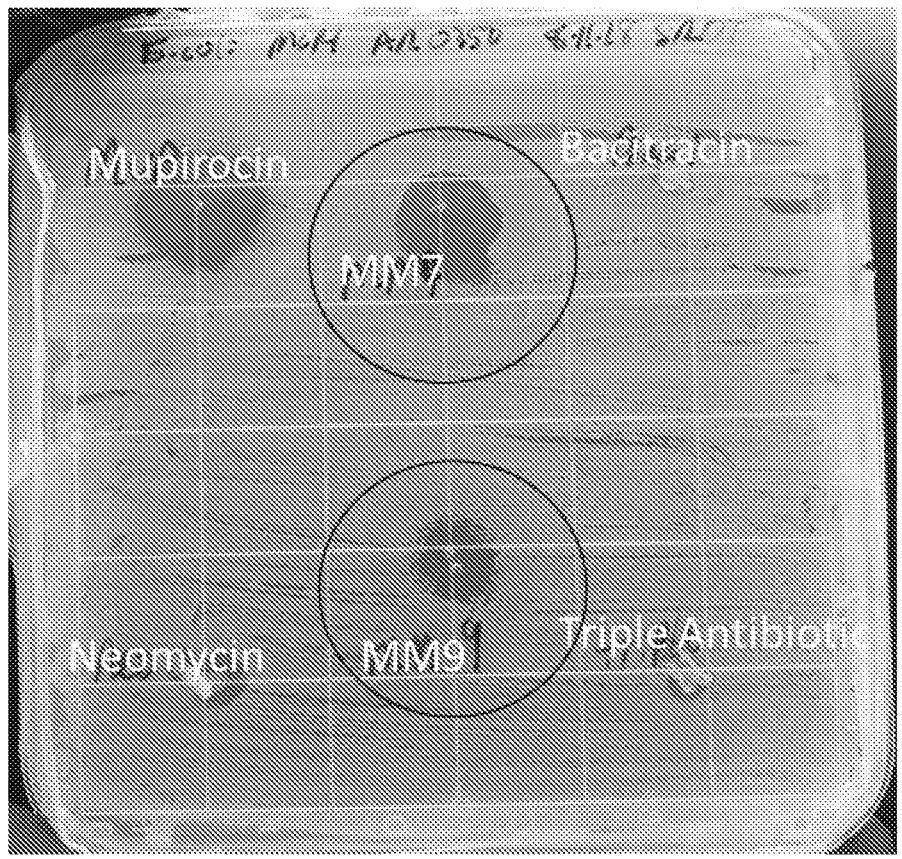

FIG. 88 shows an MHA plate of *E. coli* (AR 0350) treated with MM7, MM9, mupirocin, bacitracin, neomycin, and a triple antibiotic.

Figure 89:
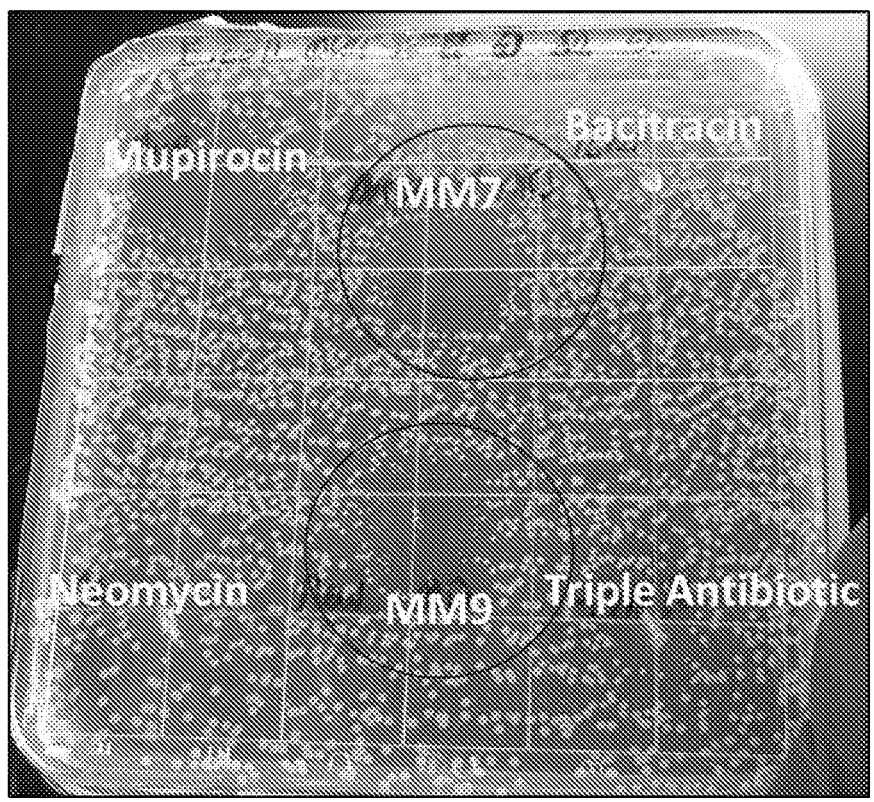

FIG. 89 shows an MHA plate of multi-drug resistant *E. coli* (AR 0348) treated with MM7, MM9, mupirocin, bacitracin, neomycin, and a triple antibiotic cream.

Figure 90:
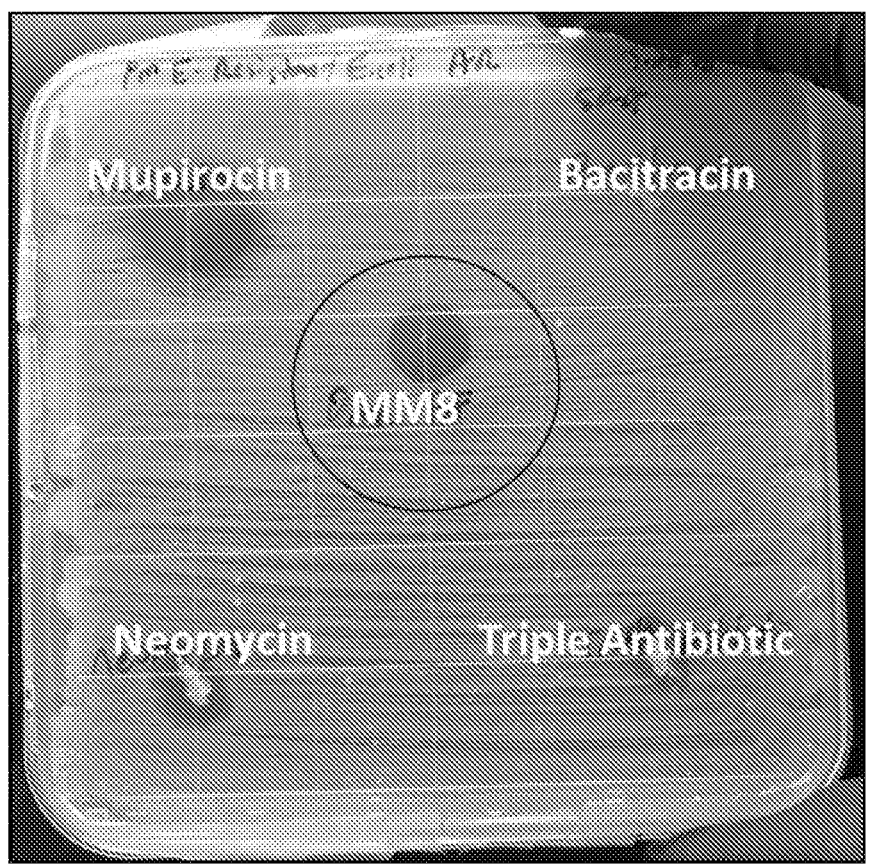

FIG. 90 shows an MHA plate of multi-drug resistant *E. coli* (AR 0346) treated with MM8, mupirocin, bacitracin, neomycin, and a triple antibiotic cream.

Figure 91:
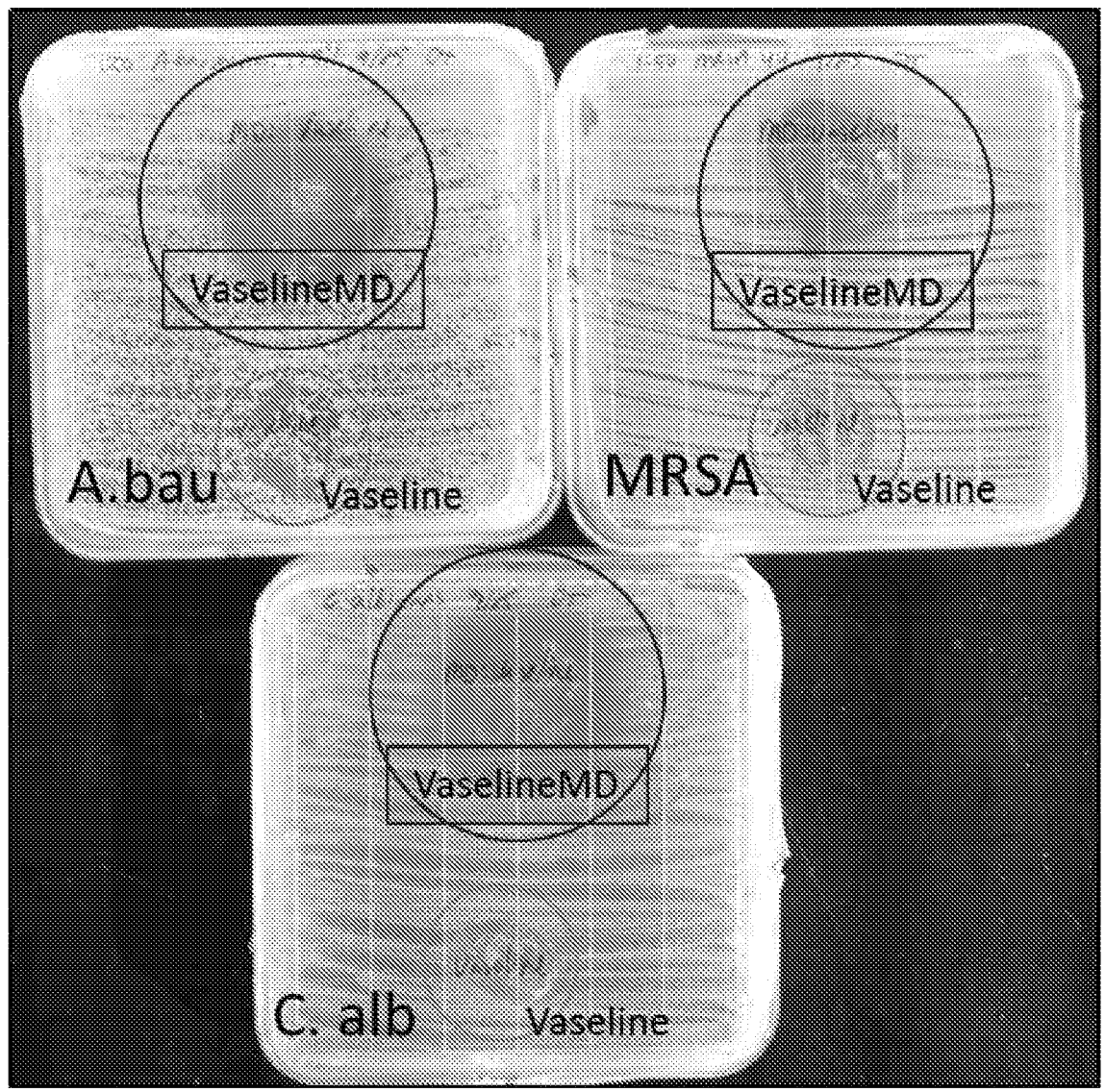

FIG. 91 shows the effects of the MM12/Petroleum jelly mixture (VaselineMD) and Petroleum jelly on killing lawns infected with *A. baumannii* ATCC 1797, MRSA BAA-44, and *C. albicans*.

Figure 92:
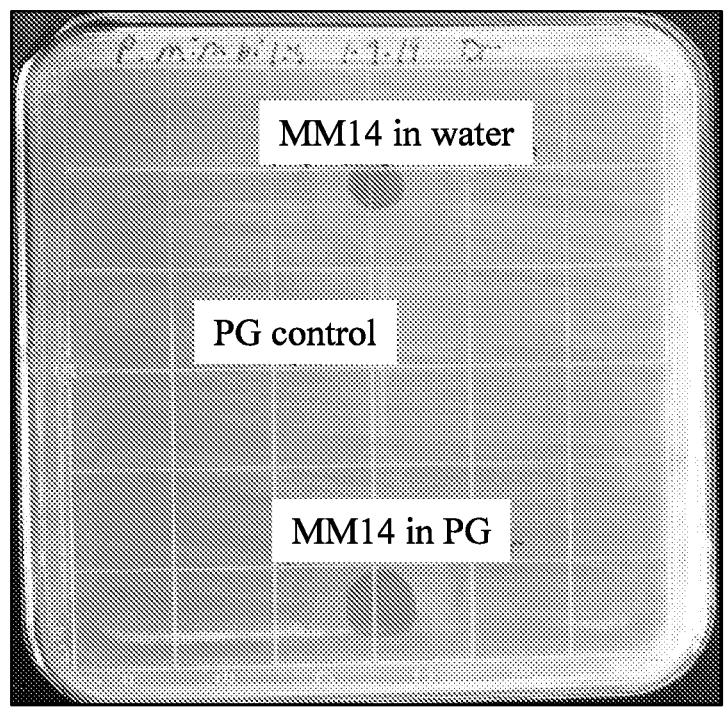

FIG. 92 shows that MM14 delivered in water or propylene glycol (PG) was effective at killing *Proteus mirabilis*.

Figure 93:
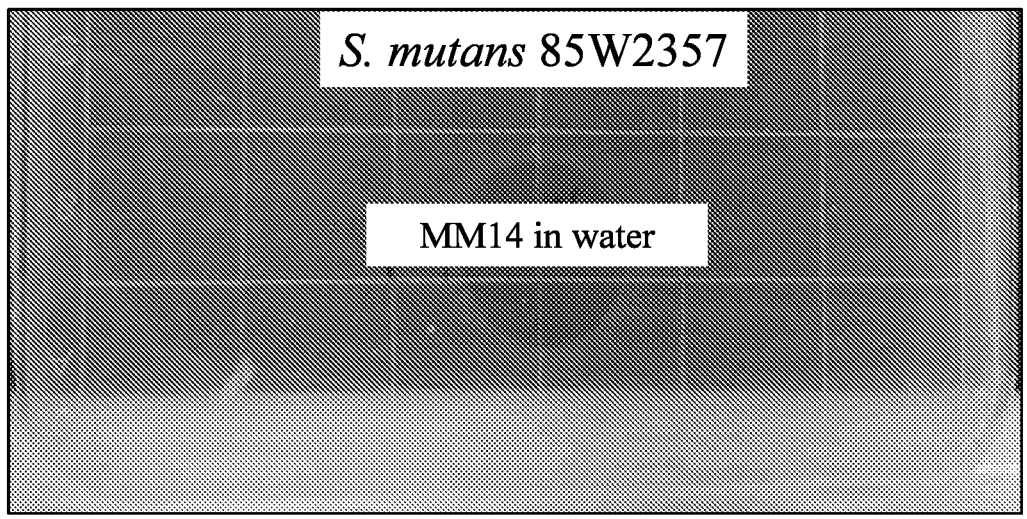

FIG. 93 shows that MM14 delivered in water was effective at killing *Streptococcus mutans*.

Figure 94:
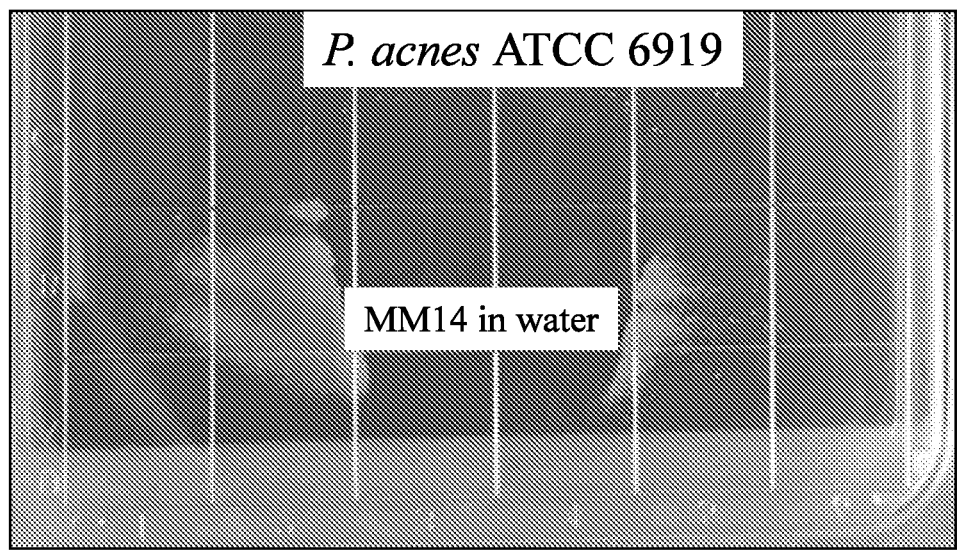

FIG. 94 shows that MM14 delivered in water was effective at killing *Propionibacterium acnes*.

Figure 95:
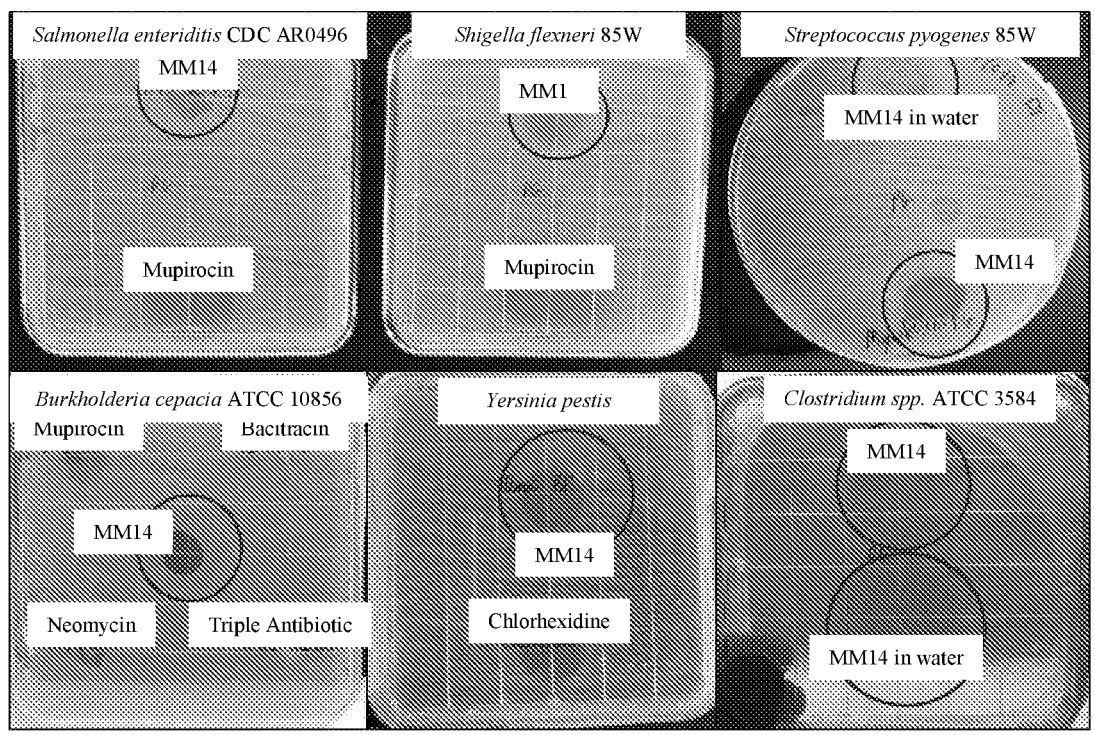

FIG. 95 shows that MM14 was effective at killing *Salmonella enteriditis, Shigella flexneri, Streptococcus pyogenes, Burkholderia cepacia. Clostridium* spp., and *Yersinia pestis*.

Figure 96:
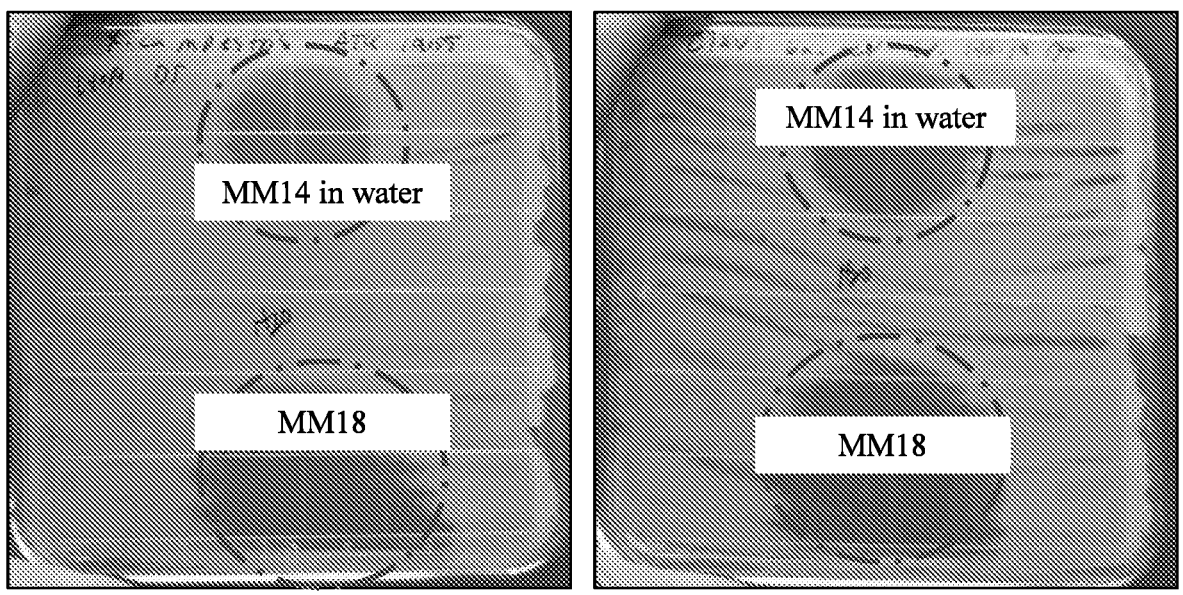

FIG. 96 shows that MM14 and MM18 were effective at killing *Xanthomonas campestris* (ATCC 19155) and *Clavibacter* sp. (ATCC 43179).

Figure 97:
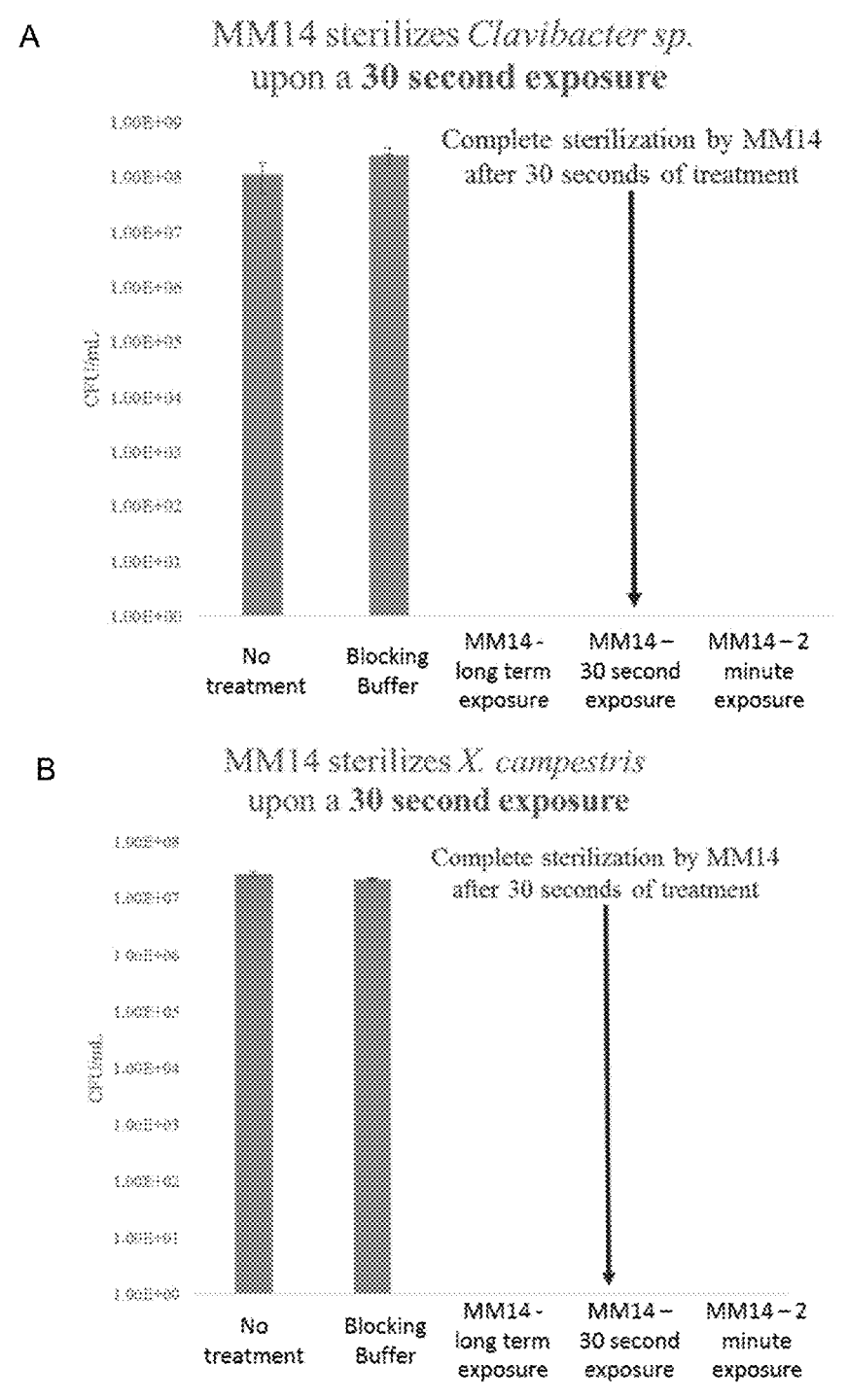

FIG. 97 Panel A shows that MM14 sterilized *Clavibacter* sp. upon a 30 second exposure. Panel B shows that MM14 sterilized *X. campestris* upon a 30 second exposure.

FIG. 98 shows the efficacy of MM18 powder against *A. baumannii* ATCC 1997.

FIG. 99 shows the anti-infective properties of MM14 combined with other preparations.

FIG. 100 shows that pretreatment of seeds with MM14 or MM18 does not have an effect on seed germination efficiency.

DETAILED DESCRIPTION

Fungi are primitive organisms that live in air, water, soil, and on other surfaces. Some types of fungus reproduce by sending spores through the air. When the spores land on and grow on the body, the spores can cause fungal infections. People with weakened immune systems or people taking medicines, such as antibiotics or corticosteroids, are at increased risk for fungal skin infections.

Fungal infections are often difficult to treat. Treatment often involves topical or oral medications. The type of antifungal used to treat an infection depends on the specific type of fungus that is causing the infection.

Applications

The present disclosure describes antifungal formulations that can be used to treat fungal infections. For example, the formulations of the disclosure can treat *Candida auris* (*C. auris*), cryptococcal meningitis, fungal eye infections, oral candidiasis, vaginal candidiasis, *Candida* vaginitis, *Tinea pedis* (athlete's foot), pulmonary apergillosis, chronic pulmonary apergillosis, toe and hand nails infected with *Trichophyton rubrum, Tinia capitis* (*Tinea tonsurans*), ringworm, mucormycosis, or blastomycosis. The formulations of the present disclosure can also be used to treat infections caused by an *Ascomycetous* fungus (e.g., pezizomycotina, saccharomycotina, and laphrinomycotina), *Trichophyton, Epidermophyton, Microsporum. Aspergillus, Blastomyces, Cryptococcus neoformans, Cryptococcus gattii, Trichophyton rubrum, Aspergillus niger, stachybotrys, Batrachochytrium dendrobatidis* (frog Bd fungus), or *Blastomyces dermatitidis.*

*C. auris* is a yeast-like fungus related to *Candida albicans. C. auris* is one of the few species of the *Candida* genus that can cause candidiasis in humans. Candidiasis can be acquired in hospitals by patients with weakened immune systems. *C. auris* can cause invasive candidiasis in which the bloodstream (fungemia), the central nervous system, and internal organs are affected. *C. auris* can easily be misidentified as other *Candida* species. The fungus causes invasive infections with a high death rate (about 57%), and causes mainly bloodstream, wound, and ear infections. *C. auris* is invasive and multiply drug-resistant in contrast to other fungal diseases, and is usually associated with outbreaks in healthcare settings like hospitals.

Meningitis, an infection of the lining of the spinal cord and brain, is the most common illness caused by *Cryptococcus*. Cryptococcal meningitis can cause coma and death, and can also infect the skin, lungs, or other parts of the body. The risk of cryptococcal infection is highest when a person's CD4 counts are below 100. Cryptococcal meningitis is a major HIV-related opportunistic infection.

Fungal eye infections are rare, but can be very serious. The most common way for someone to develop a fungal eye infection is from an eye injury, particularly if the injury was caused by plant material, such as a stick or a thorn. Inflammation or infection of the cornea is known as keratitis, and inflammation or infection of the interior of the eye is called endophthalmitis. In some embodiments, fungal eye infections are caused by Moniliaceae, Dematiaceae, and yeasts. Moniliaceae includes non-pigmented filamentary fungi, such as *Fusarium* and *Aspergillus* species; Dematiaceae includes pigmented filamentary fungi, such as *Curvularia* and *Lasiodiplodia* species; and yeasts include *Candida* species.

*Cryptococcus neoformans* and *Cryptococcus gattii* are species of fungus that can cause crytococcosis, also known as cryptococcal disease. *Cryptococcus* is a potentially fatal fungal disease that can be acquired by inhalation of the infections propagule from the environment. *Cryptococcus* does not spread from person to person.

*Batrachochytrium dendrobatidis* is a species of fungus that can cause chytridiomycosis in amphibians such as frogs. *Batrachochytrium dendrobatidis* can be introduced to amphibians through water exposure and can eventually lead to cardiac arrest and death.

A formulation of the disclosure can be used as a treatment against bacterial agents. Non-limiting examples of bacterial agents that can be treated with a formulation of the disclosure include *Bacillus anthracis* (anthrax), *Franscisella tularensis* (tularemia), *Yersinia pestis* (plague), *Clostridium botulinum* (botulism), *Coxiella burnetti* (Q fever), *Brucella* species (brucellosis), *Burkholderia mallei* (glanders), *Clostridium perfringens* (clostridial necrotizing enteritis), *Vibrio cholerae* (cholera), and *Porphyromonas gingivalis* (gingavitis, and can cause Alzheimer's Disease).

A formulation of the disclosure can be used as a treatment against viral agents. Non-limiting examples of viral agents that can be treated with a formulation of the disclosure include, for example, arenaviruses such as Lassa virus, *Junin* mammarenavirus, and Machupo virus; filoviruses such as Ebola virus, and Marburg virus; Variola major (smallpox); Nipah virus; Hantaviruses; Nairovirus (Bunyaviradae family); lentiviruses such as HIV; varicella-zoster virus; paramyxovirus; rubeola virus; rhinovirus; coronavirus; respiratory syncytial virus; influenza viruses; noroviruses; hepatitis A; rotavirus; astrovirus; and Norwalk-like viruses.

A formulation of the disclosure can be used as a treatment against plant pathogens such as *Xanthomonas campestris* and *Clavibacter* sp. *Xanthomonas campestris* is a black rot that can effect cruciferous vegetables and other plants. *Clavibacter* sp. is a bacterial canker of tomato/potato plants. Infection with *Clavibacter* sp. can begin in seeds, and infected seeds can be indistinguishable from healthy seeds.

The formulations of the disclosure can be used to treat human skin, animal skin, wounds, and body cavities, for example, the mouth, vagina, ears, or nose. The formulations of the disclosure can also be used to treat infected surfaces, such as wood, metal, glass, concrete, painted surfaces, or plastic surfaces. The formulation of the disclosure can be used to treat a surface made of a porous or non-porous material. In some embodiments, the surface can comprise horizontally or vertically aligned non-porous substrates, such as floors and walls, counter tops, table tops, medical equipment, gurneys, heart stress test room surfaces, toilet or seats. In some embodiments, the formulations of the disclosure can be used to treat complex three dimensional structures, such as faucets, tools, or other equipment. In some embodiments, the formulations of the disclosure can be used to treat and decontaminate vehicle interiors, buildings, medical facilities, articles of manufacture, buildings and infrastructure intended for demolition, military assets, airplanes, military ships, or civilian ships.

A formulation of the disclosure can be used to treat agriculture products such as seeds, plants, or crops. In some embodiments, the formulations of the disclosure can be used to treat rice seeds, rice plants, barley seeds, barley plants, flax seeds, flax plants, *Sorghum* seeds, *Sorghum* plants, tomato seeds, tomato plants, potato tubers, potatoes, mustard seeds, mustard plants, collard seeds, collard plants, rutabaga seeds, rutabaga, turnip seeds, turnips, cabbage seeds, cabbage plants, broccoli seeds, broccoli, cauliflower seeds, cauliflower, Brussel sprout seeds, Brussel sprouts, radish seeds, radishes, kale seeds, kale, turfgrass seeds, turfgrass, banana seeds, banana plants, citrus seeds, citrus plants, orange seeds, orange trees, apple seeds, apple trees, strawberry seeds, strawberry plants, blueberry seeds, blueberry plants, melon seeds, melon plants, cantaloupe seeds, cantaloupe plants, watermelon seeds, watermelon plants, *Papaya* seeds, *Papaya* plants, pea seeds, pea plants, corn seeds, corn stalks, wheat seeds, wheat, sugar cane, sugar cane seeds, or beans.

Pharmaceutical Compositions of the Invention

The pharmaceutical compositions of the disclosure comprise a cationic surfactant, a chelating agent, and at least one solvent. For example, the pharmaceutical compositions of the disclosure can comprise a cationic surfactant, such as pH-dependent primary, secondary, or tertiary amines. In some embodiments, the pharmaceutical compositions of the disclosure can comprise octenidine dihydrochloride. The pharmaceutical compositions of the disclosure can also comprise permanently charged quaternary ammonium salts, such as cetyltrimethylammonium bromide (CTAB), cetyltrimethylammonium chloride (CTAC), benzylalkonium chloride (BAC), benzethonium chloride (BZT), dimethyldioctadecylammonium chloride, or dioctadecyldimethylammonium bromide (DODAB).

A pharmaceutical composition of the invention can be used, for example, before, during, or after treatment of a subject with a second pharmaceutical agent.

A pharmaceutical composition of the invention can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, ophthalmic, nasal, vaginal, and topical administration.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral rinses to be used by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N, N'-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

The formulations of the disclosure can comprise a chelating agent, such as ethylenediaminetetraacetic acid (EDTA), diethylenetriaminepentaacetic acid (DTPA), nitrilotriacetic acid, or cyclohexane diamine tetra-acetic acid. The chelating agent of the formulations of the disclosure can be, for example, Prussian blue, citric acid, peptides, amino acids including short chain amino acids, aminopolycarboxylic acids, gluconic acid, glucoheptonic acid, organophosphonates, bisphosphonates (e.g., pamidronate), or an inorganic polyphosphate. In some embodiments, sodium, calcium, or zinc salts of DTPA can be used as a chelating agent.

The formulations of the disclosure can comprise a surfactant, for example, one or more alkanolamines, alkylarylsulfonates, amine oxides, poly(oxyalkylene) compounds (e.g., block co-polymers comprising alkylene oxide repeat units), carboxylated alcohol ethoxylates, ethoxylated alcohols, ethoxylated alkyl phenols, ethoxylated amines and amides, ethoxylated fatty acids, ethoxylated fatty esters and oils, fatty esters, fatty acid amides, glycerol esters, glycol esters, sorbitan esters, imidazoline derivatives, lechithin and lechithin derivatives, lignin and lignin derivatives, monoglycerides and monoglyceride derivatives, olefin sulfonates, phosphate esters and derivates, propoxylated and ethoxylated fatty acids or alcohols or alkyl phenols, sorbitan derivatives, sucrose esters and derivatives, sulfates or alcohols or ethoxylated alcohols or fatty esters, sulfates or sulfonates of dodecyl and tridecyl benzenes or condensed naphthalenes or petroleum, sulfosuccinates and derivatives, or tridecyl and dodecyl benzene sulfonic acids. In some embodiments, the formulations of the disclosure can comprise more than one surfactant. In some embodiments, the formulations of the disclosure can comprise sodium dodecyl sulfate (SDS), sodium lauryl sulfate, the cetrimonium cation, cetyltrimethylammonium bromide, cetyltrimethylammonium chloride, hexadecyltrimethylammonium bromide, hexadecyltrimethylammonium chloride, or a combination thereof.

The formulations of the disclosure also comprise a solvent or a mixture of solvents, such as propylene glycol (PG), dimethyl sulfoxide (DMSO), Ficoll® 400 (e.g., 7.5% w/v final), low molecular weight methylcellulose, methanol, ethanol, polyvinyl alcohol, isocetyl alchol, oleyl alcohol, or propanol. In some embodiments, the formulations of the disclosure can comprise a solvent or a mixture of solvents, for example, polyethylene glycol, water, glycerol, aloe vera extract, paraffin oil, petroleum gel, petroleum jelly, acetylated lanolin alcohol, almond oil, apricot kernel oil, avocado oil, cocoa butter, coconut butter, corn oil, cotton seed oil, evening primrose oil, hydrogenated vegetable oil, isodecyl oleate, jojoba oil, olive oil, peanut oil, PEG 8 castor oil, sandalwood seed oil, sesame oil, shark liver oil, soybean oil, or sulfated jojoba oil.

The formulations of the disclosure can also comprise additional non-comodogenic or comodogenic ingredients, for example, colloidal silicon dioxide, beeswax, butyl stearate, capric acid, caprylic acid, carnuba wax, ceteareth 20, cetyl acetate, cetyl alcohol, cetearyl alcohol, D&C red #17, D&C red #19, D&C red #21, D&C red #27, D&C red #3, D&C red #30, D&C red #33, D&C red #36, D&C red #4, D&C red #40, D&C red #9, decyl oleate, di(2-ethylhexyl)

succinate, dimethicone, dioctyl malate, diocyl succinate, eicosanoic acid, ethylhexyl palmitate, ethylhexyl pelargonate, glyceryl tricapylo/caprate, glyceryl stearate NSE, glyceryl stearate SE, glyceryl-3-diisostearate, hexylene glycol, isocetyl alcohol, isodecyl oleate, isopropyl isostearate, isopropyl linolate, isopropyl myristate, isopropyl palmitate, isostearyl isostearate, isostearyl neopentanoate, lanolin wax, laureth-23, laureth-4, lauric acid, mink oil, myristic acid, myristyl lactate, myristyl myristate, myristyl alcohol, oleth-10, oleth-20, oleth-3, oleth-3 phosphate, oleth-5, oleyl alcohol, palmitic acid, PEG 100 distearate, PEG 150 distearate, PEG 16 lanolin (Solulan 16), PEG 20 stearate, PEG 200 dilaurate, PEG 8 castor oil, PEG 8 stearate, PG caprylate/caprate, PG dicaprylate/caprate, PG dipelargonate, PG monostearate, phytantriol, polyglyceryl-3-diisostearate, PPG 10 cetyl ether, PPG 2 myristyl propionate, PPG 5 ceteth 10 phosphate, sorbitan isostearate, sorbitan oleate, squalene, steareth-10, steaateh-2, steareth-20, stearic acid, stearic acid TEA, stearyl alcohol, stearyl heptanoate, triethanolamine, water-soluble sulfur, xylene, or zinc dioxide.

The formulations of the disclosure can comprise a cationic surfactant at a concentration of about 1 mM, about 20 mM, about 50 mM, about 75 mM, about 100 mM, about 150 mM, about 200 mM, about 250 mM, about 300 mM, about 350 mM, about 400 mM, about 450 mM, or about 500 mM. In some embodiments, the formulations of the disclosure can comprise a cationic surfactant (e.g., CTAC or CTAB) at a concentration of about 1 mM. In some embodiments, the formulations of the disclosure can comprise a cationic surfactant (e.g., CTAC or CTAB) at a concentration of about 300 mM. In some embodiments, the formulations of the disclosure can comprise a cationic surfactant (e.g., CTAC or CTAB) at a concentration of about 400 mM. In some embodiments, the formulations of the disclosure can comprise a cationic surfactant (e.g., CTAC or CTAB) at a concentration of about 500 mM.

The formulations of the disclosure can comprise a chelating agent at a concentration of about 1 mM, about 20 mM, about 50 mM, about 75 mM, about 100 mM, about 150 mM, about 200 mM, about 250 mM, about 300 mM, about 350 mM, about 400 mM, about 450 mM, or about 500 mM. In some embodiments, the formulations of the disclosure can comprise a chelating agent (e.g., DTPA or EDTA) at a concentration of about 10 mM. In some embodiments, the formulations of the disclosure can comprise a chelating agent (e.g., DTPA or EDTA) at a concentration of about 250 mM. In some embodiments, the formulations of the disclosure can comprise a chelating agent (e.g., DTPA or EDTA) at a concentration of about 300 mM. In some embodiments, the formulations of the disclosure can comprise a chelating agent (e.g., DTPA or EDTA) at a concentration of about 400 mM. In some embodiments, the formulations of the disclosure can comprise a chelating agent (e.g., DTPA or EDTA) at a concentration of about 500 mM.

The formulations of the disclosure can comprise a mixture of solvents, for example, a mixture of water and an organic solvent. The formulations of the disclosure can comprise, for example, about 25%, about 50%, about 75%, or about 100% of an organic solvent. In some embodiments, the formulations of the disclosure can comprise about 25% PG or DMSO and about 75% water. In some embodiments, the formulations of the disclosure can comprise about 50% PG or DMSO and about 50% water. In some embodiments, the formulations of the disclosure can comprise about 75% PG or DMSO and about 25% water. In some embodiments, the formulations of the disclosure can be made in 100% of an organic solvent, for example, 100% PG or 100% DMSO.

The formulations of the disclosure can further comprise a dye, pigment, or colorant. The formulations of the disclosure can comprise an organic dye, pigment, or colorant; or an inorganic dye, pigment, or colorant. For example, a formulation of the disclosure can comprise a dye, such as Alcian yellow GXS (Ingrain yellow 1), Alizarin (Mordant red 11), Alizarin red S (Mordant red 3), Alizarin yellow GG (Mordant yellow 1), Alizarin yellow R (Mordant orange 1), Azophloxin (Acid red 1), Bismarck brown R (Vesuvine brown), Bismarck brown Y (Vesuvine phenylene brown), Brilliant cresyl blue (Cresyl blue BBS), Chrysoidine R (Basic orange 1), Chrysoidine Y (Basic orange 2), Congo red (Direct red 28), Crystal violet (Basic violet 3), Fuschsin acid (Acid violet 19), Gentian violet (Basic violet 1), Janus green, Lissamine fast yellow (Acid yellow 17), Malachite green, Martius yellow (Acid yellow 24), Meldola blue (phenylene blue), Metanil yellow (Acid yellow 36), Methyl orange (Acid orange 52), Methyl red (Acid red 2), Naphthalene black 12B (Amido black 10B or Acid black 1), Naphthol green B (Acid green 1), Naphthol yellow S (Acid yellow 1), Orange G (Acid orange 10), Purpurin (Verantin), Rose Bengal (Acid red 94), Sudan II (Solvent orange 7), Titan yellow (Direct yellow 9), Tropaeolin O (sulpho orange or acid orange 6), Tropaeolin OO (Acid orange 5), Tropaeolin OOO (Acid orange 7), Victoria blue 4R (Basic blue 8), Victoria blue B (Basic blue 26), Victoria blue R (Basic blue 11), or Xylene cyanol FF (Acid blue 147).

The formulations of the disclosure can further comprise viscosity modulators, such as a thickening agent. For example, the formulations of the disclosure can comprise a thickening agent, such as a starch (e.g., arrow root, cornstarch, katakuri starch, potato starch, sago, tapioca), vegetable gum (alginin, guar gum, locust bean gum, xanthan gum), a protein (e.g., collagen, egg whites, gelatin), a sugar (e.g., agar, carrageenan), or sodium pytophosphate.

The formulations of the disclosure can further comprise stabilizers. For example, the formulations of the disclosure can comprise calcium-zinc, organo-calcium, lead, and tin-based stabilizers. The formulations of the disclosure can also comprise liquid and light stabilizers, such as hindered amine light stabilizers (HALS), benzophenone, or benzotriazole. Examples of stabilizers also include tris(2,4-di-tert-butylphenyl)phosphite, antioxidants (e.g., oxygen scavengers, such as phosphite esters; persistant radical scavengers, such as butylated hydroxytoluene; antiozonants; sequestrants; ultraviolet stabilizers). The formulations of the disclosure can include gelling agents, such as alginic acid, sodium alginate, potassium alginate, ammonium alginate, calcium alginate, agar, carrageenan, locust bean gum, pectin, or gelatin. In some embodiments, a thickening agent, such as polyethylene glycol, synthetic carbomers, petroleum jelly, paraffin, and wax can be used in the formulations of the disclosure.

The formulations of the disclosure can further comprise local anesthetics. For example, the formulations of the disclosure can comprise a local anesthetic, such as lignocaine (lidocaine, Remicaine®, Petercaine®), bupivacaine (e.g., Macaine®), ropivacaine (e.g., Naropin®), prilocaine, amethocaine (e.g., Tetracaine®), procaine, cinchocaine (e.g., Dibucaine®), mepivacaine (e.g., Carbocaine®), or etidocaine.

The formulations of the disclosure can further comprise tissue permeabilizers. The formulations of the disclosure can comprise a tissue permeabilizer, such as an organic solvent (e.g., methanol, acetone) or a detergent (e.g., saponin, Triton™ X-100, Tween®-20).

The formulations of the disclosure can further comprise skin softeners. The formulations of the disclosure can comprise a skin softener, such as lentil fruit extract, hexyl laurate, hexyldecanol, hydrogenated polyisobutene, hydrolyzed glycosaminoglycans, hydrolyzed jojoba esters, isoamyl laurate, Limnanthes alba, lyceum barbarum fruit extract, methyl gluceth-20, methyl glucose sesquistearate, methylglucoside phosphate, millet seed extract, neopentyl glycol diheptanoate, octyldodecyl myristate, octyldodecyl neopentanoate, oleyl erucate, Oryza sativa cera, polyglyceryl-10 laurate, tridecyl trimellitate, trimethylsiloxysilicate, trioctyldodecyl citrate, Triticum volgare (wheat) germ extract, Triticum vulgare oil, whey protein, xymenynic acid, Cocos nucifera (coconut) fruit extract, caprylyl caprylate/caprate, ethylhexyl olivate, urea, or tocopheryl acetate.

The formulations of the disclosure can further comprise an exfoliant. The formulations of the disclosure can comprise an exfoliant, such as betaine salicylate, beta hydroxy acid, bromelain, alpha hydroxy acid, ammonium glycolate, amygdalic acid, Ananas sativus fruit extract, azelaic acid, gluconolactone, lactic acid, lactobionic acid, glycolic acid, malic acid, mandelic acid, papain, Papaya extract, polyhydroxy acid, salicylic acid, tartaric acid, or urea.

The formulations of the disclosure can further comprise amino acids, peptides, proteins, or proteases. In some embodiments, the formulations of the disclosure can comprise poly-L-lysine, arginine, bacitracin, milk hydrolysate, alcalase, collagenase, or keratinase.

The formulations of the disclosure can further comprise antibiotics. The formulations of the disclosure can comprise antibiotics, such as penicillins, cephalosporins, macrolides, fluoroquinolones, sulfonamides, tetracyclines, or aminoclycosides. For example, a formulation of the disclosure can further comprise a penicillin, such as penicillin or amoxicillin. A formulation of the disclosure can further comprise a cephalosporin, such as cephalexin. A formulation of the disclosure can further comprise a macrolide, such as erythromycin, clarithromycin, or azithromycin. A formulation of the disclosure can further comprise a fluoroquinolone, such as ciprofloxacin, levofloxacin, or ofloxacin. A formulation of the disclosure can further comprise a sulfonamide, such as co-trimoxazole or trimethoprim. A formulation of the disclosure can further comprise a tetracycline, such as tetracycline (sumycin, panmycin) or doxycycline. A formulation of the disclosure can further comprise an aminoglycoside, such as gentamicin or tobramycin.

In some embodiments, the formulations of the disclosure can comprise a cationic surfactant, a chelating agent, an organic solvent, and antibiotic, for example, polymyxin B. In some embodiments, the formulations of the disclosure can comprise: 1) CTAC or CTAB: 2) DTPA or EDTA; 3) PG or DMSO; and 4) an antibiotic, for example, polymyxin B.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, and any combination thereof.

Non-limiting examples of pharmaceutically-acceptable excipients suitable for use in the invention include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Multiple therapeutic agents can be administered in any order or simultaneously. In some embodiments, a compound of the invention is administered in combination with, before, or after an antibiotic. If simultaneously, the multiple therapeutic agents can be provided in a single, unified form, or in multiple forms, for example, as multiple separate topical treatments. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A therapeutic agent can be administered as soon as is practicable after the onset of a disease or condition is detected or suspected, and for a length of time necessary for the treatment of the disease, such as, for example, from about 1 month to about 3 months. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged topicals, vials, or ampoules. Aqueous suspension compositions can be packaged in single-dose non-reclosable containers. Multiple-dose reclosable containers can be used, for example, in combination with or without a preservative. Formulations for administration can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, and ophthalmic preparations.

Compounds can be delivered via liposomal technology. The use of liposomes as drug carriers can increase the therapeutic index of the compounds. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

In some embodiments, the pharmaceutical compositions of the disclosure can be formulated as leave-on sprays for use to treat mold. In some embodiments, the pharmaceutical compositions of the disclosure are formulated as shampoos and soaps to treat ringworm in humans or animals. In some embodiments, the pharmaceutical compositions of the disclosure are formulated as detergents to pre-treat or treat articles of clothing that carry fungal cells or spores.

The formulations of the disclosure can be combined with other preparations to endow the other preparations with anti-microbial properties. Non-limiting examples of preparations that can be combined with a formulation disclosed herein include Mouth Kote Dry Mouth Spray, Feminease® Feminine Moisturizer, and Pretz Nasal Spray.

Purity of Compounds of the Invention

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

Dosing

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

Subjects

Subjects can be, for example, elderly adults, adults, adolescents, pre-adolescents, children, toddlers, infants, and non-human animals. In some embodiments, a subject is a patient. Non-human animal subjects can be, for example, an animal (e.g., a mouse, rat, a chicken, a rabbit, a dog, a cat, a frog, or a cow). Compounds of the invention can be employed on surfaces in places where the spread of drug-resistant bacteria can be more likely, for example, hospitals, nursing homes, dormitories, homeless shelters, military barracks, schools, locker rooms, gymnasiums, prisons, poultry farms, cow pens, or pigsties. The methods of the invention can be applied to, for example, fomites, surgical instruments, tables, chairs, doors, eating utensils, bedding, beds, and keyboards.

In some embodiments, the methods of the invention can be applied to, for example, a plant infected by a fungus, bacterium, parasite, or virus. Administration can, for example, kill or inhibit the plant fungus, bacterium, parasite, or virus or kill or inhibit an agent that harms or presents a risk of harm to a plant or fungus, or lessen a likelihood of such risk. For example, agricultural applications to inhibit the spread of and damage by agriculturally-detrimental microbes are possible.

Formulations

Non limiting examples of formulations of the disclosure are shown below in TABLE 1.

TABLE 1*

| Formulation | CTAC | CTAB | DTPA | Ca-DTPA | PG | EtOH | Glycerol | DMSO | PMB |
|---|---|---|---|---|---|---|---|---|---|
| MM1 | 400 mM | — | 500 mM | — | 25% | — | — | — | — |
| MM2 | 500 mM | — | 300 mM | — | 25% | — | — | — | — |
| MM3 | 400 mM | — | 250 mM | — | 25% | — | — | — | — |
| MM4 | 400 mM | — | 500 mM | — | — | — | — | 25% | — |
| MM5 | 500 mM | — | 300 mM | — | — | — | — | 25% | — |
| MM6 | 400 mM | — | 250 mM | — | — | — | — | 25% | — |
| MM7 | 1 mM | — | 10 mM | — | 100% PG | — | — | — | — |
| MM8 | 1 mM | — | 10 mM | — | 100% PG | — | — | — | 25 µg/mL |
| MM9 | — | 1 mM | — | 10 mM | 100% PG | — | — | — | — |
| MM10 | 1 mM | — | — | 10 mM | 100% PG | — | — | — | — |
| MM11 | — | 1 mM | 10 mM | — | 100% PG | — | — | — | — |
| MM12 | 1 mM | — | 10 mM | — | — | 50% | — | — | — |
| MM13 | 1 mM | — | 10 mM | — | — | — | 25% | — | — |
| MM14 | 2 mM | — | 20 mM | — | 100% | — | — | — | — |
| MM15 | — | 2 mM | 20 mM | — | 100% | — | — | — | — |
| MM16 | — | 2 mM | — | 20 mM | 100% | — | — | — | — |
| MM17 | 2 mM | — | — | 20 mM | 100% | — | — | — | — |
| MM18 | 10 mM | — | 100 mM | — | — | 100% | — | — | — |
| MM19 | — | 10 mM | 100 mM | — | — | 100% | — | — | — |

*All formulations were prepared in sterile water. For use in inanimate surfaces, MM1, MM2, and MM3 used water instead of a 25% PG solution.
Abbreviations: cetyltrimethylammonium bromide (CTAB); cetyltrimethylammonium chloride (CTAC); diethylenetriaminepentaacetic acid (DTPA); propylene glycol (PG); dimethyl sulfoxide (DMSO); polymyxin B (PMB).

In some embodiments, a formulation of TABLE 1 comprises CTAC, DTPA or a pharmaceutically-acceptable salt thereof, and propylene glycol. In some embodiments, a formulation of TABLE 1 comprises CTAB, DTPA or a pharmaceutically-acceptable salt thereof, and propylene glycol. In some embodiments, a formulation of TABLE 1 comprises about 1 mM CTAC, about 10 mM DTPA, and propylene glycol. In some embodiments, a formulation of TABLE 1 comprises about 1 mM CTAB, about 10 mM Ca-DTPA, and propylene glycol. In some embodiments, a formulation of TABLE 1 comprises about 1 mM CTAB, about 10 mM DTPA, and propylene glycol. In some embodiments, a formulation of TABLE 1 comprises about 1 mM CTAC, about 10 mM Ca-DTPA, and propylene glycol. In some embodiments, a formulation of TABLE 1 comprises about 2 mM CTAC, about 20 mM DTPA, and propylene glycol. In some embodiments, a formulation of TABLE 1 comprises about 2 mM CTAB, about 20 mM DTPA, and propylene glycol. In some embodiments, a formulation of TABLE 1 comprises about 2 mM CTAB, about 20 mM Ca-DTPA, and propylene glycol. In some embodiments, a formulation of TABLE 1 comprises about 2 mM CTAC, about 20 mM Ca-DTPA, and propylene glycol. In some embodiments, a formulation of TABLE 1 comprises CTAC, DTPA or a pharmaceutically-acceptable salt thereof, propylene glycol, and polymyxin B. In some embodiments, a formulation of TABLE 1 comprises about 1 mM CTAC, about 10 mM DTPA, propylene glycol, and about 25 µg/mL of polymyxin B. In some embodiments, a formulation of TABLE 1 comprises CTAC, DTPA or a pharmaceutically-acceptable salt thereof, propylene glycol, and water. In some embodiments, a formulation of TABLE 1 comprises about 400 mM CTAC, about 500 mM DTPA, and a solvent mixture consisting of about 25% propylene glycol and about 75% water. In some embodiments, a formulation of TABLE 1 comprises about 500 mM CTAC, about 300 mM DTPA, and a solvent mixture consisting of about 25% propylene glycol and about 75% water. In some embodiments, a formulation of TABLE 1 comprises about 400 mM CTAC, about 250 mM DTPA, and a solvent mixture consisting of about 25% propylene glycol and about 75% water. In some embodiments, a formulation of TABLE 1 comprises CTAC, DTPA or a pharmaceutically-acceptable salt thereof, DMSO, and water. In some embodiments, a formulation of TABLE 1 comprises about 400 mM CTAC, about 500 mM DTPA, and a solvent mixture consisting of about 25% DMSO and about 75% water. In some embodiments, a formulation of TABLE 1 comprises about 500 mM CTAC, about 300 mM DTPA, and a solvent mixture consisting of about 25% DMSO and about 75% water. In some embodiments, a formulation of TABLE 1 comprises about 400 mM CTAC, about 250 mM DTPA, and a solvent mixture consisting of about 25% DMSO and about 75% water. In some embodiments, a formulation of the disclosure comprises CTAC, DTPA or a pharmaceutically-acceptable salt thereof, ethanol, and water. In some embodiments, a formulation of TABLE 1 comprises about 1 mM CTAC, about 10 mM DTPA, and a solvent mixture consisting of about 50% ethanol and about 50% water. In some embodiments, a formulation of TABLE 1 comprises CTAC, DTPA or a pharmaceutically-acceptable salt thereof, glycerol, and water. In some embodiments, a formulation of TABLE 1 comprises about 1 mM CTAC, about 10 mM DTPA, and a solvent mixture consisting of about 25% glycerol and about 75% water. In some embodiments, a formulation of TABLE 1 comprises CTAC, DTPA or a pharmaceutically-acceptable salt thereof, and water. In some embodiments, a formulation of TABLE 1 comprises about 10 mM CTAC, about 100 mM DTPA, and water. In some embodiments, a formulation of TABLE 1 comprises CTAB, DTPA or a pharmaceutically-acceptable salt thereof, and water. In some embodiments, a formulation of TABLE 1 comprises about 10 mM CTAB, about 100 mM DTPA, and water.

A pharmaceutical composition comprising, in unit dosage form, a formulation of TABLE 1 as described above can be used to kill microorganisms. In some embodiments, a method of killing a microorganism comprises administering to the microorganism a pharmaceutical composition comprising, in unit dosage form, a formulation of TABLE 1 as described above. Non-limiting examples of microorganisms that can be killed via administration a pharmaceutical composition comprising, in unit dosage form, a formulation of TABLE 1 include bacterium, gram-positive bacterium, gram-negative bacterium, *Acinetobacter baumannii, Pseudomonas aeruginosa, Escherichia coli, Burkholderia cepacia, Streptococcus pyogenes, Stenotrophomonas maltophilia, Bacillus subtilis, Mycobacterium abscessus, Staphylococcus aureus, Staphylococcus epidermis. Propionibacterium acnes, Streptococcus mutans, Bacillus anthracis, Franscisella tularensis, Yersinia pestis, Clostridium botulinum, Coxiella burnetti, Brucella species, Burkholderia mallei, Clostridium perfringens, Vibrio cholerae, Porphyromonas gingivalis, Proteus mirabilis, Salmonella enteriditis, Shigella flexneri, Xanthomonas campestris, Clavibacter* sp. fungi, *Candida auris, Trichophyton rubrum, Aspergillus niger, Candida krusei, Geomyces destructans, Trichophyton rubrum*, mold, yeast, *Candida albicans, Candida parapsilosis, Candida glabrata, Candida haemulonii, Candida duobshaemulonii, Candida tropicalis, Cryptococcus neoformans, Cryptococcus gattii, Batrachochytrium dendrobatidis*, viruses, Lassa virus, *Junin* virus, Machupo virus, Ebola virus, Marburg virus, Variola major, Nipah virus, Hantavirus, Nairovirus, Varicella-zoster virus, paramyxovirus, rubeola virus, rhinovirus, coronavirus, respiratory syncytial virus, influenza virus, norovirus, hepatitis A, rotavirus, astrovirus, and Norwalk-like virus.

A pharmaceutical composition comprising, in unit dosage form, a formulation of TABLE 1 as described above can be used to treat an infection in a subject. In some embodiments, a method of treating an infection in a subject comprises administering to a subject in need thereof a therapeutically-effective amount of a pharmaceutical composition comprising a formulation of TABLE 1 as described above. Infections treated with a pharmaceutical composition comprising, in unit dosage form, a formulation of TABLE 1 can be caused by, for example, microorganisms. Non-limiting examples of microorganisms that can cause an infection that can be treated via administration of a formulation of TABLE 1 to a subject include bacterium, gram-positive bacterium, gram-negative bacterium, *Acinetobacter baumannii, Pseudomonas aeruginosa, Escherichia coli, Burkholderia cepacia, Streptococcus pyogenes, Stenotrophomonas maltophilia, Bacillus subtilis, Mycobacterium abscessus, Staphylococcus aureus, Staphylococcus epidermis, Propionibacterium acnes, Streptococcus mutans, Bacillus anthracis. Franscisella tularensis, Yersinia pestis, Clostridium botulinum, Coxiella burnetti, Brucella species, Burkholderia mallei, Clostridium perfringens, Vibrio cholerae, Porphyromonas gingivalis, Proteus mirabilis, Salmonella enteriditis, Shigella flexneri, Xanthomonas campestris, Clavibacter* sp, fungi, *Candida auris, Trichophyton rubrum, Aspergillus niger, Candida krusei, Geomyces destructans, Trichophyton rubrum*, mold, yeast, *Candida albicans, Candida parapsilosis, Candida glabrata, Candida haemulonii, Candida duobshaemulonii, Candida tropicalis, Cryptococcus neoformans, Cryptococcus gattii, Batrachochytrium dendrobatidis*, viruses, Lassa virus, *Junin* virus, Machupo virus, Ebola virus, Marburg virus, Variola major, Nipah virus, Hantavirus, Nairovirus, Varicella-zoster virus, paramyxovirus, rubeola virus, rhinovirus, coronavirus, respiratory syncytial virus, influenza virus, norovirus, hepatitis A, rotavirus, astrovirus, and Norwalk-like virus.

A pharmaceutical composition comprising, in unit dosage form, a formulation of TABLE 1 as described above can be used to disinfect a surface. In some embodiments, a method of disinfecting a surface comprises administering to a surface in need thereof a pharmaceutical composition comprising, in unit dosage form, a formulation of TABLE 1 as described above. Surfaces that can be disinfected via administration of a pharmaceutical composition comprising, in unit dosage form, a formulation of TABLE 1 as described above can be infected with a microorganism. Non-limiting examples of microorganisms that can infect a surface that can be disinfected via administration of a pharmaceutical composition comprising, in unit dosage form, a formulation of TABLE 1 as described above include bacterium, gram-positive bacterium, gram-negative bacterium, *Acinetobacter baumannii, Pseudomonas aeruginosa, Escherichia coli, Burkholderia cepacia, Streptococcus pyogenes, Stenotrophomonas maltophilia, Bacillus subtilis, Mycobacterium abscessus, Staphylococcus aureus, Staphylococcus epidermis, Propionibacterium acnes, Streptococcus mutans, Bacillus anthracis, Franscisella tularensis, Yersinia pestis, Clostridium botulinum, Coxiella burnetti, Brucella species, Burkholderia mallei, Clostridium perfringens. Vibrio cholerae, Porphyromonas gingivalis, Proteus mirabilis, Salmonella enteriditis, Shigella flexneri, Xanthomonas campestris, Clavibacter* sp, fungi, *Candida auris, Trichophyton rubrum, Aspergillus niger, Candida krusei, Geomyces destructans, Trichophyton rubrum*, mold, yeast, *Candida albicans, Candida parapsilosis, Candida glabrata, Candida haemulonii, Candida duobshaemulonii, Candida tropicalis, Cryptococcus neoformans, Cryptococcus gattii, Batrachochytrium dendrobatidis*, viruses, Lassa virus, *Junin* virus, Machupo virus, Ebola virus, Marburg virus, Variola major, Nipah virus, Hantavirus, Nairovirus, Varicella-zoster virus, paramyxovirus, rubeola virus, rhinovirus, coronavirus, respiratory syncytial virus, influenza virus, norovirus, hepatitis A, rotavirus, astrovirus, and Norwalk-like virus.

A pharmaceutical composition comprising, in unit dosage form, a formulation of TABLE 1 as described above can be used to disinfect an agricultural product. In some embodiments, a method of disinfecting an agricultural product comprises administering to an agricultural product in need thereof a pharmaceutical composition comprising, in unit dosage form, a formulation of TABLE 1 as described above. Agricultural products that can be disinfected via administration of a pharmaceutical composition comprising, in unit dosage form, a formulation of TABLE 1 as described above can be infected with a microorganism. Non-limiting examples of microorganisms that can infect an agricultural product that can be disinfected via administration of a pharmaceutical composition comprising, in unit dosage form, a formulation of TABLE 1 as described above include bacterium, gram-positive bacterium, gram-negative bacterium, *Acinetobacter baumannii, Pseudomonas aeruginosa, Escherichia coli, Burkholderia cepacia, Streptococcus pyogenes, Stenotrophomonas maltophilia, Bacillus subtilis, Mycobacterium abscessus, Staphylococcus aureus, Staphylococcus epidermis, Propionibacterium acnes, Streptococcus mutans, Bacillus anthracis, Franscisella tularensis, Yersinia pestis, Clostridium botulinum, Coxiella burnetti,*

Brucella species, Burkholderia mallei, Clostridium perfringens, Vibrio cholerae, Porphyromonas gingivalis, Proteus mirabilis, Salmonella enteriditis, Shigella flexneri, Xanthomonas campestris, Clavibacter sp, fungi, Candida auris, Trichophyton rubrum, Aspergillus niger, Candida krusei, Geomyces destructans, Trichophyton rubrum, mold, yeast, Candida albicans, Candida parapsilosis, Candida glabrata, Candida haemulonii, Candida duobshaemulonii, Candida tropicalis, Cryptococcus neoformans, Cryptococcus gattii, Batrachochytrium dendrobatidis, viruses, Lassa virus, Junin virus, Machupo virus, Ebola virus, Marburg virus, Variola major, Nipah virus, Hantavirus, Nairovirus, Varicella-zoster virus, paramyxovirus, rubeola virus, rhinovirus, coronavirus, respiratory syncytial virus, influenza virus, norovirus, hepatitis A, rotavirus, astrovirus, and Norwalk-like virus.

EXAMPLES

Example 1: Composition of Formulations

Formulations were prepared using different concentrations of cetyltrimethylammonium bromide (CTAB) or cetyltrimethylammonium chloride (CTAC), and diethylenetriaminepentaacetic acid (DTPA) dissolved in aqueous solutions of propylene glycol (PG) or dimethyl sulfoxide (DMSO). Solutions were prepared to contain 25% by volume of PG or DMSO and 75% by volume of CTAC and DTPA. TABLE 1 shows the preparation of formulations MM1-MM19.

Example 2: Testing the Potency of MM1

Concentrated MM1 (500 mM DTPA+400 mM CTAC) was diluted 1:10, 1:100, 1:1000, and 1:10000 in an aqueous solution of 25% PG to test the potency of the MM1 solutions. 5 µL of the diluted MM1 solution was spotted on a lawn of multi drug-resistant C. auris (CDC 0385).

A 50 mL tube containing YM medium was inoculated with a culture of multi drug-resistant C. auris (CDC 0385) and incubated at 37° C. for 24 hours in a rotary shaking incubator. 100 µL of the C. auris (approximately 1×10$^8$ CFU/mL) was spread onto 100 mm×15 mm square plates containing Mueler-Hinton agar (MHA). Upon spreading the lawn of C. auris, 5 µL of the 1:10, 1:100, 1:1000, and 1:10000 dilutions of concentrated MM1 were spotted onto respective areas of the inoculated MHA plate. The plate was then incubated for 48 hours at 37° C.

Figure 1:
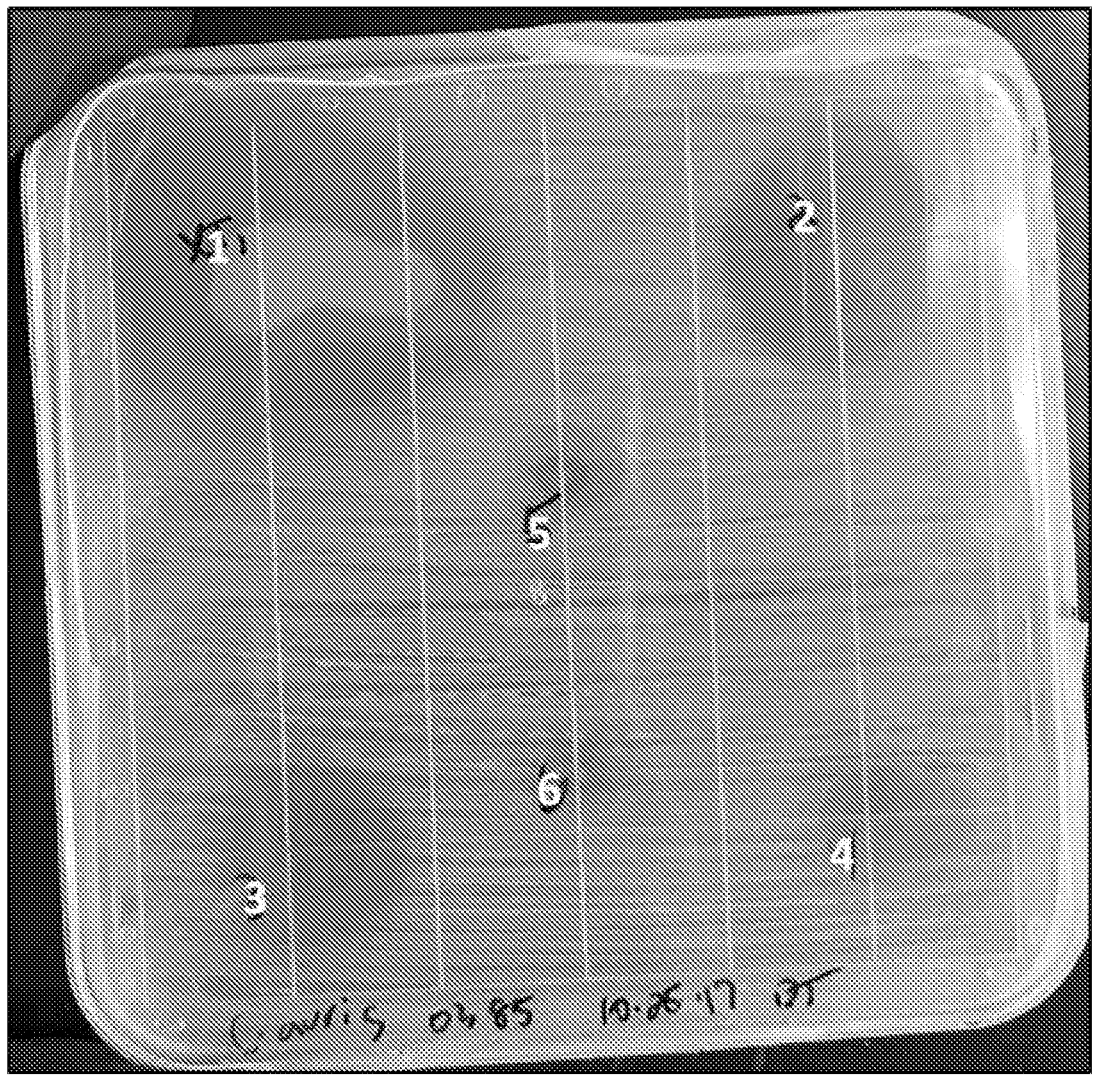
FIG. 1 shows that the concentrated MM1 was effective at killing multi drug-resistant *C. auris* (ATCC 0385) at different dilution levels.

FIG. 1 shows that the concentrated MM1 was effective at killing multi drug-resistant C. auris (CDC 0385) at different dilution levels. 1 shows the effect of concentrated MM1 without dilution; 2 shows the effect of concentrated MM1 diluted 1:10 in an aqueous solution of 25% PG; 3 shows the effect of concentrated MM1 diluted 1:100 in an aqueous solution of 25% PG; 4 shows the effect of concentrated MM1 diluted 1:1000 in an aqueous solution of 25% PG; and 5 shows the effect of concentrated MM1 diluted 1:10000 in an aqueous solution of 25% PG. The diameter of the clearance area decreased with dilution. Within the circle of death, the MM1 solutions completely killed C. auris, which was observed with decreased opacity within the fungal lawns. Increasing the volume of the diluted MM1 solutions resulted in sterilization of larger surface areas.

Example 3: Effect of Antifungal Formulations on Fungi

The formulations of EXAMPLE 1 were tested against commercially available anti-fungal formulations. The active and inactive ingredients for Derman® Antifungal cream, Equate® Athlete's Foot Antifungal Cream, Lotrimin® Ultra Athlete's Foot Cream, Tinactin® Athlete's Foot Cream, and Lamisil® Athlete's Foot Cream are shown in TABLE 2.

TABLE 2

| Formulation | Active Ingredient(s) | Inactive Ingredient(s) |
| --- | --- | --- |
| Derman® Antifungal Cream | 18% Zinc undecylenate, 5% undecylenic acid | Glycerine, nonyl phenol sulfate, polyethylene glycol 500, polyethylene glycol 4000, propylene glycol, sodium bisulfite, water, zinc stearate |
| Equate® Athlete's Foot Antifungal Cream | 1% Terbinafine hydrochloride | Benzyl alcohol, cetyl alcohol, cetyl palmitate, isopropyl myristate, polysorbate 60, purified water, sodium hydroxide, sorbitan monostearate, stearyl alcohol |
| Lotrimin® Ultra Athlete's Foot Cream | 1% Butenafine hydrochloride | Benzyl alcohol, cetyl alcohol, glycerin, glyceryl monostearate SE, polyoxyethylene (23) cetyl Ether, propylene glycol dicaprylate, purified water, sodium benzoate, stearic acid, trolamine, white petrolatum |
| Tinactin® Athlete's Foot Cream | 1% Tolnaftate | Antifungal ceteth-20, cetostearyl alcohol, chlorocresol, mineral Oil, propylene glycol, purified water, sodium phosphate monobasic, white petrolatum |
| Lamisil® Athlete's Foot Cream | 1% Terbinafine hydrochloride | Benzyl alcohol, cetyl alcohol cetyl palmitate, isopropyl myristate, polysorbate 60, purified water, sodium hydroxide, sorbitan monostearate, stearyl alcohol |

MM1, MM2, MM3, MM4, MM5, MM6, Derman® Antifungal Cream, Equate® Athlete's Foot Antifungal Cream, Lotrimin® cream, Tinactin® cream, and Lamisil® cream were tested for the efficacy in killing Candida albicans, Trichophyton rubrum, Aspergillus niger, drug-resistant Candida parapsilosis (CDC 0339), drug-resistant Candida aureus (CDC 0383), multi-drug-resistant Candida aureus (CDC 0385), and Candida krusei (CDC 0397).

Candida albicans (ATCC 26555), drug-resistant Candida parapsilosis (CDC 0339), drug-resistant C. auris (CDC 0383), multi-drug-resistant C. auris (CDC 0385), and Candida krusei (CDC 0397) were grown in YM medium for 24 hours at 37° C. in a rotary shaking incubator. Trichophyton rubrum (ATCC 28188) was grown in YM medium for 21 days at 30° C., and Aspergillus niger was grown in YM medium for 5 days at 30° C. 100 µL of approximately 1×10$^8$ CFU/mL of each culture was spread onto 100 mm×15 mm square plates containing MHA. Upon spreading a lawn of each fungal strain, 10 µL of MM1, MM2, MM3, MM4, MM5, and MM6 were spotted onto respective areas of the inoculated MHA plate. Approximately 10 µL drops of Derman® Antifungal Cream, Equate® Athlete's Foot Antifungal Cream, Lotrimin® Ultra Athlete's Foot cream, Tinactin® Athlete's Foot cream, and Lamisil® Athlete's Foot cream were tested for efficacy in killing Candida albicans, (ATCC 26555), Trichophyton rubrum (ATCC 28188), Aspergillus niger, drug-resistant Candida parapsilosis (CDC 0339), drug-resistant C. auris (CDC 0383), multidrug-resistant *C. auris* (CDC 0385), and *Candida krusei* (CDC 0397) after a 48 hour incubation at 37° C. for *Candida* species, 30 days at 28° C. for *Trichophyton rubrum*, and 7 days at 28° C. for *Aspergillus niger*.

a. *Candida albicans* (ATCC 26555)

MM1, MM2, MM3, MM4, MM5, MM6, Derman® Antifungal Cream, Equate® Athlete's Foot Antifungal Cream, Lotrimin® Ultra Athlete's Foot cream, Tinactin® Athlete's Foot cream, and Lamisil® Athlete's Foot cream were tested for the efficacy in killing *Candida albicans*. TABLE 3 shows the formulations that were used on the MHA plates infected with *Candida albicans*.

TABLE 3

| Label | Excipient (PG) |
| --- | --- |
| 1 | MM1 |
| 1A | Derman ® Antifungal Cream |
| 2 | MM2 |
| 2A | Equate ® Athlete's Foot Antifungal Cream |
| 3 | MM3 |
| 3A | Lotrimin ® Ultra Athlete's Foot cream |
| 4 | MM4 |
| 4A | Tinactin ® Athlete's Foot cream |
| 5 | MM5 |
| 5A | Lamisil ® Athlete's Foot cream |
| 6 | MM6 |
| PMB | Polymyxin B |

Figure 2:
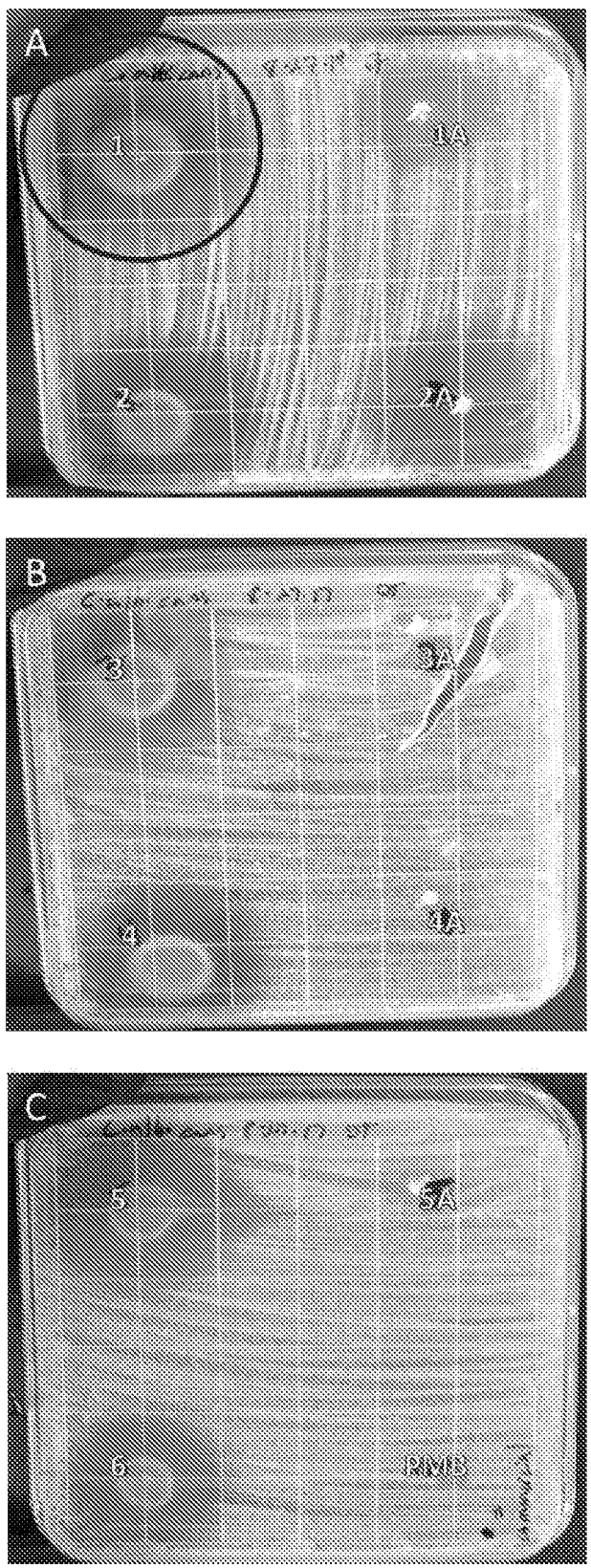
FIG. 2 PANEL A shows the diameter of clearing (cm) of *Candida albicans* when treated with MM1 (1), Derman® Antifungal Cream (1A), MM2 (2), and Equate® Athlete's Foot Antifungal Cream (2A). The bold circle encloses the diameter of clearing (cm) for *Candida albicans* treated with MM1. PANEL B shows the diameter of clearing (cm) of *Candida albicans* when treated with MM3 (3), Lotrimin® (3A), MM4 (4), and Tinactin® (4A). PANEL C shows the diameter of clearing (cm) of *Candida albicans* when treated with MM5 (5), Lamisil® (5A), MM6 (6), and Polymyxin B (PMB).

FIG. 2 PANEL A shows the diameter of clearing (cm) of *Candida albicans* when treated with MM1 (1), Derman® Antifungal Cream (1A), MM2 (2), and Equate® Athlete's Foot Antifungal Cream (2A). The bold circle encloses the diameter of clearing (cm) for *Candida albicans* treated with MM1. FIG. 2 PANEL B shows the diameter of clearing (cm) of *Candida albicans* when treated with MM3 (3), Lotrimin® Ultra Athlete's Foot Cream (3A), MM4 (4), and Tinactin® Athlete's Foot Cream (4A). FIG. 2 PANEL C shows the diameter of clearing (cm) of *Candida albicans* when treated with MM5 (5), Lamisil® Athlete's Foot Cream (5A), MM6 (6), and Polymyxin B (PMB).

Figure 3:
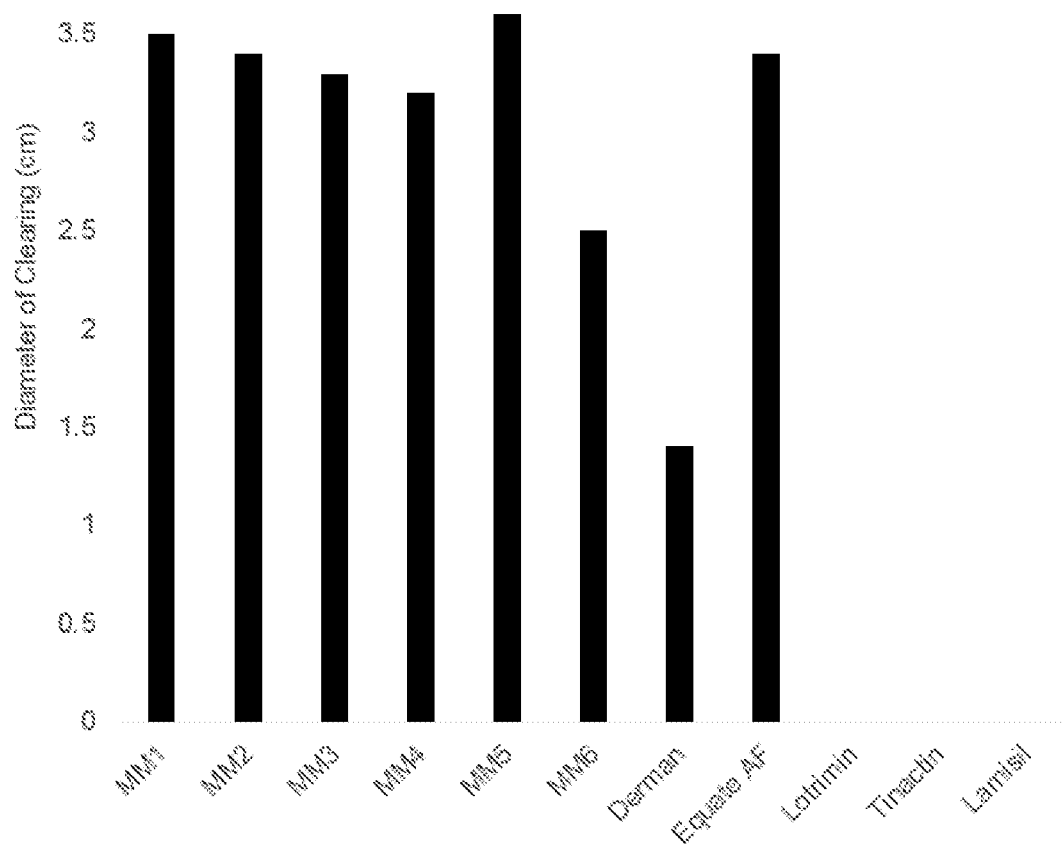
FIG. 3 shows a graph of clearance achieved by equal volumes of formulations MM1-MM6 as compared to equal volumes of commercial Derman® Antifungal Cream, Equate® Athlete's Foot Antifungal Cream, Lotrimin® Ultra Athlete's Foot Cream, Tinactin® Athlete's Foot Cream, Lamisil® Athlete's Foot Cream, and Polymyxin B against *Candida* albicans.

FIG. 3 compares the effects of the formulations in killing *Candida albicans*. The data show that MM1 was as effective as killing *Candida albicans* as Equate® Athlete's Foot Antifungal Cream. Formulations MM1-MM6 were significantly more effective at killing *Candida albicans* than Derman® Antifungal Cream, Lotrimin® Ultra Athlete's Foot Cream, Tinactin® Athlete's Foot Cream, and Lamisil® Athlete's Foot Cream were. A diameter of clearing of 0 cm indicates that the formulation did not kill *Candida albicans* and/or regrowth of the fungi was observed.

Figure 4:
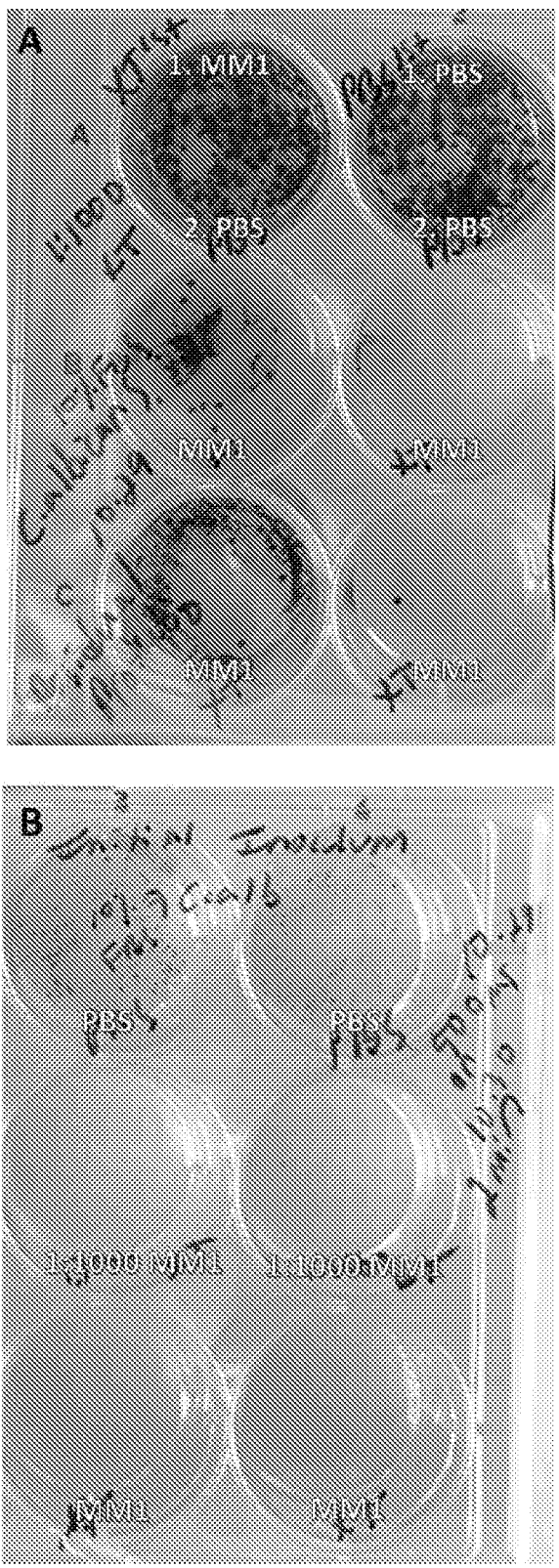
FIG. 4 PANEL A shows the residual protection of MM1 and the residual protection of a 1:1000 dilution of MM1 against *Candida albicans* on a moist agar surface. PANEL B shows the protection of MM1 and a 1:1000 dilution of MM1 against *Candida albicans* on a moist agar surface without pre-treatment with MM1. PANEL B shows that treatment with MM1 and 1:1000 MM1 resulted in killing of a pre-existing infection of *Candida* albicans.

The residual protection ability of MM1 was tested for *Candida* albicans. 3 wells of a 12-well MHA plate (FIG. 4A, left wells) were flooded with 500 µL of 1:1000 MM1 for 1 minute. The MM1 formulation was removed, and the wells were washed with 500 µL of PBS to remove any leftover MM1. Three different wells of an MHA plate (FIG. 4A, right wells) were flooded with 500 µL of PBS for 1 minute. The wells were emptied, and one well was flooded with 500 µL of PBS (positive control), and two wells were washed with 500 µL of 1:1000 MM1. The wells were dried, and a lawn of undiluted *Candida albicans* (1×10$^8$ CFU/mL) were streaked on the dried surface of the wells, and incubated at 37° C. for 48 hours. FIG. 4A shows the residual protection ability of MM1 in killing *Candida albicans*. The wells pre-treated with MM1 and washed with PBS exhibited more fungal growth than did wells pre-treated with PBS and washed with 1:1000 MM1. This result suggests that while the 1:1000 diluted MM1 formulation did not offer residual protection, washing away the MM1 and further diluting the concentration with PBS decreased the killing efficacy of MM1.

A lawn of *Candida albicans* (about 50 µL of 1×10$^8$ CFU/mL) was spread onto 6 wells of an MHA plate and incubated at 37° C. for 1 day. Wells were treated with 500 µL PBS (FIG. 4B, Row 1), 500 µL of 1:1000 MM1 (FIG. 4B, Row 2), or 500 µL of MM1 (FIG. 4B, Row 3). After 2 minutes, the solutions were removed, and the plate was incubated at 37° C. for 1 day. FIG. 4B shows that treatment with MM1 and 1:1000 MM1 resulted in killing of a pre-existing infection of *Candida albicans*.

b. *Trichophyton rubrum* (ATCC 28188)

MM1, MM2, MM3, MM4, MM5, MM6, Derman® Antifungal Cream, Equate® Athlete's Foot Antifungal Cream, Lotrimin® Ultra Athlete's Foot Cream, Tinactin® Athlete's Foot Cream, and Lamisil® Athlete's Foot Cream were tested for the efficacy in killing *Trichophyton rubrum*. TABLE 4 shows the formulations that were used on the MHA plates infected with *Trichophyton rubrum*.

TABLE 4

| Label | Excipient (PG) |
| --- | --- |
| 1 | MM1 |
| 1A | Derman ® Antifungal Cream |
| 2 | MM2 |
| 2A | Equate ® Athlete's Foot Antifungal Cream |
| 3 | MM3 |
| 3A | Lotrimin ® Ultra Athlete's Foot cream |
| 4 | MM4 |
| 4A | Tinactin ® Athlete's Foot cream |
| 5 | MM5 |
| 5A | Lamisil ® Athlete's Foot cream |
| 6 | MM6 |
| PMB | Polymyxin B |

Figure 5:
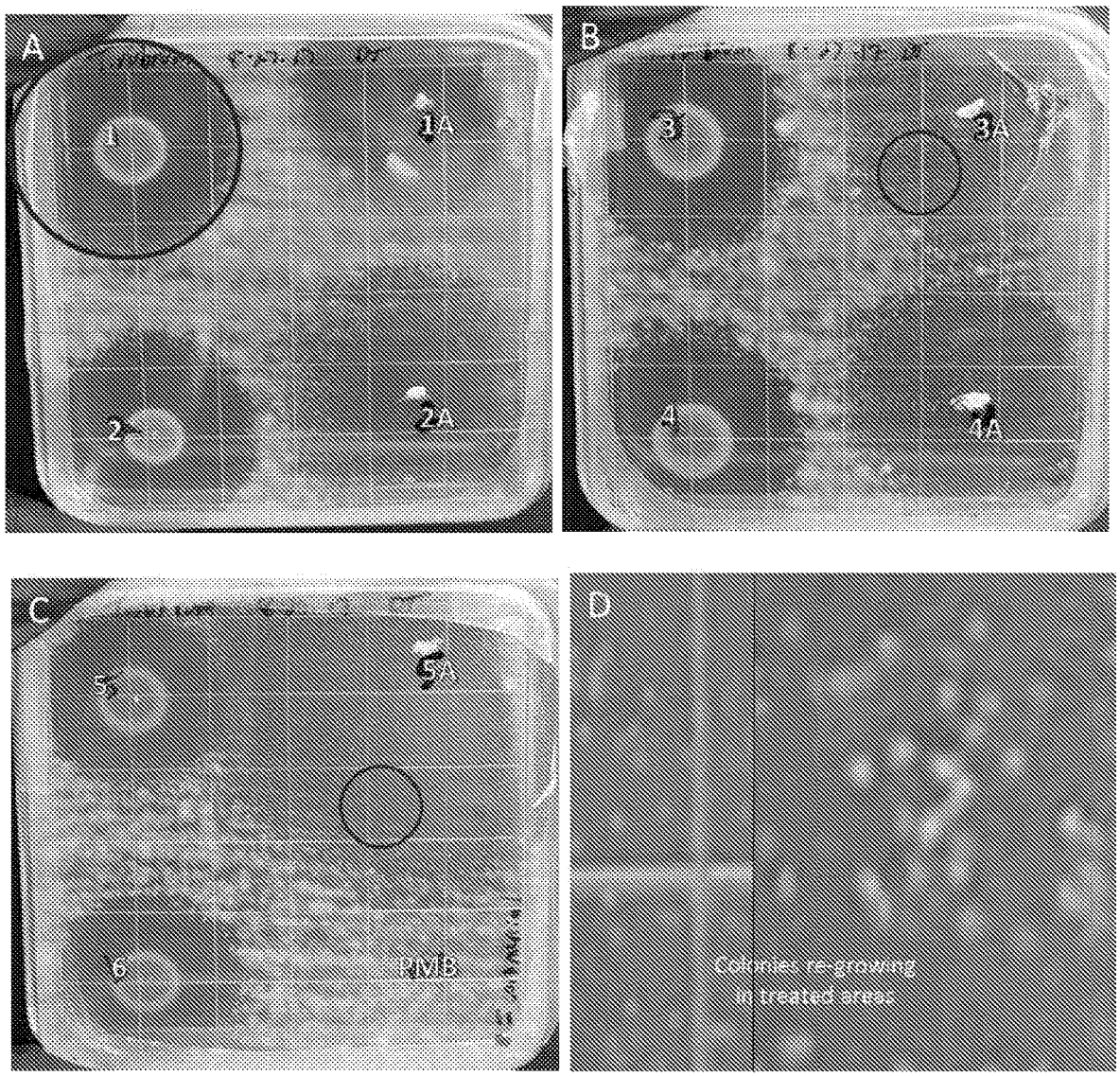
FIG. 5 PANEL A shows the diameter of clearing (cm) of *Trichophyton rubrum* when treated with MM1 (1), Derman® Antifungal Cream (1A), MM2 (2), or Equate® Athlete's Foot Antifungal Cream (2A). PANEL B shows the diameter of clearing (cm) of *Trichophyton rubrum* when treated with MM3 (3), Lotrimin® Ultra Athlete's Foot Cream (3A), MM4 (4), or Tinactin® Athlete's Foot Cream (4A). PANEL C shows the diameter of clearing (cm) of *Trichophyton rubrum* when treated with MM5 (5), Lamisil® Athlete's Foot Cream (5A), MM6 (6), or Polymyxin B (PMB). PANEL D LEFT PANEL shows a magnified image of the circle shown in PANEL C. PANEL D RIGHT PANEL shows a magnified image of the circle shown in PANEL B.

FIG. 5 PANEL A shows the diameter of clearing (cm) of *Trichophyton rubrum* when treated with MM1 (1), Derman® Antifungal Cream (1A), MM2 (2), and Equate® Athlete's Foot Antifungal Cream (2A). The bold circle encloses the diameter of clearing (cm) for *Trichophyton rubrum* treated with MM1. FIG. 5 PANEL B shows the diameter of clearing (cm) of *Trichophyton rubrum* when treated with MM3 (3), Lotrimin® Ultra Athlete's Foot Cream (3A), MM4 (4), or Tinactin® Athlete's Foot Cream (4A). FIG. 5 PANEL C shows the diameter of clearing (cm) of *Trichophyton rubrum* when treated with MM5 (5), Lamisil® Athlete's Foot Cream (5A), MM6 (6), or Polymyxin B (PMB). FIG. 5 PANEL D LEFT PANEL shows a magnified image of the circle shown in FIG. 5 PANEL C. The magnified image shows that the colonies were re-growing in the area treated with Lamisil® Athlete's Foot Cream. FIG. 5 PANEL D RIGHT PANEL shows a magnified image of the circle shown in FIG. 5 PANEL B. The magnified image shows that the colonies were re-growing in the area treated with Lotrimin® Ultra Athlete's Foot Cream.

Figure 6:
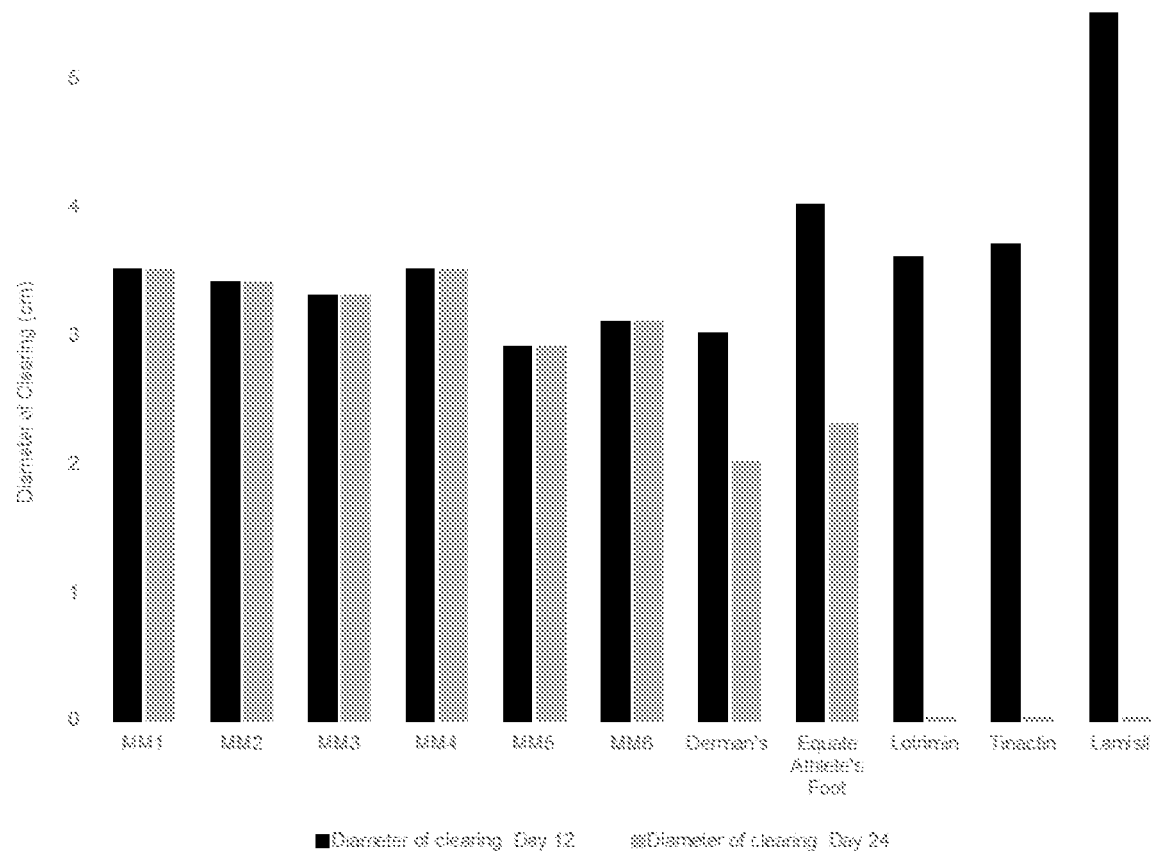
FIG. 6 compares the effects of MM1-MM6 and commercially available formulations in killing *Trichophyton rubrum* after 12 days and 24 days of treatment.

FIG. 6 compares the effects of the formulations in killing *Trichophyton rubrum* after 12 days and 24 days of treatment. The data show that MM1 and MM4 were equally effective at killing *Trichophyton rubrum* as Lotrimin® Ultra Athlete's Foot Cream and Tinactin® Athlete's Foot Cream after 12 days and after 24 days. Lamisil® Athlete's Foot Cream was the most effective at killing *Trichophyton rubrum* after 12 days of treatment. MM1-MM6 had the same diameter of clearing after 12 days and 24 days of treatment. Derman® and Equate® Athlete's Foot showed decreased diameters of clearing after 12 days. Lotrimin® Ultra Athlete's Foot Cream, Tinactin® Athlete's Foot Cream, and Lamisil® Athlete's Foot Cream showed almost complete regrowth of the fungus after 24 days of treatment. A diameter of clearing of 0 cm indicates that the formulation did not kill *Trichophyton rubrum* and/or there was regrowth of the fungi.

The ability of MM1, Derman® Antifungal Cream, Equate® Athlete's Foot Antifungal Cream, Lotrimin® Ultra Athlete's Foot Cream, Tinactin® Athlete's Foot Cream, and Lamisil® Athlete's Foot Cream to kill *Trichophyton rubrum* and stop re-growth of the fungus was tested. *Trichophyton rubrum* was grown in YM media for 21 days at 30° C. A lawn of undiluted *T. rubrum* was spread on a MHA plate. 10 μL of MM1 was spotted onto the inoculated MHA plate, and approximately 10 μL drops of Derman® Antifungal Cream, Equate® Athlete's Foot Antifungal Cream, Lotrimin® Ultra Athlete's Foot cream, Tinactin® Athlete's Foot cream, and Lamisil® Athlete's Foot cream were applied to different sections of the MHA plate to test for the efficacy in initial kill and permeant kill. The plates were incubated for 12 days and 24 days at 28° C.

TABLE 5 shows the formulations that were used on the MHA plates infected with *Trichophyton rubrum*.

TABLE 5

| Label | Excipient (PG) |
| --- | --- |
| MM1 | MM1 |
| 1 | Derman ® Antifungal Cream |
| 2 | Equate ® Athlete's Foot Antifungal Cream |
| 3 | Lotrimin ® Ultra Athlete's Foot Cream |
| 4 | Tinactin ® Athlete's Foot Cream |
| 5 | Lamisil ® Athlete's Foot Cream |

Figure 7:
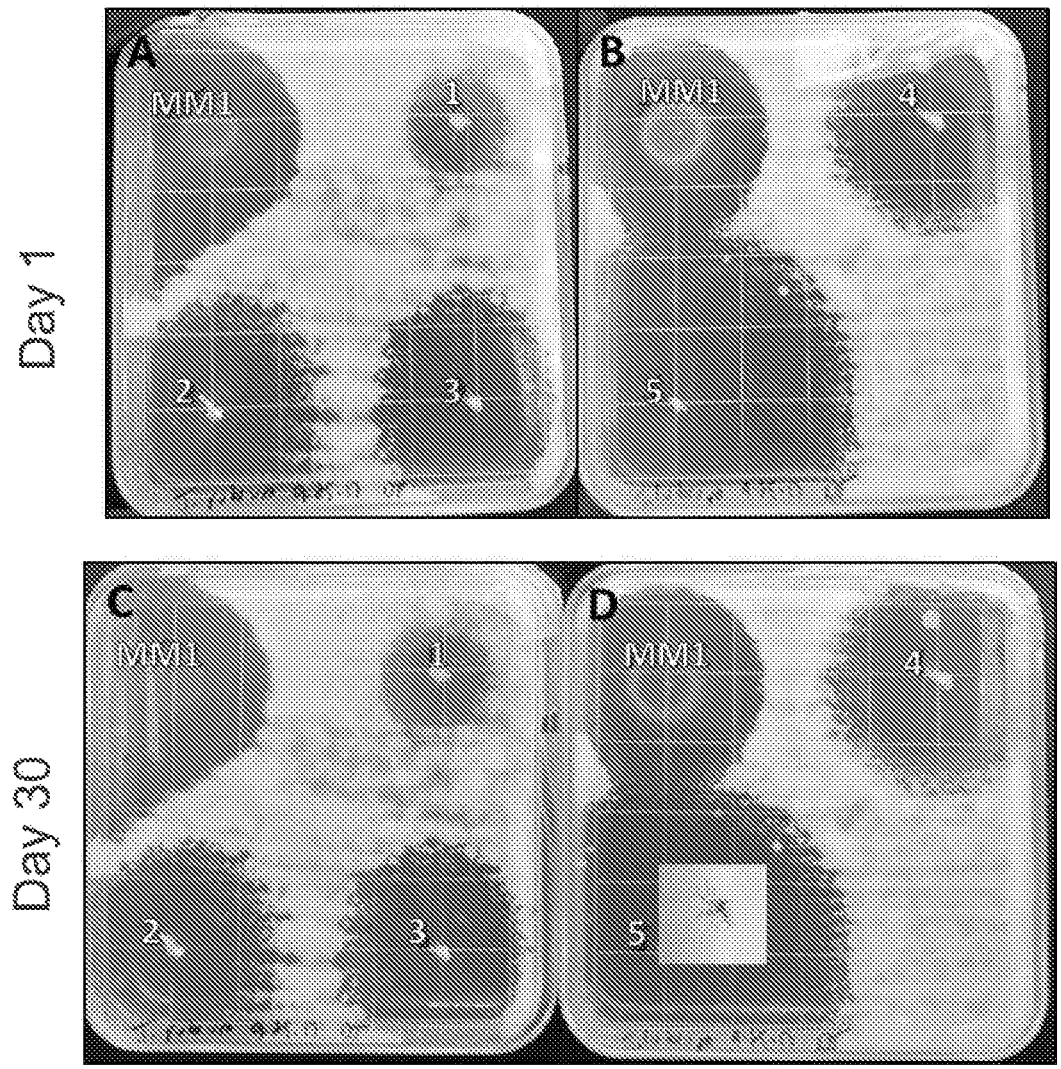
FIG. 7 PANEL A shows the diameter of clearing (cm) of *Trichophyton rubrum* when treated with MM1, Derman® (1), Equate® Athlete's Foot (2), or Lotrimin® Ultra Athlete's Foot Cream (3) after 12 days. PANEL B shows the diameter of clearing (cm) of *Trichophyton rubrum* when treated with MM1, Tinactin® Athlete's Foot Cream (4), and Lamisil® Athlete's Foot Cream (5) after 12 days. PANEL C shows the diameter of clearing (cm) of *Trichophyton rubrum* when treated with MM1, Derman® Antifungal Cream (1), Equate® Athlete's Foot (2), and Lotrimin® Ultra Athlete's Foot Cream (3) after 30 days. PANEL D shows the diameter of clearing (cm) of *Trichophyton rubrum* when treated with MM1, Tinactin® Athlete's Foot Cream, and Lamisil® Athlete's Foot Cream after 30 days.

FIG. 7 PANEL A shows the diameter of clearing (cm) of *Trichophyton rubrum* when treated with MM1, Derman® (1), Equate® Athlete's Foot (2), or Lotrimin® Ultra Athlete's Foot Cream (3) after 12 days. FIG. 7 PANEL B shows the diameter of clearing (cm) of *Trichophyton rubrum* when treated with MM1, Tinactin® Athlete's Foot Cream (4), and Lamisil® Athlete's Foot Cream (5) after 12 days. FIG. 7 PANEL C shows the diameter of clearing (cm) of *Trichophyton rubrum* when treated with MM1, Derman® Antifungal Cream (1), Equate® Athlete's Foot (2), and Lotrimin® Ultra Athlete's Foot Cream (3) after 30 days. FIG. 7 PANEL D shows the diameter of clearing (cm) of *Trichophyton rubrum* when treated with MM1, Tinactin® Athlete's Foot Cream, and Lamisil® Athlete's Foot Cream after 30 days. The box in FIG. 7 PANEL D shows that the colonies were re-growing in areas treated with Lamisil®. Colony re-growth was not observed for areas treated with MM1.

FIG. 8 compares the effects of the formulations in killing *Trichophyton rubrum*. The data show that MM1 was more effective at killing *Trichophyton rubrum* than Derman® Antifungal Cream, Equate® Athlete's Foot, Lotrimin® Ultra Athlete's Foot Cream, Tinactin® Athlete's Foot Cream, and Lamisil® Athlete's Foot Cream were 12 days after application and 30 days after application.

c. *Aspergillus niger* (Teaching Strain)

The efficacy of the disclosed formulations and commercially available products were compared using wood samples infected with *Aspergillus niger*. Three pieces of wood were inoculated using a sterile cotton tip with *A. niger* spores that were previously grown on an MHA plate. The wood samples were stored in a 28° C. incubator for one month. One piece of wood was treated with MM1, and a second piece of wood was left un-treated and used as a control. FIG. 9 PANEL A-FIG. 9 PANEL G show images of the untreated *Aspergillus niger*-infected wood sample. FIG. 9 PANEL H-FIG. 9 PANEL M show images of the *Aspergillus niger*-infected wood sample treated with MM1.

After two days of treatment with MM1, the MM1-treated wood sample and the control wood sample were swabbed under sterile conditions, plated on MHA plates, and incubated at 28° C. for 2 days and 5 days. FIG. 10 PANEL A shows the MHA plate swabbed with the MM1-treated wood sample after 2 days. FIG. 10 PANEL B shows the MHA plate swabbed with the untreated wood sample after 2 days. FIG. 10 PANEL C shows the MHA plate swabbed with the MM1-treated wood sample after 5 days. FIG. 10 PANEL D shows the MHA plate swabbed with the untreated wood sample after 5 days. The fungal burden of the wood sample treated with MM1 once was lower than the untreated wood sample. The data show that the wood sample treated with MM1 could control the pre-existing mold on the wood sample with a single treatment with MM1.

An MHA plate was infected with undiluted *Aspergillus niger* to test the toxicity of MM1. To the *Aspergillus niger*-infected MHA plate, 5 μL of MM1 and 5 μL of Lamisil® Athlete's Foot Cream (terbinafine) were spotted. The MHA plate was then incubated at 28° C. for 5 days. FIG. 11 PANEL A shows the front of the *Aspergillus niger*-infected MHA plate treated with MM1 and Lamisil® Athlete's Foot Cream after incubation for 5 days. FIG. 11 PANEL B shows the back of the *Aspergillus niger*-infected MHA plate treated with MM1 and Lamisil® Athlete's Foot Cream after incubation for 5 days. FIG. 12 compares the diameter of diffusion (cm) of the spots of the *Aspergillus niger*-infected MHA plate treated with MM1 and Lamisil® Athlete's Foot Cream. The data show that treatment of the *Aspergillus niger*-infected MHA plate with MM1 resulted in a diameter of diffusion that was over 4 times the diameter of diffusion resulting from treatment of the *Aspergillus niger*-infected MHA plate with Lamisil® Athlete's Foot Cream.

The *Aspergillus niger*-infected MHA plate was treated with MM1 and Lamisil® Athlete's Foot Cream (terbinafine), and was incubated at 28° C. for an additional 27 days (total 32 day incubation time). FIG. 13 PANEL A shows the front of the *Aspergillus niger*-infected MHA plate treated with MM1 and Lamisil® Athlete's Foot Cream after an incubation time of 32 days. FIG. 13 PANEL B shows the back of the *Aspergillus niger*-infected MHA plate treated with MM1 and Lamisil® Athlete's Foot Cream after an incubation time of 32 days. The results indicate that after 32 days of incubation, the spots treated with MM1 were more effective at killing *Aspergillus niger* than Lamisil® Athlete's Foot Cream, as indicated by the larger diameters of diffusion (cm) resulting from treatment with MM1.

To test the residual protection ability of MM1, 3 wells of a 6-well plate were treated with 500 μL of MM1 and inoculated with *Aspergillus niger*, and 3 different wells of the 6-well plate were treated with 500 μL of MHB and inoculated with *Aspergillus niger*. Of the 3 wells that were treated with 500 μL of MM1 first and inoculated with *Aspergillus niger*, one well was subsequently treated with MHB, and two wells did not receive further treatment. Of the 3 wells that were treated with 500 μL of MHB first and inoculated with *Aspergillus niger*, one well was subsequently treated with 500 μL of MHB, and two wells were subsequently treated with 500 μL of MM1. The 6-well plate was incubated for 2 days at 28° C. The well pre-treated with MHB, inoculated with *Aspergillus niger*, and treated again with the MHB control was swabbed onto an MHA plate and was incubated at 28° C. for 2 days and 7 days. The well pre-treated with MHB, inoculated with *Aspergillus niger*, and treated with MM1 was swabbed onto an MHA plate and incubated at 28° C. days for 2 days and 7 days. The 6-well plate was incubated further for 5 additional days (total incubation time of 7 days) at 28° C. The wells pre-treated with 500 µL of MM1 and wells inoculated with *Aspergillus niger* and subsequently treated with MM1 did not exhibit growth of *Aspergillus niger*.

FIG. 14 PANEL A shows the 6-well plate with 3 wells pre-treated with MM1 and 3 wells pre-treated with an MHB control. FIG. 14 PANEL B TOP PANEL shows the MHA plate swabbed with the well treated with MHB, inoculated with *Aspergillus niger*, and further treated with MHB. FIG. 14 PANEL B BOTTOM PANEL shows the MHA plate swabbed with the well pre-treated with MHB, inoculated with *Aspergillus niger*, and treated with MM1. FIG. 14 PANEL C shows the 6-well plate after incubation for 7 days. The wells show that pre-treatment of the wells with MM1 prior to inoculation with *Aspergillus niger*, and treatment with MM1 after inoculation with *Aspergillus niger* could prevent the re-growth of *Aspergillus niger* for an extended period of time.

d. Drug-Resistant *Candida parapsilosis* (CDC 0339)

The ability of MM1, Derman® Antifungal Cream, Equate® Athlete's Foot Antifungal Cream, Lotrimin® Ultra Athlete's Foot Cream, Tinactin® Athlete's Foot Cream, and Lamisil® Athlete's Foot Cream to kill drug-resistant *Candida parapsilosis* was tested. *Candida parapsilosis* (CDC 0339) was grown in YM media for 24 hours at 37° C. A lawn of undiluted *Candida parapsilosis* (~1×10$^8$ CFU/mL) was spread on an MHA plate. 10 µL of MM1 was spotted onto the inoculated MHA plate, and approximately 10 µL drops of Derman® Antifungal Cream, Equate® Athlete's Foot Antifungal Cream, Lotrimin® Ultra Athlete's Foot cream, Tinactin® Athlete's Foot cream, and Lamisil® Athlete's Foot cream were spotted onto the MHA plate to test the killing efficacy of the formulations after a 48 hour incubation at 37° C.

TABLE 6 shows the formulations that were used on the agar plates infected with drug-resistant *Candida parapsilosis*.

TABLE 6

| Label | Excipient (PG) |
| --- | --- |
| MM1 | MM1 |
| 1 | Derman ® Antifungal Cream |
| 2 | Equate ® Athlete's Foot Cream |
| 3 | Lotrimin ® Ultra Athlete's Foot Cream |
| 4 | Tinactin ® Athlete's Foot Cream |
| 5 | Lamisil ® Athlete's Foot Cream |

FIG. 15 PANEL A shows the extent of clearing of drug-resistant *Candida parapsilosis* when treated with MM1, Derman® Antifungal Cream (1), Equate® Athlete's Foot Cream (2), or Lotrimin® Ultra Athlete's Foot Cream (3) after 1 day. FIG. 15 PANEL B shows the extent of clearing of drug-resistant *Candida parapsilosis* when treated with MM1, Tinactin® Athlete's Foot Cream (4), or Lamisil® Athlete's Foot Cream (5) after 1 day. FIG. 15 PANEL C shows the extent of clearing of drug-resistant *Candida parapsilosis* when treated with MM1, Derman® Antifungal Cream (1), Equate® Athlete's Foot Cream (2), or Lotrimin® Ultra Athlete's Foot Cream (3) after 15 days. FIG. 15 PANEL D shows the extent of clearing of drug-resistant *Candida parapsilosis* when treated with MM1, Tinactin® Athlete's Foot Cream(4), or Lamisil® Athlete's Foot Cream (5) after 15 days.

FIG. 16 compares the effectiveness of MM1 and commercially available formulations in killing drug-resistant *Candida parapsilosis* after 1 day and 15 days of treatment. The data show that MM1 was more effective at killing drug-resistant *Candida parapsilosis* than Derman® Antifungal Cream, Equate® Athlete's Foot Cream, Lotrimin® Ultra Athlete's Foot Cream, Tinactin® Athlete's Foot Cream, and Lamisil® Athlete's Foot Cream after 1 day and 15 days of treatment. Derman® Antifungal Cream, Lotrimin® Ultra Athlete's Foot Cream, Tinactin® Athlete's Foot Cream, and Lamisil® Athlete's Foot Cream were ineffective at killing drug-resistant *Candida parapsilosis*, and had diameters of clearance of less than 0.25 cm.

e. Drug-Resistant *C. auris* (CDC 0383)

The ability of MM1, Derman® Antifungal Cream, Equate® Athlete's Foot Antifungal Cream, Lotrimin® cream, Tinactin® cream, and Lamisil® cream to kill drug-resistant *C. auris* (CDC 0383) was tested. Drug-resistant *Candida auris* (CDC 0383) was grown in YM media for 24 hours at 37° C. A lawn of undiluted *C. auris* (~1×10$^8$ CFU/mL) was spread on an MHA plate. 10 µL of MM1 was spotted onto the inoculated MHA plate, and approximately 10 µL drops of Derman® Antifungal Cream, Equate® Athlete's Foot Antifungal Cream, Lotrimin® Ultra Athlete's Foot cream, Tinactin® Athlete's Foot cream, and Lamisil® Athlete's Foot cream were spotted on different areas of the MHA plate to test the efficacy of killing *C. auris* of the formulations after a 48 hour incubation period at 37° C.

TABLE 7 shows the formulations that were used on the agar plates infected with drug-resistant *C. auris* (CDC 0383).

TABLE 7

| Label | Excipient (PG) |
| --- | --- |
| MM1 | MM1 |
| 1 | Derman ® Antifungal Cream |
| 2 | Equate ® Athlete's Foot Cream |
| 3 | Lotrimin ® Ultra Athlete's Foot Cream |
| 4 | Tinactin ® Athlete's Foot Cream |
| 5 | Lamisil ® Athlete's Foot Cream |

FIG. 17 PANEL A shows the diameter of clearing (cm) of drug-resistant *C. auris* (CDC 0383) when treated with MM1, Derman® Antifungal Cream (1), Equate® Athlete's Foot Cream (2), or Lotrimin® Ultra Athlete's Foot Cream (3) after 1 day. FIG. 17 PANEL B shows the diameter of clearing (cm) of drug-resistant *C. auris* (CDC 0383) when treated with MM1, Tinactin® Athlete's Foot Cream (4), or Lamisil® Athlete's Foot Cream (5) after 1 day. FIG. 17 PANEL C shows the diameter of clearing (cm) of drug-resistant *C. auris* (CDC 0383) when treated with MM1, Derman® Antifungal Cream (1), Equate® Athlete's Foot Cream (2), or Lotrimin® Ultra Athlete's Foot Cream (3) after 15 days. FIG. 17 PANEL D shows the diameter of clearing (cm) of drug-resistant *C. auris* (CDC 0383) when treated with MM1, Tinactin® Athlete's Foot Cream (4), or Lamisil® Athlete's Foot Cream (5) after 15 days.

FIG. 18 compares the effectiveness of MM1 and commercially available formulations in killing drug-resistant *C. auris* (CDC 0383) after 1 day and 15 days of treatment. The data show that MM1 was more effective at killing drug-resistant *C. auris* (CDC 0383) than Derman® Antifungal Cream, Equate® Athlete's Foot Cream, Lotrimin® Ultra Athlete's Foot Cream, Tinactin® Athlete's Foot Cream, and Lamisil® Athlete's Foot Cream were after 1 day and 15 days of treatment. Derman® Antifungal Cream and Equate® Athlete's Foot Cream resulted in a diameter of clearance that was about half that of MM1. Lotrimin® Ultra Athlete's Foot Cream, Tinactin® Athlete's Foot Cream, and Lamisil® Athlete's Foot Cream were ineffective at killing drug-resistant *C. auris* (CDC 0383), and had diameters of clearance of less than 0.25 cm.

f. Drug Resistant *C. auris* (CDC 0383)

The ability of MM1, Derman® Antifungal Cream, Equate® Athlete's Foot Antifungal Cream, Lotrimin® cream, Tinactin® cream, and Lamisil® cream to kill multi drug-resistant *C. auris* (CDC 0383) was tested. Multi-drug-resistant *Candida auris* (CDC 0383) was grown in YM media for 24 hours at 37° C. A lawn of undiluted *C. auris* (~1×10$^8$ CFU/mL) was spread on an MHA plate. 10 µL of MM1 was spotted onto the inoculated MHA plate, and approximately 10 µL drops of Derman® Antifungal Cream, Equate® Athlete's Foot Cream, Lotrimin® Ultra Athlete's Foot cream, Tinactin® Athlete's Foot cream, and Lamisil® Athlete's Foot cream were spotted on different areas of the plate to test for the efficacy of the formulations against *C. auris* after a 48 hour incubation at 37° C.

TABLE 8 shows the formulations that were used on the agar plates infected with multi drug-resistant *C. auris* (CDC 0383).

TABLE 8

| Label | Excipient (PG) |
|---|---|
| MM1 | MM1 |
| 1 | Derman ® Antifungal Cream |
| 2 | Equate ® Athlete's Foot Cream |
| 3 | Lotrimin ® Ultra Athlete's Foot Cream |
| 4 | Tinactin ® Athlete's Foot Cream |
| 5 | Lamisil ® Athlete's Foot Cream |

FIG. 19 PANEL A shows the diameter of clearing (cm) of drug-resistant *C. auris* (CDC 0383) when treated with MM1, Derman® Antifungal Cream (1), Equate® Athlete's Foot Cream (2), or Lotrimin® Ultra Athlete's Foot Cream (3). FIG. 19 PANEL B shows the diameter of clearing (cm) of drug-resistant *C. auris* (CDC 0383) when treated with MM1, Tinactin® Athlete's Foot Cream (4), or Lamisil® Athlete's Foot Cream (5).

FIG. 20 compares the effectiveness of MM1 and commercially available formulations in killing drug-resistant *C. auris* (CDC 0383). The data show that MM1 was more effective at killing drug-resistant *C. auris* (CDC 0383) than Derman® Antifungal Cream, Equate® Athlete's Foot Cream, Lotrimin® Ultra Athlete's Foot Cream, Tinactin® Athlete's Foot Cream, and Lamisil® Athlete's Foot Cream were. Treatment with Derman® Antifungal Cream resulted in a diameter of clearance that was less than half that of MM1. Treatment with Equate® Athlete's Foot Cream resulted in a diameter of clearance that was about 75% that of MM1. Lotrimin® Ultra Athlete's Foot Cream, Tinactin® Athlete's Foot Cream, and Lamisil® Athlete's Foot Cream were ineffective at killing drug-resistant *C. auris* (CDC 0383), and had diameters of clearance that were approximately zero.

g. Multi-Drug-Resistant *C. auris* (CDC 0385)

The ability of MM1, Derman® Antifungal Cream, Equate® Athlete's Foot Antifungal Cream, Lotrimin® Ultra Athlete's Foot Cream, Tinactin® Athlete's Foot Cream, and Lamisil® Athlete's Foot Cream to kill drug-resistant *C. auris* (CDC 0385) was tested. Multi-drug-resistant *Candida auris* (CDC 0385) was grown in YM media for 24 hours at 37° C. A lawn of undiluted *C. auris* (~1×10$^8$ CFU/mL) was spread on an MHA plate. 10 µL of MM1 was spotted onto the inoculated MHA plate, and approximately 10 µL drops of Derman® Antifungal Cream, Equate® Athlete's Foot Antifungal Cream, Lotrimin® Ultra Athlete's Foot cream, Tinactin® Athlete's Foot cream, and Lamisil® Athlete's Foot cream were spotted on different areas of the plate to test for the efficacies of the formulations in killing multi-drug resistant *C. auris* after a 48 hour incubation at 37° C.

TABLE 9 shows the formulations that were used on the agar plates infected with multi drug-resistant *C. auris* (CDC 0385).

TABLE 9

| Label | Excipient (PG) |
|---|---|
| MM1 | MM1 |
| 1 | Derman ® Antifungal Cream |
| 2 | Equate ® Athlete's Foot Cream |
| 3 | Lotrimin ® Ultra Athlete's Foot Cream |
| 4 | Tinactin ® Athlete's Foot Cream |
| 5 | Lamisil ® Athlete's Foot Cream |

FIG. 21 PANEL A shows the diameter of clearing (cm) of multi drug-resistant *C. auris* (CDC 0385) when treated with MM1, Derman® Antifungal Cream (1), Equate® Athlete's Foot Cream (2), or Lotrimin® Ultra Athlete's Foot Cream (3) after 1 day. FIG. 21 PANEL B shows the diameter of clearing (cm) of multi drug-resistant *C. auris* (CDC 0385) when treated with MM1, Tinactin® Athlete's Foot Cream (4), or Lamisil® Athlete's Foot Cream (5) after 1 day. FIG. 21 PANEL C shows the diameter of clearing (cm) of multi drug-resistant *C. auris* (CDC 0385) when treated with MM1, Derman® Antifungal Cream (1), Equate® Athlete's Foot Cream (2), or Lotrimin® Ultra Athlete's Foot Cream (3) after 15 days. FIG. 21 PANEL D shows the diameter of clearing (cm) of multi drug-resistant *C. auris* (CDC 0385) when treated with MM1, Tinactin® Athlete's Foot Cream (4), or Lamisil® Athlete's Foot Cream (5) after 15 days.

FIG. 22 compares the effectiveness of MM1 and commercially available formulations in killing multi drug-resistant *C. auris* (CDC 0385) after 1 day or 15 days of treatment. The data show that MM1 was more effective at killing multi drug-resistant *C. auris* (CDC 0385) than Derman® Antifungal Cream, Equate® Athlete's Foot Cream, Lotrimin® Ultra Athlete's Foot Cream, Tinactin® Athlete's Foot Cream, or Lamisil® Athlete's Foot Cream after 1 day or 15 days of treatment. Derman® Antifungal Cream resulted in a diameter of clearance that was about half that of MM1. Equate® Athlete's Foot Cream, Lotrimin® Ultra Athlete's Foot Cream, Tinactin® Athlete's Foot Cream, and Lamisil® Athlete's Foot Cream were ineffective at killing multi drug-resistant *C. auris* (CDC 0385), and had diameters of clearance of less than 0.25 cm.

The abilities of MM1 and Monistat® 3 Complete Therapy System in killing multi drug-resistant *C. auris* (CDC 0385) were compared. The active ingredient of Monistat® 3 Complete Therapy System is miconazole nitrate (2%); the inactive ingredients of Monistat® 3 Complete Therapy System are benzoic acid, cetyl alcohol, isopropyl myristate, polysorbate 60, potassium hydroxide, propylene glycol, purified water, and stearyl alcohol. Equal volumes of MM1 prepared in PBS (MM1(PBS)), MM1 prepared in PG (MM1(PG)), and Monistat® 3 Complete Therapy System were applied on a lawn of multi-drug resistant *C. auris* (CDC 0385). Multidrug-resistant *Candida auris* (CDC 0385), was grown in YM media for 24 hours at 37° C. A lawn of undiluted *C. auris* (~1×10$^8$ CFU/mL) was spread on an MHA plate. 10 μL of MM1 was spotted onto the inoculated MHA plate, and approximately 10 μL drops of Monistat® 3 Complete Therapy System was spotted on a different area of the MHA plate to test for the efficacy of killing multi drug-resistant *C. auris* after a 48 hour incubation at 37° C.

FIG. 23 compares the effectiveness of Monistat® 3 Complete Therapy System, MM1 prepared in PBS, and MM1 prepared in PG in killing multi-drug resistant *C. auris* (CDC 0385). The data show that Monistat® 3 Complete Therapy System had no effect in killing multi-drug resistant *C. auris* (CDC 0385), and had a diameter of clearance of 0 cm. MM1 (PBS) and MM1 (PG) produced large diameters of clearance, demonstrating efficacy in killing multi-drug resistant *C. auris* (CDC 0385).

The ability of MM1 in killing multi-drug resistant *C. auris* (CDC 0385) in the form of a mouthwash and douche was tested. A 12-well plate filled with MHA was inoculated with multi-drug resistant *C. auris* (CDC 0385) and incubated overnight at 37° C., and the multi-drug resistant *C. auris* (CDC 0385) was allowed to grow into a thick lawn of cells. 500 μL of 1×PBS was added to the control wells (FIG. 24, row A), and 500 μL of MM1 was added to the MM1 wells (FIG. 24, rows B and C). The PBS and MM1 solutions were removed at 0 min (30 sec), 5 min, 15 min, and 30 min after initial addition of the solutions to simulate the time and coverage that would be achieved with a typical mouthwash or douche. The plate was incubated at 37° C. for 4 days after treatment. FIG. 24 shows the 12-well plate used to simulate the use of MM1 as a mouthwash and a douche. A single exposure (30 sec rinse) to MM1 killed and limited the growth of multi-drug resistant *C. auris* (CDC 0385) on a heavily-infected biofilm/surface.

The ability of MM1 to kill multi-drug resistant *C. auris* (CDC 0385) on moist, body cavity-like pre-treated surfaces was tested. 4 wells of a 12-well plate coated with MHA were pre-treated with 500 μL MM1 or 500 μL MHB (positive growth control) for 30 seconds, 5 minutes, 15 minutes, or 30 minutes The MM1 was removed, and the wells were washed 3 times with PBS. The wells were washed with PBS were inoculated with multi-drug resistant *C. auris* (CDC 0385). The plate was then incubated for 4 days at 37° C.

FIG. 25 shows the results of 1) wells pre-treated with MM1 and inoculated with multi-drug resistant *C. auris* (CDC 0385), 2) wells pre-treated with MHB and inoculated with multi-drug resistant *C. auris* (CDC 0385), 3) wells inoculated with multi-drug resistant *C. auris* (CDC 0385) and treated with MM1, and 4) wells inoculated with multi-drug resistant *C. auris* (CDC 0385) and treated with MHB. The wells pre-treated with MM1 and inoculated with multi-drug resistant *C. auris* (CDC 0385) showed minimal growth of multi-drug resistant *C. auris* (CDC 0385), while wells pre-treated with the MHB control and inoculated with multi-drug resistant *C. auris* (CDC 0385) showed growth of multi-drug resistant *C. auris* (CDC 0385). Wells that were first inoculated with multi-drug resistant *C. auris* (CDC 0385) showed killing of the fungus upon treatment with MM1, but exhibited full growth of the fungus when treated with the MHB control. Row C has no wells.

FIG. 26 compares the effect of MM1 and the MHB control on the growth of multi-drug resistant *C. auris* (CDC 0385) when applied to a surface prior to inoculation of multi-drug resistant *C. auris* (CDC 0385) (black), or when applied to a surface after the surface was inoculated with multi-drug resistant *C. auris* (CDC 0385). The data show that MM1 was effective at preventing the growth of multi-drug resistant *C. auris* (CDC 0385) and/or killing of multi-drug resistant *C. auris* (CDC 0385). The y-axis is the optical density at 595 nm, which corresponds to cell viability.

h. *Candida krusei* (CDC 0397)

The ability of MM1, Derman® Antifungal Cream, Equate® Athlete's Foot Cream, Lotrimin® Ultra Athlete's Foot Cream, Tinactin® Athlete's Foot Cream, and Lamisil® Athlete's Foot Cream to kill *Candida krusei* (CDC 0397) was tested. *Candida krusei* (CDC 0397), was grown in YM media for 24 hours at 37° C. A lawn of undiluted *Candida krusei* (~100 μL of 1×10$^8$ CFU/mL) was spread on an MHA plate. 10 μL of MM1 was spotted onto the inoculated MHA plate, and approximately 10 μL drops of Derman® Antifungal Cream, Equate® Athlete's Foot Cream, Lotrimin® Ultra Athlete's Foot cream, Tinactin® Athlete's Foot cream, or Lamisil® Athlete's Foot cream were spotted on different areas of the plate to test for the efficacy of killing after a 48 hour incubation at 37° C.

TABLE 10 shows the formulations that were used on the agar plates infected with *Candida krusei* (CDC 0397).

TABLE 10

| Label | Excipient (PG) |
|---|---|
| MM1 | MM1 |
| 1 | Derman ® Antifungal Cream |
| 2 | Equate ® Athlete's Foot Cream |
| 3 | Lotrimin ® Ultra Athlete's Foot Cream |
| 4 | Tinactin ® Athlete's Foot Cream |
| 5 | Lamisil ® Athlete's Foot Cream |

FIG. 27 PANEL A shows the clearing of *Candida krusei* (CDC 0397) when treated with MM1, Derman® Antifungal Cream (1), Equate® Athlete's Foot Cream (2), or Lotrimin® Ultra Athlete's Foot Cream (3) after 1 day. FIG. 27 PANEL B shows the clearing of *Candida krusei* (CDC 0397) when treated with MM1, Tinactin® Athlete's Foot Cream (4), or Lamisil® Athlete's Foot Cream (5) after 1 day. FIG. 27 PANEL C shows the clearing of *Candida krusei* (CDC 0397) when treated with MM1, Derman® Antifungal Cream (1), Equate® Athlete's Foot Cream (2), or Lotrimin® Ultra Athlete's Foot Cream (3) after 15 days. FIG. 27 PANEL D shows the clearing of *Candida krusei* (CDC 0397) when treated with a single dose of MM1, Tinactin® Athlete's Foot Cream (4), or Lamisil® Athlete's Foot Cream (5) after 15 days.

FIG. 28 compares the effectiveness of MM1 and commercially available formulations in killing *Candida krusei* (CDC 0397). The data show that MM1 was more effective at killing *Candida krusei* (CDC 0397) than Derman® Antifungal Cream, Equate® Athlete's Foot Cream, Lotrimin® Ultra Athlete's Foot Cream, Tinactin® Athlete's Foot Cream, and Lamisil® Athlete's Foot Cream were. Treatment with Derman® Antifungal Cream or Equate® Athlete's Foot Cream resulted in a diameter of clearance that was about 30% of the diameter of clearance of MM1. Derman® Antifungal Cream and Equate® Athlete's Foot Cream both exhibited decreased diameters of clearance after 15 days of treatment compared to the diameter of clearance after 1 day of treatment. Treatment with Lotrimin® Ultra Athlete's Foot Cream, Tinactin® Athlete's Foot Cream, and Lamisil® Athlete's Foot Cream were ineffective at killing *Candida krusei* (CDC 0397), each of which resulted in diameters of clearance of less than 0.25 cm.

i. Unidentified Plant Fungus

An unidentified plant fungus was treated with MM1 to test the efficacy of MM1 in killing the unidentified plant fungus. A 12-well MHA plate was inoculated with an unidentified fungus swabbed from a plant and incubated for 1 day at 37° C. to establish a thick layer of fungal growth. 500 μL of 1×PBS was added to the control wells (FIG. 29, row A), and 500 μL of MM1 was added to the MM1 wells (FIG. 29, rows B and C). The PBS and MM1 solutions were removed 30 sec, 1 min, 2 min, and 3 min after initial addition of the solutions. The plate was incubated at 30° C. for 2 days after treatment to determine the killing efficiency of MM1.

FIG. 29 shows the 12-well plate used to treat an unidentified plant fungus with MM1. A 30 second exposure of the plant fungus with MM1 killed and limited the growth of the plant fungus. The wells treated with PBS were overgrown with the plant fungus.

The residual protection ability of MM1 was tested on the unidentified plant fungus. The left 3 wells of a 6-well plate were first washed with MHB for 5 minutes and then treated with 500 μL of MM1 for an additional 5 minutes. All of the MM1 was removed, and the wells were inoculated with the unidentified plant fungus. The 3 wells on the right side of the 6-well plate were first treated with 500 μL of MM1 for 5 minutes. After the 5 minute treatment, the MM1 was removed, and the wells were washed with MHB for an additional 5 minutes. The MHB was removed, and the wells were inoculated with the unidentified plant fungus. In the left half of the 6-well plate, 2 of the 3 wells were pre-treated with 500 μL MM1 and 1 of the wells was treated with MHB to serve as a positive growth control. All of the 3 wells were inoculated with the unidentified plant fungus. In the right half of the 6-well plate, 2 of the 3 wells were pre-treated with 500 μL MM1 and subsequently washed with 500 μL MHB to further determine MM1 residual protection upon dilution. The remaining well was treated with 500 μL MHB to serve as a positive growth control. All of the 3 wells were inoculated with the unidentified plant fungus.

FIG. 30 PANEL A shows a 6-well plate with 2 wells pre-treated with MM1 with no subsequent washes, 2 wells pre-treated with an MM1 and then washed with MHB to remove any remaining MM1, or 2 wells washed with only MHB which served as a positive growth control after 2 days of incubation. FIG. 30 PANEL B shows the unidentified plant fungus that was used for the residual protection assay. FIG. 30 PANEL C shows the 6-well plate with 4 wells pre-treated with MM1 and 2 wells pre-treated with an MHB control after 7 days of incubation. The results show that pre-treatment of the wells with MMJ prior to inoculation with the unidentified plant fungus inhibited growth of the plant fungus for an extended period of time.

Example 4: Antiseptic Properties of MM7 on MRSA (BAA-44), *Acinetobacter baumannii* (ATCC 1797), *Pseudomonas aeruginosa* (ATCC 2114), and Multi-Drug Resistant *C. auris* (CDC 0385)

MRSA (BAA-44), *Acinetobacter baumannii* (ATCC 1797), *Pseudomonas aeruginosa* (ATCC 2114), and multi-drug resistant *C. auris* (CDC 0385) cells were grown overnight in MHB, diluted 1:10, and plated on 4 different MHA plates. Each plate was spotted with 10 μL of MM7 and 10 μL of chlorhexidine gluconate 0.12% oral rinse. The plates were incubated at 37° C. overnight. MM7 killed MRSA (BAA-44), *Acinetobacter baumannii* (ATCC 1797), *Pseudomonas aeruginosa* (ATCC 2114), and multi-drug resistant *C. auris* (CDC 0385) cells. MM7 exhibited similar activity to the chlorohexidine gluconate 0.12% oral rinse in killing MRSA (BAA-44) and *Pseudomonas aeruginosa* (ATCC 2114). MM7 demonstrated greater efficacy at killing *Acinetobacter baumannii* (ATCC 1797) and multi-drug resistant *C. auris* (CDC 0385) than did the chlorohexidine gluconate 0.12% oral rinse.

FIG. 31 PANEL A shows the abilities of MM7 and the chlorohexidine gluconate 0.12% oral rinse in killing MRSA (BAA-44). FIG. 31 PANEL B shows the abilities of MM7 and the chlorohexidine gluconate 0.12% oral rinse in killing *Acinetobacter baumannii* (ATCC 1797). FIG. 31 PANEL C shows the abilities of MM7 and the chlorohexidine gluconate 0.12% oral rinse in killing *Pseudomonas aeruginosa* (ATCC 2114). FIG. 31 PANEL D shows the abilities of MM7 and the chlorohexidine gluconate 0.12% oral rinse in killing multi-drug resistant *C. auris* (CDC 0385).

Example 5: Preparation of MM8

A solution of DTPA was prepared by dissolving DTPA powder into a mixture of 50% sterile water and 50% 10M NaOH to obtain a 500 mM stock solution. The pH of the DTPA stock solution was adjusted to pH ~7.4 using concentrated hydrochloric acid. A solution of a 780 mM CTAC stock solution was aliquoted into a sterile 1.6 mL micro tube. A solution of polymyxin B (PMB) was prepared by dissolving 10 mg of PMB into 1 mL of sterile water, and filtering the resulting solution through a 0.22 μm filter. 20 μL of the 500 mM DPTA stock solution, 1.2 μL of the 780 mM CTAC stock solution, 2.5 μL of 10 mg/mL PMB solution, and 976 μL of PG were mixed to provide MM8. The final concentrations of the components of MM8 are shown in TABLE 11.

TABLE 11

| Formulation | CTAC | DTPA | PMB | Solvent |
| --- | --- | --- | --- | --- |
| MM8 | 1 mM | 10 mM | 25 μg/mL | PG |

Example 6: Efficacy of MM8 as an Anti-Fungal Agent

The efficacy of MM8 as an anti-fungal and anti-bacterial agent was tested. An undiluted overnight grow of fungi was spread on an MHA plate. A 1:10 dilution of bacteria (100 μL of ~1×10$^8$ CFU/mL) in MHB broth was spread on a different MHA plate. 10 μL of MM8 and chlorohexidine gluconate 0.12% oral rinse were spotted on the MHA plate containing fungi, and the plate was incubated at 28° C. for 24-48 hours. 10 μL of MM8 and chlorohexidine gluconate 0.12% oral rinse were spotted on the MHA plate containing bacteria, and the plate was incubated at 37° C. for 24-48 hours.

The toxicity of MM8 in mammalian cells was compared to the toxicity of chlorohexidine gluconate 0.12% oral rinse using HeLa cells. HeLa cells were grown in a 5% $CO_2$ humidified incubator at 37° C. HeLa cells were plated in a 96-well plate to a cell density of 4000 cells/well in DMEM with 1% penicillin/streptomycin and 10% fetal bovine serum (FBS). The cells were treated with MM8 or chlorohexidine gluconate 0.12% oral rinse concentrations of 0.004%, 0.008%, 0.016%, 0.0310%, 0.0625%, 0.125%, 0.25%, 0.5%, and 1% v/v of the compounds. The cells were incubated with the compounds for 48 hr. MTT was used to assess the cell viability after the 48 hour incubation. MTT (5 mg/mL) was added to each well at a final volume of 10%, incubated for 2 hours at 37° C. in a 5% $CO_2$ incubator, and solubilized in 100 μL of DMSO before the absorbance was read at 595 nm.

FIG. 32 shows the toxicity of chlorohexidine gluconate 0.12% oral rinse against HeLa cells. Chlorohexidine gluconate 0.12% oral rinse had an $IC_{50}$ ($GI_{50}$) of 0.09% v/v of the compound. FIG. 33 shows the toxicity of MM8 against HeLa cells. MM8 had an $IC_{50}$ ($GI_{50}$) of 0.22% v/v of the compound. TABLE 12 shows the $GI_{50}$ (% v/v) and SD % of the compounds.

TABLE 12

| Compound | $GI_{50}$ (% v/v) | SD % |
| --- | --- | --- |
| MM8 | 0.09 | 4 |
| chlorohexidine gluconate 0.12% oral rinse | 0.22 | 3 |

MM8, Lotrimin® Ultra Athlete's Foot Cream, Tinactin® Athlete's Foot Cream, Lamisil® Athlete's Foot Cream, and Monistat® 3 Complete Therapy System were tested against antibiotic-sensitive and antibiotic-resistant fungal pathogens. *Candida albicans*, drug-resistant *Candida parapsilosis* (CDC 0339), drug-resistant *C. auris* (CDC 0383), multi-drug-resistant *C. auris* (CDC 0385), *C. tropicalis* (CDC 0345), *C. haemulonii* (CDC 0393), *C. glabrata* (CDC 0315), *C. duobushaemulonii* (CDC 0394), *Candida krusei* (CDC 0397), *Cryptococcus neoformans* (H99), and *Cryptococcus gattii* (K265) were grown in YM media for 24-48 hours at 37° C. *Trichophyton rubrum* was grown in YM media for 21 days at 30° C., and *Aspergillus niger* was grown for 5 days at 30° C. Approximately $1\times10^8$ CFU/mL of each culture was spread onto 100×15 mm square petri dishes containing MHA. Upon spreading a lawn of each fungal strain, 10 μL of MM8 was spotted onto respective areas of the inoculated MHA plate, and approximately 10 μL drops of Lotrimin® Ultra Athlete's Foot Cream, Tinactin® Athlete's Foot Cream, Lamisil® Athlete's Foot Cream, and Monistat® 3 Complete Therapy System were spotted on different areas of the plate to test for the efficacy of the formulations in killing the fungal strains (48 hour incubation at 37° C. for *Candida* and Cryptococcal species, 30 days at 28° C. for *Trichophyton rubrum*, and 7 days at 28° C. for *Aspergillus niger*).

TABLE 13 shows that MM8 killed all 12 strains of the antibiotic-sensitive and antibiotic-resistant fungal pathogens. Lotrimin® Ultra Athlete's Foot Cream, Tinactin® Athlete's Foot Cream, Lamisil® Athlete's Foot Cream, and Monistat® 3 Complete Therapy System were all killed *Trichophyton rubrum*. Monistat® 3 killed 8 out of the 12 antibiotic-sensitive and antibiotic-resistant fungal pathogens. "+" indicates antifungal activity with complete clearing; "−" indicates no antifungal activity.

TABLE 13

| Organism | MM8 | Lotrimin® Ultra | Tinactin® | Lamisil® | Monistat® 3 |
| --- | --- | --- | --- | --- | --- |
| *C. albicans* | + | − | − | − | − |
| *C. auris* (CDC 0385) | + | − | − | − | − |
| *C. tropicalis* (CDC 0345) | + | − | − | − | − |
| *C. krusei* (CDC 0397) | + | − | − | − | + |
| *C. haemulonii* (CDC 0393) | + | − | − | − | + |
| *C. glabrata* (CDC 0315) | + | − | − | − | + |
| *C. duobushaemulonii* (CDC 0394) | + | − | − | − | + |
| *C. parapsilosis* (CDC 0339) | + | − | − | − | + |
| *Aspergillus niger* | + | − | − | + | + |
| *Trichophyton rubrum* (ATCC 28188) | + | + | + | + | + |
| *Cryptococcus neoformans* (H99) | + | − | − | + | + |
| *Cryptococcus gattii* (K265) | + | − | − | − | − | a. *Candida albicans* (ATCC 26555)

A solution of MM8 was prepared in water (10 mM DTPA, 1 mM CTAC, 25 μg/mL PMB). To 6 wells containing agar, 500 μL of water (control) or the MM8 solution was added. The plate was incubated for 5 days at 37'° C. The water and MM8 solution were removed from the wells. A lawn of 1:10 diluted *Candida albicans* (100 μL of ~$1\times10^7$ CFU/mL) was added to the wells. The plates were incubated for 5 days at 37° C. FIG. 34 PANEL A shows that wells that received treatment with water exhibited no protection from *Candida albicans*, while wells treated with MM8 exhibited residual protection. An analogous assay was performed on multi drug-resistant *C. auris* (CDC 0385); wells that received treatment with water exhibited no protection from *C. auris*, while wells treated with MM8 exhibited residual protection from fungal growth.

A lawn of 1:10 diluted *Candida albicans* (50 μL of ~$1\times10^7$ CFU/mL) was spread onto an agar plate. The plate was incubated for 2 days at 37° C. The plates were then treated for 5 minutes with 500 μL of water (control) or MM8 solution. The treatments were removed, and the plate was incubated for an additional 3 days at 37° C. The treatment sections were each swabbed, and a new MHA plate was inoculated to check for the presence of live cells.

FIG. 34 PANEL B TOP LEFT PANEL shows that the well pre-treated with water and inoculated with *Candida albicans* did not have residual protection from the fungus. FIG. 34 PANEL B TOP RIGHT PANEL shows that the well pre-treated with MM8 and inoculated with *Candida albicans* exhibited residual protection from the fungus. FIG. 34 PANEL B BOTTOM LEFT PANEL shows that the *Candida albicans*-infected MHA plate treated with water did not exhibit protection against the fungus. FIG. 34 PANEL B BOTTOM RIGHT PANEL shows that the *Candida albicans*-infected MHA plate treated with MM8 exhibited protection against the fungus. Analogous results were obtained upon evaluation with *C. auris* (CDC 0385). FIG. 34 PANEL C shows that the *C. auris*-infected MHA plate treated with MM8 exhibited protection against *C. auris*.

An MHA plate was swabbed with *Candida albicans*, and treated with MM8, Lotrimin® Ultra Athlete's Foot Cream, Tinactin® Athlete's Foot Cream, Lamisil® Athlete's Foot Cream, and Monistat® 3 Complete Therapy System. *Candida albicans* (ATCC 26555) or *C. auris* (CDC 0385) were grown in YM media for 24 hours at 37° C. A lawn of 1:10 diluted *Candida albicans* or *C. auris* (~100 μL of ~$1\times10^7$ CFU/mL) was spread on a MHA plate. 10 μL of MM8 was spotted onto the inoculated MHA plate, and approximately 10 μL of Lotrimin® Ultra Athlete's Foot Cream, Tinactin® Athlete's Foot Cream, Lamisil® Athlete's Foot Cream, and Monistat® 3 Complete Therapy System was spotted on the MHA plate to test for the efficacy of the formulations in killing the fungus after a 48 hour incubation at 37° C.

FIG. 35 PANEL A shows that MM8 and Monistat® 3 killed *Candida albicans*, while Lotrimin® Ultra Athlete's Foot Cream, Tinactin® Athlete's Foot Cream, and Lamisil® Athlete's Foot Cream did not kill *Candida albicans*. The circle encloses the diameter of clearance of MM8. FIG. 35 PANEL B compares the diameter of clearance (mm) of MM8, Lotrimin® Ultra Athlete's Foot Cream, Tinactin® Athlete's Foot Cream, Lamisil® Athlete's Foot Cream, and Monistat® 3 Complete Therapy System when used to treat *Candida albicans*. FIG. 36 shows that treatment with Monistat® 3 Complete Therapy System resulted in invasion of the colonies at the border of the diameter of clearance, resulting in a smaller diameter of clearance than MM8.

b. Multi Drug-Resistant *C. auris* (CDC 0385)

An MHA plate was swabbed with multi-drug resistant *C. auris* (CDC 0385), and treated with MM8, Lotrimin® Ultra Athlete's Foot Cream, Tinactin® Athlete's Foot Cream, Lamisil® Athlete's Foot Cream, and Monistat® 3 Complete Therapy System. Multi-drug-resistant *Candida auris* (CDC0385) was grown in YM media for 24 hours at 37° C. A lawn of 1:10 diluted *C. auris* (~100 μL of ~1×10$^7$ CFU/mL) was spread on a MHA plate. 10 μL of MM8 was spotted onto the inoculated MHA plate, and approximately 10 μL drop of Lotrimin® Ultra Athlete's Foot Cream, Tinactin® Athlete's Foot Cream, Lamisil® Athlete's Foot Cream, and Monistat® 3 Complete Therapy System were spotted to test for the efficacy of the formulations in killing the fungi after a 48 hour incubation at 37° C.

FIG. 37 PANEL A shows that MM8 and Monistat® 3 killed multi-drug resistant *C. auris* (CDC 0385), while Lotrimin® Ultra Athlete's Foot Cream, Tinactin® Athlete's Foot Cream, and Lamisil® Athlete's Foot Cream did not kill multi-drug resistant *C. auris* (CDC 0385). The circle encloses the diameter of clearance created by treatment with MM8. FIG. 37 PANEL B compares the diameter of clearance (mm) of MM8, Lotrimin® Ultra Athlete's Foot Cream, Tinactin® Athlete's Foot Cream, Lamisil® Athlete's Foot Cream, and Monistat® 3 Complete Therapy System when used to treat multi-drug resistant *C. auris* (CDC 0385). MM8 was the only formulation that had a diameter of clearance.

c. *Candida krusei* (CDC 0397)

An MHA plate was swabbed with *Candida krusei* (CDC 0397), and treated with MM8, Lotrimin® Ultra Athlete's Foot Cream, Tinactin® Athlete's Foot Cream, Lamisil® Athlete's Foot Cream, and Monistat® 3 Complete Therapy System. *Candida krusei* (CDC0397) was grown in YM media for 48 hours at 37° C. A lawn of undiluted *Candida krusei* (~100 μL of ~1×10$^7$ CFU/mL) was spread on an MHA plate. 10 μL of MM8 was spotted onto the inoculated MHA plate, and approximately 10 μL drops of Lotrimin® Ultra Athlete's Foot Cream, Tinactin® Athlete's Foot Cream, Lamisil® Athlete's Foot Cream, and Monistat® 3 Complete Therapy System was spotted on the MHA plate to test the efficacy of the formulations in killing fungi after a 72 hour incubation at 37° C.

FIG. 38 PANEL A shows that MM8 and Monistat® 3 killed *Candida krusei* (CDC 0397), while Lotrimin® Ultra Athlete's Foot Cream, Tinactin® Athlete's Foot Cream, and Lamisil® Athlete's Foot Cream did not kill multi-drug resistant *Candida krusei* (CDC 0397). The circle encloses the diameter of clearance created by treatment with MM8. FIG. 38 PANEL B compares the diameter of clearance (mm) of MM8, Lotrimin® Ultra Athlete's Foot Cream, Tinactin® Athlete's Foot Cream, Lamisil® Athlete's Foot Cream, and Monistat® 3 Complete Therapy System when used to treat multi drug-resistant *C. auris* (CDC 0385). MM8 was the only formulation that had a diameter of clearance. FIG. 39 shows that treatment with Monistat® 3 Complete Therapy System resulted in invasion of the colonies at the border of the diameter of clearance, resulting in a smaller diameter of clearance than MM8.

d. *Candida glabrata* (CDC 0315)

An MHA plate was swabbed with *Candida glabrata* (CDC 0315), and treated with MM8, Lotrimin® Ultra Athlete's Foot Cream, Tinactin® Athlete's Foot Cream, Lamisil® Athlete's Foot Cream, and Monistat® 3 Complete Therapy System. *Candida glabrata* (CDC0315) was grown in YM media for 24 hours at 37° C. A lawn of 1:10 diluted *Candida glabrata* (~1×10$^7$ CFU/mL) was spread on an MHA plate. 10 μL of MM8 was spotted onto the inoculated MHA plate, and approximately 10 μL drops of Lotrimin® Ultra Athlete's Foot Cream, Tinactin® Athlete's Foot Cream, Lamisil® Athlete's Foot Cream, and Monistat® 3 Complete Therapy System were spotted on the MHA plate to test the efficacy of the formulations in killing the fungi after a 48 hour incubation at 37° C.

FIG. 40 PANEL A shows that MM8 and Monistat® 3 Complete Therapy System killed *Candida glabrata* (CDC 0315), while Lotrimin® Ultra Athlete's Foot Cream, Tinactin® Athlete's Foot Cream, and Lamisil® Athlete's Foot Cream did not kill multi-drug resistant *Candida glabrata* (CDC 0315). The circle encloses the diameter of clearance created by treatment with MM8. FIG. 40 PANEL B compares the diameter of clearance (mm) of MM8, Lotrimin® Ultra Athlete's Foot Cream, Tinactin® Athlete's Foot Cream, Lamisil® Athlete's Foot Cream, and Monistat® 3 Complete Therapy System when used to treat multi-drug resistant *Candida glabrata* (CDC 0315).

e. *Candida haemulonii* (CDC 0393)

An MHA plate was swabbed with *Candida haemulonii* (CDC 0393), and treated with MM8, Lotrimin® Ultra Athlete's Foot Cream, Tinactin® Athlete's Foot Cream, Lamisil® Athlete's Foot Cream, and Monistat® 3 Complete Therapy System. *Candida haemulonii* (CDC0393) was grown in YM media for 24 hours at 37° C. A lawn of 1:10 diluted *Candida haemulonii* (~100 μL of ~1×10$^7$ CFU/mL) was spread on an MHA plate. 10 μL of MM8 was spotted onto the inoculated MHA plate, and approximately 10 μL drops of Lotrimin® Ultra Athlete's Foot Cream, Tinactin® Athlete's Foot Cream, Lamisil® Athlete's Foot Cream, and Monistat® 3 Complete Therapy System were spotted on the MHA plate to test for the efficacy of the formulations in killing the fungi after a 48 hours incubation at 37° C.

FIG. 41 PANEL A shows that MM8 and Monistat® 3 Complete Therapy System killed *Candida haemulonii* (CDC 0393), while Lotrimin® Ultra Athlete's Foot Cream, Tinactin® Athlete's Foot Cream, and Lamisil® Athlete's Foot Cream did not kill multi-drug resistant *Candida haemulonii* (CDC 0393). The circle encloses the diameter of clearance created by treatment with MM8. FIG. 41 PANEL B compares the diameter of clearance (mm) of MM8, Lotrimin® Ultra Athlete's Foot Cream, Tinactin® Athlete's Foot Cream, Lamisil® Athlete's Foot Cream, and Monistat® 3 Complete Therapy System when used to treat multi-drug resistant *Candida haemulonii* (CDC 0393). MM8 and Monistat® 3 Complete Therapy System had similar diameters of clearance (mm).

f. *Candida duobshaemulonii* (CDC 0394)

An MHA plate was swabbed with *Candida duobshaemulonii* (CDC 0394), and treated with MM8, Lotrimin® Ultra Athlete's Foot Cream, Tinactin® Athlete's Foot Cream, Lamisil® Athlete's Foot Cream, and Monistat® 3 Complete Therapy System. *Candida duobshaemulonii* (CDC0394) was grown in YM media for 48 hours at 37° C. A lawn of undiluted *Candida duobshaemulonii* (~100 µL of ~1×10$^7$ CFU/mL) was spread on an MHA plate. 10 µL of MM8 was spotted onto the inoculated MHA plate, and approximately 10 µL drops of Lotrimin® Ultra, Tinactin®, Lamisil®, and Monistat® 3 Complete Therapy System were spotted on the MHA plate to test the efficacies of the formulations in killing the fungi after a 72 hour incubation at 37° C.

FIG. 42 PANEL A shows that MM8, Lamisil® Athlete's Foot Cream, and Monistat® 3 Complete Therapy System killed *Candida duobshaemulonii* (CDC 0394), while Lotrimin® Ultra Athlete's Foot Cream and Tinactin® Athlete's Foot Cream did not kill *Candida duobshaemulonii* (CDC 0394). The circle encloses the diameter of clearance created by treatment with MM8. FIG. 42 PANEL B compares the diameter of clearance (mm) of MM8, Lotrimin® Ultra Athlete's Foot Cream, Tinactin® Athlete's Foot Cream, Lamisil® Athlete's Foot Cream, and Monistat® 3 Complete Therapy System when used to treat *Candida duobshaemulonii* (CDC 0394).

g. *Candida tropicalis* (CDC 0345)

An MHA plate was swabbed with *Candida tropicalis* (CDC 0345), and treated with MM8, Lotrimin® Ultra Athlete's Foot Cream, Tinactin® Athlete's Foot Cream, Lamisil® Athlete's Foot Cream, and Monistat® 3 Complete Therapy System. *Candida tropicalis* (CDC0345) was grown in YM media for 24 hours at 37° C. A lawn of 1:10 diluted *Candida tropicalis* (~100 µL of ~1×10$^7$ CFU/mL) was spread on an MHA plate. 10 µL of MM8 was spotted onto the inoculated MHA plate, and approximately 10 µL drops of Lotrimin® Ultra Athlete's Foot Cream, Tinactin® Athlete's Foot Cream, Lamisil® Athlete's Foot Cream, and Monistat® 3 Complete Therapy System were spotted onto the MHA plate to test the efficacies of the formulations in killing the fungi after a 48 hour incubation at 37° C.

FIG. 43 PANEL A shows that MM8 and Monistat® 3 Complete Therapy System killed *Candida tropicalis* (CDC 0345), while Lotrimin® Ultra Athlete's Foot Cream, Tinactin® Athlete's Foot Cream, and Lamisil® Athlete's Foot Cream did not kill *Candida tropicalis* (CDC 0345). The circle encloses the diameter of clearance created by treatment with MM8. FIG. 43 PANEL B compares the diameter of clearance (mm) of MM8, Lotrimin® Ultra Athlete's Foot Cream, Tinactin® Athlete's Foot Cream, Lamisil® Athlete's Foot Cream, and Monistat® 3 Complete Therapy System when used to treat *Candida tropicalis* (CDC 0345). MM8 was the only formulation that had a diameter of clearance. FIG. 44 shows that treatment with Monistat® 3 Complete Therapy System resulted in invasion of the colonies at the border of the diameter of clearance, resulting in a diameter of clearance of zero mm.

h. *Aspergillus niger*

An MHA plate was swabbed with *Aspergillus niger*, and treated with MM8, Lotrimin® Ultra Athlete's Foot Cream, Tinactin® Athlete's Foot Cream, Lamisil® Athlete's Foot Cream, and Derman® Antifungal Cream. *Aspergillus niger* was grown in YM media for 5 days at 30° C. A lawn of undiluted *A. niger* (~100 µL of ~1×10$^7$ CFU/mL) was spread on an MHA plate. 10 µL of MM8 was spotted onto the inoculated MHA plate, and approximately 10 µL drops of Lotrimin® Ultra Athlete's Foot Cream, Tinactin® Athlete's Foot Cream, Lamisil® Athlete's Foot Cream, and Monistat® 3 Complete Therapy System were spotted on the MHA plate to test the efficacies of the formulations in killing the fungi after a 5 day incubation at 30° C.

FIG. 45 PANEL A shows that MM8, Lamisil® Athlete's Foot Cream, and Derman® Antifungal Cream killed *Aspergillus niger*, while Lotrimin® Ultra Athlete's Foot Cream and Tinactin® Athlete's Foot Cream did not kill *Aspergillus niger*. The circle encloses the diameter of clearance created by treatment with MM8. FIG. 45 PANEL B compares the diameter of clearance (mm) of MM8, Lotrimin® Ultra Athlete's Foot Cream, Tinactin® Athlete's Foot Cream, Lamisil® Athlete's Foot Cream, and Derman® Antifungal Cream when used to treat *Aspergillus niger*. MM8 had a diameter of clearance that was greater than Lamisil® Athlete's Foot Cream and Derman® Antifungal Cream.

i. *Cryptococcus neoformans* (H99)

An MHA plate was swabbed with *Cryptococcus neoformans* (H99), and treated with MM8, Lotrimin® Ultra Athlete's Foot Cream, Tinactin® Athlete's Foot Cream, Lamisil® Athlete's Foot Cream, and Monistat® 3 Complete Therapy System. *Cryptococcus neoformans* (H99) was grown in YM media for 48 hours at 37° C. A lawn of 1:10 diluted *Cryptococcus neoformans* (~100 µL of ~1×10$^7$ CFU/mL) was spread on an MHA plate. 10 µL of MM8 was spotted onto the inoculated MHA plate, and approximately 10 µL drops of Lotrimin® Ultra Athlete's Foot Cream, Tinactin® Athlete's Foot Cream, Lamisil® Athlete's Foot Cream, and Monistat® 3 Complete Therapy System were spotted on the MHA plate to test the efficacies of the formulations in killing the fungi after a 48 hour incubation at 37° C.

FIG. 46 PANEL A shows that MM8 and Monistat® 3 killed *Cryptococcus neoformans* (H99), while Lotrimin® Ultra Athlete's Foot Cream, Tinactin® Athlete's Foot Cream, and Lamisil® Athlete's Foot Cream did not kill *Cryptococcus neoformans* (H99). The circle encloses the diameter of clearance created by treatment with MM8. FIG. 46 PANEL B compares the diameter of clearance (mm) of MM8, Lotrimin® Ultra Athlete's Foot Cream, Tinactin® Athlete's Foot Cream, Lamisil® Athlete's Foot Cream, and Monistat® 3 Complete Therapy System when used to treat *Cryptococcus neoformans* (H99). MM8 had a diameter of clearance that was greater than Lamisil® Athlete's Foot Cream and Derman® Antifungal Cream.

j. *Cryptococcus gattii* (K265)

An MHA plate was swabbed with *Cryptococcus gattii* (K265), and treated with MM8, Lotrimin® Ultra Athlete's Foot Cream, Tinactin® Athlete's Foot Cream, Lamisil® Athlete's Foot Cream, and Monistat® 3 Complete Therapy System. *Cryptococcus gattii* (K265) was grown in YM media for 48 hours at 37° C. A lawn of 1:10 diluted *Cryptococcus gattii* (~100 µL of ~×10$^7$ CFU/mL) was spread on an MHA plate. 10 µL of MM8 was spotted onto the inoculated MHA plate, and approximately 10 µL drops of Lotrimin® Ultra Athlete's Foot Cream, Tinactin® Athlete's Foot Cream, Lamisil® Athlete's Foot Cream, and Monistat® 3 Complete Therapy System were spotted on the MHA plate to test the efficacies of the formulations in killing the fungus after a 48 hour incubation at 37° C.

FIG. 47 PANEL A shows that MM8 and Monistat® 3 Complete Therapy System killed *Cryptococcus gattii* (K265), while Lotrimin® Ultra Athlete's Foot Cream, Tinactin® Athlete's Foot Cream, and Lamisil® Athlete's Foot Cream did not kill *Cryptococcus gattii* (K265). The circle encloses the diameter of clearance created by treatment with MM8. FIG. 47 PANEL B compares the diameter of clearance (mm) of MM8, Lotrimin® Ultra Athlete's Foot Cream, Tinactin® Athlete's Foot Cream, Lamisil® Athlete's Foot Cream, and Monistat® 3 Complete Therapy System when used to treat *Cryptococcus gattii* (K265).

k. *Geomyces destructans* (ATCC MYA4855)

An MHA plate was swabbed with *Geomyces destructans*, the causative agent of the White-nose syndrome epidemic in bats, and treated with MM8. *Geomyces destructans* was grown in YM media for 30 days at 8° C. A lawn of undiluted *Geomyces destructans* (~100 µL of ~1×10$^6$ CFU/mL) was spread on an MHA plate. 10 µL of MM8 was spotted onto the inoculated MHA plate to test for the efficacy of MM8 in killing the fungus after a 7 day incubation period at 8° C.

FIG. 48 shows that MM8 killed *Geomyces destructans*. The circle encloses the diameter of clearance created by treatment with MM8.

l. *Trichophyton rubrum* (ATCC 28188)

An MHA plate was swabbed with *Trichophyton rubrum*, and treated with MM8, Lamisil® Athlete's Foot Cream, Tinactin® Athlete's Foot Cream, Lotrimin® Ultra Athlete's Foot Cream, and Derman® Antifungal Cream. *Trichophyton rubrum* was grown in YM media for 30 days at 30° C. A lawn of undiluted *Trichophyton rubrum* (~1×10$^7$ CFU/mL) was spread on an MHA plate. 10 µL of MM8 was spotted onto the inoculated MHA plate, and approximately 10 µL drops of Lotrimin® Ultra Athlete's Foot Cream, Tinactin® Athlete's Foot Cream, Lamisil® Athlete's Foot Cream, and Monistat® 3 Complete Therapy System were spotted on the MHA plate to test the efficacies of the formulations in killing the fungus a 6 day incubation at 28° C.

FIG. 49 PANEL A shows that MM8, Lamisil® Athlete's Foot Cream, Tinactin® Athlete's Foot Cream, and Derman® Antifungal Cream killed *Trichophyton rubrum*. Lamisil® Athlete's Foot Cream was the most effective at killing *Trichophyton rubrum*. At higher concentrations (i.e., 10× concentration), MM8 was as effective at killing *Trichophyton rubrum* as Lamisil®. The circle encloses the diameter of clearance created by treatment with MM8. FIG. 49 PANEL B shows that MM8 was as effective at killing *Trichophyton rubrum* as a chlorhexidine gluconate 0.12% oral rinse. The circle encloses the diameter of clearance created by treatment with MM8.

Example 6: Efficacy of MM8 as an Anti-Bacterial Agent

MM8 was used to test the efficacy of the formulation in killing drug-resistant and drug-sensitive bacteria. Mupirocin, bacitracin, neomycin, and a triple antibiotic were used as comparisons. The formulations were used to test the killing efficacy against Vancomycin-resistant *enterococcus* (VRE), Methicillin-resistant *Staphylococcus aureus* (MRSA), multi-drug resistant carbapenem-resistant Enterobacteriaceae (CRE NDM-1 MDR), multi-drug resistant *Acinetobacter baumannii*, multi-drug resistant *Pseudomonas aeruginosa*, *Escherichia coli* (O157:H7), *Stenotrophomonas maltophilia*, *Mycobacterium abscessus*, *Streptococcus pyogenes*, and *Burkholderia cepacia*.

Vancomycin-resistant *Enterococcus* (VRE) (ATCC 51299), Methicillin-resistant *Staphylococcus aureus* (MRSA) (ATCC BAA), multi-drug-resistant carbapenem-resistant Enterobacteriaceae (CRE NDM-1 MDR) (ATCC BAA 2146), multi-drug-resistant *Acinetobacter baumannii* ((ATCC 1797), multi-drug-resistant *Pseudomonas aeruginosa* (ATCC 2114), *Escherichia coli* (O157:H7) (ATCC 51657), *Stenotrophomonas maltophilia* (ATCC 13637), *Streptococcus pyogenes*, and multi-drug-resistant *Burkholderia cepacia* (ATCC 10856) or non-pathogenic *Yesenia pestis* (Kimo 6) were grown in Mueller-Hinton broth at 37° C. overnight. *Mycobacterium abscessus* was grown in Middlebrook 7H9 broth and incubated for 48 hours at 37° C. Each strain of bacteria, with the exception of VRE and *S. maltophilia*, was diluted 1:10 (~100 µL of ~1×10$^8$ CFU/mL) and plated on an MHA plate to test for the efficacy of killing after first being treated with 10 µL of MM8 and a 10 µL spot of mupirocin, bacitracin, neomycin, and a triple antibiotic ointment. The plates were incubated for 24 to 48 hours at 37° C. before being assessed.

TABLE 14 shows that MM8 killed the 10 strains of antibiotic-sensitive and antibiotic-resistant Gram-positive and Gram-negative bacterial strains that were tested. "+" indicates antibacterial activity with complete clearing, "−" indicates no antibacterial activity.

TABLE 14

| Organism | MM8 | Mupirocin | Bacitracin | Neomycin | Triple antibiotic |
| --- | --- | --- | --- | --- | --- |
| VRE (ATCC 51299) | + | − | − | − | − |
| MRSA (ATCC BAA44) | + | + | − | − | − |
| CRE NDM-1 MDR (ATCC BAA 2146) | + | − | − | − | − |
| *A. Baumannii* MDR (ATCC 1797) | + | − | − | − | − |
| *P. aeruginosa* MDR (ATCC 2114) | + | + | − | − | − |
| *E. Coli* (O157:H7) (ATCC 51657) | + | + | − | + | + |
| *S. maltophilia* (ATCC 13637) | + | − | − | + | + |
| *M. abscessus* (ATCC 19977) | + | − | − | − | − |
| *S. pyogenes* | + | + | − | + | + |
| *B. cepacia* (ATCC 10856) | + | + | − | − | − | a. *Yesenia pestis* (Kimo 6)

An undiluted culture of non-pathogenic Kimo 6 *Yesenia pestis* (100 µL of ~1×10$^9$ CFU/mL) was swabbed on an MHA plate. The inoculated MHA plate was treated with 10 µL of MM8 and with 10 µL spots of mupirocin, bacitracin, neomycin, and a triple antibiotic ointment or with 10 µL of MM8 and a chlorhexidine gluconate 0.12% oral rinse. The plate was incubated at 37° C. for 24 hours.

FIG. 50 PANEL A shows the circle enclosing the diameter of clearance created by treatment with MM8 and demonstrates that while mupirocin and neomycin were more effective than MM8 was, MM8 was more effective than bacitracin and the triple antibiotic ointment were after an incubation period of 1 day. FIG. 50 PANEL B shows that MM8 and the chlorhexidine gluconate 0.12% oral rinse were about equally toxic to *Yesenia pestis* (Kimo 6).

b. Vancomycin-Resistant *Enterococcus* (VRE) (ATCC 51299)

An MHA plate was swabbed with VRE, and treated with MM8, mupirocin, bacitracin, neomycin, and a triple antibiotic ointment. The plate was incubated at 37° C. for 1 day, and the diameter of clearance of each formulation was measured. The plate was then incubated at 37° C. for an additional 6 days, and the diameter of clearance of each formulation was measured. An undiluted culture of VRE (~100 µL of ~1×10$^9$ CFU/mL) was plated on an MHA plate. The inoculated MHA plate was treated with 10 µL of MM8 and with 10 µL spots of mupirocin, bacitracin, neomycin, and a triple antibiotic ointment. The plate was incubated at 37° C. for an initial period of 24 hours, followed by an additional 6 day incubation to address the long-term killing efficacy of MM8.

Figure 51:
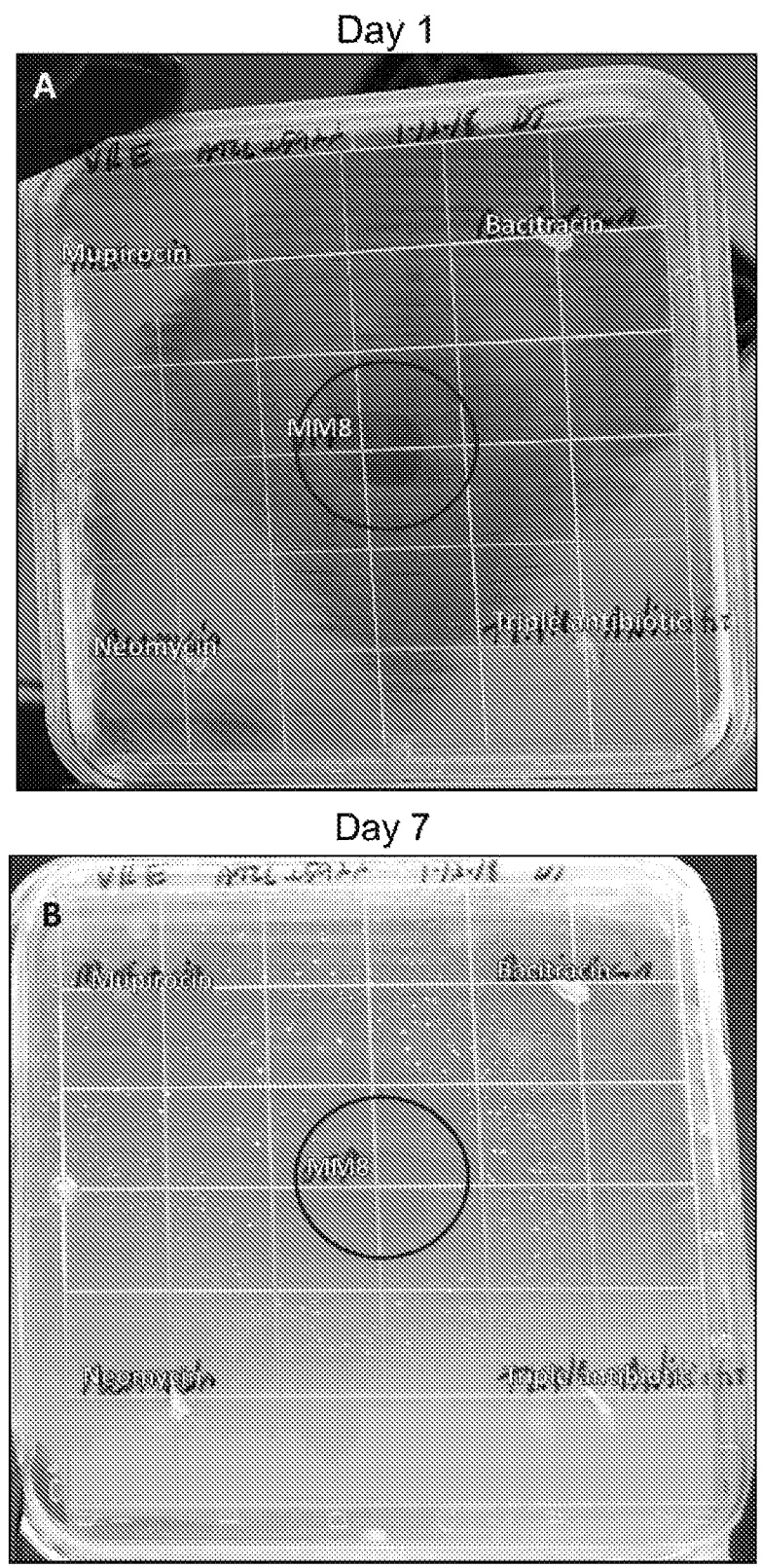

FIG. 51 PANEL A shows that MM8 and bacitracin killed VRE after an incubation period of 1 day. The circle encloses the diameter of clearance created by treatment with MM8 and demonstrates that MM8 was the most efficacious treatment compared to mupirocin, bacitracin, neomycin, and a triple antibiotic ointment. FIG. 51 PANEL B shows that after 7 days of incubation, the area of VRE treated with MM8 was the only remaining diameter of clearance, indicating that one treatment with MM8 had long-lasting effects against VRE.

c. Methicillin-Resistant *Staphylococcus aureus* (MRSA)

An MHA plate was swabbed with MRSA, and treated with MM8, mupirocin, bacitracin, neomycin, and a triple antibiotic ointment. The plate was incubated at 37° C. for 1 day, and the diameter of clearance of each formulation was measured. The plate was then incubated at 37° C. for an additional 3 days, and the diameter of clearance of each formulation was measured. A culture of MRSA (ATCC BAA44) was diluted 1:10 (~1×10$^8$ CFU/mL), and ~100 µL was plated on an MHA plate. The inoculated MHA plate was treated with 10 µL of MM8 and with 10 µL spots of mupirocin, bacitracin, neomycin, and a triple antibiotic ointment. The plate was incubated at 37° C. for 24 hours, followed by an additional 3 day incubation to address the long-term killing efficacy of MM8.

Figure 52:
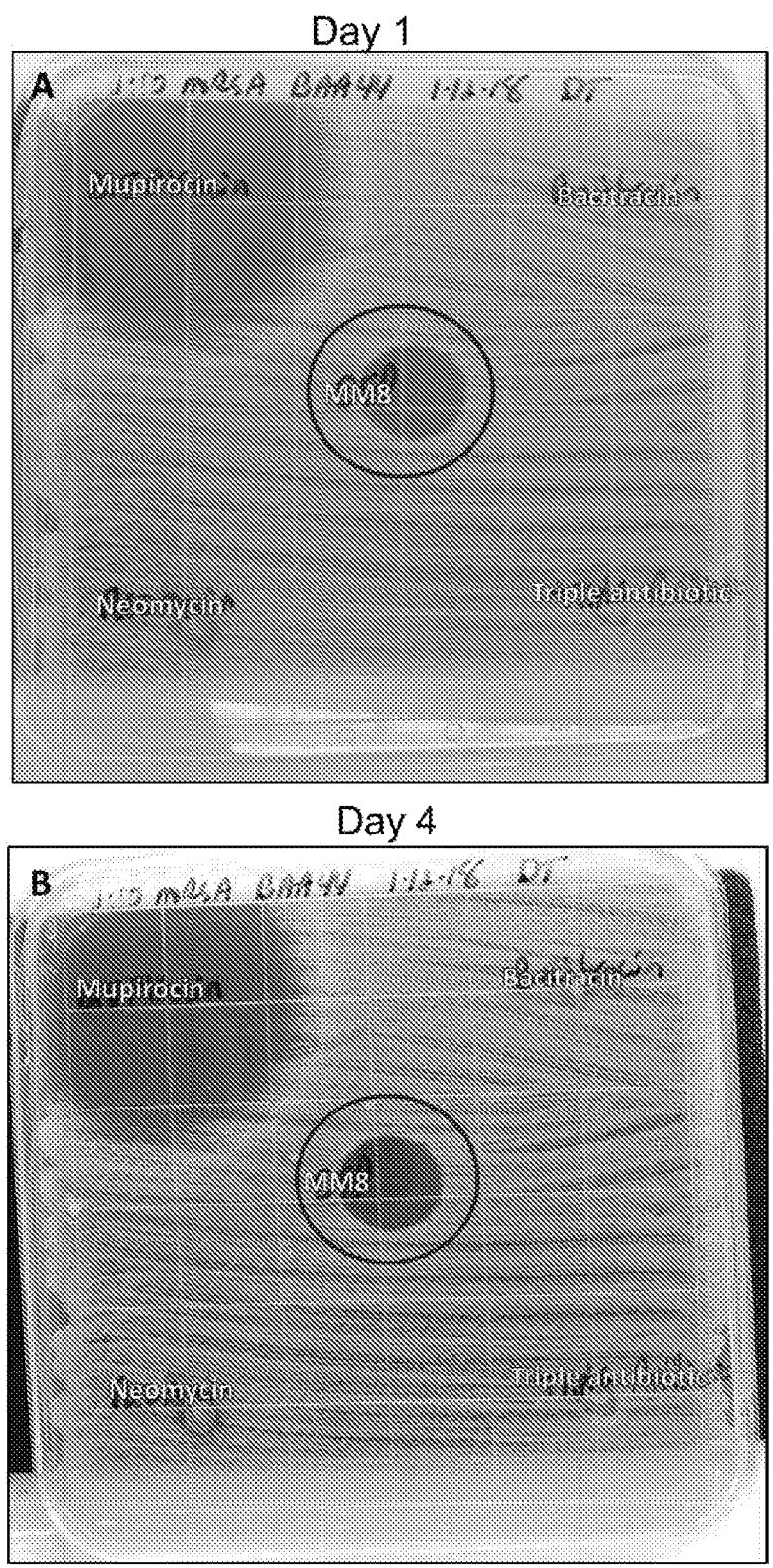

FIG. 52 PANEL A shows that MM8 and mupirocin killed MRSA after an incubation period of 1 day. The circle encloses the diameter of clearance created by treatment with MM8. FIG. 52 PANEL B shows that after 4 days of incubation, MM8 and mupirocin were the only formulations that killed MRSA. Regrowth of MRSA killed by mupirocin and MM8 was not observed.

d. Multi-Drug Resistant Carbapenem-Resistant Enterobacteriaceae (CRE NDM-1 MDR)

An MHA plate was swabbed with CRE NDM-1 MDR, and treated with MM8, mupirocin, bacitracin, neomycin, and a triple antibiotic ointment. The plate was incubated at 37° C. for 1 day, and the diameter of clearance of each formulation was measured. The plate was then incubated at 37° C. for an additional 4 days, and the diameter of clearance of each formulation was measured. A culture of CRE NDM-1 MDR was diluted 1:10 (~1×10$^8$ CFU/mL), and ~100 µL was plated on an MHA plate. The inoculated MHA plate was treated with 10 µL of MM8 and with 10 µL spots of mupirocin, bacitracin, neomycin, and a triple antibiotic ointment. The plate was incubated at 37° C. for 24 hours, followed by an additional 4 day incubation to address the long-term killing efficacy of MM8.

Figure 53:
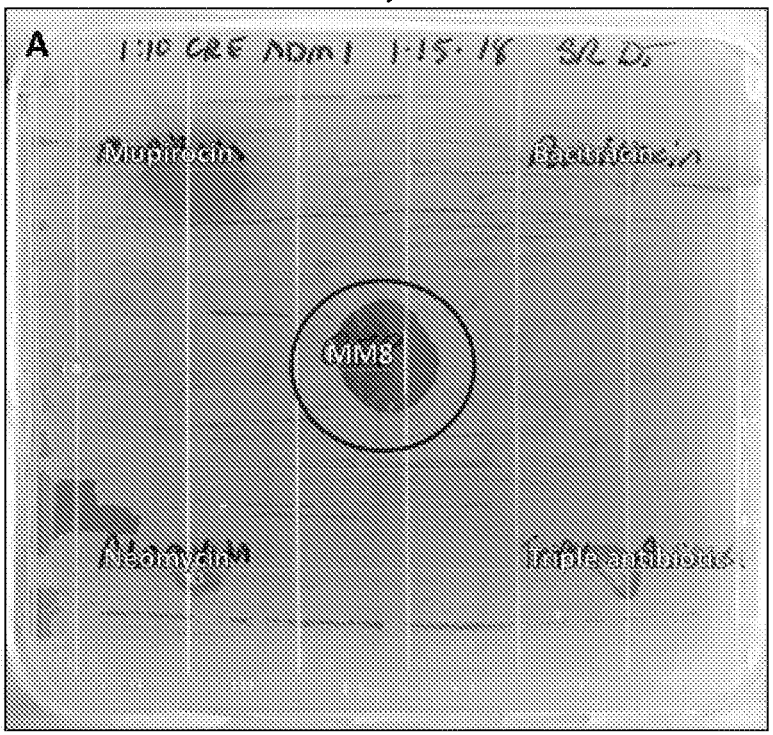
Figure 53:
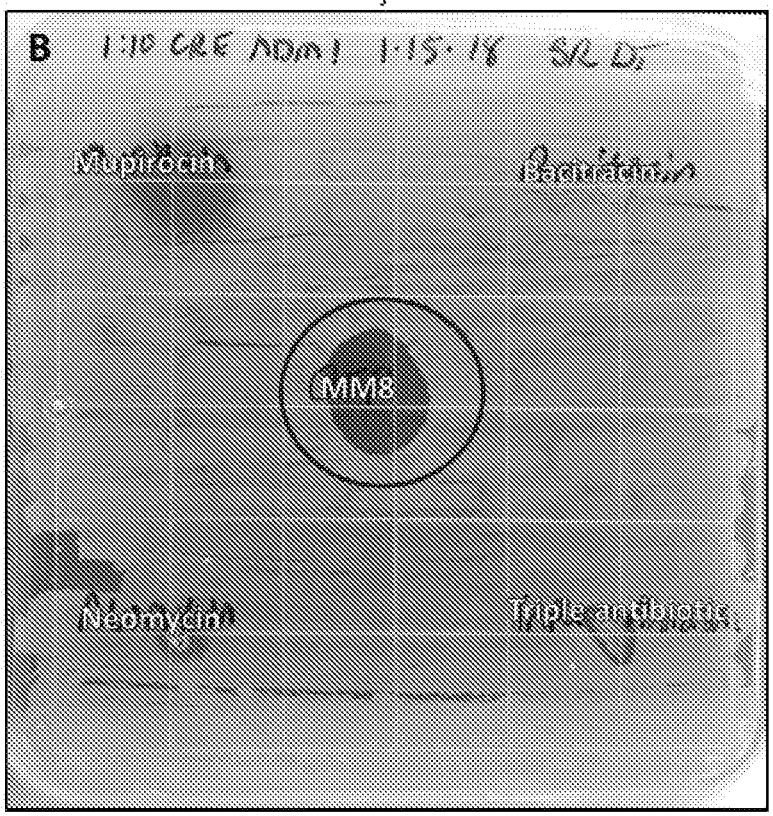

FIG. 53 PANEL A shows that MM8 and mupirocin killed CRE NDM-1 MDR after an incubation period of 1 day. The circle encloses the diameter of clearance created by treatment with MM8. FIG. 53 PANEL B shows that after 5 days of incubation, MM8 and mupirocin were the only formulations that killed CRE NDM-1 MDR. Regrowth of CRE NDM-1 MDR killed by mupirocin and MM8 was not observed.

e. Multi-Drug Resistant *Acinetobacter baumannii* (ATCC 1797)

An MHA plate was swabbed with multi-drug resistant *Acinetobacter baumannii*, and treated with MM8, mupirocin, bacitracin, neomycin, and a triple antibiotic ointment. The plate was incubated at 37° C. for 1 day, and the diameter of clearance of each formulation was measured. A culture of *A. baumannii* was diluted 1:10 (~1×10$^8$ CFU/mL), and ~100 µL was plated on an MHA plate. The inoculated MHA plate was treated with 10 µL of MM8 and with 10 µL spots of mupirocin, bacitracin, neomycin, and a triple antibiotic ointment to test for the efficacy of the formulations in killing *A. baumannii* after a 24 hour incubation at 37° C.

Figure 54:
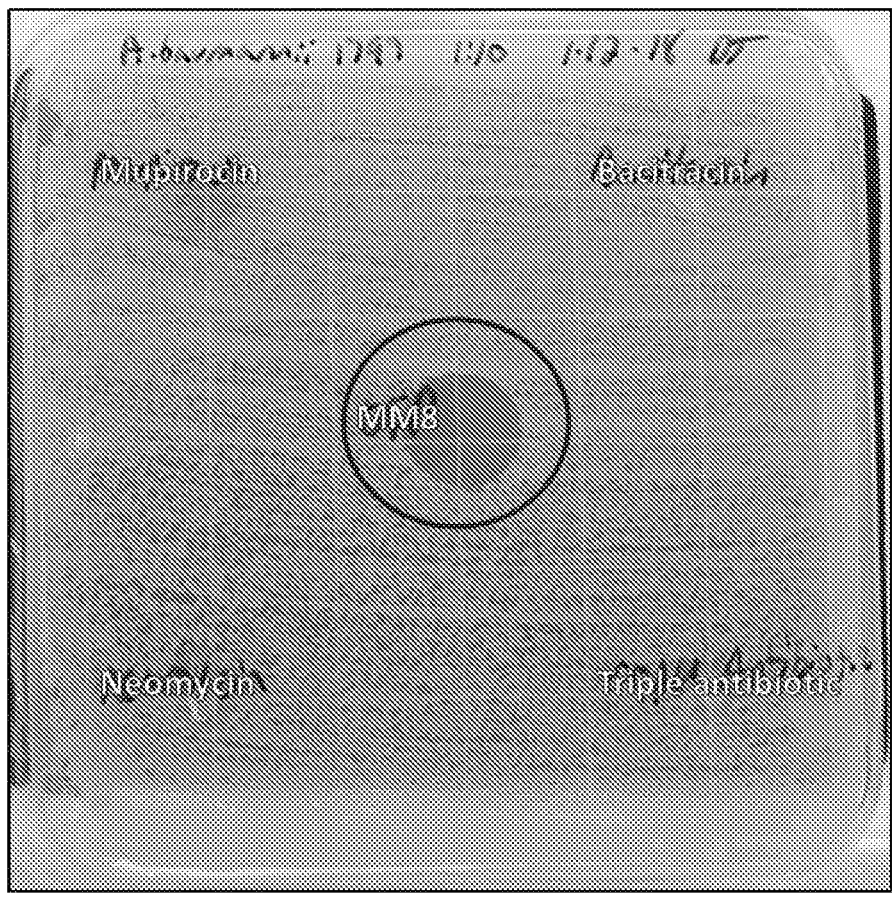

FIG. 54 shows that MM8 and mupirocin killed *A. baumannii* after an incubation period of 1 day. The circle encloses the diameter of clearance created by treatment with MM8.

f. Multi-Drug Resistant *Pseudomonas aeruginosa* (ATCC 2114)

An MHA plate was swabbed with multi-drug resistant *Pseudomonas aeruginosa*, and treated with MM8, mupirocin, bacitracin, neomycin, and a triple antibiotic ointment. The plate was incubated at 37° C. for 1 day, and the diameter of clearance of each formulation was measured. A culture of *P. aeruginosa* was diluted 1:10 (~1×10$^8$ CFU/mL), and ~100 µL was plated on an MHA plate. The inoculated MHA plate was treated with 10 µL of MM8 and with 10 µL spots of mupirocin, bacitracin, neomycin, and a triple antibiotic ointment to test the efficacies of the formulations in killing *P. aeruginosa* after a 24 hour incubation at 37° C.

Figure 55:
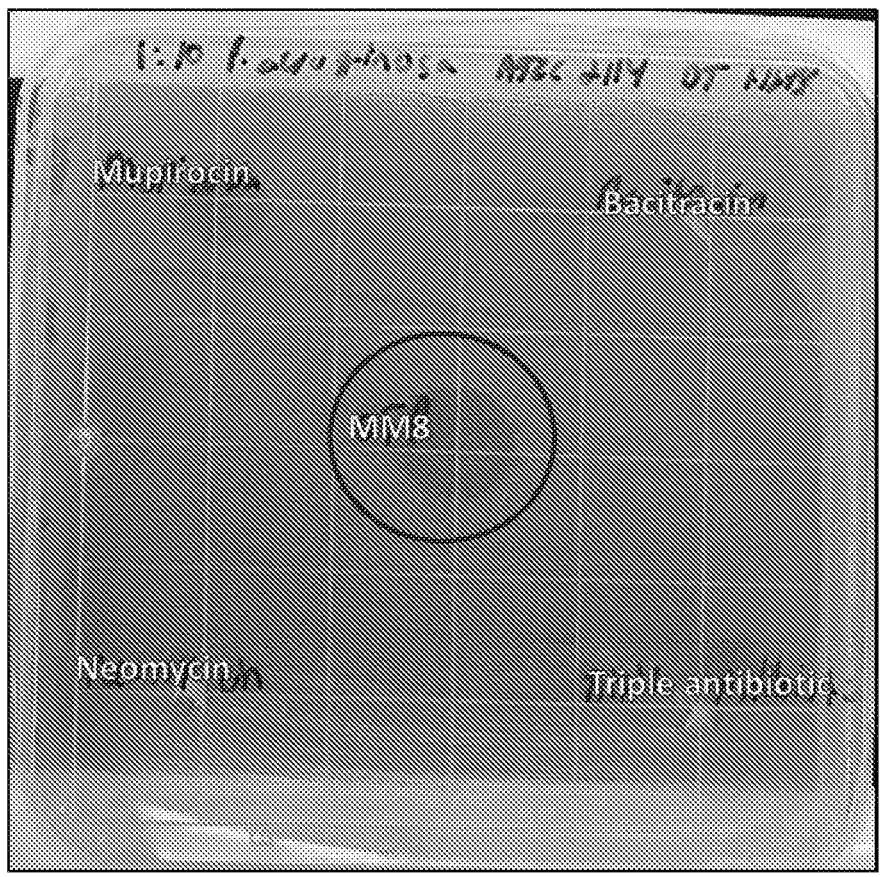

FIG. 55 shows that MM8 and mupirocin killed multi-drug resistant *Pseudomonas aeruginosa* after an incubation period of 1 day. The circle encloses the diameter of clearance created by treatment with MM8.

g. *Escherichia coli* (O157:H7) (ATCC 51657)

An MHA plate was swabbed with *Escherichia coli* (O157:H7), and treated with MM8, mupirocin, bacitracin, neomycin, and a triple antibiotic ointment. The plate was incubated at 37° C. for 1 day, and the diameter of clearance of each formulation was measured. The plate was then incubated at 37° C. for an additional 4 days, and the diameter of clearance of each formulation was measured. A culture of *E. coli* O157:H7 (ATCC 51657) was diluted 1:10 (~1×10$^8$ CFU/mL), and ~100 µL plated on an MHA plate. The inoculated MHA plate was treated with 10 µL of MM8, and 10 µL mupirocin, bacitracin, neomycin, and a triple antibiotic ointment were spotted on the MHA plate to test the efficacies of the formulations in killing *E. Coli* after a 24 hour incubation and an additional 4 day incubation at 37° C.

Figure 56:
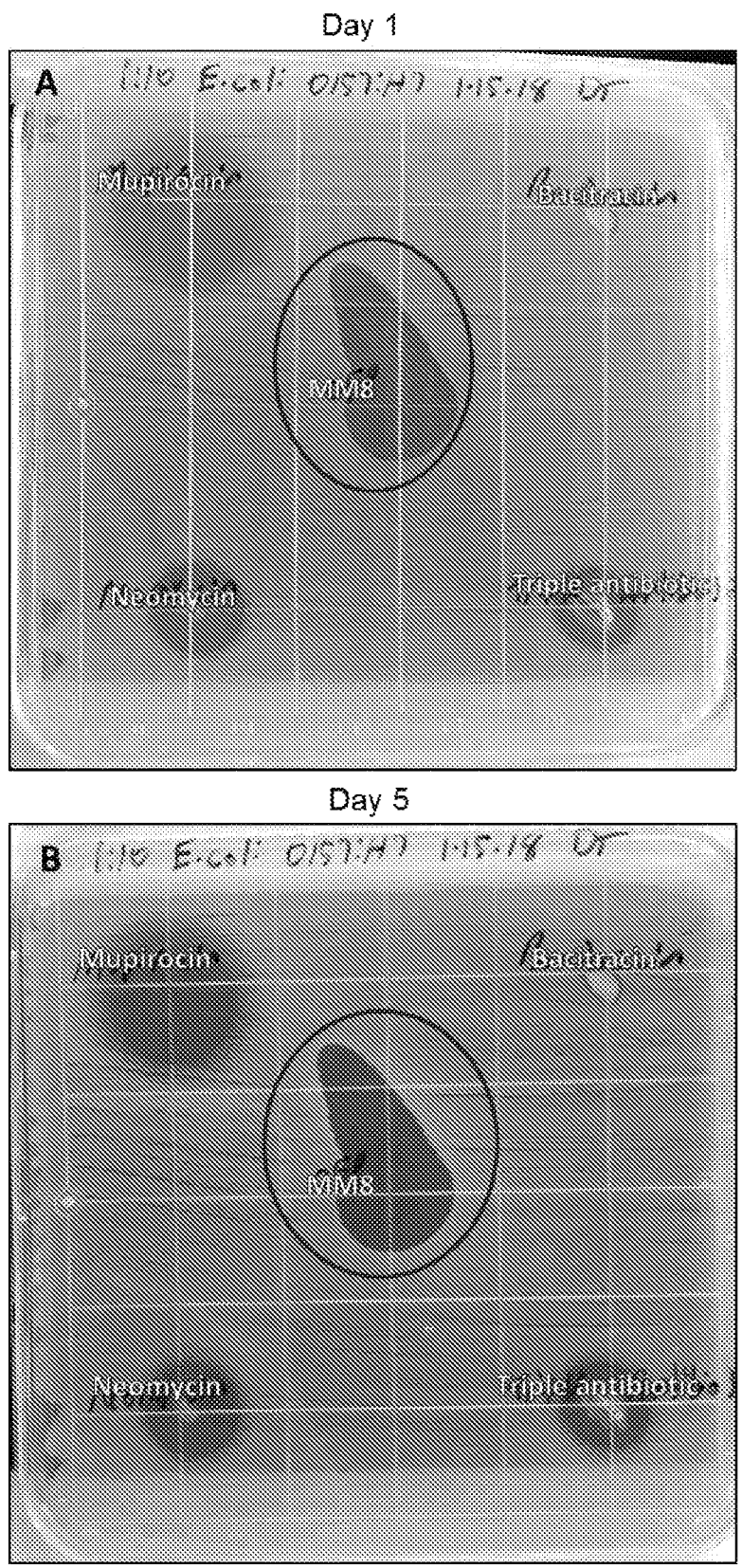

FIG. 56 PANEL A shows that MM8, mupirocin, neomycin, and the triple antibiotic ointment killed *Escherichia coli* (O157:H7) after an incubation period of 1 day. The circle encloses the diameter of clearance created by treatment with MM8. FIG. 56 PANEL B shows that after 5 days of incubation, MM8, mupirocin, neomycin, and the triple antibiotic ointment were the only formulations that killed *Escherichia coli* (O157:H7). Regrowth of *Escherichia coli* (O157:H7) killed by MM8, mupirocin, neomycin, and the triple antibiotic ointment was not observed.

h. Multi-Drug Resistant *Burkholderia cepacia* (ATCC 10856)

An MHA plate was swabbed with multi-drug resistant *Burkholderia cepacia*, and treated with MM8, mupirocin, bacitracin, neomycin, and a triple antibiotic ointment. The plate was incubated at 37° C. for 1 day, and the diameter of clearance of each formulation was measured. The plate was then incubated at 37° C. for an additional 3 days, and the diameter of clearance of each formulation was measured. A culture of *B. cepacia* was diluted 1:10 (~1×10$^8$ CFU/mL) and ~100 µL was plated on an MHA plate. The inoculated MHA plate was treated with 10 µL of MM8, and 10 µL of mupirocin, bacitracin, neomycin, and a triple antibiotic ointment were spotted on the MHA plate to test the efficacies of the formulations in killing *B. cepacia* after a 24 hour incubation and an additional 3 day incubation at 37° C.

Figure 57:
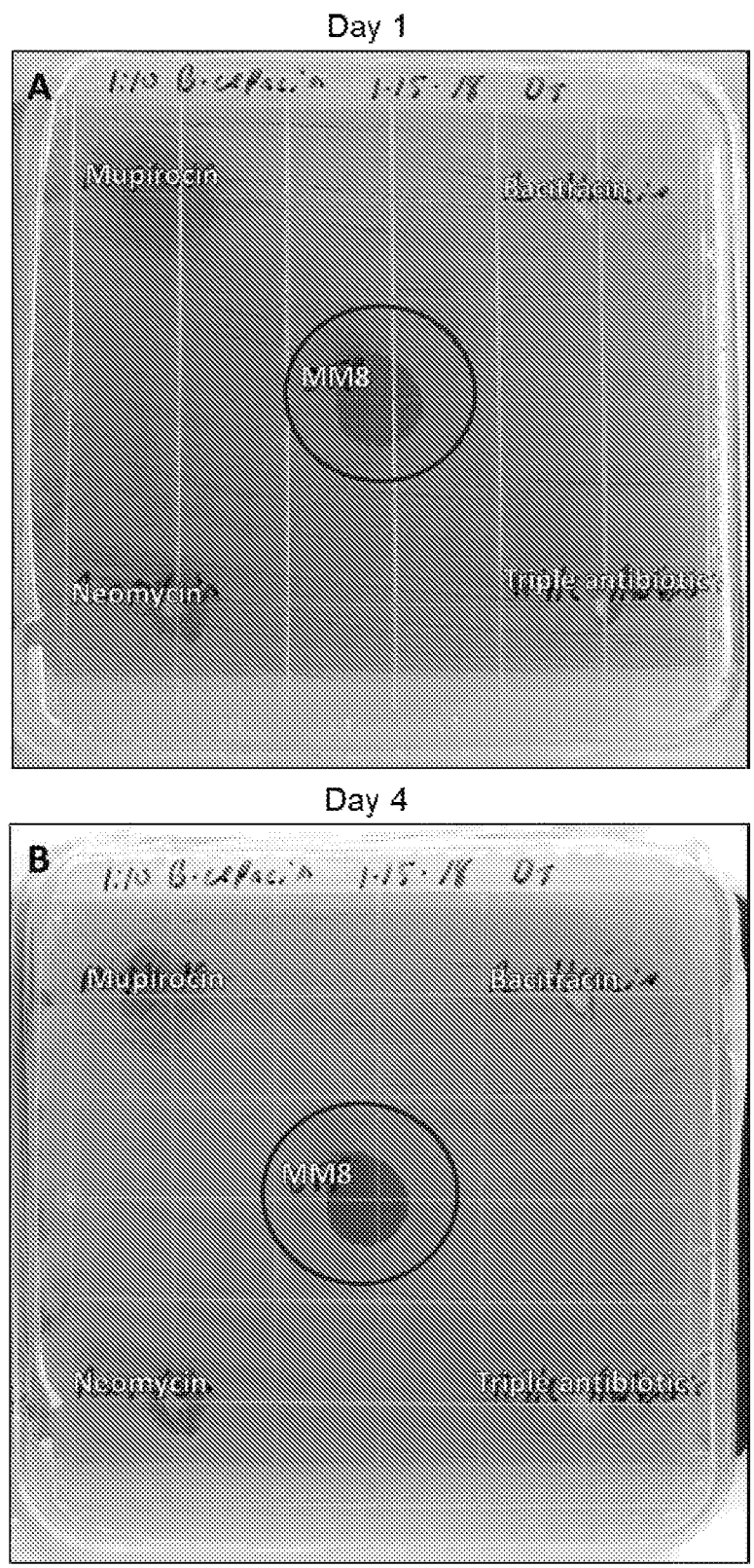

FIG. 57 PANEL A shows that MM8 was the only formulation to kill multi-drug resistant *Burkholderia cepacia* after an incubation period of 1 day. The circle encloses the diameter of clearance created by treatment with MM8. FIG. 57 PANEL B shows that after 4 days of incubation, MM8 was the only formulation that killed multi-drug resistant *Burkholderia cepacia*. Regrowth of multi-drug resistant *Burkholderia cepacia* killed by MM8 was not observed.

i. *Streptococcus pyogenes*

An MHA plate was swabbed with *Streptococcus pyogenes*, and treated with MM8, mupirocin, bacitracin, neomycin, and a triple antibiotic ointment. The plate was incubated at 37° C. for 1 day, and the diameter of clearance of each formulation was measured. The plate was then incubated at 37° C. for an additional 6 days, and the diameter of clearance of each formulation was measured. A culture of *S. pyogenes* was diluted 1:10 (~1×10$^8$ CFU/mL) and ~100 µL was plated on an MHA plate. The inoculated MHA plate was treated with 10 µL of MM8, and 10 µL of mupirocin, bacitracin, neomycin, and a triple antibiotic ointment were spotted on the MHA plate to test the efficacies of the formulations in killing *S. pyogenes* after a 24 hour incubation and an additional 6 day incubation at 37° C.

Figure 58:
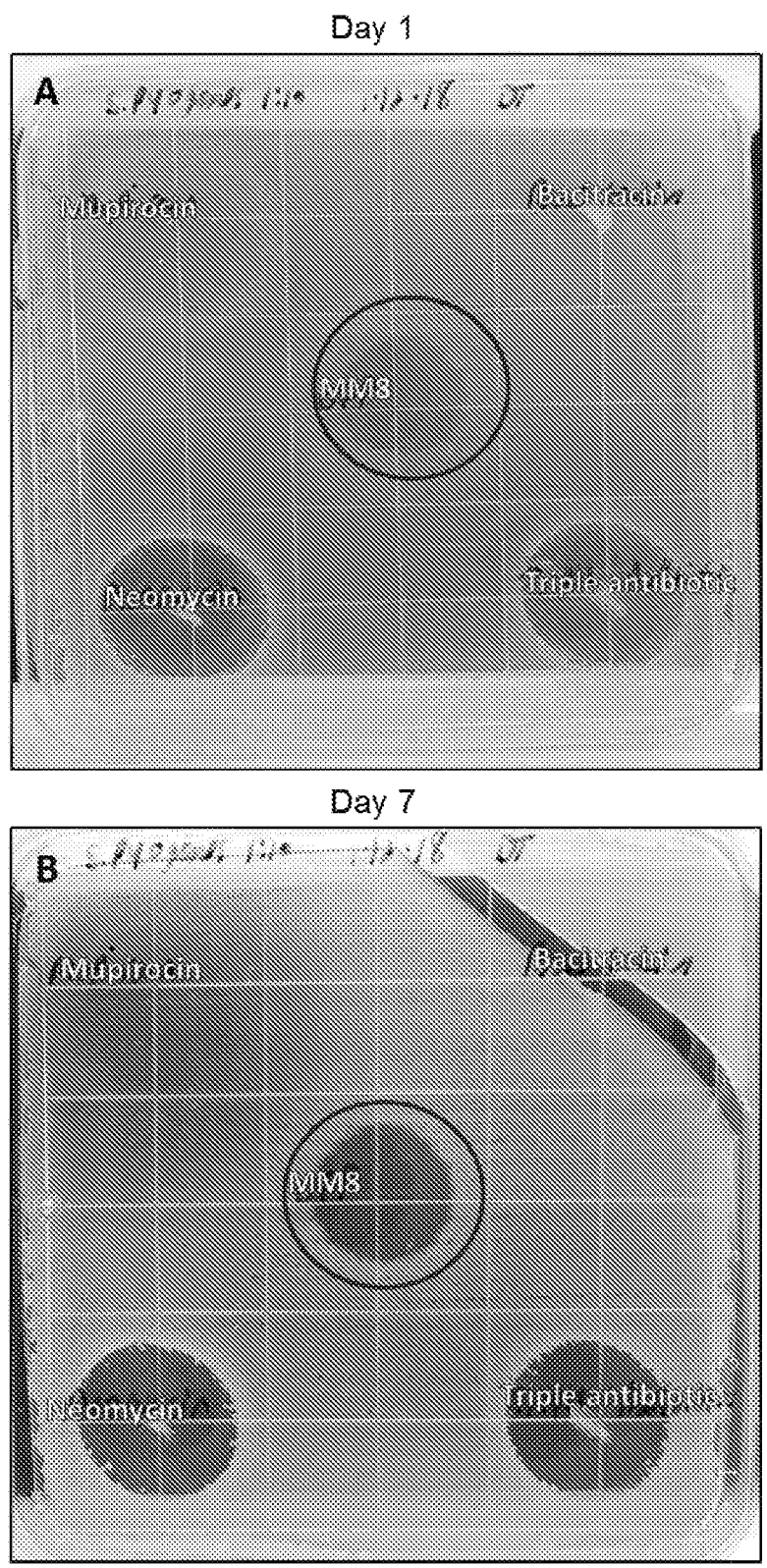
Figure 59:
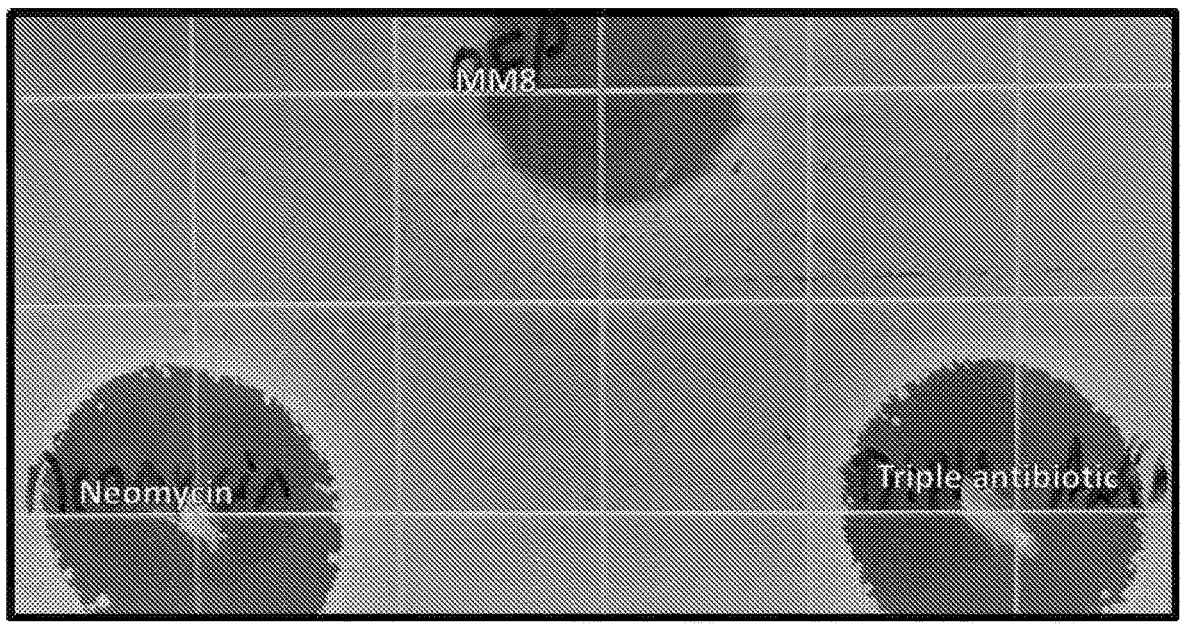

FIG. 58 PANEL A shows that MM8, mupirocin, neomycin, and the triple antibiotic ointment killed *Streptococcus pyogenes* after an incubation period of 1 day. The circle encloses the diameter of clearance created by treatment with MM8. FIG. 58 PANEL B shows that after 7 days of incubation, MM8, mupirocin, neomycin, and the triple antibiotic ointment further killed *S. pyogenes*. FIG. 59 shows that the *S. pyogenes* colonies invaded the areas treated with neomycin and the triple antibiotic, but the area treated with MM8 did not exhibit regrowth of the *Streptococcus pyogenes* colonies.

j. Polymyxin E-Resistant *Stenotrophomonas maltophilia* (ATCC 13637)

An MHA plate was swabbed with polymyxin E (PME)-resistant *Stenotrophomonas maltophilia*, and treated with MM8 and MM8 prepared with Ca-DTPA as an alternative. The plate was incubated at 37° C. for 1 day, and the diameter of clearance of each formulation was measured. A culture of polymyxin E-resistant *S. maltophilia* (ATCC 13637), previously evolved for resistance to PME in the laboratory, was prepared by growing and diluting a culture of *S. maltophilia* in 100 µg/mL PME overnight at 37° C. About 100 µL of 1:10 dilution of cells (~1×10$^8$ CFU/mL) was plated on an MHA plate. The inoculated MHA plate was treated with 10 µL of MM8 to test for the efficacy of the formulation in killing *S. maltophilia* after a 24 hour incubation at 37° C.

Figure 60:
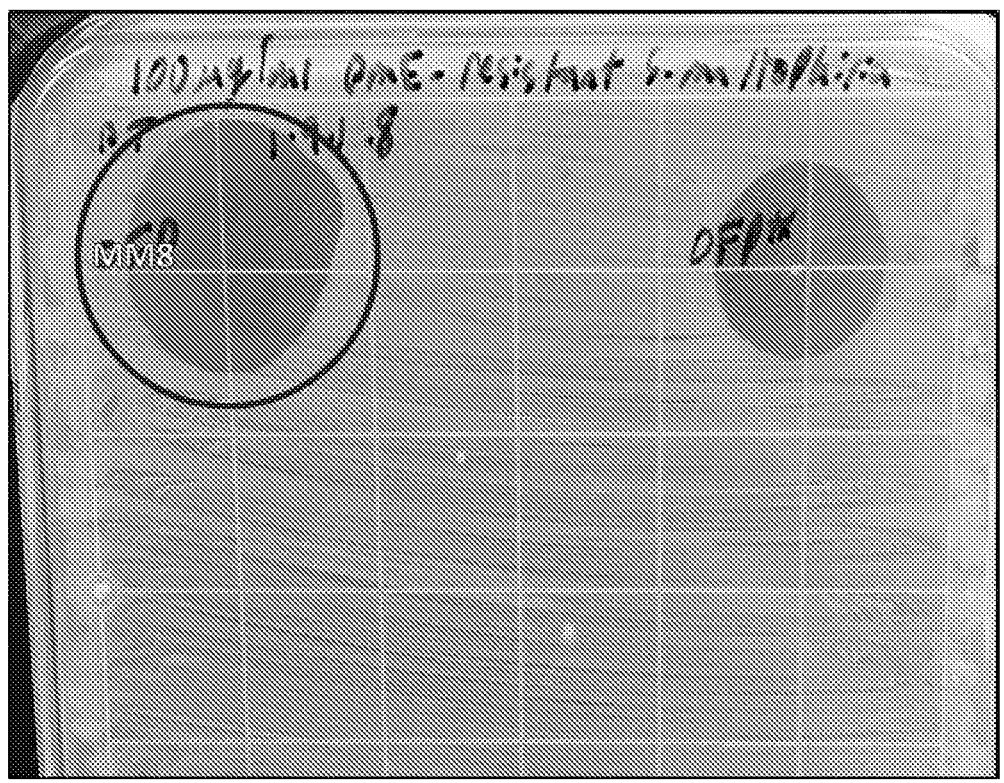

FIG. 60 shows that MM8 killed polymyxin E-resistant *Stenotrophomonas maltophilia* after an incubation period of 1 day. The circle encloses the diameter of clearance created by treatment with MM8.

k. *Bacillus subtilis* (ATCC 6633)

An MHA plate was swabbed with *Bacillus subtilis*, and treated with MM8, mupirocin, bacitracin, neomycin, and a triple antibiotic ointment. The plate was incubated at 37° C. for 1 day, and the diameter of clearance of each formulation was measured. A culture of *B. subtilis* was diluted 1:10 (~1×10$^8$ CFU/mL) and ~ 100 µL was plated on an MHA plate. The inoculated MHA plate was treated with 10 µL of MM8, and 10 µL of mupirocin, bacitracin, neomycin, and the triple antibiotic ointment was spotted on the MHA plate to test the efficacies of the formulations in killing *B. subtilis* after a 24 hour incubation at 37° C.

Figure 61:
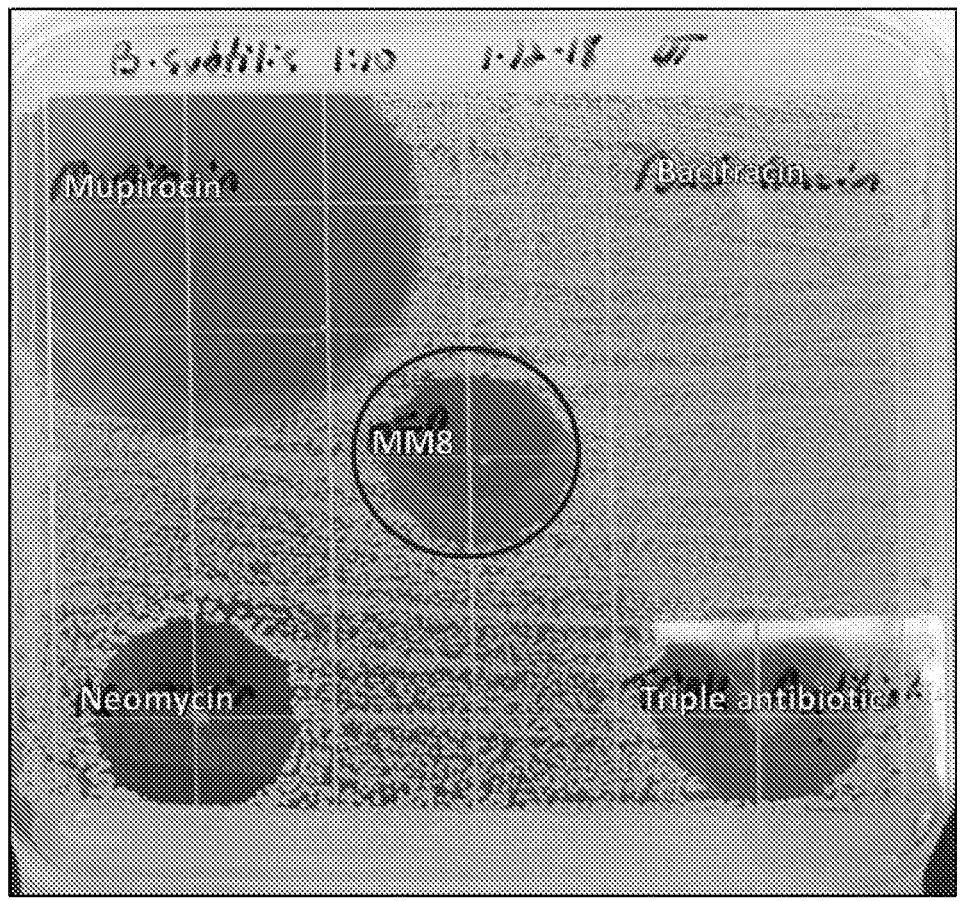

FIG. 61 shows that MM8, mupirocin, neomycin, and the triple antibiotic ointment killed *Bacillus subtilis* after an incubation period of 1 day. The circle encloses the diameter of clearance created by treatment with MM8.

l. *Mycobacterium abscessus* (ATCC 19977)

An MHA plate was swabbed with *Mycobacterium abscessus*, and treated with MM8, mupirocin, bacitracin, neomycin, and a triple antibiotic ointment. The plate was incubated at 37° C. for 2 days, and the diameter of clearance of each formulation was measured. About 100 µL of an undiluted culture of *M. abscessus* (~1×10$^9$ CFU/mL) was plated on an MHA plate. The inoculated MHA plate was treated with 10 µL of MM8, and 10 µL spots of mupirocin, bacitracin, neomycin, and the triple antibiotic ointment was spotted on the MHA plate to test the efficacies of the formulations in killing *M. abscessus* after a 48 hour incubation at 37° C. The MHA plate was then stained with MTT (blue-black) to visualize the growth of the colonies.

Figure 62:
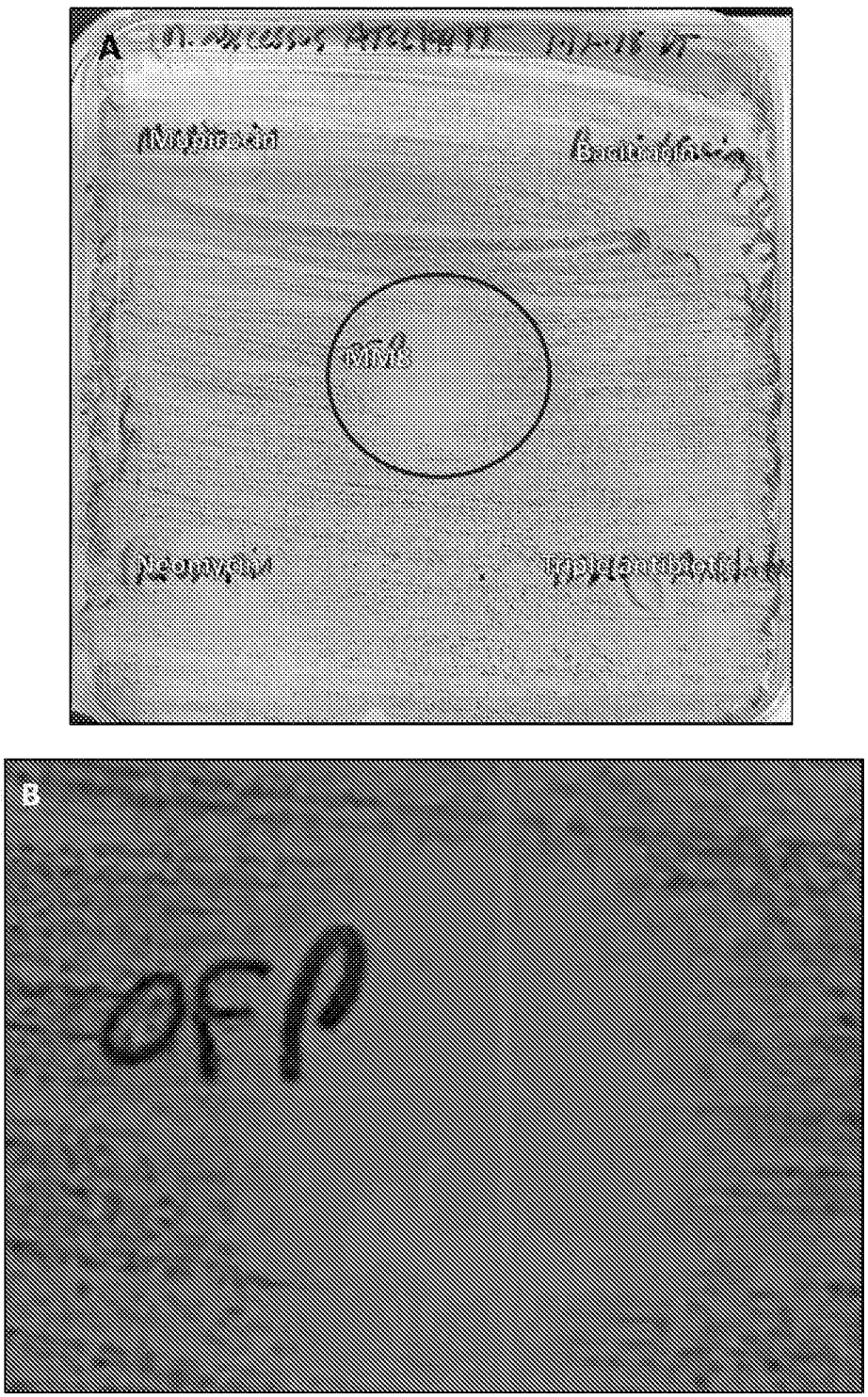

FIG. 62 PANEL A shows that MM8 was the only formulation that killed *Mycobacterium abscessus*. The circle encloses the diameter of clearance created by treatment with MM8. The plate was sprayed with a solution of 5 mg/mL MTT, which turns only viable cells purple. The area of the plate treated with MM8 appeared clear/yellow, and indicated zero viability. In contrast, the surrounding area of the plate was blue/black in color, and indicated metabolic activity and cell viability. FIG. 62 PANEL B shows an image of the MHA stained with MTT. The image shows that there was no colony regrowth in the area treated with MM8.

m. MRSA BAA-1717 (USA 300) and Multi-Drug Resistant *Burkholderia cepacia* (ATCC 10856)

An overnight grow of MRSA BAA-1717 (USA 300) was diluted 1:10 (1×10$^8$ CFU/mL), and plated on an MHA plate. An overnight grow of multi-drug resistant *Burkholderia cepacia* was diluted 1:10 (1×10$^8$ CFU/mL) and plated on a second MHA plate. The MHA plates were treated with 10 µL of MM8, mupirocin, bacitracin, neomycin, and a triple antibiotic ointment. The plates were incubated at 37° C. overnight, and the diameter of clearance of each formulation was measured.

Figure 63:
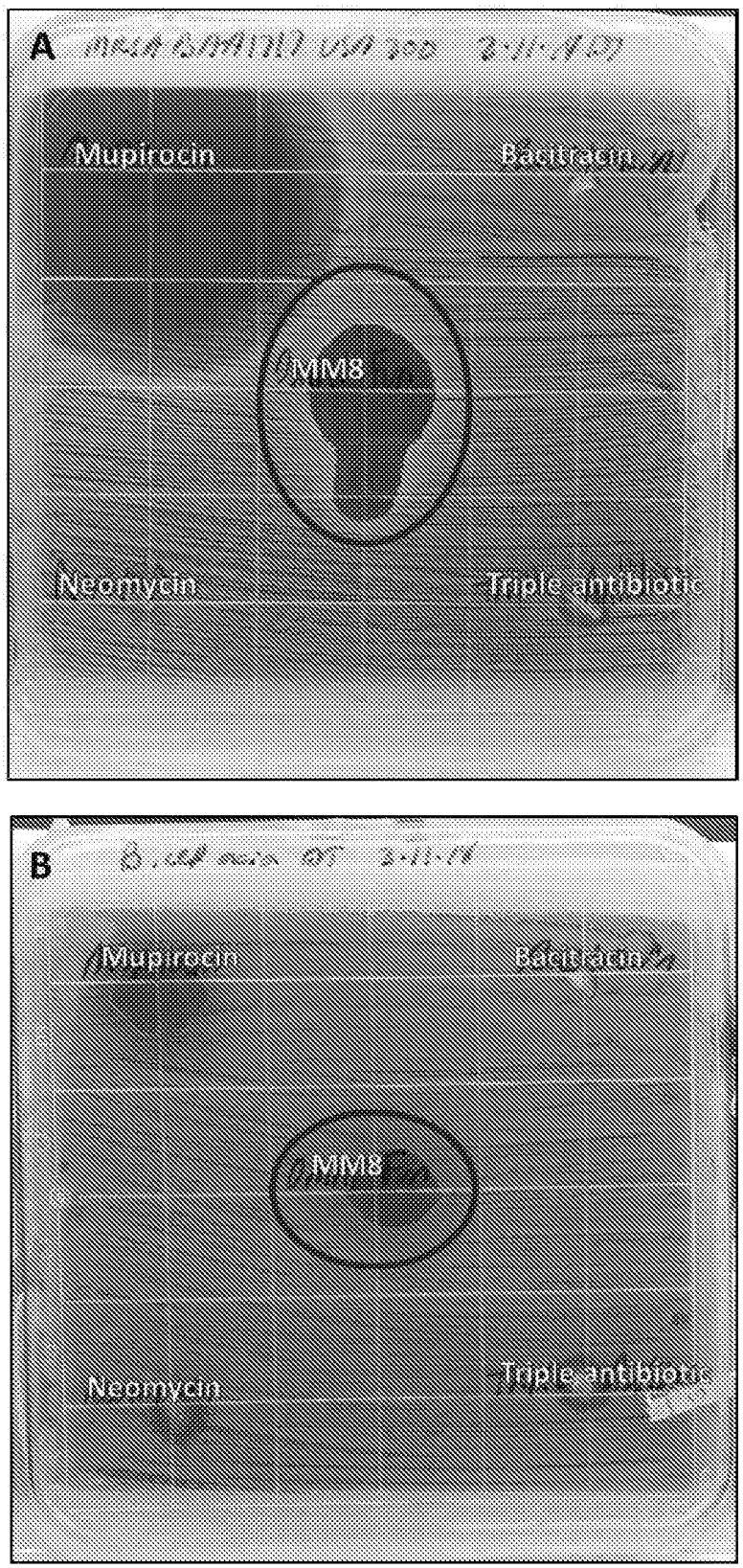

FIG. 63 PANEL A shows that MM8 and mupirocin killed MRSA BAA-1717 (USA 300). The circle encloses the diameter of clearance created by treatment with MM8. FIG. 63 PANEL B shows that MM8, mupirocin, neomycin, and the triple antibiotic ointment killed multi-drug resistant *Burkholderia cepacia*.

Example 7: Antiseptic Properties of MM8

MHA plates were swabbed with MRSA BAA-1717 (USA 300), MRSA BAA-44, *Acinetobacter baumannii* (ATCC 1797), *Pseudomonas aeruginosa* (ATCC 2114), multi-drug resistant *C. auris*, and multi-drug resistant *Burkholderia cepacia*. The MHA plates were treated with MM8 and chlorhexidine gluconate 0.12% oral rinse. The plate was incubated at 37° C. for 1 day, and the diameter of clearance of each formulation was measured. MRSA BAA-1717 (USA 300), MRSA BAA-44, *Acinetobacter baumannii* (ATCC 1797), *Pseudomonas aeruginosa* (ATCC 2114), multi-drug resistant *C. auris*, and multi-drug resistant *Burkholderia cepacia* (ATCC 10856) were grown in Mueller-Hinton broth overnight at 37° C. The cultures of bacteria were diluted 1:10 (~1×10$^8$ CFU/mL) and plated on an MHA plate, and ~100 μL of undiluted culture of *Candida albicans* (~1×10$^8$ CFU/mL) was plated on an MHA plate. The inoculated MHA plate was treated with 10 μL of MM8 and with 10 μL of chlorhexidine gluconate 0.12% oral rinse to test the efficacies of the formulations in killing the bacteria after a 24 hour incubation at 37° C.

Figure 64:
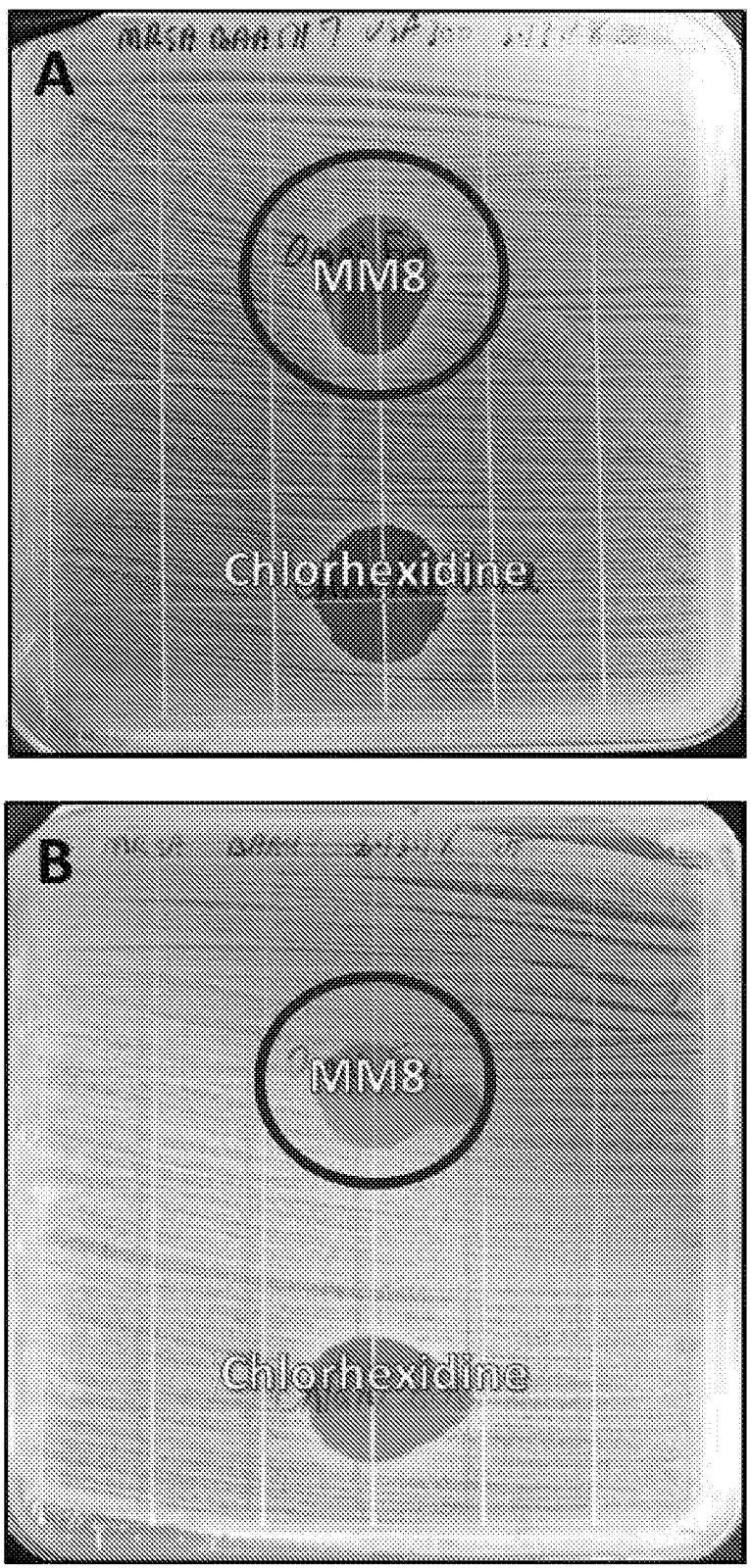
Figure 65:
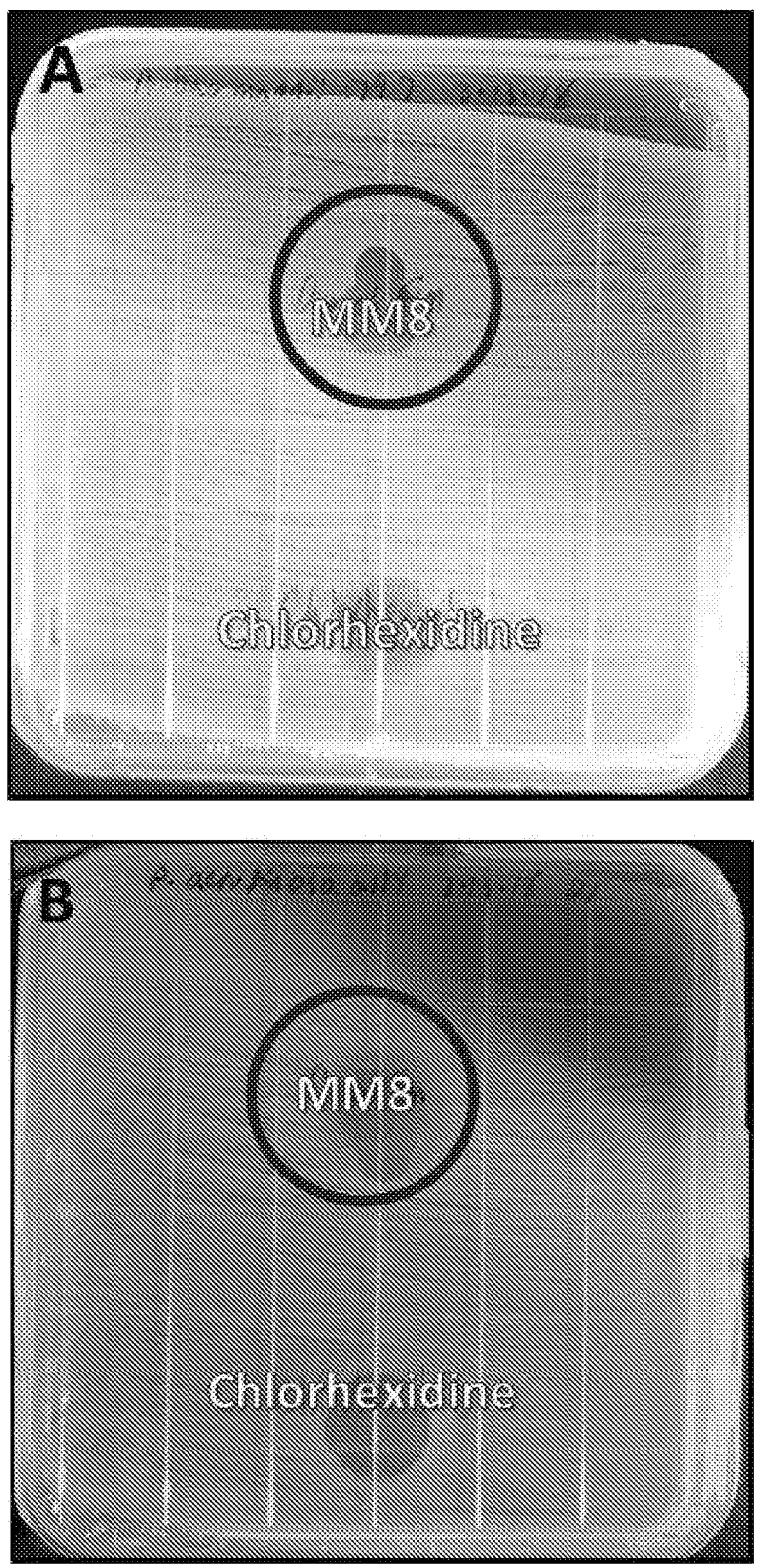
Figure 66:
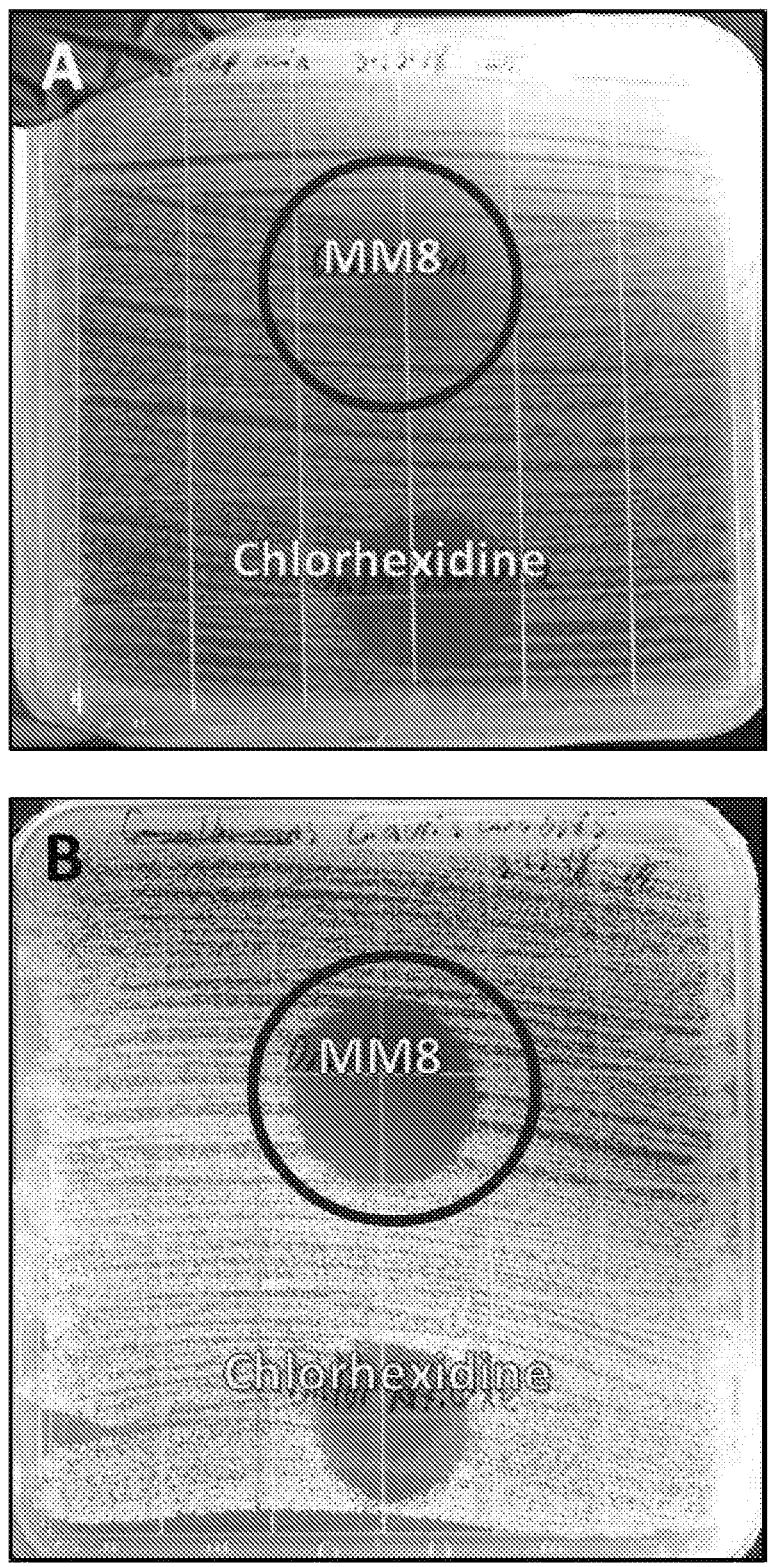

FIG. 64 PANEL A shows that MM8 and chlorhexidine gluconate 0.12% oral rinse killed MRSA BAA-1717 (USA 300). FIG. 64 PANEL B shows that MM8 and chlorhexidine gluconate 0.12% oral rinse killed MRSA BAA-44. FIG. 65 PANEL A shows that MM8 and chlorhexidine gluconate 0.12% oral rinse killed *Acinetobacter baumannii* (ATCC 1797). FIG. 65 PANEL B shows that MM8 and chlorhexidine gluconate 0.12% oral rinse killed *Pseudomonas aeruginosa* (ATCC 2114). FIG. 66 PANEL A shows that MM8 and chlorhexidine gluconate 0.12% oral rinse killed multi-drug resistant *Burkholderia cepacia*. FIG. 66 PANEL B shows that MM8 and chlorhexidine gluconate 0.12% oral rinse killed multi-drug resistant *C. auris*. The circles indicate the diameter of clearance created by treatment with MM8 after an incubation period of 1 day.

MHA plates were swabbed with *Candida albicans* and a multi-drug resistant *Candida* panel from the Center for Disease Control (CDC). The MHA plates were treated with MM8 and chlorhexidine. The plate was incubated at 37° C. for 2 days, and the diameter of clearance of each formulation was measured. *Candida albicans* (ATCC 26555) and the multi-drug-resistant *Candida* panel obtained from CDC were was grown in YM media for 24 to 48 hours at 37° C. About a 100 μL lawn of undiluted *Candida* species (~1×10$^8$ CFU/mL) was spread on an MHA plate. 10 μL of MM8 and 10 μL of chlorhexidine gluconate 0.12% oral rinse were spotted onto the inoculated MHA plate to test for the efficacies of the formulations in killing the *Candida* panel after a 48 hour incubation at 37° C.

Figure 67:
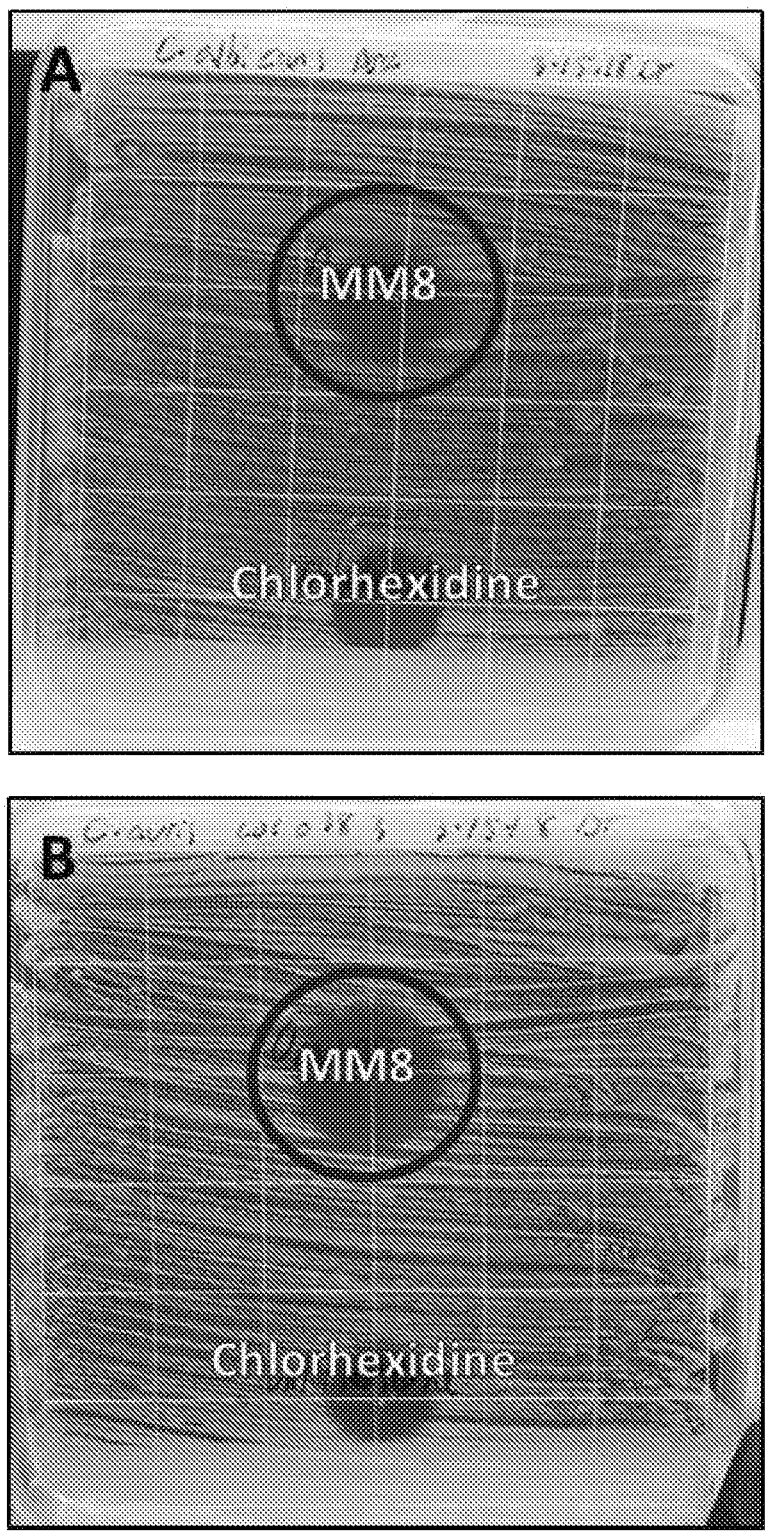
Figure 68:
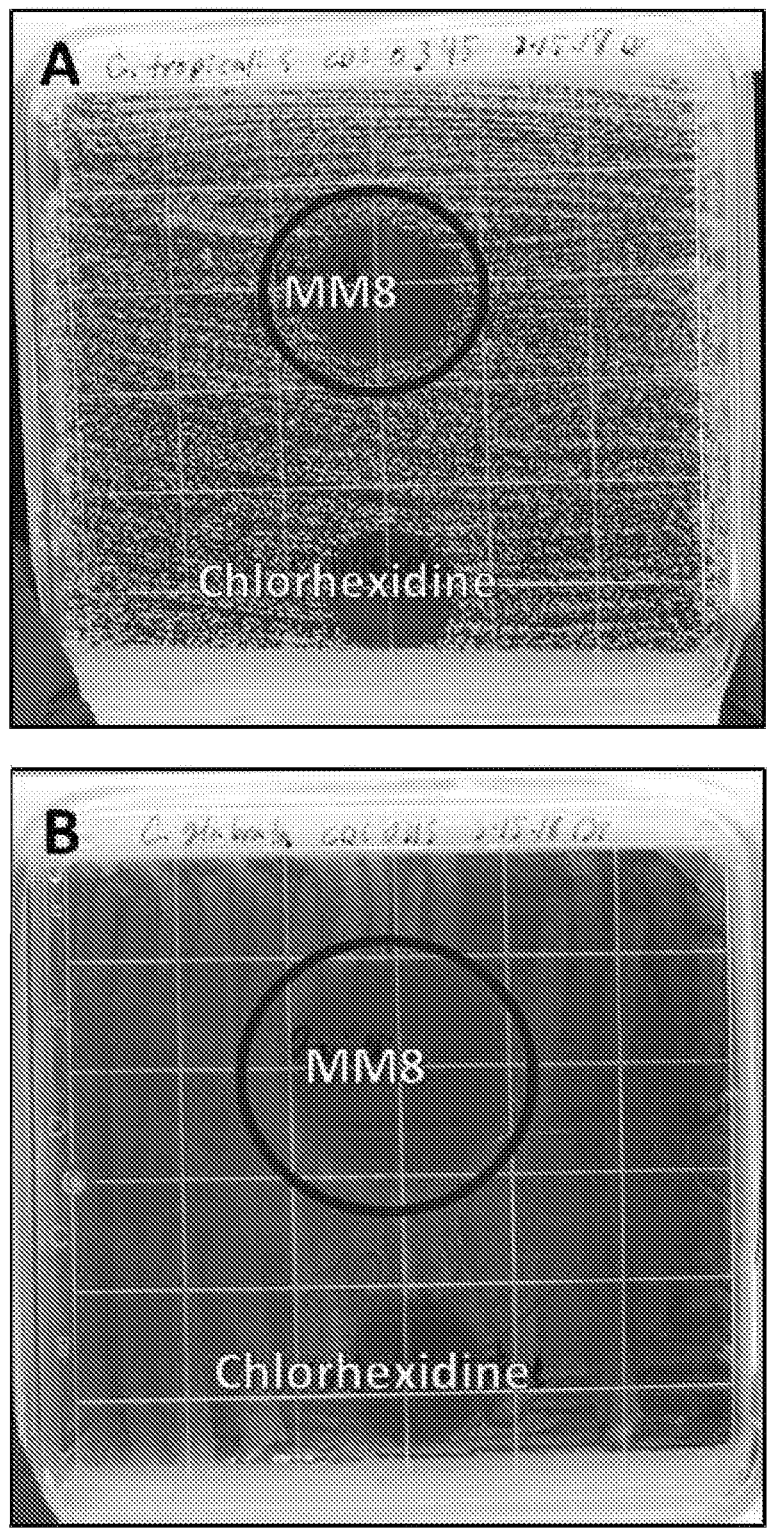

FIG. 67 PANEL A shows that MM8 and chlorhexidine gluconate 0.12% oral rinse killed *Candida albicans* (ATCC 26555). FIG. 67 PANEL B shows that MM8 and chlorhexidine gluconate 0.12% oral rinse killed *C. auris* (CDC 0383) after an incubation period of 2 days. FIG. 68 PANEL A shows that MM8 and chlorhexidine gluconate 0.12% oral rinse killed *Candida tropicalis* (CDC 0345) after an incubation period of 2 days. FIG. 68 PANEL B shows that MM8 and chlorhexidine gluconate 0.12% oral rinse killed *Candida glabrata* (CDC 0315) after an incubation period of 2 days. FIG. 69 PANEL A shows that MM8 and chlorhexidine gluconate 0.12% oral rinse killed *Candida haemulonii* (CDC 0393) after an incubation period of 2 days. FIG. 69 PANEL B shows that MM8 and chlorhexidine gluconate 0.12% oral rinse killed *Candida duobushaemulonii* (CDC 0339) after an incubation period of 2 days. FIG. 70 PANEL A shows that MM8 and chlorhexidine gluconate 0.12% oral rinse killed *Candida parapsilosis* (CDC 0339) after an incubation period of 2 days. FIG. 70 PANEL B shows that MM8 and chlorhexidine gluconate 0.12% oral rinse killed *Candida krusei* (CDC 0397) after an incubation period of 2 days. The circles indicate the diameter of clearance created by treatment with MM8.

The antiseptic properties of MM8 were also tested against *Cryptococcus gattii*, *Cryptococcus neoformans*, and *Aspergillus niger*. *Cryptococcus gattii* (K265) and *Cryptococcus neoformans* (H99) were grown in YM media for 24 to 48 hours at 37° C. and *Aspergillus niger* was grown in YM media for 5 days at 30° C. About a 100 μL lawn of undiluted *Cryptococcus gattii*, *Cryptococcus neoformans*, and *Aspergillus niger* (~1×10$^8$ CFU/mL) was spread on an MHA plate. 10 μL of MM8 and 10 μL of chlorhexidine gluconate 0.12% oral rinse were spotted onto the inoculated MHA plate to test the efficacies of the formulations in killing *Cryptococcus gattii* (K265) and *Cryptococcus neoformans* (48 hour incubation at 37° C.) and *Aspergillus niger* (5 day incubation at 28° C.).

FIG. 71 PANEL A shows that MM8 and chlorhexidine gluconate 0.12% oral rinse killed *Cryptococcus gattii*. FIG. 71 PANEL B shows that MM8 and chlorhexidine gluconate 0.12% oral rinse killed *Cryptococcus neoformans*. FIG. 72 PANEL A shows the front side of an MHA plate infected with *Aspergillus niger*, which shows that MM8 and chlorhexidine gluconate 0.12% oral rinse killed *Aspergillus niger*. FIG. 72 PANEL B shows the back side of an MHA plate infected with *Aspergillus niger*, which shows that MM8 and chlorhexidine gluconate 0.12% oral rinse killed *Aspergillus niger*.

Example 8: Effect of Treatment with MM1 and MM8 Against Fungal and Bacterial Biofilms The efficacy of MM1 and MM8 in killing fungal biofilms was tested using *Staphylococcus epidermis* (ATCC 35984), *C. auris*, and *Candida albicans* biofilms. *C. albicans* (ATCC 26555) and *C. auris* (CDC 0385) were grown overnight at 37° C. in 1:10 YM media (10% YM media and 90% sterile water). The culture was diluted 1:100 into 10% Mueller-Hinton broth and 90% sterile water. Diluted *Candida albicans* and *C. auris* were plated at a volume of 100 μL in a 96-well TC-treated plate, and the plate was incubated at 37° C. in a non-shaking incubator. After 24 hours of incubation, the media was removed and replaced with 1:10 YM, and the plate was incubated for an additional 24 hours at 37° C. After the second day of incubation, the media was removed, and the wells were washed three times with 1:10 YM before being treated with 100 μL of 100 μM PAO (positive killing control), water (positive growth control), chlorhexidine gluconate 0.12% oral rinse, MM8, MM8 with no polymyxin B, and MM1 for 15 minutes at 37° C. All treatments were removed, and 100 μL 1:10 YM was added. The plate was incubated for an additional 3 days at 37° C. The wells were washed three times with 1:10 YM, and 100 μL of a 5 mg/ml solution of MTT was added to the wells. The plate was incubated overnight at 37° C. The following day, all of the MTT was removed and replaced by solubilization solution. The optical density was read at 595 nm to assess cell viability as a measure of treatment efficacy.

*Staphylococcus epidermidis* (ATCC 35984) was grown overnight at 37° C. in 1:10 MHB (10% Mueller-Hinton broth and 900% sterile water). The culture was diluted 1:100 into 10% Mueller-Hinton broth and 90% sterile water. The diluted *S. epidermidis* cells were plated at a volume of 100 μL in a 96-well TC-treated plate, and the plate was incubated at 37° C. in a non-shaking incubator. After 24 hours of incubation, the media was removed and replaced with 1:10 MHB, and the plate was incubated an additional 24 hours at 37° C. After the second day of incubation, the media was removed, and the wells were washed three times with 1:10 MHB before being treated with 100 μL of 100 μM PAO (positive killing control), water (positive growth control), chlorhexidine gluconate 0.12% oral rinse, MM8, MM8 with no polymyxin B, and MM1 for 15 minutes at 37° C. All treatments were removed, and 100 μL 1:10 MHB was added. The plate was incubated for an additional 3 days at 37° C. The wells were washed three times with 1:10 MHB, and 100 μL of a 5 mg/ml solution of MTT was added to the wells.

The plate was incubated overnight at 37° C. The following day, all of the MTT was removed and replaced with a solubilization solution. The optical density was read at 595 nm to assess cell viability as a measure of treatment efficacy.

FIG. 73 shows that chlorhexidine gluconate 0.12% oral rinse, MM1, and MM8 were equally effective at a pre-established *Staphylococcus epidermis* biofilm after 15 minutes of treatment. FIG. 74 PANEL A shows the colorimetric results of treating an 8-day old biofilm of *C. auris* with PAO, no treatment, chlorhexidine gluconate 0.12% oral rinse, MM7, or MM8. FIG. 74 PANEL B shows that chlorhexidine gluconate 0.12% oral rinse, MM7, and MM8 were the most effective at killing a pre-established, multi-drug resistant *C. auris* biofilm. FIG. 75 PANEL A shows the colorimetric results of treating a 6-day old biofilm of *Candida albicans* with PAO, no treatment, chlorhexidine gluconate 0.12% oral rinse, MM1, and MM8. FIG. 75 PANEL B shows that chlorhexidine gluconate 0.12% oral rinse, MM1, and MM8 were the most effective at killing a pre-established, multi-drug resistant *Candida albicans* biofilm.

The antiseptic properties of MM8 were tested against *Bacillus subtilis* (ATCC 6633)-infected (dead) chicken skin. Skin was removed from store-purchased chicken thighs, washed, and infected with 500 μL of a *B. subtilis* culture (~1×10$^9$ CFU/mL). The bacteria were rubbed into the skin sample for 15 seconds, and residual liquid was dabbed off with a paper towel. The skin sample was cut in half; one piece was treated with water, and the second piece was treated with various concentrations of MM8. Treatment with either water or MM8 was followed by 15 sec of rubbing into the skin and subsequent 20 min incubation at room temperature. 200 μl of water was placed on each skin sample, rubbed, and collected. 10 μL of the water was spread onto and MHA plate and incubated overnight at 37° C.

FIG. 76 PANEL A shows chicken skin samples that were infected with *B. subtilis* and decontaminated using concentrated MM8. FIG. 76 PANEL B shows the colony counts post treatment with water (TOP) and 5× concentrated MM8 (BOTTOM). FIG. 76 PANEL C shows colony counts post treatment with water (TOP) or 2× concentrated MM8 (BOTTOM). FIG. 76 PANEL D shows colony counts post treatment with water (TOP) or 1×MM8 (BOTTOM).

A culture of MRSA BAA-44 and multi-drug-resistant *Acinetobacter baumannii* (ATCC 1797) was grown in Mueller-Hinton broth or YM media overnight or for 24 hours at 37° C. 100 μL of an undiluted bacterial culture (~1×10$^9$ CFU/mL) were plated on MHA plates. To test for the efficacy of the formulations in killing *A. baumannii* after a 24 hour incubation, the inoculated MHA plates were treated with 10 μL of 1) MM8 or chlorhexidine gluconate 0.12% oral rinse; or 2) MM8 or chlorhexidine gluconate 0.12% oral rinse with 20% fetal bovine serum. FIG. 77 PANEL A shows that 20% FBS did not decrease the efficacy of MM8 or chlorhexidine gluconate 0.12% oral rinse in Gram-positive MRSA. FIG. 77 PANEL B shows that 20% FBS did not decrease MM8 killing efficiency in Gram-negative multi drug-resistant *A. baumannii*, but that 20% FBS decreased the efficacy of chlorhexidine gluconate 0.12% oral rinse in multi drug-resistant *A. baumannii*.

Example 9: Formulations with MM8 and EDTA

MM8$_{10}$ was formulated to include MM8 and 10 mM of ethylenediaminetetracetic acid (EDTA). MM8$_{100}$ was formulated to include MM8 and 100 mM of EDTA. An MHA plate was treated with multi-drug resistant *Burkholderia cepacia*, *Acinetobacter baumannii* (ATCC 1797), MRSA BAA-44, multi-drug resistant *C. auris* (CDC 0385), and *P. aeruginosa* (ATCC 2114). The MHA plates with *Acinetobacter baumannii* (ATCC 1797), MRSA BAA-44, and multi-drug resistant *C. auris* (CDC 0385) were treated with MM8$_{10}$. The MHA plates with multi-drug resistant *C. auris* (CDC 0385), *P. aeruginosa* (ATCC 2114), MRSA BAA-44, and multi-drug resistant *Burkholderia cepacia* were treated with MM8$_{100}$. The plates were then incubated at 37° C. for 1 day. Cultures of multi-drug-resistant *Burkholderia cepacia* (ATCC 10856), *Acinetobacter baumannii* (ATCC 1797), MRSA BAA-44, multi-drug-resistant *C. auris* (CDC 0385), and *P. aeruginosa* (ATCC 2114) were grown in Mueller-Hinton broth or YM media overnight or for 24 hours at 37° C. About 100 μL of undiluted bacterial and *Candida* cultures (~1×10$^9$ CFU/mL) were plated on MHA plates. The inoculated MHA plates were treated with 10 μL of MM8 and with 10 μL MM8$_{10}$ to test the efficacy of killing after a 24 hour incubation for bacterial plates and 48 hour incubation for the *C. auris* at 37° C.

FIG. 78 PANEL A shows that MM8$_{10}$ was not more effective at killing *Acinetobacter baumannii* (ATCC 1797) than was MM8 alone. FIG. 78 PANEL B shows that MM8$_{10}$ was not more effective at killing MRSA BAA-44 than was MM8 alone. FIG. 79 PANEL A shows that MM8$_{10}$ was more effective at killing multi-drug resistant *C. auris* than MM8 alone. FIG. 79 PANEL B shows that MM8$_{100}$ was more effective at killing multi-drug resistant *C. auris* than was MM8 alone.

FIG. 80 PANEL A shows that MM8$_{100}$ was more effective at killing *P. aeruginosa* (ATCC 2114) than was MM8 alone. FIG. 80 PANEL B shows that MM8$_{100}$ was more effective at killing MMRSA BAA-44 than was MM8 alone. For the areas treated with MM8$_{100}$, an improvement in the size and edge tightness of the diameters of clearance was observed. FIG. 81 shows that MM8$_{100}$ was more effective at killing *Burkholderia cepacia* (ATCC 10856) than was MM8 alone.

Example 10: Comparison of Hemolytic Activity

Chlorhexidine gluconate 0.12% oral rinse and MM8 were compared for hemolytic activity. 5 μL of CellLytic® B, chlorhexidine gluconate 0.12% oral rinse, or MM8 were spotted on a standard blood agar plate. Hemolysis was allowed to proceed for 6 hours at room temperature. Hemolysis results in red blood cells lysing, and areas on a blood agar plate with hemolysis turning either yellow or clear. FIG. 82 shows that CellLytic® B created a dramatic clearance while chlorhexidine gluconate 0.12% oral rinse and MM8 did not affect the color of the plate. The data show that MM8 was less hemolytic than was chlorhexidine gluconate 0.12% oral rinse.

Example 11: Efficacy of Formulations Against Anaerobic Oral Bacteria and Facial Bacteria The efficacy of diluted MM1 and MM8 against anaerobic oral bacteria and facial bacteria were tested. Cultures of *Propionibacterium acnes* (ATCC 6919) and *Streptococcus mutans* (85 W 2357) were grown in tryptic soy broth (TSB) media containing 10% sheep blood. The cultures were incubated under anaerobic conditions for 4 days at 37° C. About 100 μL of the undiluted bacterial cultures (~1×10$^9$ CFU/mL) were plated on MHA plates. The inoculated MHA plates were treated with 10 μL of MM8, a 1:2 dilution of MM8 in water, and a 1:10 dilution of MM1. The plates were incubated under anaerobic condition for either 11 days (*P. acnes*) or 2 days (*S. mutans*) at 37° C. FIG. 83 shows that MM8, a 1:2 aqueous dilution of MM8, and a 1:10 aqueous dilution of MM1 were equally effective in killing anaerobic bacteria *Propionibacterium acnes* (ATCC 6919) and *Streptococcus mutans* (85 W 2357).

Example 12: Evaluating Blood Hemolysis of MM7

5 µL of cell lysis buffer (CLB; positive control), MM7 (MycoDelens), 4% benzoyl peroxide, 10% benzoyl peroxide, and 2% salicylic acid were spotted on a blood agar plate. The blood agar plate was refrigerated overnight and assessed for blood hemolysis. Clear sections on the plate indicated blood hemolysis.

FIG. 84 shows a blood agar plate spotted with cell lysis buffer, MM7, 4% benzoyl peroxide, 10% benzoyl peroxide, and 2% salicylic acid. The data show that the cell lysis buffer caused complete cell hemolysis, MM7 caused little to no hemolysis, benzoyl peroxide (4% and 10%) caused complete hemolysis, and 2% salicylic acid caused little to no hemolysis.

Example 13: Evaluating the Efficacy of MM7, MM8, MM12, and MM13 in Killing MRSA BAA-44, Multi-Drug Resistant *A. baumannii* (ATCC 1797), Multi-Drug Resistant *P. aeruginosa* (ATCC 2114), and *C. albicans*

Overnight growths of MRSA BAA-44, multi-drug resistant *A. baumannii* (ATCC 1797), multi-drug resistant *P. aeruginosa* (ATCC 2114), and *C. albicans* were made in MHB. Each bacteria and yeast was spread undiluted onto different MHA plates. 10 µL drops of MM7, MM8, MM12, MM13, and vehicle controls (25% ethanol in PG and 50% ethanol in PG) were spotted onto different areas of each MHA plate. The MHA plates were incubated at 37° C. overnight and evaluated.

FIG. 85 PANEL A shows a MHA plate of MRSA BAA-44 treated with MM7, MM8, MM12, MM13, and vehicle controls. PANEL B shows a MHA plate of *A. baumannii* treated with MM7, MM8, MM12, MM13, and vehicle controls. PANEL C shows a MHA plate of *P. aeruginosa* treated with MM7, MM8, MM12, MM13, and vehicle controls. PANEL D shows a MHA plate of *C. albicans* treated with MM7, MM8, MM12, MM13, and vehicle controls. The data show that treatments with MM7, MM8, MM12, and MM13 were able to kill MRSA BAA-44, multi-drug resistant *A. baumannii*, multi-drug resistant *P. aeruginosa*, and *C. albicans* (ATCC 26555) after an incubation period of 1 day.

Example 14: Evaluating the Efficacy of MM7, MM9, MM10, and MM1 on MRSA BAA-44, Multi-Drug Resistant *A. baumannii* (ATCC 1797), Multi-Drug Resistant *P. aeruginosa* (ATCC 2114) and *C. albicans*

Overnight growths of MRSA, *A. baumannii*, *P. aeruginosa*, and *C. albicans* were made in MHB. The MRSA, *A. baumannii*, and *P. aeruginosa* samples were diluted 1:10, and the *C. albicans* sample was used undiluted. The samples were spread onto different MHA plates. 10 µL drops of MM7, MM9, MM10, and MM11 were spotted onto different areas of each plate. The plates were incubated at 37° C. overnight.

FIG. 86 PANEL A shows a MHA plate of *A. baumannii* treated with MM7, MM9, MM10, and MM11. PANEL B shows a MHA plate of MRSA BAA-44 treated with MM7, MM9, MM10, and MM11. PANEL C shows a MHA plate of *P. aeruginosa* treated with MM7, MM9, MM10, and MM11. PANEL D shows a MHA plate of *C. albicans* treated with MM7, MM9, MM10, and MM11. The data show that MM7, MM9, MM10, and MM11 were effective at killing MRSA BAA-44, multi-drug resistant *A. baumannii*, multi-drug resistant *P. aeruginosa*, and *C. albicans* after an incubation period of 1 day.

Overnight growths of MRSA BAA-44, multi-drug resistant *A. baumannii* (ATCC 1797), multi-drug resistant *P. aeruginosa* (ATCC 2114), and *C. albicans* were made in MHB. MRSA BAA-44, multi-drug resistant *A. baumannii*, and multi-drug resistant *P. aeruginosa* were diluted 1:10, and *C. albicans* was used undiluted. Each bacterial strain was spread onto a different MHA plate. 10 µL drops of MM7, MM9, MM10, and MM11 were spotted onto the different MHA plates. The plates were incubated overnight at 37° C., and were misted with a stock of 5 mg/mL MTT.

FIG. 87 PANEL A shows a MHA plate of MRSA BAA-44 treated with MM7, MM9, MM10, and MM11. PANEL B shows a MHA plate of *A. baumannii* (ATCC 1797) treated with MM7, MM9, MM10, and MM11. PANEL C shows a MHA plate of *P. aeruginosa* (ATCC 2114) treated with MM7, MM9, MM10, and MM11. PANEL D shows a MHA plate of *C. albicans* treated with MM7, MM9, MM10, and MM11. The data show that MM7, MM9, MM10, and MM11 were effective at killing MRSA BAA-44, multi-drug resistant *A. baumannii*, multi-drug resistant *P. aeruginosa*, and *C. albicans* after an incubation period of 1 day.

Example 16: Evaluating the Efficacy of Formulations of the Disclosure in Killing Colisitin-Resistant Bacteria An overnight growth of MCR-1 *E. coli* (AR 0350) was made in MHB, and was spread undiluted onto a MHA plate. 10 µL drops of MM7, MM9, mupirocin, bacitracin, neomycin, and a triple antibiotic ointment were spotted onto different areas of the MHA plate. The plate was incubated at 37° C. for 1 day.

FIG. 88 shows a MHA plate of *E. coli* treated with MM7, MM9, mupirocin, bacitracin, neomycin, and a triple antibiotic. The data show that only MM7, MM9, and mupirocin fully killed MCR-1 *E. coli* (AR 0350; colisitin-resistance only) after an incubation period of 1 day.

An overnight growth of multi-drug resistant *E. coli* (AR 0348) was made in MHB. The samples were diluted 1:1000, and spread onto a MHA plate. 10 µL of MM7, MM9, mupirocin, bacitracin, neomycin, and a triple antibiotic cream were spotted onto different areas of the MHA plate. The plate was incubated at 37° C. for 1 day.

FIG. 89 shows a MHA plate of multi-drug resistant *E. coli* treated with MM7, MM9, mupirocin, bacitracin, neomycin, and a triple antibiotic cream. The data show that only MM7, MM9, and mupirocin fully killed multi-drug resistant *E. coli* (AR 0348) after an incubation period of 1 day.

An overnight growth of multi-drug resistant *E. coli* (AR 0346) was made in MHB. The samples were diluted 1:1000, and spread onto a MHA plate. 10 µL of MM8, mupirocin, bacitracin, neomycin, and a triple antibiotic cream were spotted onto different areas of the MHA plate. The plate was incubated at 37° C. for 3 days.

FIG. 90 shows a MHA plate of multi-drug resistant *E. coli* (AR 0346) treated with MM8, mupirocin, bacitracin, neomycin, and a triple antibiotic cream. The data show that only MM8 and mupirocin fully killed multi-drug resistant *E. coli* (AR 0346) after an incubation period of 3 days.

Example 17: Evaluating the Efficacy of Formulations Mixed with Petroleum Jelly MM12 was mixed with an equal volume of petroleum jelly (VaselineMD) until a suspension was formed. The MM12/petroleum jelly mixture was applied to a lawn of multi drug-resistant *A. baumannii*, MRSA BAA-44, or *C. albicans* by gently rubbing the MM12/petroleum jelly mixture into the lawn. The efficacy of the formulation was evaluated after 24 hours. MM12 retained antibacterial and antifungal potency even when mixed with an equal volume of petroleum jelly. The petroleum jelly did not contribute to the toxicity observed in the treatment of lawns with the MM12/petroleum jelly mixture. FIG. 91 shows the effects of the MM12/petroleum jelly mixture (VaselineMD) and petroleum jelly on killing lawns infected with *A. baumannii* ATCC 1797, MRSA BAA-44, and *C. albicans*.

Example 18: Evaluating the Efficacy of MycoDelens as a Disinfectant Using a Time-Kill Kinetic Assay An overnight grow of bacteria was prepared in MHB or an overnight grow of *C. albicans* was prepared in YM media. To 1.6 mL tubes of the samples, 100 µL of MHB, 100 µL of MM12-neutralizing blocking buffer, 100 µL of MM12, were added sequentially. Then, 90 µL of the blocking buffer and 10 µL of cells in MM12 were added to the tubes at appropriate time points. The resulting mixtures were incubated at room temperature for 10 minutes. Approximately $1 \times 10E^8$ CFU/mL of cells were added to each tube. 10 µL of a sample was removed from the MycoDelens tube at t=5 seconds, 30 seconds, or 2 minutes, and the sample was added to 90 µL of blocking buffer. The samples were incubated for an additional 10 minutes at 37° C. The samples were diluted by 10-fold, and drip-streaked to determine colony counts.

The data show that MM12 eradicated a starting population of cells of about 10E5 to about 10E7 pathogens within less than 2 minutes of exposure. TABLE 15 shows the results of the experiment. * indicates experiments conducted in triplicate.

Example 19: Evaluating the Efficacy of MM14 Against Antibiotic-Sensitive and Antibiotic-Resistant Gram Positive and Gram Negative Bacteria The efficacy of MM14 in killing drug-resistant and drug-sensitive bacteria was tested as described below. Mupirocin Ointment USP, 2% (Glenmark Pharmaceuticals Ltd, Mahwah, N.J.), Actavis Bacitracin Zinc Ointment, 1 oz (Actavis Generics, Parsippany-Troy Hills, N.J.), Vitacilina Neomycin Sulfate ointment First Aid (Teresa Cecena DBA Genesis, San Ysidro, Calif.) and Equate Triple Antibiotic Ointment, 1 oz (Walmart, Bentonville, Ark.) were used as comparisons for MM14 in the majority of the efficacy screenings. MM7, along with the above mentioned ointments, was screened against VRE ATCC 51299, MRSA ATCC BAA-44, CRE NDM-1 ATCC BAA-2146, multi-drug resistant *A. baumannii* ATCC BAA-1797, multi-drug resistant *P. aeruginosa* ATCC BAA-2114, *E. coli* O157:H7 ATCC 51657, *S. maltophilia* ATCC 13637, *M. abscessus* ATCC 19977, *B. cepacia* ATCC 10856, *S. flexneri* 85 W 2332, *S. enteriditis* CDC AR0496, *S. pyogenes* 85 W 1180, *Y. pestis* KIM6, *Clostridium* spp. ATCC 3584, *N. gonorrhea* CDC AR0214, *P. acnes* ATCC 6919, multi-drug-resistant *E. coli* CDC AR0493, and *S. mutans* 85 W2357. For the screening procedure, approximately $1 \times 108$ CFU/mL were plated on a MIA plate. Following the seeding of the bacterial lawn, 10 µL of MM14 and a 10 µL spot of Mupirocin Ointment, Actavis Bacitracin Zinc Ointment, Vitacilina Neomycin Sulfate Ointment, and Equate Triple Antibiotic Ointment were added to the plate. The plates were subsequently incubated for 24 to 48 hours at 37° C. before being visually assessed for antimicrobial susceptibility.

As shown in TABLE 16, MM14 had antimicrobial activity against all 17 strains of antibiotic-sensitive and antibiotic-resistant Gram-positive and Gram-negative bacterial strains that were tested. Moreover, MM14 was the most, and often only, effective treatment against the diverse panel of bacterial strains that were evaluated. For example, MM14 was the only effective treatment against VRE ATCC 25922, CRE NDM-1 ATCC BAA-2146, *A. baumannii* ATCC BAA-1797, and *M. abscessus* ATCC 19977. Prescription Mupirocin Ointment was the leading competitor with respect to broad spectrum antibacterial activity.

TABLE 15

| Organism | Challenge suspension (CFU/mL) | Exposure Time | Post-exposure Population (CFU/mL) | $Log_{10}$ Reduction | Percent Reduction |
|---|---|---|---|---|---|
| * MDR *A. baumannii* ATCC 1797 | $4.8 \times 10^8$ | 5 seconds | $3.4 \times 10^4$ | 4 | 99.99% |
|  |  | 30 seconds | 0 | 8 | 100% |
| * MRSA BAA-44 | $4.0 \times 10^7$ | 5 seconds | 0 | 7 | 100% |
|  |  | 30 seconds | 0 | 7 | 100% |
| *S. maltophilia* | $1.2 \times 10^7$ | 5 seconds | 0 | 7 | 100% |
|  |  | 30 seconds | 0 | 7 | 100% |
| *C. albicans* | $6.2 \times 10^5$ | 5 seconds | $6.3 \times 10^4$ | 1 | 89.83% |
|  |  | 30 seconds | 0 | 5 | 100% |
| *E. coli* | $2.4 \times 10^7$ | 30 seconds | 0 | 7 | 100% |
|  |  | 2 minutes | 0 | 7 | 100% |
| * *P. aeruginosa* | $8.9 \times 10^8$ | 30 seconds | 0 | 8 | 100% |
|  |  | 2 minutes | 0 | 8 | 100% |
| * *K. pneumoniae* | $1.7 \times 10^8$ | 30 seconds | $2.3 \times 10^3$ | 5 | 99.90% |
|  |  | 2 minutes | 0 | 8 | 100% |
| **S. enteritidis* | $3.4 \times 10^8$ | 30 seconds | $1.8 \times 10^6$ | 2 | 99.5% |
|  |  | 2 minutes | 0 | 8 | 100% |
| **S. pyogenes* | $1.9 \times 10^7$ | 30 seconds | 0 | 7 | 100% |
|  |  | 2 minutes | 0 | 7 | 100% |
| *VRE | $2.0 \times 10^7$ | 30 seconds | 0 | 7 | 100% |
|  |  | 2 minutes | 0 | 7 | 100% |

TABLE 16

| Organism | MM14 | Mupirocin | Bacitracin | Neomycin | Triple Antibiotic |
|---|---|---|---|---|---|
| VRE ATCC 25922 | + | – | – | – | – |
| MRSA ATCC BAA-44 | + | + | – | – | – |
| CRE NDM-1 (MDR) ATCC BAA-2146 | + | – | – | – | – |
| A. baumannii MDR ATCC 1797 | + | – | – | – | – |
| P. aeruginosa MDR ATCC 2114 | + | + | – | – | – |
| E. coli CDC AR0493 | + | + | – | – | – |
| E. coli O157:H7 | + | + | – | + | + |
| Shigella flexneri 85W 2332 | + | + | NT | NT | NT |
| Salmonella enteriditis CDC AR0496 | + | + | NT | NT | NT |
| Streptococcus pyogenes 85W 1180 | + | + | – | + | + |
| Burkholderia cepacia ATCC 10856 | + | + | – | – | – |
| Yersinia pestis KIM6 | + | + | – | – | – |
| Clostridium spp. ATCC 3584 | + | NT | NT | NT | NT |
| Neisseria gonorrhea CDC AR0214 | + | NT | NT | NT | NT |
| Mycobacterium abscessus ATCC19977 | + | – | – | – | – |
| Streptococcus mutans 85W2357 | + | NT | NT | NT | NT |
| Propionibacterium acnes ATCC 6919 | + | NT | NT | NT | NT |

"+" = antibacterial activity with complete clearing;
"–" = no antibacterial activity;
NT = not tested

Example 18: Evaluating the Efficacy of MM14 and MM118 as a Disinfectant Via a Time-Kill Kinetic Assay The disinfectant properties of MM14 and MM18 were evaluated on each of the bacterial and fungal species. All bacterial species were grown in MH broth for 12 hours in a rotary shaking incubator (100 rpm) at 37° C. *Candida albicans* ATCC 26555 was grown in YM for 18 hours in a rotary shaking incubator at 37° C. 1.6 mL Eppendorf tubes were prepared as follows: 1) 90 µL of either MH or YM; 2) 90 µL of Letheen neutralizing buffer (LET aka blocking buffer; 5 g/L beef extract, 0.7 g/L lecithin, 5 g/L polysorbate 80, and 5 g/L sodium chloride); 3) 90 µL MycoDelens or MycoAmet; and 4) 90 µL LET. 10 µL of undiluted cell suspension (ranging from 1×10⁵ to 1×10⁸ CFU/mL) were added to each of the above described tubes and incubated either 30 seconds, 2 minutes, 10 minutes, or 15 minutes at room temperature. After a designated amount of time, 10 µL of cell suspension was removed from 3) and re-suspended into 4) to neutralize the toxicity of MM14 and MM18. The samples were placed into a CytoOne 96-well microtiter plate (USA Scientific, Orlando, Fla.), diluted 10-fold, and drip-streaked onto 100 mm×15 mm Mueller-Hinton agar (MHA) plates (Simport Scientific Inc., Saint-Mathieu-de-Beloeil, QC). The MHA plates were incubated for 12 hours at 37° C. and the efficacy of the disinfectant properties of MM14 and MM18 were evaluated in terms of colony forming units with respect to the population of remaining viable bacteria and fungi.

The data show that MM14 and MM18 eradicated a starting population of cells of about 1×10⁵ to about 1×10⁷ pathogens within less than 2 minutes of exposure. TABLE 17 shows the results of the experiment. * indicates experiments conducted with MM18 as opposed to MM14. All experiments were performed in triplicate.

TABLE 17

| Organism | Challenge suspension (CFU/mL) | Exposure Time | Post-exposure Population (CFU/mL) | $Log_{10}$ Reduction | Percent Reduction |
|---|---|---|---|---|---|
| MDR A. baumannii ATCC 1797 | $4.8 \times 10^8$ | 5 seconds | $3.4 \times 10^4$ | 4 | 99.99% |
|  |  | 30 seconds | 0 | 8 | 100% |
| MRSA ATCC BAA-44 | $4.0 \times 10^7$ | 5 seconds | 0 | 7 | 100% |
|  |  | 30 seconds | 0 | 7 | 100% |
| S. maltophilia ATCC 13637 | $5.2 \times 10^7$ | 30 seconds | 0 | 7 | 100% |
|  |  | 2 minutes | 0 | 7 | 100% |
| C. albicans ATCC 26555 | $8.5 \times 10^5$ | 30 seconds | 0 | 5 | 100% |
|  |  | 2 minutes | 0 | 5 | 100% |
| E. coli ATCC 2340 | $4.8 \times 10^7$ | 30 seconds | $4.0 \times 10^6$ | 1 | 91.67% |
|  |  | 2 minutes | 0 | 7 | 100% |
| P. aeruginosa ATCC 2114 | $8.9 \times 10^8$ | 30 seconds | 0 | 8 | 100% |
|  |  | 2 minutes | 0 | 8 | 100% |

TABLE 17-continued

| Organism | Challenge suspension (CFU/mL) | Exposure Time | Post-exposure Population (CFU/mL) | $Log_{10}$ Reduction | Percent Reduction |
|---|---|---|---|---|---|
| K. pneumoniae ATCC 2342 | $1.7 \times 10^8$ | 30 seconds | $2.3 \times 10^3$ | 5 | 99.90% |
| | | 2 minutes | 0 | 8 | 100% |
| S. enteritidis 85W 2310 | $3.4 \times 10^8$ | 30 seconds | $1.8 \times 10^6$ | 2 | 99.5% |
| | | 2 minutes | 0 | 8 | 100% |
| S. enteritidis CDC AR 0496 | $1.8 \times 10^8$ | 30 seconds | $1.1 \times 10^6$ | 2 | 99.5% |
| | | 2 minutes | 0 | 0 | 100% |
| S. pyogenes 85W 1180 | $1.9 \times 10^7$ | 30 seconds | 0 | 7 | 100% |
| | | 2 minutes | 0 | 7 | 100% |
| VRE ATCC 51299 | $2.0 \times 10^7$ | 30 seconds | 0 | 7 | 100% |
| | | 2 minutes | 0 | 7 | 100% |
| S. flexneri 85W2332 | $2.0 \times 10^7$ | 30 seconds | 0 | 7 | 100% |
| | | 2 minutes | 0 | 7 | 100% |
| Y. pestis Kim6 | $2.0 \times 10^6$ | 30 seconds | 0 | 6 | 100% |
| | | 2 minutes | 0 | 6 | 100% |
| *P. mirabilis 85W 1895 | $2.5 \times 10^8$ | *15 minutes | 0 | 8 | 100% |
| B. cepacia | $5.4 \times 10^7$ | *10 minutes | 0 | 7 | 100% |
| | | 15 minutes | 0 | 7 | 100% |

*Indicates experiments conducted with MM18 as opposed to MM14. All experiments performed in triplicate.

Example 20: The Effect of MM14 on P. mirabilis

The efficacy of MM14 in killing Proteus mirabilis (P. mirabilis), an oral bacterium that causes Alzheimer's Disease, was tested. In brief P. mirabilis, 85 W 1895 was grown in Mueller-Hinton (MH) broth at 37° C. for 12 hours in a rotary shaking incubator. For the screening procedure, approximately $1 \times 10^8$ CFU/mL were plated on an MHA plate. Following the seeding of the bacterial lawn, 10 µL of MM14 was added to the plate. The plate was subsequently incubated for 18 hours at 37° C. before being visually assessed for antimicrobial susceptibility. As shown in FIG. 92, MM14 eradicated P. mirabilis when delivered in both water and PG.

Example 21: The Effect of MM14 on S. mutans

MM14 was screened against Streptococcus mutans (S. mutans) 85 W2357, a cavity causing bacteria. S. mutans was grown in Brain Heart Infusion broth at 37° C. for 12 hours in a rotary shaking incubator. For the screening procedure, approximately $1 \times 10^8$ CFU/mL were plated on MHA plate. Following the seeding of the bacterial lawn, 10 µL of MM14 was added to the plate. The plate was subsequently incubated for 24 to 48 hours at 37° C. before being visually assessed for antimicrobial susceptibility. As shown in FIG. 93, MM14 eradicated S. mutans growth.

Example 22: The Effect of MM14 on P. acnes

MM14 was screened against Propionibacterium acnes (P. acnes) ATCC 6919, an acne-causing bacteria. P. acnes was grown in TSB with 5% defibrinated sheep blood in an anaerobic chamber in the presence of a gas mixture consisting of 80% $N_2$, 10% $CO_2$, and 10% $H_2$ in a rotary shaking incubator (100 rpm) at 37° C. for 11 days. For the screening procedure, approximately $1 \times 10^8$ CFU/mL were plated on an MHA plate. Following the seeding of the bacterial lawn, 10 µL of MM14 was added to the plate. The plate was subsequently incubated for an additional 11 days at 37° C. in an anaerobic chamber before being visually assessed for antimicrobial susceptibility. As shown in FIG. 94, MM14 eradicated P. acnes growth.

Example 23: The Effect of MM14 on Salmonella enteriditis, Shigella flexneri, Streptococcus pyogenes, Burkholderia Cepacia, Clostridium Spp, and Yersinia pestis Burkholderia cepacia ATCC 10856, Streptococcus pyogenes 85 W, and Yersinia pestis (KIM6) were grown in Mueller-Hinton broth at 37° C. for 12 hours in a rotary shaking incubator (100 rpm). Shigella flexneri 85 W 2332 and Salmonella enteriditis CDC AR0496 were grown in Brain Heart Infusion broth (BHI) at 37° C. for 12 hours in a rotary shaking incubator. Clostridium spp. ATCC 3584 was grown in Trypticase Soy broth (BD™ Tryptic Soy Broth (TSB) BD, Franklin Lakes, N.J.) in an anaerobic chamber in the presence of a gas mixture consisting of 80% $N_2$, 10% $CO_2$, and 10% $H_2$ (BD BBL™ $CO_2$ generator, Franklin Lakes, N.J.) at 37° C. for 10 days. The efficacy of MM14 in killing the above mentioned pathogens was tested and compared to various commercially available products. Mupirocin Ointment USP, 2%, Actavis Bacitracin Zinc Ointment, Vitacilina Neomycin Sulfate ointment First Aid, Equate Triple Antibiotic Ointment, and Chlorhexidine gluconate 0.12% were used as comparisons for MM14 in the majority of the efficacy screenings. MM14, along with the above mentioned ointments, was screened against Burkholderia cepacia (B. cepacia) ATCC 10856, Shigella flexneri (S. flexneri) 85 W 2332, Salmonella enteriditis (S. enteriditis) CDC AR0496, Streptococcus pyogenes (S. pyogenes) 85 W 1180, Yersinia pestis (Y. pestis) KIM6, and Clostridium spp. ATCC 3584. For the screening procedure, approximately $1 \times 10^8$ CFU/mL were plated on an MHA plate. Following the seeding of the bacterial lawn, 10 µL of MM14 and a 10 µL spot of Mupirocin Ointment, Actavis Bacitracin Zinc Ointment, Vitacilina Neomycin Sulfate Ointment, Chlorhexidine gluconate 0.12%, and Equate Triple Antibiotic Ointment were added to the MHA plate. The plates were subsequently incubated for 24 to 48 hours (all pathogens with the exception of Clostridium spp. Which was incubated for 20 days) at 37° C. before being visually assessed for antimicrobial susceptibility. Result shown in FIG. 95 indicated that MM14 was able to eradicate each of the pathogens tested.

Example 24: Sterilization Efficacy of MM14 and MM18 on *X. campestris* 19155 and *Clavibacter* sp. ATCC 43179

The sterilization efficacy of MM14 and MM18 on *Xanthomonas campestris* (*X. campestris*) ATCC 19155 and *Clavibacter* sp, two pathogens associated with crop destruction, was assessed. *X. campestris* ATCC 19155 and *Clavibacter* sp. ATCC 43179 were grown in BHI broth at 26° C. for 12 hours in a rotary shaking incubator (100 rpm). To screen MM14 and MM18 against the pathogens, approximately $1 \times 10^8$ CFU/mL were plated on a BHI plate. Following the seeding of the bacterial lawn, 10 µL of MM14 and 10 µL MM18 were added to the BHI plate. The plates were subsequently incubated for 18 hours at 26° C. before being visually assessed for antimicrobial susceptibility. Results are shown in FIG. 96 and indicated that both MM14 and MM18 eradicated *X. campestris* ATCC 19155 and *Clavibacter* sp. ATCC 43179.

Example 25: Quantification of MM14 Sterilization Efficacy on *X. campestris* 19155 and *Clavibacter* sp. ATCC 43179

The disinfectant properties of MM14 were quantified on each of *X. campestris* 19155 and *Clavibacter* sp. ATCC 43179. Each bacterial species was grown in BHI broth for 12 hours in a rotary shaking incubator (100 rpm) at 26° C. 1.6 mL Eppendorf tubes were prepared as follows: 1) 90 µL of either BHI; 2) 90 µL of Letheen neutralizing buffer (LET blocking buffer; 5 g/L beef extract, 0.7 g/L lecithin, 5 g/L polysorbate 80, and 5 g/L sodium chloride); 3) 90 µL MM14; and 4) 90 µL LET. 10 µL of undiluted cell suspension ($1 \times 10^8$ CFU/mL) were added to each of the above described tubes and incubated either 30 seconds or 2 minutes at room temperature. After a designated amount of time, 10 µL of cell suspension was removed from 3) and re-suspended into 4) in order to neutralize the toxicity of MM14. The samples were placed into a CytoOne 96-well microtiter plate, diluted 10-fold, and drip-streaked onto 100 mm×15 mm BHI plates. The BHI plates were incubated for 12 hours at 26° C. and the efficacy of the disinfectant properties of MM14 were evaluated in terms of colony forming units with respect to the population of remaining viable bacteria and fungi. As can be seen in FIG. 97, MM14 caused complete sterilization of both *X. campestris* and *Clavibacter* sp. after 30 seconds of treatment.

Example 26: The Effect of MM14 and MM18 on *Porphyromonas gingivalis* (*P. gingivalis*)

*P. gingivalis* is grown anaerobically (80% $N_2$, 10% $CO_2$, 10% $H_2$) in Trypticase soy broth (TSB) enriched with 0.25% yeast extract, 2.5 µg/ml hemin, 5.0 µg/ml menadione, and 0.01% dithiothreitol (DTT) at 37° C. for 48 hours. A TSA plate is then inoculated with approximately $1 \times 10^7$ cells/mL. Following the seeding of the bacterial lawn, 10 µL of MM14, 10 µL MM18, 10 µL Chlorhexidine gluconate 0.12%, 10 µL Listerine Naturals Antiseptic Mouthwash, and 10 µL Crest Pro-Health Multiprotection Rinse, are then added to separate areas on the plate. The plate is then subsequently incubated for 48 hours in anaerobic conditions at 37° C. before being visually assessed for antimicrobial susceptibility.

Example 27: Testing the Efficacy of MM18 Powder on *A. baumannii* ATCC 1997

Figure 98:
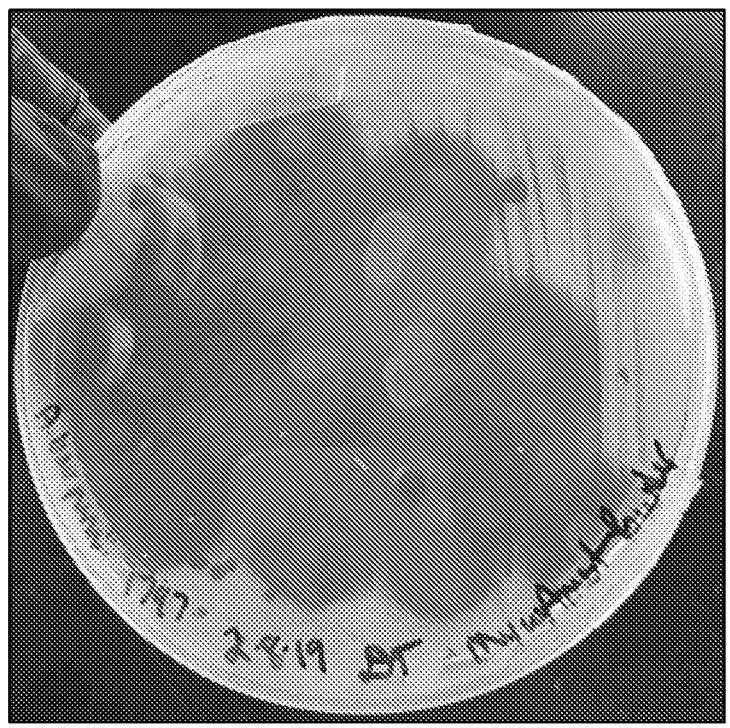

To obtain MM18 in powder form, a liquid formulation of MM18 was left in a sterile T75 tissue culture flask with a vented cap until 100 mL of the liquid dried into a glass-like consistency at the bottom of the flask. A mortal and pestle was then used to turn the dried MM18 into a powder. A MHA plate was then inoculated with a lawn of *A. baumannii* ATCC BAA-1797. To test the efficacy of MM18 powder against *A. baumannii*, MM18 poser was sprinkled onto the surface of the inoculated plate. Following an 18 hour incubation at 37° C., the plate was visually assessed for antimicrobial susceptibility. As can be seen in FIG. 98, the MM18 powder eradicated *A. baumannii* in the areas in which it was added.

Example 28: Testing the Efficacy of MM14 and MM15 as Anti-Viral Agents

To determine the efficacy of MM14 and MM15 as antiviral agents, human cervical adenocarcinoma (HeLa) cells are cultured in T25 tissue culture flasks in Dulbecco's Modified Eagle's Medium (DMEM) with 10% fetal bovine serum (FBS) in a 37° C. incubator with 5% $CO_2$ until confluency. To prepare a stock viral culture (e.g. vaccinia virus), HeLa cells are split and plated into 6-well plates, allowed to attach for 12 hours at 37° C. in a 5% $CO_2$ incubator, are be infected with 0.1 plaque forming units (PFU) per cell, and delivered in a minimal volume that covers the surface of the HeLa cells. The samples are incubated at 37° C. in 5% $CO_2$ for 30 minutes. Following the incubation, the inoculum is aspirated and replaced with fresh DMEM and FBS before being incubated again at 37° C. in 5% $CO_2$ for 48 hours. Following the 48 hour incubation, the supernatant is discarded and the infected HeLa cells are re-suspended in 1 mM Tris pH 9.0. Three freeze-thaw cycles are performed, and the sample is purified through a sucrose cushion. For purification with a sucrose cushion, following the freeze-thaw cycles, the sample is mixed by vortex and spun by centrifuge for 10 minutes at 1.2 K. The resulting supernatant is collected and saved, while the pellet is re-suspended in 15 mL of 1 mM Tris pH 9.0 before being mixed by vortex and spun by centrifuge for 10 minutes at 1.2 K. The resulting supernatants are also collected. 15 mL of 36% w/v sucrose in 1 mM Tris pH 9.0 is added to an ultracentrifuge tube to which 20 mL of viral sample is slowly added, taking extra care that the samples do not mix. Lastly, the viral titer of the stock is determined. The samples are then spun in an ultracentrifuge for 1 hour at 20 K at 4° C. Following ultracentrifugation, the supernatant is aspirated and the pellet is re-suspended in 1 mL of 1 mM Tris pH 9.0.

After determining the vial titer, a plaque assay is performed as follows: 10 µL of virus stock is mixed with 10 µL of sterile 0.25 mg/ml trypsin. The mix is incubated in a 37° C. water bath and mixed by vortex every 10 minutes during the incubation. Immediately following the incubation, dilutions ranging from 10-2 to 10-10 are prepared in DMEM plus FBS. The medium is aspirated from the 6-wells plates and 200 µL of the virus dilution is added to 1 mL of DMEM plus FBS. This viral mix is distributed into each well of the 6-well plates. The sample treatments include a negative control as well as wells treated with 50%, 10%, 5%, 1%, and 0.5% v/v of MM14 and/or MM15. The plates are incubated at 37° C. for 30 minutes in 5% $CO_2$. Following the incubation, the inocula is aspirated and replaced with 3 mL of DMEM with 2% FBS. The plates are then incubated at 37°

C. in 5% $CO_2$ for 48 hours. To enumerate PFU/cell, the medium is aspirated from each well following the 48 hour incubation. 2 mL of crystal violet (0.1% crystal violet in 20% ethanol) is added and the plates are incubated at room temperature for 10 minutes. The stain is then aspirated, the wells are washed with water, and the number of plaques is counted.

Example 29: Anti-Infective Properties of MM14 Combined with Other Preparations

Figure 99:
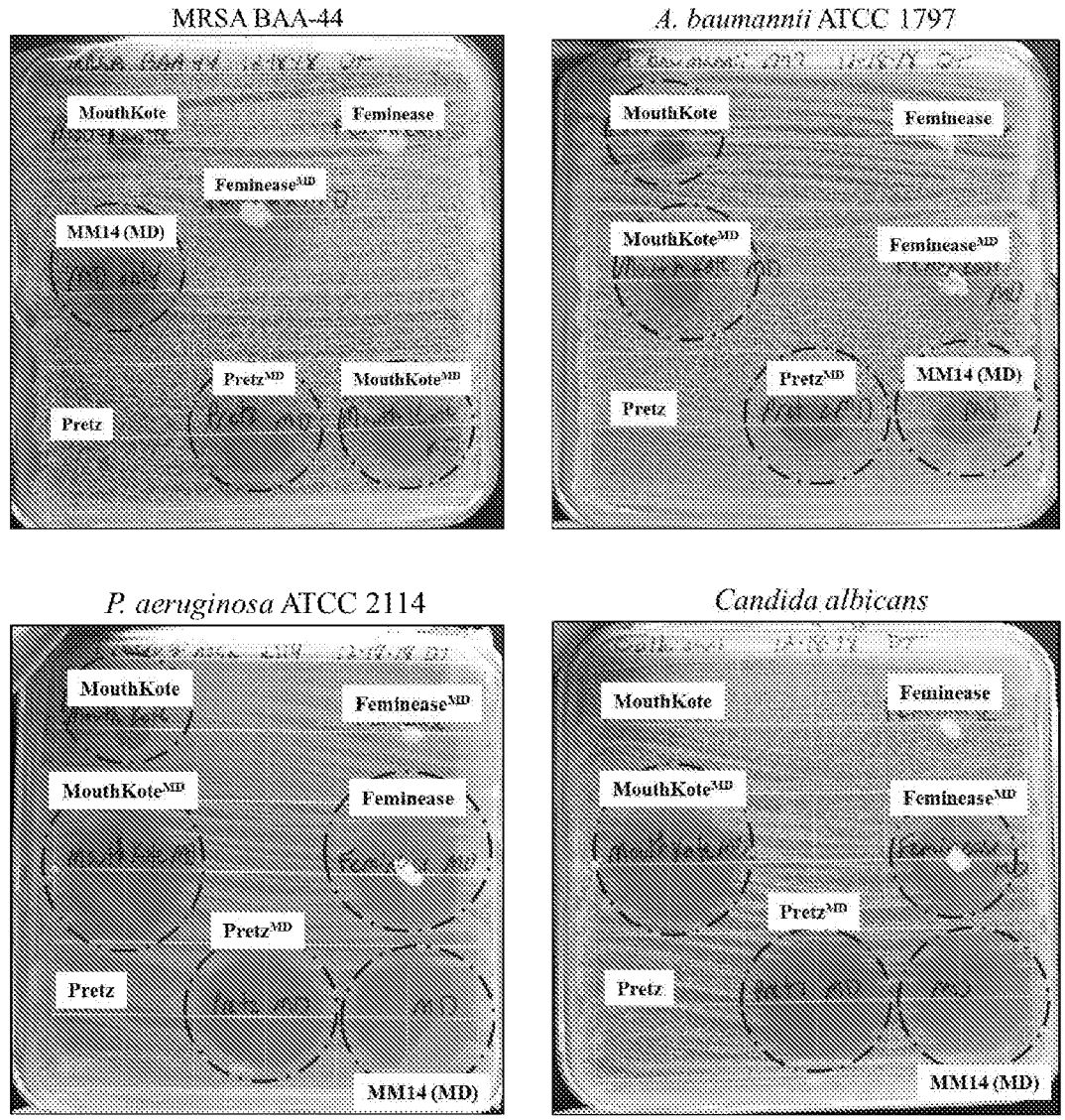

The efficacy of MM14 in killing MRSA BAA-44, *P. aeruginosa* ATCC 2114, *A. baumannii* ATCC 1797, and *C. albicans* ATCC 26555 when combined with other preparations was tested as described below. Organisms were grown in Mueller-Hinton (MH) broth at 37° C. for 12 hours in a rotary shaking incubator. For the screening procedure, approximately $1 \times 10^8$ CFU/mL were plated on an MHA plate. Following the seeding of the bacterial lawn, 10 μL of MM14, Feminease® Feminine Moisturizer, Pretz Nasal Spray, Mouth Kote Dry Mouth Spray, Feminease® Feminine Moisturizer+MM14, Pretz Nasal Spray+MM14, and Mouth Kote Dry Mouth Spray+MM14 were added to the plate. The plate was subsequently incubated for 18 hours at 37° C. before being visually assessed for antimicrobial susceptibility. As can be seen in FIG. 99 adding MM14 to the existing preparations endowed the preparations with-infective properties.

Example 30: Evaluating Seed Germination after Treatment with MM14 and MM18

Figure 100:
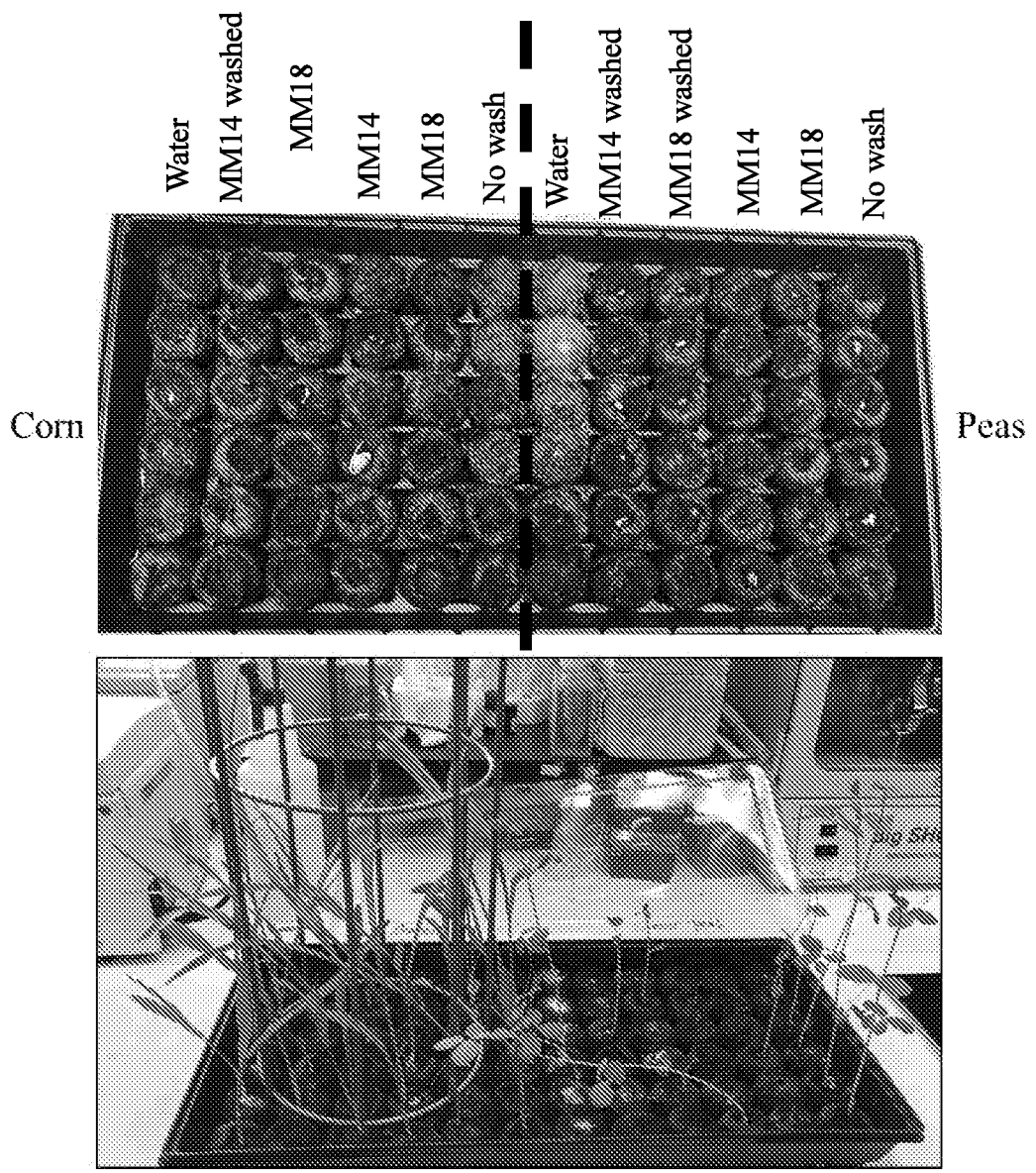

To assess the potential of MM14 and MM18 to protect crops from infection, the effect of MM14 and MM18 on seed germination was assessed. Sweet snap pea and corn seeds were separated into 6 treatment groups as follows: 1) no treatment, 2) sterile water wash, 3) MM14 wash, 4) MM18 wash, 5) MM14 wash and subsequent water wash, and 6) MM18 wash and subsequent water wash. Seeds were treated for 10 minutes before being planted into soil. Seeds were watered and left in sunlight for two weeks before evaluating germination efficiency. As can be seen in FIG. 100, no significant differences were seen in germination efficiency among treatment groups.

Embodiments

The following non-limiting embodiments provide illustrative examples of the invention, but do not limit the scope of the invention.

Embodiment 1. A pharmaceutical composition comprising, in a unit dosage form: a) a cationic surfactant, wherein the cationic surfactant is a cetyltrimethylammonium halide; b) a chelating agent, wherein the chelating agent is diethylenetriaminepentaacetic acid (DTPA) or a pharmaceutically-acceptable salt thereof: and c) a solvent.

Embodiment 2. The pharmaceutical composition of embodiment 1, wherein the cetyltrimethylammonium halide is cetyltrimethylammonium bromide.

Embodiment 3. The pharmaceutical composition of embodiment 1, wherein the cetyltrimethylammonium halide is cetyltrimethylammonium chloride.

Embodiment 4. The pharmaceutical composition of any one of embodiments 1-3, wherein the cationic surfactant is present at a concentration of about 1 mM to about 500 mM.

Embodiment 5. The pharmaceutical composition of any one of embodiments 1-4, wherein cationic surfactant is present at a concentration of about 1 mM.

Embodiment 6. The pharmaceutical composition of any one of embodiments 1-4, wherein the cationic surfactant is present at a concentration of about 400 mM.

Embodiment 7. The pharmaceutical composition of any one of embodiments 1-4, wherein the cationic surfactant is present at a concentration of about 500 mM.

Embodiment 8. The pharmaceutical composition of any one of embodiments 1-7, wherein the chelating agent is present at a concentration of about 10 mM to about 500 mM.

Embodiment 9. The pharmaceutical composition of any one of embodiments 1-8, wherein the chelating agent is present at a concentration of about 10 mM.

Embodiment 10. The pharmaceutical composition of any one of embodiments 1-8, wherein the chelating agent is present at a concentration of about 250 mM.

Embodiment 11. The pharmaceutical composition of any one of embodiments 1-8, wherein the chelating agent is present at a concentration of about 300 mM.

Embodiment 12. The pharmaceutical composition of any one of embodiments 1-8, wherein the chelating agent is present at a concentration of about 500 mM.

Embodiment 13. The pharmaceutical composition of any one of embodiments 1-12, wherein the solvent is an organic solvent.

Embodiment 14. The pharmaceutical composition of any one of embodiments 1-12, wherein the solvent comprises propylene glycol.

Embodiment 15. The pharmaceutical composition of any one of embodiments 1-12, wherein the solvent comprises petroleum jelly.

Embodiment 16. The pharmaceutical composition of any one of embodiments 1-12, wherein the solvent comprises an organic solvent and an aqueous solvent.

Embodiment 17. The pharmaceutical composition of embodiment 16, wherein the organic solvent is present in an amount of about 25%.

Embodiment 18. The pharmaceutical composition of embodiment 16, wherein the organic solvent is present in an amount of about 50%.

Embodiment 19. The pharmaceutical composition of embodiment 16, wherein the organic solvent is propylene glycol and the aqueous solvent is water.

Embodiment 20. The pharmaceutical composition of any one of embodiments 16-18, wherein the organic solvent is dimethyl sulfoxide and the aqueous solvent is water.

Embodiment 21. The pharmaceutical composition of any one of embodiments 16-18, wherein the organic solvent is ethanol and the aqueous solvent is water.

Embodiment 22. The pharmaceutical composition of any one of embodiments 16-18, wherein the organic solvent is glycerol and the aqueous solvent is water.

Embodiment 23. The pharmaceutical composition of any one of embodiments 1-22, wherein the pharmaceutical composition further comprises an antibiotic.

Embodiment 24. The pharmaceutical composition of embodiment 23, wherein the antibiotic is polymyxin B.

Embodiment 25. A method of killing a microorganism comprising administering to the microorganism a therapeutically-effective amount of a pharmaceutical composition, wherein the pharmaceutical composition comprises, in a unit dosage form: a) a cationic surfactant, wherein the cationic surfactant is a cetyltrimethylammonium halide; b) a chelating agent, wherein the chelating agent is diethylenetriaminepentaacetic acid (DTPA) or a pharmaceutically-acceptable salt thereof; and c) a solvent.

Embodiment 26. The method of embodiment 25, wherein the microorganism is a bacterium Embodiment 27. The method of embodiment 25, wherein the microorganism is a fungus.

Embodiment 28. The method of embodiment 27, wherein the fungus is a mold.

Embodiment 29. The method of embodiment 25, wherein the microorganism is a yeast.

Embodiment 30. The method of embodiment 25, wherein the microorganism is a virus.

Embodiment 31. The method of any one of embodiments 25-30, wherein the cetyltrimethylammonium halide is cetyltrimethylammonium bromide.

Embodiment 32. The method of any one of embodiments 25-30, wherein the cetyltrimethylammonium halide is cetyltrimethylammonium chloride.

Embodiment 33. The method of any one of embodiments 25-32, wherein the cationic surfactant is present at a concentration of about 1 mM to about 500 mM.

Embodiment 34. The method of any one of embodiments 25-33, wherein the cationic surfactant is present at a concentration of about 1 mM.

Embodiment 35. The method of any one of embodiments 25-33, wherein the cationic surfactant is present at a concentration of about 400 mM.

Embodiment 36. The method of any one of embodiments 25-33, wherein the cationic surfactant is present at a concentration of about 500 mM.

Embodiment 37. The method of any one of embodiments 25-36, wherein the chelating agent is present at a concentration of about 10 mM to about 500 mM.

Embodiment 38. The method of any one of embodiments 25-37, wherein the chelating agent is present at a concentration of about 10 mM.

Embodiment 39. The method of any one of embodiments 25-37, wherein the chelating agent is present at a concentration of about 250 mM.

Embodiment 40. The method of any one of embodiments 25-37, wherein the chelating agent is present at a concentration of about 300 mM.

Embodiment 41. The method of any one of embodiments 25-37, wherein the chelating agent is present at a concentration of about 500 mM.

Embodiment 42. The method of any one of embodiments 25-41, wherein the solvent is an organic solvent.

Embodiment 43. The method of any one of embodiments 25-41, wherein the solvent comprises propylene glycol Embodiment 44. The method of any one of embodiments 25-41, wherein the solvent comprises petroleum jelly.

Embodiment 45. The method of any one of embodiments 25-41, wherein the solvent comprises an organic solvent and an aqueous solvent.

Embodiment 46. The method of embodiment 45, wherein the organic solvent is present in an amount of about 25%.

Embodiment 47. The method of embodiment 45, wherein the organic solvent is present in an amount of about 50%.

Embodiment 48. The method of any one of embodiments 45-47, wherein the organic solvent is propylene glycol and the aqueous solvent is water.

Embodiment 49. The method of any one of embodiments 45-47, wherein the organic solvent is dimethyl sulfoxide and the aqueous solvent is water.

Embodiment 50. The method of any one of embodiments 45-47, wherein the organic solvent is ethanol and the aqueous solvent is water.

Embodiment 51. The method of any one of embodiments 45-47, wherein the organic solvent is glycerol and the aqueous solvent is water.

Embodiment 52. The method of any one of embodiments 25-51, wherein the pharmaceutical composition further comprises an antibiotic.

Embodiment 53. The method of embodiment 52, wherein the antibiotic is polymyxin B.

Embodiment 54. The method of any one of embodiments 25-53, wherein the microorganism is on a plant.

Embodiment 55. A method of treating an infection comprising administering to a subject in need thereof a therapeutically-effective amount of a pharmaceutical composition, wherein the pharmaceutical composition comprises, in unit dosage form: a) a cationic surfactant, wherein the cationic surfactant is a cetyltrimethylammonium halide; b) a chelating agent, wherein the chelating agent is diethylenetriaminepentaacetic acid (DTPA) or a pharmaceutically-acceptable salt thereof; and c) a solvent.

Embodiment 56. The method of embodiment 55, wherein the microorganism is a bacterium Embodiment 57. The method of embodiment 55, wherein the microorganism is a fungus.

Embodiment 58. The method of embodiment 57, wherein the fungus is a mold.

Embodiment 59. The method of embodiment 55, wherein the microorganism is a yeast.

Embodiment 60. The method of embodiment 55, wherein the microorganism is a virus.

Embodiment 61. The method of any one of embodiments 55-60, wherein the cetyltrimethylammonium halide is cetyltrimethylammonium bromide.

Embodiment 62. The method of any one of embodiments 55-60, wherein the cetyltrimethylammonium halide is cetyltrimethylammonium chloride.

Embodiment 63. The method of any one of embodiments 55-62, wherein the cationic surfactant is present at a concentration of about 1 mM to about 500 mM.

Embodiment 64. The method of any one of embodiments 55-63, wherein the cationic surfactant is present at a concentration of about 1 mM.

Embodiment 65. The method of any one of embodiments 55-63, wherein the cationic surfactant is present at a concentration of about 400 mM.

Embodiment 66. The method of any one of embodiments 55-63, wherein the cationic surfactant is present at a concentration of about 500 mM.

Embodiment 67. The method of any one of embodiments 55-66, wherein the chelating agent is present at a concentration of about 10 mM to about 500 mM.

Embodiment 68. The method of any one of embodiments 55-67, wherein the chelating agent is present at a concentration of about 10 mM.

Embodiment 69. The method of any one of embodiments 55-67, wherein the chelating agent is present at a concentration of about 250 mM.

Embodiment 70. The method of any one of embodiments 55-67, wherein the chelating agent is present at a concentration of about 300 mM.

Embodiment 71. The method of any one of embodiments 55-67, wherein the chelating agent is present at a concentration of about 500 mM.

Embodiment 72. The method of any one of embodiments 55-71, wherein the solvent is an organic solvent.

Embodiment 73. The method of any one of embodiments 55-71, wherein the solvent comprises propylene glycol Embodiment 74. The method of any one of embodiments 55-71, wherein the solvent comprises petroleum jelly.

Embodiment 75. The method of any one of embodiments 55-71, wherein the solvent comprises an organic solvent and an aqueous solvent.

Embodiment 76. The method of embodiment 75, wherein the organic solvent is present in an amount of about 25%.

Embodiment 77. The method of embodiment 75, wherein the organic solvent is present in an amount of about 50%.

Embodiment 78. The method of any one of embodiments 75-77, wherein the organic solvent is propylene glycol and the aqueous solvent is water.

Embodiment 79. The method of any one of embodiments 75-77, wherein the organic solvent is dimethyl sulfoxide and the aqueous solvent is water.

Embodiment 80. The method of any one of embodiments 75-77, wherein the organic solvent is ethanol and the aqueous solvent is water.

Embodiment 81. The method of any one of embodiments 75-77, wherein the organic solvent is glycerol and the aqueous solvent is water.

Embodiment 82. The method of any one of embodiments 55-81, wherein the pharmaceutical composition further comprises an antibiotic.

Embodiment 83. The method of embodiment 82, wherein the antibiotic is polymyxin B.

Embodiment 84. A method of disinfecting a surface comprising administering to a surface in need thereof an effective amount of a pharmaceutical composition, wherein the pharmaceutical composition comprises, in unit dosage form: a) a cationic surfactant, wherein the cationic surfactant is a cetyltrimethylammonium halide; b) a chelating agent, wherein the chelating agent is diethylenetriaminepentaacetic acid (DTPA) or a pharmaceutically-acceptable salt thereof; and c) a solvent.

Embodiment 85. The method of embodiment 84, wherein the microorganism is a bacterium Embodiment 86. The method of embodiment 84, wherein the microorganism is a fungus.

Embodiment 87. The method of embodiment 86, wherein the fungus is a mold.

Embodiment 88. The method of embodiment 84, wherein the microorganism is a yeast.

Embodiment 89. The method of embodiment 84, wherein the microorganism is a virus.

Embodiment 90. The method of any one of embodiments 84-89, wherein the cetyltrimethylammonium halide is cetyltrimethylammonium bromide.

Embodiment 91. The method of any one of embodiments 84-89, wherein the cetyltrimethylammonium halide is cetyltrimethylammonium chloride.

Embodiment 92. The method of any one of embodiments 84-91, wherein the cationic surfactant is present at a concentration of about 1 mM to about 500 mM.

Embodiment 93. The method of any one of embodiments 84-92, wherein the cationic surfactant is present at a concentration of about 1 mM.

Embodiment 94. The method of any one of embodiments 84-92, wherein the cationic surfactant is present at a concentration of about 400 mM.

Embodiment 95. The method of any one of embodiments 84-92, wherein the cationic surfactant is present at a concentration of about 500 mM.

Embodiment 96. The method of any one of embodiments 84-95, wherein the chelating agent is present at a concentration of about 10 mM to about 500 mM.

Embodiment 97. The method of any one of embodiments 84-96, wherein the chelating agent is present at a concentration of about 10 mM.

Embodiment 98. The method of any one of embodiments 84-96, wherein the chelating agent is present at a concentration of about 250 mM.

Embodiment 99. The method of any one of embodiments 84-96, wherein the chelating agent is present at a concentration of about 300 mM.

Embodiment 100. The method of any one of embodiments 84-96, wherein the chelating agent is present at a concentration of about 500 mM.

Embodiment 101. The method of any one of embodiments 84-100, wherein the solvent is an organic solvent.

Embodiment 102. The method of any one of embodiments 84-100, wherein the solvent comprises propylene glycol Embodiment 103. The method of any one of embodiments 84-100, wherein the solvent comprises petroleum jelly.

Embodiment 104. The method of any one of embodiments 84-100, wherein the solvent comprises an organic solvent and an aqueous solvent.

Embodiment 105. The method of embodiment 104, wherein the organic solvent is present in an amount of about 25%.

Embodiment 106. The method of embodiment 104, wherein the organic solvent is present in an amount of about 50%.

Embodiment $10^7$. The method of any one of embodiments 104-106, wherein the organic solvent is propylene glycol and the aqueous solvent is water.

Embodiment 108. The method of any one of embodiments 104-106, wherein the organic solvent is dimethyl sulfoxide and the aqueous solvent is water.

Embodiment 109. The method of any one of embodiments 104-106, wherein the organic solvent is ethanol and the aqueous solvent is water.

Embodiment 110. The method of any one of embodiments 104-106, wherein the organic solvent is glycerol and the aqueous solvent is water.

Embodiment 111. The method of any one of embodiments 84-110, wherein the pharmaceutical composition further comprises an antibiotic.

Embodiment 112. The method of embodiment 111, wherein the antibiotic is polymyxin B.

Embodiment 113. A method of disinfecting an agricultural product, the method comprising contacting the agricultural product with an effective amount of a composition, wherein the composition comprises, in unit dosage form: a) a cationic surfactant, wherein the cationic surfactant is a cetyltrimethylammonium halide; b) a chelating agent, wherein the chelating agent is diethylenetriaminepentaacetic acid (DTPA) or a pharmaceutically-acceptable salt thereof: and c) a solvent.

Embodiment 114. The method of embodiment 113, wherein the agricultural product is a seed.

Embodiment 115. The method of embodiment 113, wherein the agricultural product is a plant.

Embodiment 116. The method of embodiment 113, wherein the agricultural product is a food-bearing plant.

Embodiment 117. The method of any one of embodiments 113-116, wherein the agricultural product is infected with a bacterium.

Embodiment 118. The method of any one of embodiments 113-116, wherein the agricultural product is infected with a fungus.

Embodiment 119. The method of embodiment 118, wherein the fungus is a mold.

Embodiment 120. The method of any one of embodiments 113-116, wherein the agricultural product is infected with a yeast.

Embodiment 121. The method of any one of embodiments 113-116, wherein the agricultural product is infected with a virus.

Embodiment 122. The method of any one of embodiments 113-121, wherein the cetyltrimethylammonium halide is cetyltrimethylammonium bromide.

Embodiment 123. The method of any one of embodiments 113-121, wherein the cetyltrimethylammonium halide is cetyltrimethylammonium chloride.

Embodiment 124. The method of any one of embodiments 113-123, wherein the cationic surfactant is present at a concentration of about 1 mM to about 500 mM.

Embodiment 125. The method of any one of embodiments 113-124, wherein the cationic surfactant is present at a concentration of about 1 mM.

Embodiment 126. The method of any one of embodiments 113-124, wherein the cationic surfactant is present at a concentration of about 400 mM.

Embodiment 127. The method of any one of embodiments 113-124, wherein the cationic surfactant is present at a concentration of about 500 mM.

Embodiment 128. The method of any one of embodiments 113-127, wherein the chelating agent is present at a concentration of about 10 mM to about 500 mM.

Embodiment 129. The method of any one of embodiments 113-128, wherein the chelating agent is present at a concentration of about 10 mM.

Embodiment 130. The method of any one of embodiments 113-128, wherein the chelating agent is present at a concentration of about 250 mM.

Embodiment 131. The method of any one of embodiments 113-128, wherein the chelating agent is present at a concentration of about 300 mM.

Embodiment 132. Embodiment 131. The method of any one of embodiments 113-128, wherein the chelating agent is present at a concentration of about 500 mM.

Embodiment 133. The method of any one of embodiments 113-132, wherein the solvent is an organic solvent.

Embodiment 134. The method of any one of embodiments 113-132, wherein the solvent comprises propylene glycol.

Embodiment 135. The method of any one of embodiments 113-132, wherein the solvent comprises petroleum jelly.

Embodiment 136. The method of any one of claims 113-132, wherein the solvent comprises an organic solvent and an aqueous solvent.

Embodiment 137. The method of embodiment 136, wherein the organic solvent is present in an amount of about 25%.

Embodiment 138. The method of embodiment 136, wherein the organic solvent is present in an amount of about 50%.

Embodiment 139. The method of any one of embodiments 136-138, wherein the organic solvent is propylene glycol and the aqueous solvent is water.

Embodiment 140. The method of any one of embodiments 136-138, wherein the organic solvent is dimethyl sulfoxide and the aqueous solvent is water.

Embodiment 141. The method of any one of embodiments 136-138, wherein the organic solvent is ethanol and the aqueous solvent is water.

Embodiment 142. The method of any one of embodiments 136-138, wherein the organic solvent is glycerol and the aqueous solvent is water.

Embodiment 143. The method of any one of embodiments 113-142, wherein the pharmaceutical composition further comprises an antibiotic.

Embodiment 144. The method of embodiment 143, wherein the antibiotic is polymyxin B.

What is claimed is:

1. A pharmaceutical composition comprising, in a unit dosage form:
   a) a cationic surfactant, wherein the cationic surfactant is a cetyltrimethylammonium halide;
   b) a chelating agent, wherein the chelating agent is diethylenetriaminepentaacetic acid (DTPA) or a pharmaceutically-acceptable salt thereof, and wherein the pharmaceutical composition comprises the chelating agent at a concentration of from about 200 mM to about 500 mM; and
   c) a solvent,
   wherein the pharmaceutical composition further comprises an antibiotic.

2. The pharmaceutical composition of claim 1, wherein the cetyltrimethylammonium halide is cetyltrimethylammonium bromide.

3. The pharmaceutical composition of claim 1, wherein the cetyltrimethylammonium halide is cetyltrimethylammonium chloride.

4. The pharmaceutical composition of claim 1, wherein the cationic surfactant is present in the pharmaceutical composition at a concentration of from about 1 mM to about 500 mM.

5. The pharmaceutical composition of claim 1, wherein the solvent comprises an organic solvent and an aqueous solvent.

6. The pharmaceutical composition of claim 5, wherein the organic solvent is propylene glycol and the aqueous solvent is water.

7. The pharmaceutical composition of claim 5, wherein the organic solvent is dimethyl sulfoxide and the aqueous solvent is water.

8. The pharmaceutical composition of claim 1, wherein the antibiotic is polymyxin B.

9. A method of killing a microorganism comprising administering to the microorganism a therapeutically-effective amount of a pharmaceutical composition, wherein the pharmaceutical composition comprises, in a unit dosage form:
   a) a cationic surfactant, wherein the cationic surfactant is a cetyltrimethylammonium halide;
   b) a chelating agent, wherein the chelating agent is diethylenetriaminepentaacetic acid (DTPA) or a pharmaceutically-acceptable salt thereof, and wherein the pharmaceutical composition comprises the chelating agent at a concentration of from about 200 mM to about 500 mM; and
   c) a solvent,
   wherein the solvent comprises dimethyl sulfoxide and water.

10. The method of claim 9, wherein the microorganism is a bacterium.

11. The method of claim 9, wherein the microorganism is a virus.

12. The method of claim 9, wherein the cetyltrimethylammonium halide is cetyltrimethylammonium bromide.

13. The method of claim 9, wherein the cetyltrimethylammonium halide is cetyltrimethylammonium chloride.

14. The method of claim 9, wherein the cationic surfactant is present at a concentration of from about 1 mM to about 500 mM.

15. A method of killing a microorganism comprising administering to the microorganism a therapeutically-effective amount of a pharmaceutical composition, wherein the pharmaceutical composition comprises, in a unit dosage form:
- a) a cationic surfactant, wherein the cationic surfactant is a cetyltrimethylammonium halide;
- b) a chelating agent, wherein the chelating agent is diethylenetriaminepentaacetic acid (DTPA) or a pharmaceutically-acceptable salt thereof, and wherein the pharmaceutical composition comprises the chelating agent at a concentration of from about 200 mM to about 500 mM; and
- c) a solvent, wherein the pharmaceutical composition further comprises an antibiotic.

16. The method of claim 15, wherein the cetyltrimethylammonium halide is cetyltrimethylammonium bromide or cetyltrimethylammonium chloride.

17. The method of claim 15, wherein the cationic surfactant is present at a concentration of from about 1 mM to about 500 mM.

18. The method of claim 15, wherein the solvent comprises an organic solvent and an aqueous solvent.

19. The method of claim 15, wherein the microorganism is a bacterium.

20. The method of claim 15, wherein the antibiotic is polymyxin B.

* * * * *